(12) United States Patent
Srivastava et al.

(10) Patent No.: US 12,018,235 B2
(45) Date of Patent: *Jun. 25, 2024

(54) MANNANASE VARIANTS AND POLYNUCLEOTIDES ENCODING SAME

(71) Applicant: Novozymes A/S, Bagsvaerd (DK)

(72) Inventors: Vivek Srivastava, Bangalore (IN); Markus Klinger, Vaerloese (DK); Rakhi Saikia, Bangalore (IN); Vijaya Shankar Nataraj, Bangalore (IN); Sohel Dalal, Bangalore (IN); Jens Erik Nielsen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 258 days.

This patent is subject to a terminal disclaimer.

(21) Appl. No.: 16/605,091

(22) PCT Filed: Apr. 26, 2018

(86) PCT No.: PCT/EP2018/060729
§ 371 (c)(1),
(2) Date: Oct. 14, 2019

(87) PCT Pub. No.: WO2018/206302
PCT Pub. Date: Nov. 15, 2018

(65) Prior Publication Data
US 2021/0130743 A1  May 6, 2021

(30) Foreign Application Priority Data

May 8, 2017 (IN) .............................. 201741016141

(51) Int. Cl.
*C12N 9/24* (2006.01)
*C11D 3/386* (2006.01)

(52) U.S. Cl.
CPC ...... *C11D 3/38636* (2013.01); *C11D 3/38618* (2013.01); *C12N 9/2491* (2013.01); *C11D 2111/12* (2024.01); *C11D 2111/14* (2024.01)

(58) Field of Classification Search
None
See application file for complete search history.

(56) References Cited

U.S. PATENT DOCUMENTS

| | | | | |
|---|---|---|---|---|
| 11,492,605 B2 * | 11/2022 | Srivastava | ............ | C12N 9/2437 |
| 2004/0259749 A1 * | 12/2004 | Braeckman | ........ | C11D 17/0086 510/220 |
| 2016/0115465 A1 * | 4/2016 | Hua | ..................... | C12N 9/2491 435/254.11 |

FOREIGN PATENT DOCUMENTS

| | | | |
|---|---|---|---|
| WO | 1999/64619 A2 | 12/1999 | |
| WO | 2015/149641 A1 | 10/2015 | |
| WO | 2016/007929 A2 | 1/2016 | |
| WO | 2016/054176 A1 | 4/2016 | |
| WO | WO-2017079751 A1 * | 5/2017 | ............. A23L 29/06 |

OTHER PUBLICATIONS

Singh et al., Curr. Protein Pept. Sci. 18:Jan. 11, 2017 (Year: 2017).*
Zhang et al., Structure 26:1474-1485, 2018 (Year: 2018).*
Ma et al., Extremophiles 8:447-454, 2004 (Year: 2004).*
UniProt Database Accession No. A0A1H3HAJ0, Sep. 2021, 1 page (Year: 2021).*
UniProt Database Accession No. Q6QHT4, Apr. 2017, 1 page (Year: 2017).*
Goswami et al., Front. Onc. 9:297, 2019, 25 pages (Year: 2019).*
Betts et al., Bioinformatics for Geneticists, Chapter 14, Amino Acid Properties and Consequences of Substitutions, pp. 289-316, 2003 (Year: 2003).*
Adams et al., WO 2016-007929 A2—Database Accession No. BCK93993.
Ademark et al, 1998, J Biotechnol, vol. 63, pp. 199-210.
Araujo et al, 1990, J Appl Bacteriol, vol. 68, pp. 253-261.
Bewley et al, 1997, Planta, vol. 203, pp. 454-459.
Couturier et al., 2013, PLOS One, vol. 8, No. 11, p. e79800.
Dhawan et al., 2007, CRC Critical Reviews in Biotechnology, vol. 27, No. 4, pp. 197-216.
Dutta et al., 1997, Plant Physiol, vol. 113, pp. 155-161.
Halstead et al., 2000, FEMS Microbial Lett, vol. 192, pp. 197-203.
Henrissat et al., 1991, J Biochem, vol. 280, pp. 309-316.
Kauppinen et al., WO 1999-064619 A2—EBI Accession No. AAY54127.
Kauppinen et al., WO 1999-064619 A2—EBI Accession No. AAY54122.
Lee et al., 2003, Poultry Science, vol. 82, pp. 1925-1931.
McCutchen et al., 1996, Biotechnol Bioeng, vol. 52, pp. 332-339.
Moreira et al., 2008, Appl Microbiol Biotechnol, vol. 79, pp. 165-178.
Puchart et al., 2004, Biochem Biophys Acta, vol. 1674, pp. 239-250.
Suurnakki et al., 1997, Adv Biochem ENG Biotechnol, vol. 57, pp. 261-287.
Xu et al., 2002, Eur J Biochem, vol. 269, pp. 1753-1760.
Zhou et al., 2016, Applied Biochemistry and Biotechnol; Part A: Enz Engineering and Biotech, vol. 180, No. 1, pp. 122-135.

* cited by examiner

*Primary Examiner* — David Steadman
(74) *Attorney, Agent, or Firm* — Kelly K. Reynolds

(57) ABSTRACT

The present invention relates to mannanase variants. The present invention also relates to polynucleotides encoding the variants; nucleic acid constructs, vectors, and host cells comprising the polynucleotides; and methods of using the variants.

16 Claims, No Drawings
Specification includes a Sequence Listing.

MANNANASE VARIANTS AND POLYNUCLEOTIDES ENCODING SAME

CROSS-REFERENCE TO RELATED APPLICATIONS

This application is a 35 U.S.C. 371 national application of international application no. PCT/EP2018/060729 filed Apr. 26, 2018 which claims priority or the benefit under 35 U.S.C. 119 of International application no. IN 201741016141 filed May 8, 2017 the contents of which are fully incorporated herein by reference.

Reference to a Sequence Listing

This application contains a Sequence Listing in computer readable form, which is incorporated herein by reference.

BACKGROUND OF THE INVENTION

Field of the Invention

The present invention relates to mannanase variants exhibiting mannanase activity, compositions comprising the mannanase variants, polynucleotides encoding the variants, methods of producing the variants, and methods of using the variants.

Description of the Related Art

Endo-1,4-mannanases (EC 3.2.1.78) are involved in the random hydrolysis of (1→4)-β-D-mannosidic linkages in mannans, galactomannans, glucomannans and galactoglucomannans (Ademark et al. (1998) J. Biotechnol. 63:199-210).

Mannan containing polysaccharides are often a major component of the hemicellulose fraction in woods, both softwood and hardwood.

Essentially unsubstituted linear beta-1,4-mannan is found in fruits of several palm trees, such as palm kernels and coconuts. Unsubstituted beta-1,4-mannan which is present e.g. in ivory nuts resembles cellulose in the conformation of the individual polysaccharide chains, and is water-insoluble. In leguminous seeds, water-soluble galactomannan is the main storage carbohydrate comprising up to 20% of the total dry weight. See Moreira et al., (2008) Appl. Microbiol. Biotechnol. 79:165-178. Galactomannans have a linear beta-1,4-mannan backbone substituted with single alpha-1,6-galactose, optionally substituted with acetyl groups. Glucomannans are linear polysaccharides with a backbone of beta-1,4-linked mannose and glucose alternating in a more or less regular manner, the backbone optionally being substituted with galactose and/or acetyl groups. Mannans, galactomannans, glucomannans and galactoglucomannans (i.e. glucomannan backbones with branched galactose) contribute to more than 50% of the softwood hemicellulose. Moreover, the cellulose of many red algae contains a significant amount of mannose.

Mannanases have been identified in several *Bacillus* organisms, but also from other bacteria, fungi, plants, and animals. See, Araujo A. et al., (1990) I. App. Bacteriol. 68:253-261; Dutta S. et al., (1997) Plant Physiol. 113: 155-161; Puchar V. et al, (2004) Biochim. Biophys. Acta 1674:239-250. Genes encoding these enzymes from a number of organisms have also been cloned and sequenced, many if not all have been classified also as members of glycosyl hydrolase (GH) family 5 or 26, based on their sequences. See, e.g., Bewley D. J., (1997) Planta 203:454-459; Halstead J. R. et al., (2000) FEMS Microl. Lett. 192: 197-203; Xu B. et al., (2002) Eur. J. Biochem. 269: 1753-1760; Henrissat, B. (1991) Biochem. J. 280:309-316.

Beta-mannanases have been used in commercial applications in, for example, industries such as the paper and pulp industry, foodstuff and feed industry, pharmaceutical industry and energy industry. Lee J. T., et al., (2003) Poult. Sci. 82: 1925-1931; McCutchen M. C., et al., (1996) Biotechnol. Bioeng. 52:332-339; Suurnakki A., et al., (1997) Adv. Biochem. Eng. Biotechnol, 57:261-287.

Within the household care industry, it has been known to use mannanases in e.g. laundry detergents. In WO 1999/064619 an alkaline mannanase, which exhibites mannanase activity also in the alkaline pH range when applied in cleaning compositions, is disclosed.

In WO 2016/054176 other mannanases exhibiting beta-mannanase activity are disclosed.

However, mannanases with improved stability, in particular when used in detergents, have not been disclosed in the prior art. As can be seen from the data herein disclosed, the stability of a wild-type mannanase can be significantly improved by protein engineering. Viewed from a commercial side, providing a mannanase having an improved stability, will have a great impact for the detergent producing industry.

Thus, it is the object of the present invention to provide mannanase variants with improved stability compared to its parent.

SUMMARY OF THE INVENTION

The present invention relates to an isolated mannanase variant, wherein said variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, e.g. at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

The present invention also relates to a composition comprising a variant as herein disclosed, use of such a composition in a domestic or industrial cleaning process, an isolatedpolynucleotide encoding the variants; nucleic acid constructs, vectors, and host cells comprising the polynucleotides; and methods of producing the variants as well as methods of dishwashing or laundering in automatic machines using a composition herein disclosed.

Definitions

Before the invention is described in further details, it is to be understood that the present variants, compositions and methods are not limited to particular embodiments described, as such may, of course, differ. It is also to be understood that the terminology used herein is for the purpose of describing particular embodiments only, and is not intended to be limiting, since the scope of the present invention will be limited only by the appended claims.

Thus, prior to discussing the invention in further detail, the following terms will first be defined. In accordance with the detailed description, the following abbreviations and definitions apply. Note that the singular forms "a", "an", and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Certain ranges are presented herein with numerical values being preceded by the term "about". The term "about" as used herein, is to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless term is otherwise specifically defined in context. In another example, the phrase a "pH value of about 9" refers to pH values of from 8.1 to 9.9, unless the pH value is specifically defined otherwise.

Mannanase: The term "mannanase" or "galactomannanase" as used herein refers to a mannanase enzyme defined as the officially named mannan endo-1,4-beta-mannosidase and having the alternative names beta-mannanase and endo-1,4-mannanase. The mannanase term also means a polypeptide or polypeptide domain of an enzyme that has the ability to catalyze the cleavage or hydrolysis of (1→4) beta-D-mannosidic linkages of mannans, galactomannans, glucomannans, and galactoglucomannans. Thus, it means that the mannanase has mannanase activity (EC 3.2.1.78). For purposes of the present invention, mannanase activity is determined according to the procedure described in the Examples. In one aspect, the variants of the present invention have at least 20%, e.g., at least 40%, at least 50%, at least 60%, at least 70%, at least 80%, at least 90%, at least 95%, or at least 100% of the mannanase activity of the mature polypeptide of SEQ ID NO: 1.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Comprising: The term "comprising" as used herein refers to, including, but not limited to, the component(s) or feature(s) after the term "comprising". The component(s) or feature(s) after the term "comprising" are required or mandatory, but the embodiment, may further include other non-mandatory or optional component(s) or feature(s).

Consisting of: The term "consisting of" as used herein refers to, including, and limited to, the component(s) or feature(s) after the term "consisting of". The component(s) or feature(s) after the term "consisting of" are therefore required or mandatory, and no other non-mandatory or optional component(s) or feature(s) are present in the embodiments.

Expression: The term "expression" includes any step involved in the production of a variant including, but not limited to, transcription, post-transcriptional modification, translation, post-translational modification, and secretion.

Expression vector: The term "expression vector" as used herein, refers to a linear or circular DNA molecule that comprises a polynucleotide encoding a variant and is operably linked to control sequences that provide for its expression. Such control sequences may include a promotor to affect transcription, an optional operator sequence to control transcription, a sequence encoding suitable ribosome-binding sites on the mRNA, and sequence which control termination of transcription and translation. Different cell types may be used with different expression vectors.

Fragment: The term "fragment" means a polypeptide having one or more (e.g., several) amino acids absent from the amino and/or carboxyl terminus of a mature polypeptide; wherein the fragment has mannanase activity. In one aspect, a fragment contains at least 250 amino acid residues (e.g., amino acids 250 to 300 of SEQ ID NO: 2), at least 260 amino acid residues (e.g., amino acids 260 to 300 of SEQ ID NO: 2), at least 270 amino acid residues (e.g., amino acids 270 to 300 of SEQ ID NO: 2), or at least 285 amino acid residues (e.g., amino acids 285 to 300 of SEQ ID NO: 2.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication. Host cells useful in the present invention are generally prokaryotic or eukaryotic host, including any transformable microorganism in which expression can be achieved. Host cells are transformed or transfected with vectors constructed using recombinant DNA techniques. Such transformed host cells may be capable of one or both of replicating the vectors encoding the variant of the present invention and expressing the desired peptide product.

Improved property: The term "improved property" as used herein, refers to a characteristic associated with a variant that is improved compared to the parent. Such improved properties include, but are not limited to, catalytic efficiency, catalytic rate, in-detergent stability, chemical stability, oxidation stability, pH activity, pH stability, specific activity, stability under storage conditions, substrate binding, substrate cleavage, substrate specificity, substrate stability, surface properties, thermal activity, and thermostability.

In-detergent stability: The term "in-detergent stability" as used herein, refers to the stability of a mannanase enzyme, being both a wild-type, parent or variant, when it has been incubated in a detergent. For the purposes of the present invention, in-detergent stability may be determined as shown in Example 3.

Isolated: The term "isolated" as used herein, refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" as used herein, refers to a polypeptide in its final form following translation and any post-translational modifications, such as N-terminal processing, C-terminal truncation, glycosylation, phosphorylation, etc. In one aspect, the mature polypeptide is amino acids 1 to 298 of SEQ ID NO: 1 based on the SignalP 3.0 predictions (Using neural networks (NN) and hidden Markov models (HMM) trained on Gram-positive bacteria) that predicts amino acids −28 to −1 of SEQ ID NO: 1 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" as used herein, refers to a polynucleotide that encodes a mature polypeptide having mannanase activity. In one aspect, the mature polypeptide coding sequence is nucleotides 218 to 1111 of SEQ ID NO: 3.

Mutant: The term "mutant" as used herein, refers to a polynucleotide encoding a variant.

Nucleic acid construct: The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" as used herein, refers to a configuration in which a control sequence is placed at an appropriate position relative to the coding sequence of a polynucleotide such that the control sequence directs expression of the coding sequence. Thus, "operably linked" means that a regulatory region or functional domain having a known or desired activity, such as a promoter, terminator, signal sequence or enhancer region, is attached to or linked to a target (e.g., a gene or polypeptide) in such a manner as to allow the regulatory region or functional domain to control the expression, secretion or function of that target according to its known or desired activity.

Parent or parent mannanase: The term "parent", "parent mannanase" or "parent polypeptide" as used herein refers to any polypeptide with mannanase activity to which a modification is made to produce the enzyme variants of the present invention. In the present invention, it is to be understood, that a parent polypeptide both refers to a naturally-occurring polypeptide that does not include a man-made substitution, insertion, or deletion at one or more amino acid positions and to non-naturally-occurring polypeptides such as hybrids, or polypeptides comprising man-made modifications. Similarly, the term "parent" with respect to a polynucleotide, refers to both a naturally-occurring polynucleotide that does not include a man-made nucleoside change and to non-naturally-occurring polynucleotides such as hybrids, or polynucleotides comprising man-made modifications. A polynucleotide encoding a parent polypeptide is not limited to a naturally-occurring polynucleotide, but rather encompasses any polynucleotide encoding the parent polypeptide. The parent mannanase may be any mannanase having at least 58%, 60%, such as at least 62%, at least 65%, at least 70%, at least 75%, at least 80%, at least 85%, at least 90%, at least 95%, or 100% sequence identity to SEQ ID NO: 1 or 2. In one particular aspect of the present invention, the parent mannanase is the polypeptide of SEQ ID NO: 2 or a polypeptide having at least 58% sequence identity to SEQ ID NO: 2.

Polypeptide or enzyme: The terms "polypeptide" and "enzyme" may be used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.) as well as other modifcations known in the art.

Sequence identity: The relatedness between two amino acid sequences or between two nucleotide sequences is described by the parameter "sequence identity". As used herein, "percent (%) sequence identity" with respect to the amino acid or nucleotide sequence identified herein is defined as the percentage of amino acid residues or nucleotides in a candidate sequence that are identical with the amino acid residues or nucleotides in a mannanase sequence as set out in the sequence of SEQ ID NO: 1 or the sequence of SEQ ID NO: 2, or for nucleotides the sequence of SEQ ID NO: 3, after aligning the sequences and introducing gaps, if necessary, to achieve the maximum percent sequence identity, and not considering any conservative substitutions as part of the sequence identity.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62

(EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Variant: The term "variant" as used herein, refers to a polypeptide having mannanase activity comprising an modification, i.e., a substitution or deletion, at one position. A substitution means replacement of the amino acid occupying a position with a different amino acid; and a deletion means removal of the amino acid occupying a position. The variants of the present invention have at least 20%, e.g., at least 40%, at least 50%, at least 60%, at least 70%, at least 80%, at least 90%, at least 95%, or at least 100% of the mannanase activity of the mature polypeptide of SEQ ID NO: 1 or SEQ ID NO: 2.

Wild-type mannanase: The term "wild-type mannanase" as used herein, refers to a mannanase expressed by a naturally occurring microorganism, such as a bacterium, yeast, or filamentous fungus found in nature.

Sequences Referred to in the Invention

SEQ ID NO: 1 is a parent mannanase including the signal peptide.
SEQ ID NO: 2 is the mature polypeptide of SEQ ID NO: 1.
SEQ ID NO: 3 is a nucleotide sequence encoding the polypeptide of SEQ ID NO: 1.
SEQ ID NO: 4 is a mature protease.

Conventions for Designation of Variants

For purposes of the present invention, the mature polypeptide disclosed in SEQ ID NO: 2 is used to determine the corresponding amino acid residue in another mannanase. The amino acid sequence of another mannanase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another mannanase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 53709-64; Katoh and Toh, 2010, Bioinformatics 26:1899-1900), and EMBOSS EMMA employing ClustalW (1.83 or later; Thompson et al., 1994, Nucleic Acids Research 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
| --- | --- |
| 195 | 195 195a 195b |
| G | G-K-A |

Multiple modifications. Variants comprising multiple modifications are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different modifications. Where different modifications can be introduced at a position, the different modifications are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated mannanase variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, e.g. at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

The inventors of the present invention has found that a modification in one of the above listed positions of (a) provides a mannanase variants which have an improved stability compared to the parent mannanase, i.e. a mannanase not comprising a modification in any one of the listed positions. Thus, the improvement of the mannanase variants is observed when the variant has at least one of (a) listed positions. When combining (a) listed positions with any other modification, it has been observed that the stability is maintained. Thus, these positions are believed to be important for stability of mannanases. In particular, the stability may be observed as stability in detergent compositions. Such detergent stability may be determined as described in Example 3, i.e. by incubating the variants in detergent e.g. for 24 hrs at 40° C. or for 16 hrs at 45° C., and then measureing the residual activity. The residual activity is correlated/compared to the residual activity of a parent mannanase incubated at 4° C. for the equal amount of hours. The improvement of the mannanase variants are given as half-life improvement factor (HIF).

Thus, the present invention provides variants of a parent mannanase, wherein the variant comprises at least one substitution in one or more of the positions 260, 288, 294, and 295, wherein numbering is according to SEQ ID NO: 2, and at least one second (or further) substitution in a position which is in any other position in the amino acid sequence. The term "second substitution" or "further substitution" as used herein, are to be understood as being a substitution which is not in any of the following positions 260, 288, 294, and 295. However, the variant according to the invention may comprise more than one substitution in any one of the positions 260, 288, 294, and 295. Furthermore, the term "second substitution" is to be understood as "at least one second substitution", i.e. the second substitution may be in one or more positions.

The stability in detergent compositions may herein be referred to a "in detergent stability" and falls under the definition elsewhere described herein. The terms may be used interchangeably, but constitute the same meaning and purpose for the present invention. The stability has been determined as described in the Examples.

As can be seen from the Examples, all the disclosed variants have an improved stability, in particular when tested under stress. Such stress in according to the present invention may be increased by altering (i.e. raising the pH), incubating for a longer/extended time period, altered (i.e raised) temperature and/or in the presence of a protease.

It is to be understood that the variants of the present invention comprises at least two modifications, such as substitutions, which means that the variants may comprise a substitution in one of the positions listed in (a) and then the second/further substitution(s) is in any other positions herein disclosed. However, it is also to be understood that variants of the present invention may be variants that comprise a substitution in more than one of the listed positions in (a), i.e. in two, three or all four positions. Thus, embodiments of the present invention encompass variants comprising or consisting of a substitution in the following positions: 260+288, 260+294, 260+295, 288+294, 288+295, 294+295, 260+288+294, 260+288+295, 260+294+295, 288+294+295, and 260+288+294+295.

In one embodiment, the mannanase variant comprises a modification in the positions corresponding to positions 260 and 288 of SEQ ID NO: 2, and a second modification selected from any other position in said variant.

In one embodiment, the mannanase variant comprises a modification in the positions corresponding to positions 260 and 294 of SEQ ID NO: 2, and a second modification selected from any other position in said variant.

In one embodiment, the mannanase variant comprises a modification in the positions corresponding to positions 260 and 295 of SEQ ID NO: 2, and a second modification selected from any other position in said variant.

In one embodiment, the mannanase variant comprises a modification in the positions corresponding to positions 288 and 294 of SEQ ID NO: 2, and a second modification selected from any other position in said variant.

In one embodiment, the mannanase variant comprises a modification in the positions corresponding to positions 288 and 295 of SEQ ID NO: 2, and a second modification selected from any other position in said variant.

In one embodiment, the mannanase variant comprises a modification in the positions corresponding to positions 294 and 295 of SEQ ID NO: 2, and a second modification selected from any other position in said variant.

In one embodiment, the mannanase variant comprises a modification in the positions corresponding to positions 260, 288, and 294 of SEQ ID NO: 2, and a second modification selected from any other position in said variant.

In one embodiment, the mannanase variant comprises a modification in the positions corresponding to positions 260, 288, and 295 of SEQ ID NO: 2, and a second modification selected from any other position in said variant.

In one embodiment, the mannanase variant comprises a modification in the positions corresponding to positions 260, 294, and 295 of SEQ ID NO: 2, and a second modification selected from any other position in said variant.

In one embodiment, the mannanase variant comprises a modification in the positions corresponding to positions 288, 294, and 295 of SEQ ID NO: 2, and a second modification selected from any other position in said variant.

In one embodiment, the mannanase variant comprises a modification in the positions corresponding to positions 260, 288, 294, and 295 of SEQ ID NO: 2, and a second modification selected from any other position in said variant.

In one embodiment, the alteration is a substitution. In one embodiment, the substitution in the position corresponding to position 260 of SEQ ID NO: 2, is F, Y, L, or T, preferably F. In one embodiment, the substitution in the position corresponding to position 288 of SEQ ID NO: 2, is I. In one embodiment, the substitution in the position corresponding to position 294 of SEQ ID NO: 2, is P, K, I, R, V, or H, preferably P. In one embodiment, the substitution in the position corresponding to position 295 of SEQ ID NO: 2, is K, V, P, L, R, A, N, M, or I, preferably P or V.

In one embodiment, the alteration is a deletion.

In an embodiment, the at least one second substitution is in at least one or more positions selected from the positions: 1, 2, 3, 4, 5, 6, 8, 11, 13, 14, 18, 30, 32, 33, 34, 35, 37, 41, 45, 47, 57, 59, 60, 63, 65, 70, 71, 74, 77, 78, 80, 82, 83, 93, 95, 97, 98, 100, 104, 108, 111, 114, 116, 118, 119, 131, 133, 135, 136, 139, 142, 143, 150, 169, 172, 174, 176, 177, 180, 183, 184, 185, 196, 200, 202, 203, 205, 210, 213, 228, 229, 234, 235, 241, 243, 244, 250, 254, 257, 262, 266, 268, 270, 272, 273, 276, 279, 280, 283, 286, 290, 296, and 298, wherein numbering is according to SEQ ID NO: 2.

When the Improvement Factor (IF) is more than 1.0, it means that the variant tested has an improved property, such as improved stability, compared to the parent mannanase.

The substitution may be made in any one of the positions corresponding to positions: 1, 2, 3, 5, 6, 8, 9, 10, 11, 13, 14, 16, 17, 18, 19, 21, 35, 37, 38, 39, 41, 44, 45, 47, 59, 60, 62, 65, 67, 68, 70, 71, 74, 77, 78, 79, 80, 81, 82, 83, 93, 95, 96, 97, 98, 100, 104, 107, 110, 111, 114, 115, 116, 118, 119, 132, 133, 135, 136, 139, 142, 143, 147, 150, 152, 154, 164, 167, 169, 174, 175, 176, 177, 180, 181, 183, 184, 185, 199, 200, 202, 203, 205, 206, 210, 212, 213, 214, 215, 226, 229, 234, 235, 241, 242, 243, 244, 254, 257, 258, 259, 260, 261, 267, 270, 273, 276, 279, 280, 283, 285, 286, 288, 289, 290, 292, 293, 294, 295, 296, 299, and 301, wherein numbering is according to SEQ ID NO: 2.

Unless specifically disclosed herein, the numbering of amino acid residues or positions, are done according to SEQ ID NO: 2.

In one embodiment, the one or more positions are selected from the positions 14, 37, 47, 77, 81, 82, 83, 93, 98, 116, 135, 136, 241, 242, 257, and 258 of the polypeptide of SEQ ID NO: 2.

In particular, the mannanase variant comprises two modifications in positions selected from the group of position sets: 14+260, 14+288, 14+294, 14+295, 37+260, 37+288, 37+294, 37+295, 47+260, 47+288, 47+294, 47+295, 77+260, 77+288, 77+294, 77+295, 81+260, 81+288, 81+294, 81+295, 82+260, 82+288, 82+294, 82+295, 83+260, 83+288, 83+294, 83+295, 93+260, 93+288, 93+294, 93+295, 98+260, 98+288, 98+294, 98+295, 116+260, 116+288, 116+294, 116+295, 135+260, 135+288, 135+294, 135+295, 136+260, 136+288, 136+294, 136+295, 241+260, 241+288, 241+294, 241+295, 242+260, 242+288, 242+294, 242+295, 257+260, 257+288, 257+294, 257+295, 258+260, 258+288, 258+294, 258+295, and 260+288, wherein numbering is according to SEQ ID NO: 2.

In one embodiment, the at least two substitutions are selected from the group of positions: 14+260, 14+288, 14+294, 14+295, 37+260, 37+288, 37+294, 37+295, 47+260, 47+288, 47+294, 47+295, 77+260, 77+288, 77+294, 77+295, 81+260, 81+288, 81+294, 81+295, 82+260, 82+288, 82+294, 82+295, 83+260, 83+288, 83+294, 83+295, 93+260, 93+288, 93+294, 93+295, 98+260, 98+288, 98+294, 98+295, 116+260, 116+288, 116+294, 116+295, 135+260, 135+288, 135+294, 135+295, 136+260, 136+288, 136+294, 136+295, 241+260, 241+288, 241+294, 241+295, 242+260, 242+288, 242+294, 242+295, 257+260, 257+288, 257+294, 257+295, 258+260, 258+288, 258+294, 258+295, and 260+288, wherein numbering is according to SEQ ID NO: 2.

In one embodiment, the at least second substitution is in one or both of positions 93 and 136 of the polypeptide of SEQ ID NO: 2.

Specifically, the invention relates to mannanase variants comprising a substitution in the following group of positions: 14+93+260, 14+93+288, 14+93+294, 14+93+295, 37+93+260, 37+93+288, 37+93+294, 37+93+295, 47+93+260, 47+93+288, 47+93+294, 47+93+295, 77+93+260, 77+93+288, 77+93+294, 77+93+295, 81+93+260, 81+93+288, 81+93+294, 81+93+295, 82+93+260, 82+93+288, 82+93+294, 82+93+295, 83+93+260, 83+93+288, 83+93+294, 83+93+295, 93+98+260, 93+98+288, 93+98+294, 93+98+295, 93+116+260, 93+116+288, 93+116+294, 93+116+295, 93+135+260, 93+135+288, 93+135+294, 93+135+295, 93+136+260, 93+136+288, 93+136+294, 93+136+295, 93+241+260, 93+241+288, 93+241+294, 93+241+295, 93+242+260, 93+242+288, 93+242+294, 93+242+295, 93+257+260, 93+257+288, 93+257+294, 93+257+295, 93+258+260, 93+258+288, 93+258+294, 93+258+295, and 93+260+288, wherein numbering is according to SEQ ID NO: 2.

In another embodiment, the invention relates to mannanase variants comprising a substitution in the following group of positions: 14+136+260, 14+136+288, 14+136+294, 14+136+295, 37+136+260, 37+136+288, 37+136+294, 37+136+295, 47+136+260, 47+136+288, 47+136+294, 47+136+295, 77+136+260, 77+136+288, 77+136+294, 77+136+295, 81+136+260, 81+136+288, 81+136+294, 81+136+295, 82+136+260, 82+136+288, 82+136+294, 82+136+295, 83+136+260, 83+136+288, 83+136+294, 83+136+295, 93+136+260, 93+136+288, 93+136+294, 93+136+295, 98+136+260, 98+136+288, 98+136+294, 98+136+295, 116+136+260, 116+136+288, 116+136+294, 116+136+295, 135+136+260, 135+136+288, 135+136+294, 135+136+295, 136+241+260, 136+241+288, 136+241+294, 136+241+295, 136+242+260, 136+242+288, 136+242+294, 136+242+295, 136+257+260, 136+257+288, 136+257+294, 136+257+295, 136+258+260, 136+258+288, 136+258+294, 136+258+295,and 136+260+288, wherein numbering is according to SEQ ID NO: 2.

In another embodiment, the invention relates to mannanase variants comprising a substitution in the following group of positions: 14+93+136+260, 14+93+136+288, 14+93+136+294, 14+93+136+295, 37+93+136+260, 37+93+136+288, 37+93+136+294, 37+93+136+295, 47+93+136+260, 47+93+136+288, 47+93+136+294, 47+93+136+295, 77+93+136+260, 77+93+136+288, 77+93+136+294, 77+93+136+295, 81+93+136+260, 81+93+136+288, 81+93+136+294, 81+93+136+295, 82+93+136+260, 82+93+136+288, 82+93+136+294, 82+93+136+295, 83+93+136+260, 83+93+136+288, 83+93+136+294, 83+93+136+295, 93+136+260, 93+136+288, 93+136+294, 93+136+295, 93+98+136+260, 93+98+136+288, 93+98+136+294, 93+98+136+295, 93+116+136+260, 93+116+136+288, 93+116+136+294, 93+116+136+295, 93+135+136+260, 93+135+136+288, 93+135+136+294, 93+135+136+295, 93+136+260, 93+136+288, 93+136+294, 93+136+295, 93+136+241+260, 93+136+241+288, 93+136+241+294, 93+136+241+295, 93+136+242+260, 93+136+242+288, 93+136+242+294, 93+136+242+295, 93+136+257+260, 93+136+257+288, 93+136+257+294, 93+136+257+295, 93+136+258+260, 93+136+258+288, 93+136+258+294, 93+136+258+295, and 93+136+260+288, wherein numbering is according to SEQ ID NO: 2.

In one embodiment, the at least two substitutions are selected from A1G, A1V, N2E, S3P, G4D, F5H, Y6H, Y6M, Y6F, Y6W, Y6H, S8T, S8P, S8R, T11K, T11R, Y13F, D14S, D14K, N18V, N18R, A30T, Y32F, Y32W, K33Q, D34G, Q35L, T37P, E41V, E41N, N45G, G47S, G47A, D57N, G59Q, Q60R, K63R, K63Q, D65E, R70K, N71S, S74K, E77T, E77N, D78G, H80K, V82R, V82I, V82S, A83P, A83S, Y93Q, Y93A, S95D, A97R, S98P, S98D, N100Y, D104A, D104G, E108S, S111A, S111K, S111R, I114Q, I114M, I114W, K116R, D118K, T119R, S131T, E133R, E133Q, D135P, A136P, D139A, D139R, K142M, K142V, K142S, K142R, Q143R, N150T, N150R, N150S, Q169A, Q169R, Q169K, H172R, Y174R, Y174L, Y174W, Y174F, R176Q, E177S, E177Y, N180R, P183T, P183G, Q184E, Q184K, R185G, Y196W, Y196F, N200T, S202R, Q203T, R205K, R210L, R210G, R210M, N213V, N213D, T228S, N229D, E234F, E234Y, A235K, A235R, S241C, Q243K, Q243E, R244K, R244V, A250G, K254Y, G257W, G257E, G257A, G257G, W260F, W260Y, W260L, W260T, Y262F, S266A, D268N, A270D, N272M, N272T, N273E, N273D, A276E, A276W, A276D, N279D, N279E, T280L, N283W, N283H, Y286W, Y286F, L288I, E290A, L294P, L294K, L294I, L294R, L294V, L294H, S295K, S295V, S295P, S295L, S295R, S295A, S295N, S295M, S295I, T296S, and F298Y.

Accordingly, the at least two substitutions may be any combination of those listed herein. Such at least two substitutions may be selected from the group consisting of: A1G+N2E, A1G+S3P, A1G+G4D, A1G+F5H, A1G+Y6H, A1G+Y6M, A1G+Y6F, A1G+Y6W, A1G+Y6H, A1G+S8T, A1G+S8P, A1G+S8R, A1G+T11K, A1G+T11R, A1G+Y13F, A1G+D14S, A1G+D14K, A1G+N18V, A1G+N18R, A1G+A30T, A1G+Y32F, A1G+Y32W, A1G+K33Q, A1G+D34G, A1G+Q35L, A1G+T37P, A1G+E41V, A1G+E41N, A1G+N45G, A1G+G47S, A1G+G47A, A1G+D57N, A1G+G59Q, A1G+Q60R, A1G+K63R, A1G+K63Q, A1G+D65E, A1G+R70K, A1G+N71S, A1G+S74K, A1G+E77T, A1G+E77N, A1G+D78G, A1G+H80K, A1G+V82R, A1G+V82I, A1G+V82S, A1G+A83P, A1G+A83S, A1G+Y93Q, A1G+Y93A, A1G+S95D, A1G+A97R, A1G+S98P, A1G+S98D, A1G+N100Y, A1G+D104A, A1G+D104G, A1G+E108S, A1G+S111A, A1G+S111K, A1G+S111R, A1G+I114Q, A1G+I114M, A1G+I114W, A1G+K116R, A1G+D118K, A1G+T119R, A1G+S131T, A1G+E133R, A1G+E133Q, A1G+D135P, A1G+A136P, A1G+D139A, A1G+D139R, A1G+K142M, A1G+K142V, A1G+K142S, A1G+K142R, A1G+Q143R, A1G+N150T, A1G+N150R, A1G+N150S, A1G+Q169A, A1G+Q169R, A1G+Q169K, A1G+H172R, A1G+Y174R, A1G+Y174L, A1G+Y174W, A1G+Y174F, A1G+R176Q, A1G+E177S, A1G+E177Y, A1G+N180R, A1G+P183T, A1G+P183G, A1G+Q184E, A1G+Q184K, A1G+R185G, A1G+Y196W, A1G+Y196F, A1G+N200T, A1G+S202R, A1G+Q203T, A1G+R205K, A1G+R210L, A1G+R210G, A1G+R210M, A1G+N213V, A1G+N213D, A1G+T228S, A1G+N229D, A1G+E234F, A1G+E234Y, A1G+A235K, A1G+A235R, A1G+S241C, A1G+Q243K, A1G+Q243E, A1G+R244K, A1G+R244V, A1G+A250G, A1G+K254Y, A1G+G257W, A1G+G257E, A1G+G257A, A1G+W260F, A1G+Y262F, A1G+S266A, A1G+D268N, A1G+A270D, A1G+N272M, A1G+N272T, A1G+N273E, A1G+N273D, A1G+A276E, A1G+A276W, A1G+A276D, A1G+N279D, A1G+N279E, A1G+T280L, A1G+N283W, A1G+N283H, A1G+Y286W, A1G+Y286F, A1G+L288I, A1G+E290A, A1G+L294P, A1G+L294K, A1G+L294I, A1G+L294R, A1G+L294V, A1G+L294H, A1G+S295K, A1G+S295V, A1G+S295P, A1G+S295L, A1G+S295R, A1G+S295A, A1G+S295N, A1G+S295M, A1G+S295I, A1G+T296S, A1G+F298Y, A1V+N2E, A1V+S3P, A1V+G4D, A1V+F5H, A1V+Y6H, A1V+Y6M, A1V+Y6F, A1V+Y6W, A1V+Y6H, A1V+S8T, A1V+S8P, A1V+S8R, A1V+T11K, A1V+T11R, A1V+Y13F, A1V+D14S, A1V+D14K, A1V+N18V, A1V+N18R, A1V+A30T, A1V+Y32F, A1V+Y32W, A1V+K33Q, A1V+D34G, A1V+Q35L, A1V+T37P, A1V+E41V, A1V+E41N, A1V+N45G, A1V+G47S, A1V+G47A, A1V+D57N, A1V+G59Q, A1V+Q60R, A1V+K63R, A1V+K63Q, A1V+D65E, A1V+R70K, A1V+N71S, A1V+S74K, A1V+E77T, A1V+E77N, A1V+D78G, A1V+H80K, A1V+V82R, A1V+V82I, A1V+V82S, A1V+A83P, A1V+A83S, A1V+Y93Q, A1V+Y93A, A1V+S95D, A1V+A97R, A1V+S98P, A1V+S98D, A1V+N100Y, A1V+D104A, A1V+D104G, A1V+E108S, A1V+S111A, A1V+S111K, A1V+S111R, A1V+I114Q, A1V+I114M, A1V+I114W, A1V+K116R, A1V+D118K, A1V+T119R, A1V+S131T, A1V+E133R, A1V+E133Q, A1V+D135P, A1V+A136P, A1V+D139A, A1V+D139R, A1V+K142M, A1V+K142V, A1V+K142S, A1V+K142R, A1V+Q143R, A1V+N150T, A1V+N150R, A1V+N150S, A1V+Q169A, A1V+Q169R, A1V+Q169K, A1V+H172R, A1V+Y174R, A1V+Y174L, A1V+Y174W, A1V+Y174F, A1V+R176Q, A1V+E177S, A1V+E177Y, A1V+N180R, A1V+P183T, A1V+P183G, A1V+Q184E, A1V+Q184K, A1V+R185G, A1V+Y196W, A1V+Y196F, A1V+N200T, A1V+S202R, A1V+Q203T, A1V+R205K, A1V+R210L, A1V+R210G, A1V+R210M, A1V+N213V, A1V+N213D, A1V+T228S, A1V+N229D, A1V+E234F, A1V+E234Y, A1V+A235K, A1V+A235R, A1V+S241C, A1V+Q243K, A1V+Q243E, A1V+R244K, A1V+R244V, A1V+A250G, A1V+K254Y, A1V+G257W, A1V+G257E, A1V+G257A, A1V+W260F, A1V+W260Y, A1V+W260L, A1V+W260T, A1V+Y262F, A1V+S266A, A1V+D268N, A1V+A270D, A1V+N272M, A1V+N272T, A1V+N273E, A1V+N273D, A1V+A276E, A1V+A276W, A1V+A276D, A1V+N279D, A1V+N279E, A1V+T280L, A1V+N283W, A1V+N283H, A1V+Y286W, A1V+Y286F, A1V+L288I, A1V+E290A, A1V+L294P, A1V+L294K, A1V+L294I, A1V+L294R, A1V+L294V, A1V+L294H, A1V+S295K, A1V+S295V, A1V+S295P, A1V+S295L, A1V+S295R, A1V+S295A, A1V+S295N, A1V+S295M, A1V+S295I, A1V+T296S, A1V+F298Y, N2E+S3P, N2E+ G4D, N2E+F5H, N2E+Y6H, N2E+Y6M, N2E+Y6F, N2E+ Y6W, N2E+Y6H, N2E+S8T, N2E+S8P, N2E+S8R, N2E+ T11K, N2E+T11R, N2E+Y13F, N2E+D14S, N2E+D14K, N2E+N18V, N2E+N18R, N2E+A30T, N2E+Y32F, N2E+ Y32W, N2E+K33Q, N2E+D34G, N2E+Q35L, N2E+T37P, N2E+E41V, N2E+E41N, N2E+N45G, N2E+G47S, N2E+ G47A, N2E+D57N, N2E+G59Q, N2E+Q60R, N2E+K63R, N2E+K63Q, N2E+D65E, N2E+R70K, N2E+N71S, N2E+ S74K, N2E+E77T, N2E+E77N, N2E+D78G, N2E+H80K, N2E+V82R, N2E+V82I, N2E+V82S, N2E+A83P, N2E+ A83S, N2E+Y93Q, N2E+Y93A, N2E+S95D, N2E+A97R, N2E+S98P, N2E+S98D, N2E+N100Y, N2E+D104A, N2E+ D104G, N2E+E108S, N2E+S111A, N2E+S111K, N2E+ S111R, N2E+I114Q, N2E+I114M, N2E+I114W, N2E+ K116R, N2E+D118K, N2E+T119R, N2E+S131T, N2E+ E133R, N2E+E133Q, N2E+D135P, N2E+A136P, N2E+ D139A, N2E+D139R, N2E+K142M, N2E+K142V, N2E+ K142S, N2E+K142R, N2E+Q143R, N2E+N150T, N2E+ N150R, N2E+N150S, N2E+Q169A, N2E+Q169R, N2E+ Q169K, N2E+H172R, N2E+Y174R, N2E+Y174L, N2E+ Y174W, N2E+Y174F, N2E+R176Q, N2E+E177S, N2E+ E177Y, N2E+N180R, N2E+P183T, N2E+P183G, N2E+ Q184E, N2E+Q184K, N2E+R185G, N2E+Y196W, N2E+ Y196F, N2E+N200T, N2E+S202R, N2E+Q203T, N2E+ R205K, N2E+R210L, N2E+R210G, N2E+R210M, N2E+ N213V, N2E+N213D, N2E+T228S, N2E+N229D, N2E+ E234F, N2E+E234Y, N2E+A235K, N2E+A235R, N2E+ S241C, N2E+Q243K, N2E+Q243E, N2E+R244K, N2E+ R244V, N2E+A250G, N2E+K254Y, N2E+G257W, N2E+ G257E, N2E+G257A, N2E+W260F, N2E+W260Y, N2E+ W260L, N2E+W260T, N2E+Y262F, N2E+S266A, N2E+ D268N, N2E+A270D, N2E+N272M, N2E+N272T, N2E+ N273E, N2E+N273D, N2E+A276E, N2E+A276W, N2E+ A276D, N2E+N279D, N2E+N279E, N2E+T280L, N2E+ N283W, N2E+N283H, N2E+Y286W, N2E+Y286F, N2E+ L288I, N2E+E290A, N2E+L294P, N2E+L294K, N2E+ L294I, N2E+L294R, N2E+L294V, N2E+L294H, N2E+ S295K, N2E+S295V, N2E+S295P, N2E+S295L, N2E+ S295R, N2E+S295A, N2E+S295N, N2E+S295M, N2E+ S295I, N2E+T296S, N2E+F298Y, S3P+G4D, S3P+F5H, S3P+Y6H, S3P+Y6M, S3P+Y6F, S3P+Y6W, S3P+Y6H, S3P+S8T, S3P+S8P, S3P+S8R, S3P+T11K, S3P+T11R, S3P+Y13F, S3P+D14S, S3P+D14K, S3P+N18V, S3P+ N18R, S3P+A30T, S3P+Y32F, S3P+Y32W, S3P+K33Q, S3P+D34G, S3P+Q35L, S3P+T37P, S3P+E41V, S3P+ E41N, S3P+N45G, S3P+G47S, S3P+G47A, S3P+D57N, S3P+G59Q, S3P+Q60R, S3P+K63R, S3P+K63Q, S3P+ D65E, S3P+R70K, S3P+N71S, S3P+S74K, S3P+E77T, S3P+E77N, S3P+D78G, S3P+H80K, S3P+V82R, S3P+ V82I, S3P+V82S, S3P+A83P, S3P+A83S, S3P+Y93Q, S3P+Y93A, S3P+S95D, S3P+A97R, S3P+S98P, S3P+ S98D, S3P+N100Y, S3P+D104A, S3P+D104G, S3P+ E108S, S3P+S111A, S3P+S111K, S3P+S111R, S3P+I114Q, S3P+I114M, S3P+I114W, S3P+K116R, S3P+D118K, S3P+ T119R, S3P+S131T, S3P+E133R, S3P+E133Q, S3P+ D135P, S3P+A136P, S3P+D139A, S3P+D139R, S3P+ K142M, S3P+K142V, S3P+K142S, S3P+K142R, S3P+ Q143R, S3P+N150T, S3P+N150R, S3P+N150S, S3P+ Q169A, S3P+Q169R, S3P+Q169K, S3P+H172R, S3P+ Y174R, S3P+Y174L, S3P+Y174W, S3P+Y174F, S3P+ R176Q, S3P+E177S, S3P+E177Y, S3P+N180R, S3P+ P183T, S3P+P183G, S3P+Q184E, S3P+Q184K, S3P+ R185G, S3P+Y196W, S3P+Y196F, S3P+N200T, S3P+ S202R, S3P+Q203T, S3P+R205K, S3P+R210L, S3P+ R210G, S3P+R210M, S3P+N213V, S3P+N213D, S3P+ T228S, S3P+N229D, S3P+E234F, S3P+E234Y, S3P+ A235K, S3P+A235R, S3P+S241C, S3P+Q243K, S3P+ Q243E, S3P+R244K, S3P+R244V, S3P+A250G, S3P+ K254Y, S3P+G257W, S3P+G257E, S3P+G257A, S3P+ W260F, S3P+W260Y, S3P+W260L, S3P+W260T, S3P+ Y262F, S3P+S266A, S3P+D268N, S3P+A270D, S3P+ N272M, S3P+N272T, S3P+N273E, S3P+N273D, S3P+ A276E, S3P+A276W, S3P+A276D, S3P+N279D, S3P+ N279E, S3P+T280L, S3P+N283W, S3P+N283H, S3P+ Y286W, S3P+Y286F, S3P+L288I, S3P+E290A, S3P+ L294P, S3P+L294K, S3P+L294I, S3P+L294R, S3P+ L294V, S3P+L294H, S3P+S295K, S3P+S295V, S3P+ S295P, S3P+S295L, S3P+S295R, S3P+S295A, S3P+ S295N, S3P+S295M, S3P+S295I, S3P+T296S, S3P+ F298Y, G4D+F5H, G4D+Y6H, G4D+Y6M, G4D+Y6F, G4D+Y6W, G4D+Y6H, G4D+S8T, G4D+S8P, G4D+S8R, G4D+T11K, G4D+T11R, G4D+Y13F, G4D+D14S, G4D+ D14K, G4D+N18V, G4D+N18R, G4D+A30T, G4D+Y32F, G4D+Y32W, G4D+K33Q, G4D+D34G, G4D+Q35L, G4D+T37P, G4D+E41V, G4D+E41N, G4D+N45G, G4D+ G47S, G4D+G47A, G4D+D57N, G4D+G59Q, G4D+ Q60R, G4D+K63R, G4D+K63Q, G4D+D65E, G4D+R70K, G4D+N71S, G4D+S74K, G4D+E77T, G4D+E77N, G4D+ D78G, G4D+H80K, G4D+V82R, G4D+V82I, G4D+V82S, G4D+A83P, G4D+A83S, G4D+Y93Q, G4D+Y93A, G4D+ S95D, G4D+A97R, G4D+S98P, G4D+S98D, G4D+N100Y, G4D+D104A, G4D+D104G, G4D+E108S, G4D+S111A, G4D+S111K, G4D+S111R, G4D+I114Q, G4D+I114M, G4D+I114W, G4D+K116R, G4D+D118K, G4D+T119R, G4D+S131T, G4D+E133R, G4D+E133Q, G4D+D135P, G4D+A136P, G4D+D139A, G4D+D139R, G4D+K142M, G4D+K142V, G4D+K142S, G4D+K142R, G4D+Q143R, G4D+N150T, G4D+N150R, G4D+N150S, G4D+Q169A, G4D+Q169R, G4D+Q169K, G4D+H172R, G4D+Y174R, G4D+Y174L, G4D+Y174W, G4D+Y174F, G4D+R176Q, G4D+E177S, G4D+E177Y, G4D+N180R, G4D+P183T, G4D+P183G, G4D+Q184E, G4D+Q184K, G4D+R185G, G4D+Y196W, G4D+Y196F, G4D+N200T, G4D+S202R, G4D+Q203T, G4D+R205K, G4D+R210L, G4D+R210G, G4D+R210M, G4D+N213V, G4D+N213D, G4D+T228S, G4D+N229D, G4D+E234F, G4D+E234Y, G4D+A235K, G4D+A235R, G4D+S241C, G4D+Q243K, G4D+Q243E, G4D+R244K, G4D+R244V, G4D+A250G, G4D+K254Y, G4D+G257W, G4D+G257E, G4D+G257A, G4D+W260F, G4D+W260Y, G4D+W260L, G4D+W260T, G4D+Y262F, G4D+S266A, G4D+D268N, G4D+A270D, G4D+N272M, G4D+N272T, G4D+N273E, G4D+N273D, G4D+A276E, G4D+A276W, G4D+A276D, G4D+N279D, G4D+N279E, G4D+T280L, G4D+N283W, G4D+N283H, G4D+Y286W, G4D+Y286F, G4D+L288I, G4D+E290A, G4D+L294P, G4D+L294K, G4D+L294I, G4D+L294R, G4D+L294V, G4D+L294H, G4D+S295K, G4D+S295V, G4D+S295P, G4D+S295L, G4D+S295R, G4D+S295A, G4D+S295N, G4D+S295M, G4D+S295I, G4D+T296S, G4D+F298Y, F5H+Y6H, F5H+Y6M, F5H+Y6F, F5H+Y6W, F5H+Y6H, F5H+S8T, F5H+S8P, F5H+S8R, F5H+T11K, F5H+T11R, F5H+Y13F, F5H+D14S, F5H+D14K, F5H+N18V, F5H+N18R, F5H+A30T, F5H+Y32F, F5H+Y32W, F5H+K33Q, F5H+D34G, F5H+Q35L, F5H+T37P, F5H+E41V, F5H+E41N, F5H+N45G, F5H+G47S, F5H+G47A, F5H+D57N, F5H+G59Q, F5H+Q60R, F5H+K63R, F5H+K63Q, F5H+D65E, F5H+R70K, F5H+N71S, F5H+S74K, F5H+E77T, F5H+E77N, F5H+D78G, F5H+H80K, F5H+V82R, F5H+V82I, F5H+V82S, F5H+A83P, F5H+A83S, F5H+Y93Q, F5H+Y93A, F5H+S95D, F5H+A97R, F5H+S98P, F5H+

S98D, F5H+N100Y, F5H+D104A, F5H+D104G, F5H+
E108S, F5H+S111A, F5H+S111K, F5H+S111R, F5H+
I114Q, F5H+I114M, F5H+I114W, F5H+K116R, F5H+
D118K, F5H+T119R, F5H+S131T, F5H+E133R, F5H+
E133Q, F5H+D135P, F5H+A136P, F5H+D139A, F5H+
D139R, F5H+K142M, F5H+K142V, F5H+K142S, F5H+
K142R, F5H+Q143R, F5H+N150T, F5H+N150R, F5H+
N150S, F5H+Q169A, F5H+Q169R, F5H+Q169K, F5H+
H172R, F5H+Y174R, F5H+Y174L, F5H+Y174W, F5H+
Y174F, F5H+R176Q, F5H+E177S, F5H+E177Y, F5H+
N180R, F5H+P183T, F5H+P183G, F5H+Q184E, F5H+
Q184K, F5H+R185G, F5H+Y196W, F5H+Y196F, F5H+
N200T, F5H+S202R, F5H+Q203T, F5H+R205K, F5H+
R210L, F5H+R210G, F5H+R210M, F5H+N213V, F5H+
N213D, F5H+T228S, F5H+N229D, F5H+E234F, F5H+
E234Y, F5H+A235K, F5H+A235R, F5H+S241C, F5H+
Q243K, F5H+Q243E, F5H+R244K, F5H+R244V, F5H+
A250G, F5H+K254Y, F5H+G257W, F5H+G257E, F5H+
G257A, F5H+W260F, F5H+W260Y, F5H+W260L, F5H+
W260T, F5H+Y262F, F5H+S266A, F5H+D268N, F5H+
A270D, F5H+N272M, F5H+N272T, F5H+N273E, F5H+
N273D, F5H+A276E, F5H+A276W, F5H+A276D, F5H+
N279D, F5H+N279E, F5H+T280L, F5H+N283W, F5H+
N283H, F5H+Y286W, F5H+Y286F, F5H+L288I, F5H+
E290A, F5H+L294P, F5H+L294K, F5H+L294I, F5H+
L294R, F5H+L294V, F5H+L294H, F5H+S295K, F5H+
S295V, F5H+S295P, F5H+S295L, F5H+S295R, F5H+
S295A, F5H+S295N, F5H+S295M, F5H+S295I, F5H+
T296S, F5H+F298Y, Y6H+S8T, Y6H+S8P, Y6H+S8R,
Y6H+T11K, Y6H+T11R, Y6H+Y13F, Y6H+D14S, Y6H+
D14K, Y6H+N18V, Y6H+N18R, Y6H+A30T, Y6H+Y32F,
Y6H+Y32W, Y6H+K33Q, Y6H+D34G, Y6H+Q35L, Y6H+
T37P, Y6H+E41V, Y6H+E41N, Y6H+N45G, Y6H+G47S,
Y6H+G47A, Y6H+D57N, Y6H+G59Q, Y6H+Q60R, Y6H+K63R, Y6H+K63Q, Y6H+D65E, Y6H+R70K, Y6H+N71S, Y6H+S74K, Y6H+E77T, Y6H+E77N, Y6H+D78G, Y6H+H80K, Y6H+V82R, Y6H+V82I, Y6H+V82S, Y6H+A83P, Y6H+A83S, Y6H+Y93Q, Y6H+Y93A, Y6H+S95D, Y6H+A97R, Y6H+S98P, Y6H+S98D, Y6H+N100Y, Y6H+D104A, Y6H+D104G, Y6H+E108S, Y6H+S111A, Y6H+S111K, Y6H+S111R, Y6H+I114Q, Y6H+I114M, Y6H+I114W, Y6H+K116R, Y6H+D118K, Y6H+T119R, Y6H+S131T, Y6H+E133R, Y6H+E133Q, Y6H+D135P, Y6H+A136P, Y6H+D139A, Y6H+D139R, Y6H+K142M, Y6H+K142V, Y6H+K142S, Y6H+K142R, Y6H+Q143R, Y6H+N150T, Y6H+N150R, Y6H+N150S, Y6H+Q169A, Y6H+Q169R, Y6H+Q169K, Y6H+H172R, Y6H+Y174R, Y6H+Y174L, Y6H+Y174W, Y6H+Y174F, Y6H+R176Q, Y6H+E177S, Y6H+E177Y, Y6H+N180R, Y6H+P183T, Y6H+P183G, Y6H+Q184E, Y6H+Q184K, Y6H+R185G, Y6H+Y196W, Y6H+Y196F, Y6H+N200T, Y6H+S202R, Y6H+Q203T, Y6H+R205K, Y6H+R210L, Y6H+R210G, Y6H+R210M, Y6H+N213V, Y6H+N213D, Y6H+T228S, Y6H+N229D, Y6H+E234F, Y6H+E234Y, Y6H+A235K, Y6H+A235R, Y6H+S241C, Y6H+Q243K, Y6H+Q243E, Y6H+R244K, Y6H+R244V, Y6H+A250G, Y6H+K254Y, Y6H+G257W, Y6H+G257E, Y6H+G257A, Y6H+W260F, Y6H+W260Y, Y6H+W260L, Y6H+W260T, Y6H+Y262F, Y6H+S266A, Y6H+D268N, Y6H+A270D, Y6H+N272M, Y6H+N272T, Y6H+N273E, Y6H+N273D, Y6H+A276E, Y6H+A276W, Y6H+A276D, Y6H+N279D, Y6H+N279E, Y6H+T280L, Y6H+N283W, Y6H+N283H, Y6H+Y286W, Y6H+Y286F, Y6H+L288I, Y6H+E290A, Y6H+L294P, Y6H+L294K, Y6H+L294I, Y6H+L294R, Y6H+L294V, Y6H+L294H, Y6H+S295K, Y6H+S295V, Y6H+S295P, Y6H+S295L, Y6H+S295R, Y6H+S295A, Y6H+S295N, Y6H+S295M, Y6H+S295I, Y6H+T296S, Y6H+F298Y, Y6M+S8T, Y6M+S8P, Y6M+S8R, Y6M+T11K, Y6M+T11R, Y6M+Y13F, Y6M+D14S, Y6M+D14K, Y6M+N18V, Y6M+N18R, Y6M+A30T, Y6M+Y32F, Y6M+Y32W, Y6M+K33Q, Y6M+D34G, Y6M+Q35L, Y6M+T37P, Y6M+E41V, Y6M+E41N, Y6M+N45G, Y6M+G47S, Y6M+G47A, Y6M+D57N, Y6M+G59Q, Y6M+Q60R, Y6M+K63R, Y6M+K63Q, Y6M+D65E, Y6M+R70K, Y6M+N71S, Y6M+S74K, Y6M+E77T, Y6M+E77N, Y6M+D78G, Y6M+H80K, Y6M+V82R, Y6M+V82I, Y6M+V82S, Y6M+A83P, Y6M+A83S, Y6M+Y93Q, Y6M+Y93A, Y6M+S95D, Y6M+A97R, Y6M+S98P, Y6M+S98D, Y6M+N100Y, Y6M+D104A, Y6M+D104G, Y6M+E108S, Y6M+S111A, Y6M+S111K, Y6M+S111R, Y6M+I114Q, Y6M+I114M, Y6M+I114W, Y6M+K116R, Y6M+D118K, Y6M+T119R, Y6M+S131T, Y6M+E133R, Y6M+E133Q, Y6M+D135P, Y6M+A136P, Y6M+D139A, Y6M+D139R, Y6M+K142M, Y6M+K142V, Y6M+K142S, Y6M+K142R, Y6M+Q143R, Y6M+N150T, Y6M+N150R, Y6M+N150S, Y6M+Q169A, Y6M+Q169R, Y6M+Q169K, Y6M+H172R, Y6M+Y174R, Y6M+Y174L, Y6M+Y174W, Y6M+Y174F, Y6M+R176Q, Y6M+E177S, Y6M+E177Y, Y6M+N180R, Y6M+P183T, Y6M+P183G, Y6M+Q184E, Y6M+Q184K, Y6M+R185G, Y6M+Y196W, Y6M+Y196F, Y6M+N200T, Y6M+S202R, Y6M+Q203T, Y6M+R205K, Y6M+R210L, Y6M+R210G, Y6M+R210M, Y6M+N213V, Y6M+N213D, Y6M+T228S, Y6M+N229D, Y6M+E234F, Y6M+E234Y, Y6M+A235K, Y6M+A235R, Y6M+S241C, Y6M+Q243K, Y6M+Q243E, Y6M+R244K, Y6M+R244V, Y6M+A250G, Y6M+K254Y, Y6M+G257W, Y6M+G257E, Y6M+G257A, Y6M+W260F, Y6M+W260Y, Y6M+W260L, Y6M+W260T, Y6M+Y262F, Y6M+S266A, Y6M+D268N, Y6M+A270D, Y6M+N272M, Y6M+N272T, Y6M+N273E, Y6M+N273D, Y6M+A276E, Y6M+A276W, Y6M+A276D, Y6M+N279D, Y6M+N279E, Y6M+T280L, Y6M+N283W, Y6M+N283H, Y6M+Y286W, Y6M+Y286F, Y6M+L288I, Y6M+E290A, Y6M+L294P, Y6M+L294K, Y6M+L294I, Y6M+L294R, Y6M+L294V, Y6M+L294H, Y6M+S295K, Y6M+S295V, Y6M+S295P, Y6M+S295L, Y6M+S295R, Y6M+S295A, Y6M+S295N, Y6M+S295M, Y6M+S295I, Y6M+T296S, Y6M+F298Y, Y6F+S8T, Y6F+S8P, Y6F+S8R, Y6F+T11K, Y6F+T11R, Y6F+Y13F, Y6F+D14S, Y6F+D14K, Y6F+N18V, Y6F+N18R, Y6F+A30T, Y6F+Y32F, Y6F+Y32W, Y6F+K33Q, Y6F+D34G, Y6F+Q35L, Y6F+T37P, Y6F+E41V, Y6F+E41N, Y6F+N45G, Y6F+G47S, Y6F+G47A, Y6F+D57N, Y6F+G59Q, Y6F+Q60R, Y6F+K63R, Y6F+K63Q, Y6F+D65E, Y6F+R70K, Y6F+N71S, Y6F+S74K, Y6F+E77T, Y6F+E77N, Y6F+D78G, Y6F+H80K, Y6F+V82R, Y6F+V82I, Y6F+V82S, Y6F+A83P, Y6F+A83S, Y6F+Y93Q, Y6F+Y93A, Y6F+S95D, Y6F+A97R, Y6F+S98P, Y6F+S98D, Y6F+N100Y, Y6F+D104A, Y6F+D104G, Y6F+E108S, Y6F+S111A, Y6F+S111K, Y6F+S111R, Y6F+I114Q, Y6F+I114M, Y6F+I114W, Y6F+K116R, Y6F+D118K, Y6F+T119R, Y6F+S131T, Y6F+E133R, Y6F+E133Q, Y6F+D135P, Y6F+A136P, Y6F+D139A, Y6F+D139R, Y6F+K142M, Y6F+K142V, Y6F+K142S, Y6F+K142R, Y6F+Q143R, Y6F+N150T, Y6F+N150R, Y6F+N150S, Y6F+Q169A, Y6F+Q169R, Y6F+Q169K, Y6F+H172R, Y6F+Y174R, Y6F+Y174L, Y6F+Y174W, Y6F+Y174F, Y6F+R176Q, Y6F+E177S, Y6F+E177Y, Y6F+N180R, Y6F+P183T, Y6F+P183G, Y6F+Q184E, Y6F+Q184K, Y6F+R185G, Y6F+Y196W, Y6F+Y196F, Y6F+N200T, Y6F+S202R, Y6F+Q203T, Y6F+R205K, Y6F+R210L, Y6F+R210G, Y6F+R210M, Y6F+N213V, Y6F+N213D, Y6F+T228S, Y6F+N229D, Y6F+E234F, Y6F+E234Y, Y6F+A235K, Y6F+A235R, Y6F+S241C, Y6F+Q243K, Y6F+Q243E, Y6F+R244K, Y6F+R244V, Y6F+A250G, Y6F+K254Y, Y6F+

G257W, Y6F+G257E, Y6F+G257A, Y6F+W260F, Y6F+
W260Y, Y6F+W260L, Y6F+W260T, Y6F+Y262F, Y6F+
S266A, Y6F+D268N, Y6F+A270D, Y6F+N272M, Y6F+
N272T, Y6F+N273E, Y6F+N273D, Y6F+A276E, Y6F+
A276W, Y6F+A276D, Y6F+N279D, Y6F+N279E, Y6F+
T280L, Y6F+N283W, Y6F+N283H, Y6F+Y286W, Y6F+
Y286F, Y6F+L288I, Y6F+E290A, Y6F+L294P, Y6F+
L294K, Y6F+L294I, Y6F+L294R, Y6F+L294V, Y6F+
L294H, Y6F+S295K, Y6F+S295V, Y6F+S295P, Y6F+
S295L, Y6F+S295R, Y6F+S295A, Y6F+S295N, Y6F+
S295M, Y6F+S295I, Y6F+T296S, Y6F+F298Y, Y6W+S8T,
Y6W+S8P, Y6W+S8R, Y6W+T11K, Y6W+T11R, Y6W+
Y13F, Y6W+D14S, Y6W+D14K, Y6W+N18V, Y6W+
N18R, Y6W+A30T, Y6W+Y32F, Y6W+Y32W, Y6W+
K33Q, Y6W+D34G, Y6W+Q35L, Y6W+T37P, Y6W+
E41V, Y6W+E41N, Y6W+N45G, Y6W+G47S, Y6W+
G47A, Y6W+D57N, Y6W+G59Q, Y6W+Q60R, Y6W+
K63R, Y6W+K63Q, Y6W+D65E, Y6W+R70K, Y6W+
N71S, Y6W+S74K, Y6W+E77T, Y6W+E77N, Y6W+
D78G, Y6W+H80K, Y6W+V82R, Y6W+V82I, Y6W+
V82S, Y6W+A83P, Y6W+A83S, Y6W+Y93Q, Y6W+
Y93A, Y6W+S95D, Y6W+A97R, Y6W+S98P, Y6W+
S98D, Y6W+N100Y, Y6W+D104A, Y6W+D104G, Y6W+
E108S, Y6W+S111A, Y6W+S111K, Y6W+S111R, Y6W+
I114Q, Y6W+I114M, Y6W+I114W, Y6W+K116R, Y6W+
D118K, Y6W+T119R, Y6W+S131T, Y6W+E133R, Y6W+
E133Q, Y6W+D135P, Y6W+A136P, Y6W+D139A, Y6W+
D139R, Y6W+K142M, Y6W+K142V, Y6W+K142S,
Y6W+K142R, Y6W+Q143R, Y6W+N150T, Y6W+N150R,
Y6W+N150S, Y6W+Q169A, Y6W+Q169R, Y6W+Q169K,
Y6W+H172R, Y6W+Y174R, Y6W+Y174L, Y6W+
Y174W, Y6W+Y174F, Y6W+R176Q, Y6W+E177S, Y6W+
E177Y, Y6W+N180R, Y6W+P183T, Y6W+P183G, Y6W+
Q184E, Y6W+Q184K, Y6W+R185G, Y6W+Y196W,
Y6W+Y196F, Y6W+N200T, Y6W+S202R, Y6W+Q203T,
Y6W+R205K, Y6W+R210L, Y6W+R210G, Y6W+R210M,
Y6W+N213V, Y6W+N213D, Y6W+T228S, Y6W+N229D,
Y6W+E234F, Y6W+E234Y, Y6W+A235K, Y6W+A235R,
Y6W+S241C, Y6W+Q243K, Y6W+Q243E, Y6W+R244K,
Y6W+R244V, Y6W+A250G, Y6W+K254Y, Y6W+G257W,
Y6W+G257E, Y6W+G257A, Y6W+W260F, Y6W+
W260Y, Y6W+W260L, Y6W+W260T, Y6W+Y262F,
Y6W+S266A, Y6W+D268N, Y6W+A270D, Y6W+
N272M, Y6W+N272T, Y6W+N273E, Y6W+N273D,
Y6W+A276E, Y6W+A276W, Y6W+A276D, Y6W+
N279D, Y6W+N279E, Y6W+T280L, Y6W+N283W,
Y6W+N283H, Y6W+Y286W, Y6W+Y286F, Y6W+L288I,
Y6W+E290A, Y6W+L294P, Y6W+L294K, Y6W+L294I,
Y6W+L294R, Y6W+L294V, Y6W+L294H, Y6W+S295K,
Y6W+S295V, Y6W+S295P, Y6W+S295L, Y6W+S295R,
Y6W+S295A, Y6W+S295N, Y6W+S295M, Y6W+S295I,
Y6W+T296S, Y6W+F298Y, Y6H+S8T, Y6H+S8P, Y6H+
S8R, Y6H+T11K, Y6H+T11R, Y6H+Y13F, Y6H+D14S,
Y6H+D14K, Y6H+N18V, Y6H+N18R, Y6H+A30T, Y6H+
Y32F, Y6H+Y32W, Y6H+K33Q, Y6H+D34G, Y6H+Q35L,
Y6H+T37P, Y6H+E41V, Y6H+E41N, Y6H+N45G, Y6H+
G47S, Y6H+G47A, Y6H+D57N, Y6H+G59Q, Y6H+Q60R,
Y6H+K63R, Y6H+K63Q, Y6H+D65E, Y6H+R70K, Y6H+
N71S, Y6H+S74K, Y6H+E77T, Y6H+E77N, Y6H+D78G,
Y6H+H80K, Y6H+V82R, Y6H+V82I, Y6H+V82S, Y6H+
A83P, Y6H+A83S, Y6H+Y93Q, Y6H+Y93A, Y6H+S95D,
Y6H+A97R, Y6H+S98P, Y6H+S98D, Y6H+N100Y, Y6H+
D104A, Y6H+D104G, Y6H+E108S, Y6H+S111A, Y6H+
S111K, Y6H+S111R, Y6H+I114Q, Y6H+I114M, Y6H+
I114W, Y6H+K116R, Y6H+D118K, Y6H+T119R, Y6H+
S131T, Y6H+E133R, Y6H+E133Q, Y6H+D135P, Y6H+
A136P, Y6H+D139A, Y6H+D139R, Y6H+K142M, Y6H+
K142V, Y6H+K142S, Y6H+K142R, Y6H+Q143R, Y6H+
N150T, Y6H+N150R, Y6H+N150S, Y6H+Q169A, Y6H+
Q169R, Y6H+Q169K, Y6H+H172R, Y6H+Y174R, Y6H+
Y174L, Y6H+Y174W, Y6H+Y174F, Y6H+R176Q, Y6H+
E177S, Y6H+E177Y, Y6H+N180R, Y6H+P183T, Y6H+
P183G, Y6H+Q184E, Y6H+Q184K, Y6H+R185G, Y6H+
Y196W, Y6H+Y196F, Y6H+N200T, Y6H+S202R, Y6H+
Q203T, Y6H+R205K, Y6H+R210L, Y6H+R210G, Y6H+
R210M, Y6H+N213V, Y6H+N213D, Y6H+T228S, Y6H+
N229D, Y6H+E234F, Y6H+E234Y, Y6H+A235K, Y6H+
A235R, Y6H+S241C, Y6H+Q243K, Y6H+Q243E, Y6H+
R244K, Y6H+R244V, Y6H+A250G, Y6H+K254Y, Y6H+
G257W, Y6H+G257E, Y6H+G257A, Y6H+W260F, Y6H+
W260Y, Y6H+W260L, Y6H+W260T, Y6H+Y262F, Y6H+
S266A, Y6H+D268N, Y6H+A270D, Y6H+N272M, Y6H+
N272T, Y6H+N273E, Y6H+N273D, Y6H+A276E, Y6H+
A276W, Y6H+A276D, Y6H+N279D, Y6H+N279E, Y6H+
T280L, Y6H+N283W, Y6H+N283H, Y6H+Y286W, Y6H+
Y286F, Y6H+L288I, Y6H+E290A, Y6H+L294P, Y6H+
L294K, Y6H+L294I, Y6H+L294R, Y6H+L294V, Y6H+
L294H, Y6H+S295K, Y6H+S295V, Y6H+S295P, Y6H+
S295L, Y6H+S295R, Y6H+S295A, Y6H+S295N, Y6H+
S295M, Y6H+S295I, Y6H+T296S, Y6H+F298Y, S8T+
T11K, S8T+T11R, S8T+Y13F, S8T+D14S, S8T+D14K,
S8T+N18V, S8T+N18R, S8T+A30T, S8T+Y32F, S8T+
Y32W, S8T+K33Q, S8T+D34G, S8T+Q35L, S8T+T37P,
S8T+E41V, S8T+E41N, S8T+N45G, S8T+G47S, S8T+
G47A, S8T+D57N, S8T+G59Q, S8T+Q60R, S8T+K63R,
S8T+K63Q, S8T+D65E, S8T+R70K, S8T+N71S, S8T+
S74K, S8T+E77T, S8T+E77N, S8T+D78G, S8T+H80K,
S8T+V82R, S8T+V82I, S8T+V82S, S8T+A83P, S8T+
A83S, S8T+Y93Q, S8T+Y93A, S8T+S95D, S8T+A97R,
S8T+S98P, S8T+S98D, S8T+N100Y, S8T+D104A, S8T+
D104G, S8T+E108S, S8T+S111A, S8T+S111K, S8T+
S111R, S8T+I114Q, S8T+I114M, S8T+I114W, S8T+
K116R, S8T+D118K, S8T+T119R, S8T+S131T, S8T+
E133R, S8T+E133Q, S8T+D135P, S8T+A136P, S8T+
D139A, S8T+D139R, S8T+K142M, S8T+K142V, S8T+
K142S, S8T+K142R, S8T+Q143R, S8T+N150T, S8T+
N150R, S8T+N150S, S8T+Q169A, S8T+Q169R, S8T+
Q169K, S8T+H172R, S8T+Y174R, S8T+Y174L, S8T+
Y174W, S8T+Y174F, S8T+R176Q, S8T+E177S, S8T+
E177Y, S8T+N180R, S8T+P183T, S8T+P183G, S8T+
Q184E, S8T+Q184K, S8T+R185G, S8T+Y196W, S8T+
Y196F, S8T+N200T, S8T+S202R, S8T+Q203T, S8T+
R205K, S8T+R210L, S8T+R210G, S8T+R210M, S8T+
N213V, S8T+N213D, S8T+T228S, S8T+N229D, S8T+
E234F, S8T+E234Y, S8T+A235K, S8T+A235R, S8T+
S241C, S8T+Q243K, S8T+Q243E, S8T+R244K, S8T+
R244V, S8T+A250G, S8T+K254Y, S8T+G257W, S8T+
G257E, S8T+G257A, S8T+W260F, S8T+W260Y, S8T+
W260L, S8T+W260T, S8T+Y262F, S8T+S266A, S8T+
D268N, S8T+A270D, S8T+N272M, S8T+N272T, S8T+
N273E, S8T+N273D, S8T+A276E, S8T+A276W, S8T+
A276D, S8T+N279D, S8T+N279E, S8T+T280L, S8T+
N283W, S8T+N283H, S8T+Y286W, S8T+Y286F, S8T+
L288I, S8T+E290A, S8T+L294P, S8T+L294K, S8T+
L294I, S8T+L294R, S8T+L294V, S8T+L294H, S8T+
S295K, S8T+S295V, S8T+S295P, S8T+S295L, S8T+
S295R, S8T+S295A, S8T+S295N, S8T+S295M, S8T+
S295I, S8T+T296S, S8T+F298Y, S8P+T11K, S8P+T11R,
S8P+Y13F, S8P+D14S, S8P+D14K, S8P+N18V, S8P+
N18R, S8P+A30T, S8P+Y32F, S8P+Y32W, S8P+K33Q,
S8P+D34G, S8P+Q35L, S8P+T37P, S8P+E41V, S8P+
E41N, S8P+N45G, S8P+G47S, S8P+G47A, S8P+D57N,
S8P+G59Q, S8P+Q60R, S8P+K63R, S8P+K63Q, S8P+
D65E, S8P+R70K, S8P+N71S, S8P+S74K, S8P+E77T,

S8P+E77N, S8P+D78G, S8P+H80K, S8P+V82R, S8P+ V82I, S8P+V82S, S8P+A83P, S8P+A83S, S8P+Y93Q, S8P+Y93A, S8P+S95D, S8P+A97R, S8P+S98P, S8P+ S98D, S8P+N100Y, S8P+D104A, S8P+D104G, S8P+ E108S, S8P+S111A, S8P+S111K, S8P+S111R, S8P+I114Q, S8P+I114M, S8P+I114W, S8P+K116R, S8P+D118K, S8P+ T119R, S8P+S131T, S8P+E133R, S8P+E133Q, S8P+ D135P, S8P+A136P, S8P+D139A, S8P+D139R, S8P+ K142M, S8P+K142V, S8P+K142S, S8P+K142R, S8P+ Q143R, S8P+N150T, S8P+N150R, S8P+N150S, S8P+ Q169A, S8P+Q169R, S8P+Q169K, S8P+H172R, S8P+ Y174R, S8P+Y174L, S8P+Y174W, S8P+Y174F, S8P+ R176Q, S8P+E177S, S8P+E177Y, S8P+N180R, S8P+ P183T, S8P+P183G, S8P+Q184E, S8P+Q184K, S8P+ R185G, S8P+Y196W, S8P+Y196F, S8P+N200T, S8P+ S202R, S8P+Q203T, S8P+R205K, S8P+R210L, S8P+ R210G, S8P+R210M, S8P+N213V, S8P+N213D, S8P+ T228S, S8P+N229D, S8P+E234F, S8P+E234Y, S8P+ A235K, S8P+A235R, S8P+S241C, S8P+Q243K, S8P+ Q243E, S8P+R244K, S8P+R244V, S8P+A250G, S8P+ K254Y, S8P+G257W, S8P+G257E, S8P+G257A, S8P+ W260F, S8P+W260Y, S8P+W260L, S8P+W260T, S8P+ Y262F, S8P+S266A, S8P+D268N, S8P+A270D, S8P+ N272M, S8P+N272T, S8P+N273E, S8P+N273D, S8P+ A276E, S8P+A276W, S8P+A276D, S8P+N279D, S8P+ N279E, S8P+T280L, S8P+N283W, S8P+N283H, S8P+ Y286W, S8P+Y286F, S8P+L288I, S8P+E290A, S8P+ L294P, S8P+L294K, S8P+L294I, S8P+L294R, S8P+ L294V, S8P+L294H, S8P+S295K, S8P+S295V, S8P+ S295P, S8P+S295L, S8P+S295R, S8P+S295A, S8P+ S295N, S8P+S295M, S8P+S295I, S8P+T296S, S8P+ F298Y, S8R+T11K, S8R+T11R, S8R+Y13F, S8R+D14S, S8R+D14K, S8R+N18V, S8R+N18R, S8R+A30T, S8R+ Y32F, S8R+Y32W, S8R+K33Q, S8R+D34G, S8R+Q35L, S8R+T37P, S8R+E41V, S8R+E41N, S8R+N45G, S8R+ G47S, S8R+G47A, S8R+D57N, S8R+G59Q, S8R+Q60R, S8R+K63R, S8R+K63Q, S8R+D65E, S8R+R70K, S8R+ N71S, S8R+S74K, S8R+E77T, S8R+E77N, S8R+D78G, S8R+H80K, S8R+V82R, S8R+V82I, S8R+V82S, S8R+ A83P, S8R+A83S, S8R+Y93Q, S8R+Y93A, S8R+S95D, S8R+A97R, S8R+S98P, S8R+S98D, S8R+N100Y, S8R+ D104A, S8R+D104G, S8R+E108S, S8R+S111A, S8R+ S111K, S8R+S111R, S8R+I114Q, S8R+I114M, S8R+ I114W, S8R+K116R, S8R+D118K, S8R+T119R, S8R+ S131T, S8R+E133R, S8R+E133Q, S8R+D135P, S8R+ A136P, S8R+D139A, S8R+D139R, S8R+K142M, S8R+ K142V, S8R+K142S, S8R+K142R, S8R+Q143R, S8R+ N150T, S8R+N150R, S8R+N150S, S8R+Q169A, S8R+ Q169R, S8R+Q169K, S8R+H172R, S8R+Y174R, S8R+ Y174L, S8R+Y174W, S8R+Y174F, S8R+R176Q, S8R+ E177S, S8R+E177Y, S8R+N180R, S8R+P183T, S8R+ P183G, S8R+Q184E, S8R+Q184K, S8R+R185G, S8R+ Y196W, S8R+Y196F, S8R+N200T, S8R+S202R, S8R+ Q203T, S8R+R205K, S8R+R210L, S8R+R210G, S8R+ R210M, S8R+N213V, S8R+N213D, S8R+T228S, S8R+ N229D, S8R+E234F, S8R+E234Y, S8R+A235K, S8R+ A235R, S8R+S241C, S8R+Q243K, S8R+Q243E, S8R+ R244K, S8R+R244V, S8R+A250G, S8R+K254Y, S8R+ G257W, S8R+G257E, S8R+G257A, S8R+W260F, S8R+ W260Y, S8R+W260L, S8R+W260T, S8R+Y262F, S8R+ S266A, S8R+D268N, S8R+A270D, S8R+N272M, S8R+ N272T, S8R+N273E, S8R+N273D, S8R+A276E, S8R+ A276W, S8R+A276D, S8R+N279D, S8R+N279E, S8R+ T280L, S8R+N283W, S8R+N283H, S8R+Y286W, S8R+ Y286F, S8R+L288I, S8R+E290A, S8R+L294P, S8R+ L294K, S8R+L294I, S8R+L294R, S8R+L294V, S8R+ L294H, S8R+S295K, S8R+S295V, S8R+S295P, S8R+ S295L, S8R+S295R, S8R+S295A, S8R+S295N, S8R+ S295M, S8R+S295I, S8R+T296S, S8R+F298Y, T11K+ Y13F, T11K+D14S, T11K+D14K, T11K+N18V, T11K+ N18R, T11K+A30T, T11K+Y32F, T11K+Y32W, T11K+ K33Q, T11K+D34G, T11K+Q35L, T11K+T37P, T11K+ E41V, T11K+E41N, T11K+N45G, T11K+G47S, T11K+ G47A, T11K+D57N, T11K+G59Q, T11K+Q60R, T11K+ K63R, T11K+K63Q, T11K+D65E, T11K+R70K, T11K+ N71S, T11K+S74K, T11K+E77T, T11K+E77N, T11K+ D78G, T11K+H80K, T11K+V82R, T11K+V82I, T11K+ V82S, T11K+A83P, T11K+A83S, T11K+Y93Q, T11K+ Y93A, T11K+S95D, T11K+A97R, T11K+S98P, T11K+ S98D, T11K+N100Y, T11K+D104A, T11K+D104G, T11K+E108S, T11K+S111A, T11K+S111K, T11K+S111R, T11K+I114Q, T11K+I114M, T11K+I114W, T11K+K116R, T11K+D118K, T11K+T119R, T11K+S131T, T11K+E133R, T11K+E133Q, T11K+D135P, T11K+A136P, T11K+ D139A, T11K+D139R, T11K+K142M, T11K+K142V, T11K+K142S, T11K+K142R, T11K+Q143R, T11K+ N150T, T11K+N150R, T11K+N150S, T11K+Q169A, T11K+Q169R, T11K+Q169K, T11K+H172R, T11K+ Y174R, T11K+Y174L, T11K+Y174W, T11K+Y174F, T11K+R176Q, T11K+E177S, T11K+E177Y, T11K+ N180R, T11K+P183T, T11K+P183G, T11K+Q184E, T11K+Q184K, T11K+R185G, T11K+Y196W, T11K+ Y196F, T11K+N200T, T11K+S202R, T11K+Q203T, T11K+R205K, T11K+R210L, T11K+R210G, T11K+ R210M, T11K+N213V, T11K+N213D, T11K+T228S, T11K+N229D, T11K+E234F, T11K+E234Y, T11K+ A235K, T11K+A235R, T11K+S241C, T11K+Q243K, T11K+Q243E, T11K+R244K, T11K+R244V, T11K+ A250G, T11K+K254Y, T11K+G257W, T11K+G257E, T11K+G257A, T11K+W260F, T11K+W260Y, T11K+ W260L, T11K+W260T, T11K+Y262F, T11K+S266A, T11K+D268N, T11K+A270D, T11K+N272M, T11K+ N272T, T11K+N273E, T11K+N273D, T11K+A276E, T11K+A276W, T11K+A276D, T11K+N279D, T11K+ N279E, T11K+T280L, T11K+N283W, T11K+N283H, T11K+Y286W, T11K+Y286F, T11K+L288I, T11K+E290A, T11K+L294P, T11K+L294K, T11K+L294I, T11K+L294R, T11K+L294V, T11K+L294H, T11K+S295K, T11K+S295V, T11K+S295P, T11K+S295L, T11K+S295R, T11K+S295A, T11K+S295N, T11K+S295M, T11K+S295I, T11K+T296S, T11K+F298Y, T11R+Y13F, T11R+D14S, T11R+D14K, T11R+N18V, T11R+N18R, T11R+A30T, T11R+Y32F, T11R+Y32W, T11R+K33Q, T11R+D34G, T11R+Q35L, T11R+T37P, T11R+E41V, T11R+E41N, T11R+N45G, T11R+G47S, T11R+G47A, T11R+D57N, T11R+G59Q, T11R+Q60R, T11R+K63R, T11R+K63Q, T11R+D65E, T11R+R70K, T11R+N71S, T11R+S74K, T11R+E77T, T11R+E77N, T11R+D78G, T11R+H80K, T11R+V82R, T11R+V82I, T11R+V82S, T11R+A83P, T11R+A83S, T11R+Y93Q, T11R+Y93A, T11R+S95D, T11R+A97R, T11R+S98P, T11R+S98D, T11R+N100Y, T11R+D104A, T11R+D104G, T11R+E108S, T11R+S111A, T11R+S111K, T11R+S111R, T11R+I114Q, T11R+I114M, T11R+I114W, T11R+K116R, T11R+D118K, T11R+T119R, T11R+S131T, T11R+E133R, T11R+E133Q, T11R+D135P, T11R+A136P, T11R+D139A, T11R+D139R, T11R+K142M, T11R+K142V, T11R+K142S, T11R+K142R, T11R+Q143R, T11R+N150T, T11R+N150R, T11R+N150S, T11R+Q169A, T11R+Q169R, T11R+Q169K, T11R+H172R, T11R+Y174R, T11R+Y174L, T11R+Y174W, T11R+Y174F, T11R+R176Q, T11R+E177S, T11R+E177Y, T11R+N180R, T11R+P183T, T11R+P183G, T11R+Q184E, T11R+Q184K, T11R+R185G, T11R+Y196W, T11R+Y196F, T11R+N200T, T11R+S202R, T11R+Q203T, T11R+R205K,

T11R+R210L, T11R+R210G, T11R+R210M, T11R+ N213V, T11R+N213D, T11R+T228S, T11R+N229D, T11R+E234F, T11R+E234Y, T11R+A235K, T11R+A235R, T11R+S241C, T11R+Q243K, T11R+Q243E, T11R+ R244K, T11R+R244V, T11R+A250G, T11R+K254Y, T11R+G257W, T11R+G257E, T11R+G257A, T11R+ W260F, T11R+W260Y, T11R+W260L, T11R+W260T, T11R+Y262F, T11R+S266A, T11R+D268N, T11R+ A270D, T11R+N272M, T11R+N272T, T11R+N273E, T11R+N273D, T11R+A276E, T11R+A276W, T11R+ A276D, T11R+N279D, T11R+N279E, T11R+T280L, T11R+N283W, T11R+N283H, T11R+Y286W, T11R+ Y286F, T11R+L288I, T11R+E290A, T11R+L294P, T11R+ L294K, T11R+L294I, T11R+L294R, T11R+L294V, T11R+ L294H, T11R+S295K, T11R+S295V, T11R+S295P, T11R+ S295L, T11R+S295R, T11R+S295A, T11R+S295N, T11R+ S295M, T11R+S295I, T11R+T296S, T11R+F298Y, Y13F+ D14S, Y13F+D14K, Y13F+N18V, Y13F+N18R, Y13F+ A30T, Y13F+Y32F, Y13F+Y32W, Y13F+K33Q, Y13F+ D34G, Y13F+Q35L, Y13F+T37P, Y13F+E41V, Y13F+ E41N, Y13F+N45G, Y13F+G47S, Y13F+G47A, Y13F+ D57N, Y13F+G59Q, Y13F+Q60R, Y13F+K63R, Y13F+ K63Q, Y13F+D65E, Y13F+R70K, Y13F+N71S, Y13F+ S74K, Y13F+E77T, Y13F+E77N, Y13F+D78G, Y13F+ H80K, Y13F+V82R, Y13F+V82I, Y13F+V82S, Y13F+ A83P, Y13F+A83S, Y13F+Y93Q, Y13F+Y93A, Y13F+ S95D, Y13F+A97R, Y13F+S98P, Y13F+S98D, Y13F+ N100Y, Y13F+D104A, Y13F+D104G, Y13F+E108S, Y13F+S111A, Y13F+S111K, Y13F+S111R, Y13F+I114Q, Y13F+I114M, Y13F+I114W, Y13F+K116R, Y13F+D118K, Y13F+T119R, Y13F+S131T, Y13F+E133R, Y13F+E133Q, Y13F+D135P, Y13F+A136P, Y13F+D139A, Y13F+D139R, Y13F+K142M, Y13F+K142V, Y13F+K142S, Y13F+ K142R, Y13F+Q143R, Y13F+N150T, Y13F+N150R, Y13F+N150S, Y13F+Q169A, Y13F+Q169R, Y13F+ Q169K, Y13F+H172R, Y13F+Y174R, Y13F+Y174L, Y13F+Y174W, Y13F+Y174F, Y13F+R176Q, Y13F+ E177S, Y13F+E177Y, Y13F+N180R, Y13F+P183T, Y13F+ P183G, Y13F+Q184E, Y13F+Q184K, Y13F+R185G, Y13F+Y196W, Y13F+Y196F, Y13F+N200T, Y13F+ S202R, Y13F+Q203T, Y13F+R205K, Y13F+R210L, Y13F+R210G, Y13F+R210M, Y13F+N213V, Y13F+ N213D, Y13F+T228S, Y13F+N229D, Y13F+E234F, Y13F+E234Y, Y13F+A235K, Y13F+A235R, Y13F+ S241C, Y13F+Q243K, Y13F+Q243E, Y13F+R244K, Y13F+R244V, Y13F+A250G, Y13F+K254Y, Y13F+ G257W, Y13F+G257E, Y13F+G257A, Y13F+W260F, Y13F+W260Y, Y13F+W260L, Y13F+W260T, Y13F+ Y262F, Y13F+S266A, Y13F+D268N, Y13F+A270D, Y13F+N272M, Y13F+N272T, Y13F+N273E, Y13F+ N273D, Y13F+A276E, Y13F+A276W, Y13F+A276D, Y13F+N279D, Y13F+N279E, Y13F+T280L, Y13F+ N283W, Y13F+N283H, Y13F+Y286W, Y13F+Y286F, Y13F+L288I, Y13F+E290A, Y13F+L294P, Y13F+L294K, Y13F+L294I, Y13F+L294R, Y13F+L294V, Y13F+L294H, Y13F+S295K, Y13F+S295V, Y13F+S295P, Y13F+S295L, Y13F+S295R, Y13F+S295A, Y13F+S295N, Y13F+ S295M, Y13F+S295I, Y13F+T296S, Y13F+F298Y, D14S+ N18V, D14S+N18R, D14S+A30T, D14S+Y32F, D14S+ Y32W, D14S+K33Q, D14S+D34G, D14S+Q35L, D14S+ T37P, D14S+E41V, D14S+E41N, D14S+N45G, D14S+ G47S, D14S+G47A, D14S+D57N, D14S+G59Q, D14S+ Q60R, D14S+K63R, D14S+K63Q, D14S+D65E, D14S+ R70K, D14S+N71S, D14S+S74K, D14S+E77T, D14S+ E77N, D14S+D78G, D14S+H80K, D14S+V82R, D14S+ V82I, D14S+V82S, D14S+A83P, D14S+A83S, D14S+ Y93Q, D14S+Y93A, D14S+S95D, D14S+A97R, D14S+ S98P, D14S+S98D, D14S+N100Y, D14S+D104A, D14S+ D104G, D14S+E108S, D14S+S111A, D14S+S111K, D14S+S111R, D14S+I114Q, D14S+I114M, D14S+I114W, D14S+K116R, D14S+D118K, D14S+T119R, D14S+S131T, D14S+E133R, D14S+E133Q, D14S+D135P, D14S+A136P, D14S+D139A, D14S+D139R, D14S+K142M, D14S+ K142V, D14S+K142S, D14S+K142R, D14S+Q143R, D14S+N150T, D14S+N150R, D14S+N150S, D14S+ Q169A, D14S+Q169R, D14S+Q169K, D14S+H172R, D14S+Y174R, D14S+Y174L, D14S+Y174W, D14S+ Y174F, D14S+R176Q, D14S+E177S, D14S+E177Y, D14S+N180R, D14S+P183T, D14S+P183G, D14S+Q184E, D14S+Q184K, D14S+R185G, D14S+Y196W, D14S+ Y196F, D14S+N200T, D14S+S202R, D14S+Q203T, D14S+R205K, D14S+R210L, D14S+R210G, D14S+ R210M, D14S+N213V, D14S+N213D, D14S+T228S, D14S+N229D, D14S+E234F, D14S+E234Y, D14S+ A235K, D14S+A235R, D14S+S241C, D14S+Q243K, D14S+Q243E, D14S+R244K, D14S+R244V, D14S+ A250G, D14S+K254Y, D14S+G257W, D14S+G257E, D14S+G257A, D14S+W260F, D14S+W260Y, D14S+ W260L, D14S+W260T, D14S+Y262F, D14S+S266A, D14S+D268N, D14S+A270D, D14S+N272M, D14S+ N272T, D14S+N273E, D14S+N273D, D14S+A276E, D14S+A276W, D14S+A276D, D14S+N279D, D14S+ N279E, D14S+T280L, D14S+N283W, D14S+N283H, D14S+Y286W, D14S+Y286F, D14S+L288I, D14S+E290A, D14S+L294P, D14S+L294K, D14S+L294I, D14S+L294R, D14S+L294V, D14S+L294H, D14S+S295K, D14S+S295V, D14S+S295P, D14S+S295L, D14S+S295R, D14S+S295A, D14S+S295N, D14S+S295M, D14S+S295I, D14S+T296S, D14S+F298Y, D14K+N18V, D14K+N18R, D14K+A30T, D14K+Y32F, D14K+Y32W, D14K+K33Q, D14K+D34G, D14K+Q35L, D14K+T37P, D14K+E41V, D14K+E41N, D14K+N45G, D14K+G47S, D14K+G47A, D14K+D57N, D14K+G59Q, D14K+Q60R, D14K+K63R, D14K+K63Q, D14K+D65E, D14K+R70K, D14K+N71S, D14K+S74K, D14K+E77T, D14K+E77N, D14K+D78G, D14K+H80K, D14K+V82R, D14K+V82I, D14K+V82S, D14K+A83P, D14K+A83S, D14K+Y93Q, D14K+Y93A, D14K+S95D, D14K+A97R, D14K+S98P, D14K+S98D, D14K+N100Y, D14K+D104A, D14K+D104G, D14K+E108S, D14K+S111A, D14K+S111K, D14K+S111R, D14K+I114Q, D14K+I114M, D14K+I114W, D14K+K116R, D14K+D118K, D14K+T119R, D14K+S131T, D14K+E133R, D14K+E133Q, D14K+D135P, D14K+A136P, D14K+D139A, D14K+D139R, D14K+K142M, D14K+K142V, D14K+K142S, D14K+K142R, D14K+Q143R, D14K+N150T, D14K+N150R, D14K+N150S, D14K+Q169A, D14K+Q169R, D14K+Q169K, D14K+H172R, D14K+Y174R, D14K+Y174L, D14K+Y174W, D14K+Y174F, D14K+R176Q, D14K+E177S, D14K+E177Y, D14K+N180R, D14K+P183T, D14K+P183G, D14K+Q184E, D14K+Q184K, D14K+R185G, D14K+Y196W, D14K+Y196F, D14K+N200T, D14K+S202R, D14K+Q203T, D14K+R205K, D14K+R210L, D14K+R210G, D14K+R210M, D14K+N213V, D14K+N213D, D14K+T228S, D14K+N229D, D14K+E234F, D14K+E234Y, D14K+A235K, D14K+A235R, D14K+S241C, D14K+Q243K, D14K+Q243E, D14K+R244K, D14K+R244V, D14K+A250G, D14K+K254Y, D14K+G257W, D14K+G257E, D14K+G257A, D14K+W260F, D14K+W260Y, D14K+W260L, D14K+W260T, D14K+Y262F, D14K+S266A, D14K+D268N, D14K+A270D, D14K+N272M, D14K+N272T, D14K+N273E, D14K+N273D, D14K+A276E, D14K+A276W, D14K+A276D, D14K+N279D, D14K+N279E, D14K+T280L, D14K+N283W, D14K+N283H,

D14K+Y286W, D14K+Y286F, D14K+L288I, D14K+E290A, D14K+L294P, D14K+L294K, D14K+L294I, D14K+L294R, D14K+L294V, D14K+L294H, D14K+S295K, D14K+S295V, D14K+S295P, D14K+S295L, D14K+S295R, D14K+S295A, D14K+S295N, D14K+S295M, D14K+S295I, D14K+T296S, D14K+F298Y, N18V+A30T, N18V+Y32F, N18V+Y32W, N18V+K33Q, N18V+D34G, N18V+Q35L, N18V+T37P, N18V+E41V, N18V+E41N, N18V+N45G, N18V+G47S, N18V+G47A, N18V+D57N, N18V+G59Q, N18V+Q60R, N18V+K63R, N18V+K63Q, N18V+D65E, N18V+R70K, N18V+N71S, N18V+S74K, N18V+E77T, N18V+E77N, N18V+D78G, N18V+H80K, N18V+V82R, N18V+V82I, N18V+V82S, N18V+A83P, N18V+A83S, N18V+Y93Q, N18V+Y93A, N18V+S95D, N18V+A97R, N18V+S98P, N18V+S98D, N18V+N100Y, N18V+D104A, N18V+D104G, N18V+E108S, N18V+S111A, N18V+S111K, N18V+S111R, N18V+I114Q, N18V+I114M, N18V+I114W, N18V+K116R, N18V+D118K, N18V+T119R, N18V+S131T, N18V+E133R, N18V+E133Q, N18V+D135P, N18V+A136P, N18V+D139A, N18V+D139R, N18V+K142M, N18V+K142V, N18V+K142S, N18V+K142R, N18V+Q143R, N18V+N150T, N18V+N150R, N18V+N150S, N18V+Q169A, N18V+Q169R, N18V+Q169K, N18V+H172R, N18V+Y174R, N18V+Y174L, N18V+Y174W, N18V+Y174F, N18V+R176Q, N18V+E177S, N18V+E177Y, N18V+N180R, N18V+P183T, N18V+P183G, N18V+Q184E, N18V+Q184K, N18V+R185G, N18V+Y196W, N18V+Y196F, N18V+N200T, N18V+S202R, N18V+Q203T, N18V+R205K, N18V+R210L, N18V+R210G, N18V+R210M, N18V+N213V, N18V+N213D, N18V+T228S, N18V+N229D, N18V+E234F, N18V+E234Y, N18V+A235K, N18V+A235R, N18V+S241C, N18V+Q243K, N18V+Q243E, N18V+R244K, N18V+R244V, N18V+A250G, N18V+K254Y, N18V+G257W, N18V+G257E, N18V+G257A, N18V+W260F, N18V+W260Y, N18V+W260L, N18V+W260T, N18V+Y262F, N18V+S266A, N18V+D268N, N18V+A270D, N18V+N272M, N18V+N272T, N18V+N273E, N18V+N273D, N18V+A276E, N18V+A276W, N18V+A276D, N18V+N279D, N18V+N279E, N18V+T280L, N18V+N283W, N18V+N283H, N18V+Y286W, N18V+Y286F, N18V+L288I, N18V+E290A, N18V+L294P, N18V+L294K, N18V+L294I, N18V+L294R, N18V+L294V, N18V+L294H, N18V+S295K, N18V+S295V, N18V+S295P, N18V+S295L, N18V+S295R, N18V+S295A, N18V+S295N, N18V+S295M, N18V+S295I, N18V+T296S, N18V+F298Y, N18R+A30T, N18R+Y32F, N18R+Y32W, N18R+K33Q, N18R+D34G, N18R+Q35L, N18R+T37P, N18R+E41V, N18R+E41N, N18R+N45G, N18R+G47S, N18R+G47A, N18R+D57N, N18R+G59Q, N18R+Q60R, N18R+K63R, N18R+K63Q, N18R+D65E, N18R+R70K, N18R+N71S, N18R+S74K, N18R+E77T, N18R+E77N, N18R+D78G, N18R+H80K, N18R+V82R, N18R+V82I, N18R+V82S, N18R+A83P, N18R+A83S, N18R+Y93Q, N18R+Y93A, N18R+S95D, N18R+A97R, N18R+S98P, N18R+S98D, N18R+N100Y, N18R+D104A, N18R+D104G, N18R+E108S, N18R+S111A, N18R+S111K, N18R+S111R, N18R+I114Q, N18R+I114M, N18R+I114W, N18R+K116R, N18R+D118K, N18R+T119R, N18R+S131T, N18R+E133R, N18R+E133Q, N18R+D135P, N18R+A136P, N18R+D139A, N18R+D139R, N18R+K142M, N18R+K142V, N18R+K142S, N18R+K142R, N18R+Q143R, N18R+N150T, N18R+N150R, N18R+N150S, N18R+Q169A, N18R+Q169R, N18R+Q169K, N18R+H172R, N18R+Y174R, N18R+Y174L, N18R+Y174W, N18R+Y174F, N18R+R176Q, N18R+E177S, N18R+E177Y, N18R+N180R, N18R+P183T, N18R+P183G, N18R+Q184E, N18R+Q184K, N18R+R185G, N18R+Y196W, N18R+Y196F, N18R+N200T, N18R+S202R, N18R+Q203T, N18R+R205K, N18R+R210L, N18R+R210G, N18R+R210M, N18R+N213V, N18R+N213D, N18R+T228S, N18R+N229D, N18R+E234F, N18R+E234Y, N18R+A235K, N18R+A235R, N18R+S241C, N18R+Q243K, N18R+Q243E, N18R+R244K, N18R+R244V, N18R+A250G, N18R+K254Y, N18R+G257W, N18R+G257E, N18R+G257A, N18R+W260F, N18R+W260Y, N18R+W260L, N18R+W260T, N18R+Y262F, N18R+S266A, N18R+D268N, N18R+A270D, N18R+N272M, N18R+N272T, N18R+N273E, N18R+N273D, N18R+A276E, N18R+A276W, N18R+A276D, N18R+N279D, N18R+N279E, N18R+T280L, N18R+N283W, N18R+N283H, N18R+Y286W, N18R+Y286F, N18R+L288I, N18R+E290A, N18R+L294P, N18R+L294K, N18R+L294I, N18R+L294R, N18R+L294V, N18R+L294H, N18R+S295K, N18R+S295V, N18R+S295P, N18R+S295L, N18R+S295R, N18R+S295A, N18R+S295N, N18R+S295M, N18R+S295I, N18R+T296S, N18R+F298Y, A30T+Y32F, A30T+Y32W, A30T+K33Q, A30T+D34G, A30T+Q35L, A30T+T37P, A30T+E41V, A30T+E41N, A30T+N45G, A30T+G47S, A30T+G47A, A30T+D57N, A30T+G59Q, A30T+Q60R, A30T+K63R, A30T+K63Q, A30T+D65E, A30T+R70K, A30T+N71S, A30T+S74K, A30T+E77T, A30T+E77N, A30T+D78G, A30T+H80K, A30T+V82R, A30T+V82I, A30T+V82S, A30T+A83P, A30T+A83S, A30T+Y93Q, A30T+Y93A, A30T+S95D, A30T+A97R, A30T+S98P, A30T+S98D, A30T+N100Y, A30T+D104A, A30T+D104G, A30T+E108S, A30T+S111A, A30T+S111K, A30T+S111R, A30T+I114Q, A30T+I114M, A30T+I114W, A30T+K116R, A30T+D118K, A30T+T119R, A30T+S131T, A30T+E133R, A30T+E133Q, A30T+D135P, A30T+A136P, A30T+D139A, A30T+D139R, A30T+K142M, A30T+K142V, A30T+K142S, A30T+K142R, A30T+Q143R, A30T+N150T, A30T+N150R, A30T+N150S, A30T+Q169A, A30T+Q169R, A30T+Q169K, A30T+H172R, A30T+Y174R, A30T+Y174L, A30T+Y174W, A30T+Y174F, A30T+R176Q, A30T+E177S, A30T+E177Y, A30T+N180R, A30T+P183T, A30T+P183G, A30T+Q184E, A30T+Q184K, A30T+R185G, A30T+Y196W, A30T+Y196F, A30T+N200T, A30T+S202R, A30T+Q203T, A30T+R205K, A30T+R210L, A30T+R210G, A30T+R210M, A30T+N213V, A30T+N213D, A30T+T228S, A30T+N229D, A30T+E234F, A30T+E234Y, A30T+A235K, A30T+A235R, A30T+S241C, A30T+Q243K, A30T+Q243E, A30T+R244K, A30T+R244V, A30T+A250G, A30T+K254Y, A30T+G257W, A30T+G257E, A30T+G257A, A30T+W260F, A30T+W260Y, A30T+W260L, A30T+W260T, A30T+Y262F, A30T+S266A, A30T+D268N, A30T+A270D, A30T+N272M, A30T+N272T, A30T+N273E, A30T+N273D, A30T+A276E, A30T+A276W, A30T+A276D, A30T+N279D, A30T+N279E, A30T+T280L, A30T+N283W, A30T+N283H, A30T+Y286W, A30T+Y286F, A30T+L288I, A30T+E290A, A30T+L294P, A30T+L294K, A30T+L294I, A30T+L294R, A30T+L294V, A30T+L294H, A30T+S295K, A30T+S295V, A30T+S295P, A30T+S295L, A30T+S295R, A30T+S295A, A30T+S295N, A30T+S295M, A30T+S295I, A30T+T296S, A30T+F298Y, Y32F+K33Q, Y32F+D34G, Y32F+Q35L, Y32F+T37P, Y32F+E41V, Y32F+E41N, Y32F+N45G, Y32F+G47S, Y32F+G47A, Y32F+D57N, Y32F+G59Q, Y32F+Q60R, Y32F+K63R, Y32F+K63Q, Y32F+D65E, Y32F+R70K, Y32F+N71S, Y32F+S74K, Y32F+E77T, Y32F+E77N, Y32F+D78G, Y32F+H80K,

Y32F+V82R, Y32F+V82I, Y32F+V82S, Y32F+A83P, Y32F+A83S, Y32F+Y93Q, Y32F+Y93A, Y32F+S95D, Y32F+A97R, Y32F+S98P, Y32F+S98D, Y32F+N100Y, Y32F+D104A, Y32F+D104G, Y32F+E108S, Y32F+S111A, Y32F+S111K, Y32F+S111R, Y32F+I114Q, Y32F+I114M, Y32F+I114W, Y32F+K116R, Y32F+D118K, Y32F+T119R, Y32F+S131T, Y32F+E133R, Y32F+E133Q, Y32F+D135P, Y32F+A136P, Y32F+D139A, Y32F+D139R, Y32F+K142M, Y32F+K142V, Y32F+K142S, Y32F+K142R, Y32F+Q143R, Y32F+N150T, Y32F+N150R, Y32F+N150S, Y32F+Q169A, Y32F+Q169R, Y32F+Q169K, Y32F+H172R, Y32F+Y174R, Y32F+Y174L, Y32F+Y174W, Y32F+Y174F, Y32F+R176Q, Y32F+E177S, Y32F+E177Y, Y32F+N180R, Y32F+P183T, Y32F+P183G, Y32F+Q184E, Y32F+Q184K, Y32F+R185G, Y32F+Y196W, Y32F+Y196F, Y32F+N200T, Y32F+S202R, Y32F+Q203T, Y32F+R205K, Y32F+R210L, Y32F+R210G, Y32F+R210M, Y32F+N213V, Y32F+N213D, Y32F+T228S, Y32F+N229D, Y32F+E234F, Y32F+E234Y, Y32F+A235K, Y32F+A235R, Y32F+S241C, Y32F+Q243K, Y32F+Q243E, Y32F+R244K, Y32F+R244V, Y32F+A250G, Y32F+K254Y, Y32F+G257W, Y32F+G257E, Y32F+G257A, Y32F+W260F, Y32F+W260Y, Y32F+W260L, Y32F+W260T, Y32F+Y262F, Y32F+S266A, Y32F+D268N, Y32F+A270D, Y32F+N272M, Y32F+N272T, Y32F+N273E, Y32F+N273D, Y32F+A276E, Y32F+A276W, Y32F+A276D, Y32F+N279D, Y32F+N279E, Y32F+T280L, Y32F+N283W, Y32F+N283H, Y32F+Y286W, Y32F+Y286F, Y32F+L288I, Y32F+E290A, Y32F+L294P, Y32F+L294K, Y32F+L294I, Y32F+L294R, Y32F+L294V, Y32F+L294H, Y32F+S295K, Y32F+S295V, Y32F+S295P, Y32F+S295L, Y32F+S295R, Y32F+S295A, Y32F+S295N, Y32F+S295M, Y32F+S295I, Y32F+T296S, Y32F+F298Y, Y32W+K33Q, Y32W+D34G, Y32W+Q35L, Y32W+T37P, Y32W+E41V, Y32W+E41N, Y32W+N45G, Y32W+G47S, Y32W+G47A, Y32W+D57N, Y32W+G59Q, Y32W+Q60R, Y32W+K63R, Y32W+K63Q, Y32W+D65E, Y32W+R70K, Y32W+N71S, Y32W+S74K, Y32W+E77T, Y32W+E77N, Y32W+D78G, Y32W+H80K, Y32W+V82R, Y32W+V82I, Y32W+V82S, Y32W+A83P, Y32W+A83S, Y32W+Y93Q, Y32W+Y93A, Y32W+S95D, Y32W+A97R, Y32W+S98P, Y32W+S98D, Y32W+N100Y, Y32W+D104A, Y32W+D104G, Y32W+E108S, Y32W+S111A, Y32W+S111K, Y32W+S111R, Y32W+I114Q, Y32W+I114M, Y32W+I114W, Y32W+K116R, Y32W+D118K, Y32W+T119R, Y32W+S131T, Y32W+E133R, Y32W+E133Q, Y32W+D135P, Y32W+A136P, Y32W+D139A, Y32W+D139R, Y32W+K142M, Y32W+K142V, Y32W+K142S, Y32W+K142R, Y32W+Q143R, Y32W+N150T, Y32W+N150R, Y32W+N150S, Y32W+Q169A, Y32W+Q169R, Y32W+Q169K, Y32W+H172R, Y32W+Y174R, Y32W+Y174L, Y32W+Y174W, Y32W+Y174F, Y32W+R176Q, Y32W+E177S, Y32W+E177Y, Y32W+N180R, Y32W+P183T, Y32W+P183G, Y32W+Q184E, Y32W+Q184K, Y32W+R185G, Y32W+Y196W, Y32W+Y196F, Y32W+N200T, Y32W+S202R, Y32W+Q203T, Y32W+R205K, Y32W+R210L, Y32W+R210G, Y32W+R210M, Y32W+N213V, Y32W+N213D, Y32W+T228S, Y32W+N229D, Y32W+E234F, Y32W+E234Y, Y32W+A235K, Y32W+A235R, Y32W+S241C, Y32W+Q243K, Y32W+Q243E, Y32W+R244K, Y32W+R244V, Y32W+A250G, Y32W+K254Y, Y32W+G257W, Y32W+G257E, Y32W+G257A, Y32W+W260F, Y32W+W260Y, Y32W+W260L, Y32W+W260T, Y32W+Y262F, Y32W+S266A, Y32W+D268N, Y32W+A270D, Y32W+N272M, Y32W+N272T, Y32W+N273E, Y32W+N273D, Y32W+A276E, Y32W+A276W, Y32W+A276D, Y32W+N279D, Y32W+N279E, Y32W+T280L, Y32W+N283W, Y32W+N283H, Y32W+Y286W, Y32W+Y286F, Y32W+L288I, Y32W+E290A, Y32W+L294P, Y32W+L294K, Y32W+L294I, Y32W+L294R, Y32W+L294V, Y32W+L294H, Y32W+S295K, Y32W+S295V, Y32W+S295P, Y32W+S295L, Y32W+S295R, Y32W+S295A, Y32W+S295N, Y32W+S295M, Y32W+S295I, Y32W+T296S, Y32W+F298Y, K33Q+D34G, K33Q+Q35L, K33Q+T37P, K33Q+E41V, K33Q+E41N, K33Q+N45G, K33Q+G47S, K33Q+G47A, K33Q+D57N, K33Q+G59Q, K33Q+Q60R, K33Q+K63R, K33Q+K63Q, K33Q+D65E, K33Q+R70K, K33Q+N71S, K33Q+S74K, K33Q+E77T, K33Q+E77N, K33Q+D78G, K33Q+H80K, K33Q+V82R, K33Q+V82I, K33Q+V82S, K33Q+A83P, K33Q+A83S, K33Q+Y93Q, K33Q+Y93A, K33Q+S95D, K33Q+A97R, K33Q+S98P, K33Q+S98D, K33Q+N100Y, K33Q+D104A, K33Q+D104G, K33Q+E108S, K33Q+S111A, K33Q+S111K, K33Q+S111R, K33Q+I114Q, K33Q+I114M, K33Q+I114W, K33Q+K116R, K33Q+D118K, K33Q+T119R, K33Q+S131T, K33Q+E133R, K33Q+E133Q, K33Q+D135P, K33Q+A136P, K33Q+D139A, K33Q+D139R, K33Q+K142M, K33Q+K142V, K33Q+K142S, K33Q+K142R, K33Q+Q143R, K33Q+N150T, K33Q+N150R, K33Q+N150S, K33Q+Q169A, K33Q+Q169R, K33Q+Q169K, K33Q+H172R, K33Q+Y174R, K33Q+Y174L, K33Q+Y174W, K33Q+Y174F, K33Q+R176Q, K33Q+E177S, K33Q+E177Y, K33Q+N180R, K33Q+P183T, K33Q+P183G, K33Q+Q184E, K33Q+Q184K, K33Q+R185G, K33Q+Y196W, K33Q+Y196F, K33Q+N200T, K33Q+S202R, K33Q+Q203T, K33Q+R205K, K33Q+R210L, K33Q+R210G, K33Q+R210M, K33Q+N213V, K33Q+N213D, K33Q+T228S, K33Q+N229D, K33Q+E234F, K33Q+E234Y, K33Q+A235K, K33Q+A235R, K33Q+S241C, K33Q+Q243K, K33Q+Q243E, K33Q+R244K, K33Q+R244V, K33Q+A250G, K33Q+K254Y, K33Q+G257W, K33Q+G257E, K33Q+G257A, K33Q+W260F, K33Q+W260Y, K33Q+W260L, K33Q+W260T, K33Q+Y262F, K33Q+S266A, K33Q+D268N, K33Q+A270D, K33Q+N272M, K33Q+N272T, K33Q+N273E, K33Q+N273D, K33Q+A276E, K33Q+A276W, K33Q+A276D, K33Q+N279D, K33Q+N279E, K33Q+T280L, K33Q+N283W, K33Q+N283H, K33Q+Y286W, K33Q+Y286F, K33Q+L288I, K33Q+E290A, K33Q+L294P, K33Q+L294K, K33Q+L294I, K33Q+L294R, K33Q+L294V, K33Q+L294H, K33Q+S295K, K33Q+S295V, K33Q+S295P, K33Q+S295L, K33Q+S295R, K33Q+S295A, K33Q+S295N, K33Q+S295M, K33Q+S295I, K33Q+T296S, K33Q+F298Y, D34G+Q35L, D34G+T37P, D34G+E41V, D34G+E41N, D34G+N45G, D34G+G47S, D34G+G47A, D34G+D57N, D34G+G59Q, D34G+Q60R, D34G+K63R, D34G+K63Q, D34G+D65E, D34G+R70K, D34G+N71S, D34G+S74K, D34G+E77T, D34G+E77N, D34G+D78G, D34G+H80K, D34G+V82R, D34G+V82I, D34G+V82S, D34G+A83P, D34G+A83S, D34G+Y93Q, D34G+Y93A, D34G+S95D, D34G+A97R, D34G+S98P, D34G+S98D, D34G+N100Y, D34G+D104A, D34G+D104G, D34G+E108S, D34G+S111A, D34G+S111K, D34G+S111R, D34G+I114Q, D34G+I114M, D34G+I114W, D34G+K116R, D34G+D118K, D34G+T119R, D34G+S131T, D34G+E133R, D34G+E133Q, D34G+D135P, D34G+A136P, D34G+D139A, D34G+D139R, D34G+K142M, D34G+K142V, D34G+K142S, D34G+K142R, D34G+Q143R, D34G+N150T, D34G+N150R, D34G+N150S, D34G+Q169A, D34G+Q169R, D34G+Q169K, D34G+H172R, D34G+Y174R, D34G+Y174L, D34G+Y174W, D34G+Y174F, D34G+R176Q, D34G+E177S, D34G+E177Y, D34G+N180R, D34G+

P183T, D34G+P183G, D34G+Q184E, D34G+Q184K, D34G+R185G, D34G+Y196W, D34G+Y196F, D34G+N200T, D34G+S202R, D34G+Q203T, D34G+R205K, D34G+R210L, D34G+R210G, D34G+R210M, D34G+N213V, D34G+N213D, D34G+T228S, D34G+N229D, D34G+E234F, D34G+E234Y, D34G+A235K, D34G+A235R, D34G+S241C, D34G+Q243K, D34G+Q243E, D34G+R244K, D34G+R244V, D34G+A250G, D34G+K254Y, D34G+G257W, D34G+G257E, D34G+G257A, D34G+W260F, D34G+W260Y, D34G+W260L, D34G+W260T, D34G+Y262F, D34G+S266A, D34G+D268N, D34G+A270D, D34G+N272M, D34G+N272T, D34G+N273E, D34G+N273D, D34G+A276E, D34G+A276W, D34G+A276D, D34G+N279D, D34G+N279E, D34G+T280L, D34G+N283W, D34G+N283H, D34G+Y286W, D34G+Y286F, D34G+L288I, D34G+E290A, D34G+L294P, D34G+L294K, D34G+L294I, D34G+L294R, D34G+L294V, D34G+L294H, D34G+S295K, D34G+S295V, D34G+S295P, D34G+S295L, D34G+S295R, D34G+S295A, D34G+S295N, D34G+S295M, D34G+S295I, D34G+T296S, D34G+F298Y, Q35L+T37P, Q35L+E41V, Q35L+E41N, Q35L+N45G, Q35L+G47S, Q35L+G47A, Q35L+D57N, Q35L+G59Q, Q35L+Q60R, Q35L+K63R, Q35L+K63Q, Q35L+D65E, Q35L+R70K, Q35L+N71S, Q35L+S74K, Q35L+E77T, Q35L+E77N, Q35L+D78G, Q35L+H80K, Q35L+V82R, Q35L+V82I, Q35L+V82S, Q35L+A83P, Q35L+A83S, Q35L+Y93Q, Q35L+Y93A, Q35L+S95D, Q35L+A97R, Q35L+S98P, Q35L+S98D, Q35L+N100Y, Q35L+D104A, Q35L+D104G, Q35L+E108S, Q35L+S111A, Q35L+S111K, Q35L+S111R, Q35L+I114Q, Q35L+I114M, Q35L+I114W, Q35L+K116R, Q35L+D118K, Q35L+T119R, Q35L+S131T, Q35L+E133R, Q35L+E133Q, Q35L+D135P, Q35L+A136P, Q35L+D139A, Q35L+D139R, Q35L+K142M, Q35L+K142V, Q35L+K142S, Q35L+K142R, Q35L+Q143R, Q35L+N150T, Q35L+N150R, Q35L+N150S, Q35L+Q169A, Q35L+Q169R, Q35L+Q169K, Q35L+H172R, Q35L+Y174R, Q35L+Y174L, Q35L+Y174W, Q35L+Y174F, Q35L+R176Q, Q35L+E177S, Q35L+E177Y, Q35L+N180R, Q35L+P183T, Q35L+P183G, Q35L+Q184E, Q35L+Q184K, Q35L+R185G, Q35L+Y196W, Q35L+Y196F, Q35L+N200T, Q35L+S202R, Q35L+Q203T, Q35L+R205K, Q35L+R210L, Q35L+R210G, Q35L+R210M, Q35L+N213V, Q35L+N213D, Q35L+T228S, Q35L+N229D, Q35L+E234F, Q35L+E234Y, Q35L+A235K, Q35L+A235R, Q35L+S241C, Q35L+Q243K, Q35L+Q243E, Q35L+R244K, Q35L+R244V, Q35L+A250G, Q35L+K254Y, Q35L+G257W, Q35L+G257E, Q35L+G257A, Q35L+W260F, Q35L+W260Y, Q35L+W260L, Q35L+W260T, Q35L+Y262F, Q35L+S266A, Q35L+D268N, Q35L+A270D, Q35L+N272M, Q35L+N272T, Q35L+N273E, Q35L+N273D, Q35L+A276E, Q35L+A276W, Q35L+A276D, Q35L+N279D, Q35L+N279E, Q35L+T280L, Q35L+N283W, Q35L+N283H, Q35L+Y286W, Q35L+Y286F, Q35L+L288I, Q35L+E290A, Q35L+L294P, Q35L+L294K, Q35L+L294I, Q35L+L294R, Q35L+L294V, Q35L+L294H, Q35L+S295K, Q35L+S295V, Q35L+S295P, Q35L+S295L, Q35L+S295R, Q35L+S295A, Q35L+S295N, Q35L+S295M, Q35L+S295I, Q35L+T296S, Q35L+F298Y, T37P+E41V, T37P+E41N, T37P+N45G, T37P+G47S, T37P+G47A, T37P+D57N, T37P+G59Q, T37P+Q60R, T37P+K63R, T37P+K63Q, T37P+D65E, T37P+R70K, T37P+N71S, T37P+S74K, T37P+E77T, T37P+E77N, T37P+D78G, T37P+H80K, T37P+V82R, T37P+V82I, T37P+V82S, T37P+A83P, T37P+A83S, T37P+Y93Q, T37P+Y93A, T37P+S95D, T37P+A97R, T37P+S98P, T37P+S98D, T37P+N100Y, T37P+D104A, T37P+D104G, T37P+E108S, T37P+S111A, T37P+S111K, T37P+S111R, T37P+I114Q, T37P+I114M, T37P+I114W, T37P+K116R, T37P+D118K, T37P+T119R, T37P+S131T, T37P+E133R, T37P+E133Q, T37P+D135P, T37P+A136P, T37P+D139A, T37P+D139R, T37P+K142M, T37P+K142V, T37P+K142S, T37P+K142R, T37P+Q143R, T37P+N150T, T37P+N150R, T37P+N150S, T37P+Q169A, T37P+Q169R, T37P+Q169K, T37P+H172R, T37P+Y174R, T37P+Y174L, T37P+Y174W, T37P+Y174F, T37P+R176Q, T37P+E177S, T37P+E177Y, T37P+N180R, T37P+P183T, T37P+P183G, T37P+Q184E, T37P+Q184K, T37P+R185G, T37P+Y196W, T37P+Y196F, T37P+N200T, T37P+S202R, T37P+Q203T, T37P+R205K, T37P+R210L, T37P+R210G, T37P+R210M, T37P+N213V, T37P+N213D, T37P+T228S, T37P+N229D, T37P+E234F, T37P+E234Y, T37P+A235K, T37P+A235R, T37P+S241C, T37P+Q243K, T37P+Q243E, T37P+R244K, T37P+R244V, T37P+A250G, T37P+K254Y, T37P+G257W, T37P+G257E, T37P+G257A, T37P+W260F, T37P+W260Y, T37P+W260L, T37P+W260T, T37P+Y262F, T37P+S266A, T37P+D268N, T37P+A270D, T37P+N272M, T37P+N272T, T37P+N273E, T37P+N273D, T37P+A276E, T37P+A276W, T37P+A276D, T37P+N279D, T37P+N279E, T37P+T280L, T37P+N283W, T37P+N283H, T37P+Y286W, T37P+Y286F, T37P+L288I, T37P+E290A, T37P+L294P, T37P+L294K, T37P+L294I, T37P+L294R, T37P+L294V, T37P+L294H, T37P+S295K, T37P+S295V, T37P+S295P, T37P+S295L, T37P+S295R, T37P+S295A, T37P+S295N, T37P+S295M, T37P+S295I, T37P+T296S, T37P+F298Y, E41V+N45G, E41V+G47S, E41V+G47A, E41V+D57N, E41V+G59Q, E41V+Q60R, E41V+K63R, E41V+K63Q, E41V+D65E, E41V+R70K, E41V+N71S, E41V+S74K, E41V+E77T, E41V+E77N, E41V+D78G, E41V+H80K, E41V+V82R, E41V+V82I, E41V+V82S, E41V+A83P, E41V+A83S, E41V+Y93Q, E41V+Y93A, E41V+S95D, E41V+A97R, E41V+S98P, E41V+S98D, E41V+N100Y, E41V+D104A, E41V+D104G, E41V+E108S, E41V+S111A, E41V+S111K, E41V+S111R, E41V+I114Q, E41V+I114M, E41V+I114W, E41V+K116R, E41V+D118K, E41V+T119R, E41V+S131T, E41V+E133R, E41V+E133Q, E41V+D135P, E41V+A136P, E41V+D139A, E41V+D139R, E41V+K142M, E41V+K142V, E41V+K142S, E41V+K142R, E41V+Q143R, E41V+N150T, E41V+N150R, E41V+N150S, E41V+Q169A, E41V+Q169R, E41V+Q169K, E41V+H172R, E41V+Y174R, E41V+Y174L, E41V+Y174W, E41V+Y174F, E41V+R176Q, E41V+E177S, E41V+E177Y, E41V+N180R, E41V+P183T, E41V+P183G, E41V+Q184E, E41V+Q184K, E41V+R185G, E41V+Y196W, E41V+Y196F, E41V+N200T, E41V+S202R, E41V+Q203T, E41V+R205K, E41V+R210L, E41V+R210G, E41V+R210M, E41V+N213V, E41V+N213D, E41V+T228S, E41V+N229D, E41V+E234F, E41V+E234Y, E41V+A235K, E41V+A235R, E41V+S241C, E41V+Q243K, E41V+Q243E, E41V+R244K, E41V+R244V, E41V+A250G, E41V+K254Y, E41V+G257W, E41V+G257E, E41V+G257A, E41V+W260F, E41V+W260Y, E41V+W260L, E41V+W260T, E41V+Y262F, E41V+S266A, E41V+D268N, E41V+A270D, E41V+N272M, E41V+N272T, E41V+N273E, E41V+N273D, E41V+A276E, E41V+A276W, E41V+A276D, E41V+N279D, E41V+N279E, E41V+T280L, E41V+N283W, E41V+N283H, E41V+Y286W, E41V+Y286F, E41V+L288I, E41V+E290A, E41V+L294P, E41V+L294K, E41V+L294I, E41V+L294R, E41V+L294V, E41V+L294H, E41V+S295K, E41V+S295V, E41V+S295P, E41V+S295L, E41V+S295R, E41V+S295A, E41V+S295N, E41V+

S295M, E41V+S295I, E41V+T296S, E41V+F298Y, E41N+
N45G, E41N+G47S, E41N+G47A, E41N+D57N, E41N+
G59Q, E41N+Q60R, E41N+K63R, E41N+K63Q, E41N+
D65E, E41N+R70K, E41N+N71S, E41N+S74K, E41N+
E77T, E41N+E77N, E41N+D78G, E41N+H80K, E41N+
V82R, E41N+V82I, E41N+V82S, E41N+A83P, E41N+
A83S, E41N+Y93Q, E41N+Y93A, E41N+S95D, E41N+
A97R, E41N+S98P, E41N+S98D, E41N+N100Y, E41N+
D104A, E41N+D104G, E41N+E108S, E41N+S111A,
E41N+S111K, E41N+S111R, E41N+I114Q, E41N+I114M,
E41N+I114W, E41N+K116R, E41N+D118K, E41N+
T119R, E41N+S131T, E41N+E133R, E41N+E133Q,
E41N+D135P, E41N+A136P, E41N+D139A, E41N+
D139R, E41N+K142M, E41N+K142V, E41N+K142S,
E41N+K142R, E41N+Q143R, E41N+N150T, E41N+
N150R, E41N+N150S, E41N+Q169A, E41N+Q169R,
E41N+Q169K, E41N+H172R, E41N+Y174R, E41N+
Y174L, E41N+Y174W, E41N+Y174F, E41N+R176Q,
E41N+E177S, E41N+E177Y, E41N+N180R, E41N+P183T,
E41N+P183G, E41N+Q184E, E41N+Q184K, E41N+
R185G, E41N+Y196W, E41N+Y196F, E41N+N200T,
E41N+S202R, E41N+Q203T, E41N+R205K, E41N+
R210L, E41N+R210G, E41N+R210M, E41N+N213V,
E41N+N213D, E41N+T228S, E41N+N229D, E41N+
E234F, E41N+E234Y, E41N+A235K, E41N+A235R,
E41N+S241C, E41N+Q243K, E41N+Q243E, E41N+
R244K, E41N+R244V, E41N+A250G, E41N+K254Y,
E41N+G257W, E41N+G257E, E41N+G257A, E41N+
W260F, E41N+W260Y, E41N+W260L, E41N+W260T,
E41N+Y262F, E41N+S266A, E41N+D268N, E41N+
A270D, E41N+N272M, E41N+N272T, E41N+N273E,
E41N+N273D, E41N+A276E, E41N+A276W, E41N+
A276D, E41N+N279D, E41N+N279E, E41N+T280L,
E41N+N283W, E41N+N283H, E41N+Y286W, E41N+
Y286F, E41N+L288I, E41N+E290A, E41N+L294P, E41N+
L294K, E41N+L294I, E41N+L294R, E41N+L294V,
E41N+L294H, E41N+S295K, E41N+S295V, E41N+S295P,
E41N+S295L, E41N+S295R, E41N+S295A, E41N+
S295N, E41N+S295M, E41N+S295I, E41N+T296S,
E41N+F298Y, N45G+G47S, N45G+G47A, N45G+D57N,
N45G+G59Q, N45G+Q60R, N45G+K63R, N45G+K63Q,
N45G+D65E, N45G+R70K, N45G+N71S, N45G+S74K,
N45G+E77T, N45G+E77N, N45G+D78G, N45G+H80K,
N45G+V82R, N45G+V82I, N45G+V82S, N45G+A83P,
N45G+A83S, N45G+Y93Q, N45G+Y93A, N45G+S95D,
N45G+A97R, N45G+S98P, N45G+S98D, N45G+N100Y,
N45G+D104A, N45G+D104G, N45G+E108S, N45G+
S111A, N45G+S111K, N45G+S111R, N45G+I114Q,
N45G+I114M, N45G+I114W, N45G+K116R, N45G+
D118K, N45G+T119R, N45G+S131T, N45G+E133R,
N45G+E133Q, N45G+D135P, N45G+A136P, N45G+
D139A, N45G+D139R, N45G+K142M, N45G+K142V,
N45G+K142S, N45G+K142R, N45G+Q143R, N45G+
N150T, N45G+N150R, N45G+N150S, N45G+Q169A,
N45G+Q169R, N45G+Q169K, N45G+H172R, N45G+
Y174R, N45G+Y174L, N45G+Y174W, N45G+Y174F,
N45G+R176Q, N45G+E177S, N45G+E177Y, N45G+
N180R, N45G+P183T, N45G+P183G, N45G+Q184E,
N45G+Q184K, N45G+R185G, N45G+Y196W, N45G+
Y196F, N45G+N200T, N45G+S202R, N45G+Q203T,
N45G+R205K, N45G+R210L, N45G+R210G, N45G+
R210M, N45G+N213V, N45G+N213D, N45G+T228S,
N45G+N229D, N45G+E234F, N45G+E234Y, N45G+
A235K, N45G+A235R, N45G+S241C, N45G+Q243K,
N45G+Q243E, N45G+R244K, N45G+R244V, N45G+
A250G, N45G+K254Y, N45G+G257W, N45G+G257E,
N45G+G257A, N45G+W260F, N45G+W260Y, N45G+
W260L, N45G+W260T, N45G+Y262F, N45G+S266A,
N45G+D268N, N45G+A270D, N45G+N272M, N45G+
N272T, N45G+N273E, N45G+N273D, N45G+A276E,
N45G+A276W, N45G+A276D, N45G+N279D, N45G+
N279E, N45G+T280L, N45G+N283W, N45G+N283H,
N45G+Y286W, N45G+Y286F, N45G+L288I, N45G+
E290A, N45G+L294P, N45G+L294K, N45G+L294I,
N45G+L294R, N45G+L294V, N45G+L294H, N45G+
S295K, N45G+S295V, N45G+S295P, N45G+S295L,
N45G+S295R, N45G+S295A, N45G+S295N, N45G+
S295M, N45G+S295I, N45G+T296S, N45G+F298Y,
G47S+D57N, G47S+G59Q, G47S+Q60R, G47S+K63R,
G47S+K63Q, G47S+D65E, G47S+R70K, G47S+N71S,
G47S+S74K, G47S+E77T, G47S+E77N, G47S+D78G,
G47S+H80K, G47S+V82R, G47S+V82I, G47S+V82S,
G47S+A83P, G47S+A83S, G47S+Y93Q, G47S+Y93A,
G47S+S95D, G47S+A97R, G47S+S98P, G47S+S98D,
G47S+N100Y, G47S+D104A, G47S+D104G, G47S+
E108S, G47S+S111A, G47S+S111K, G47S+S111R, G47S+
I114Q, G47S+I114M, G47S+I114W, G47S+K116R, G47S+
D118K, G47S+T119R, G47S+S131T, G47S+E133R,
G47S+E133Q, G47S+D135P, G47S+A136P, G47S+
D139A, G47S+D139R, G47S+K142M, G47S+K142V,
G47S+K142S, G47S+K142R, G47S+Q143R, G47S+
N150T, G47S+N150R, G47S+N150S, G47S+Q169A,
G47S+Q169R, G47S+Q169K, G47S+H172R, G47S+
Y174R, G47S+Y174L, G47S+Y174W, G47S+Y174F,
G47S+R176Q, G47S+E177S, G47S+E177Y, G47S+
N180R, G47S+P183T, G47S+P183G, G47S+Q184E,
G47S+Q184K, G47S+R185G, G47S+Y196W, G47S+
Y196F, G47S+N200T, G47S+S202R, G47S+Q203T,
G47S+R205K, G47S+R210L, G47S+R210G, G47S+
R210M, G47S+N213V, G47S+N213D, G47S+T228S,
G47S+N229D, G47S+E234F, G47S+E234Y, G47S+
A235K, G47S+A235R, G47S+S241C, G47S+Q243K,
G47S+Q243E, G47S+R244K, G47S+R244V, G47S+
A250G, G47S+K254Y, G47S+G257W, G47S+G257E,
G47S+G257A, G47S+W260F, G47S+W260Y, G47S+
W260L, G47S+W260T, G47S+Y262F, G47S+S266A,
G47S+D268N, G47S+A270D, G47S+N272M, G47S+
N272T, G47S+N273E, G47S+N273D, G47S+A276E,
G47S+A276W, G47S+A276D, G47S+N279D, G47S+
N279E, G47S+T280L, G47S+N283W, G47S+N283H,
G47S+Y286W, G47S+Y286F, G47S+L288I, G47S+E290A,
G47S+L294P, G47S+L294K, G47S+L294I, G47S+L294R,
G47S+L294V, G47S+L294H, G47S+S295K, G47S+S295V,
G47S+S295P, G47S+S295L, G47S+S295R, G47S+S295A,
G47S+S295N, G47S+S295M, G47S+S295I, G47S+T296S,
G47S+F298Y, G47A+D57N, G47A+G59Q, G47A+Q60R,
G47A+K63R, G47A+K63Q, G47A+D65E, G47A+R70K,
G47A+N71S, G47A+S74K, G47A+E77T, G47A+E77N,
G47A+D78G, G47A+H80K, G47A+V82R, G47A+V82I,
G47A+V82S, G47A+A83P, G47A+A83S, G47A+Y93Q,
G47A+Y93A, G47A+S95D, G47A+A97R, G47A+S98P,
G47A+S98D, G47A+N100Y, G47A+D104A, G47A+
D104G, G47A+E108S, G47A+S111A, G47A+S111K,
G47A+S111R, G47A+I114Q, G47A+I114M, G47A+
I114W, G47A+K116R, G47A+D118K, G47A+T119R,
G47A+S131T, G47A+E133R, G47A+E133Q, G47A+
D135P, G47A+A136P, G47A+D139A, G47A+D139R,
G47A+K142M, G47A+K142V, G47A+K142S, G47A+
K142R, G47A+Q143R, G47A+N150T, G47A+N150R,
G47A+N150S, G47A+Q169A, G47A+Q169R, G47A+
Q169K, G47A+H172R, G47A+Y174R, G47A+Y174L,
G47A+Y174W, G47A+Y174F, G47A+R176Q, G47A+
E177S, G47A+E177Y, G47A+N180R, G47A+P183T,
G47A+P183G, G47A+Q184E, G47A+Q184K, G47A+

R185G, G47A+Y196W, G47A+Y196F, G47A+N200T, G47A+S202R, G47A+Q203T, G47A+R205K, G47A+R210L, G47A+R210G, G47A+R210M, G47A+N213V, G47A+N213D, G47A+T228S, G47A+N229D, G47A+E234F, G47A+E234Y, G47A+A235K, G47A+A235R, G47A+S241C, G47A+Q243K, G47A+Q243E, G47A+R244K, G47A+R244V, G47A+A250G, G47A+K254Y, G47A+G257W, G47A+G257E, G47A+G257A, G47A+W260F, G47A+W260Y, G47A+W260L, G47A+W260T, G47A+Y262F, G47A+S266A, G47A+D268N, G47A+A270D, G47A+N272M, G47A+N272T, G47A+N273E, G47A+N273D, G47A+A276E, G47A+A276W, G47A+A276D, G47A+N279D, G47A+N279E, G47A+T280L, G47A+N283W, G47A+N283H, G47A+Y286W, G47A+Y286F, G47A+L288I, G47A+E290A, G47A+L294P, G47A+L294K, G47A+L294I, G47A+L294R, G47A+L294V, G47A+L294H, G47A+S295K, G47A+S295V, G47A+S295P, G47A+S295L, G47A+S295R, G47A+S295A, G47A+S295N, G47A+S295M, G47A+S295I, G47A+T296S, G47A+F298Y, D57N+G59Q, D57N+Q60R, D57N+K63R, D57N+K63Q, D57N+D65E, D57N+R70K, D57N+N71S, D57N+S74K, D57N+E77T, D57N+E77N, D57N+D78G, D57N+H80K, D57N+V82R, D57N+V82I, D57N+V82S, D57N+A83P, D57N+A83S, D57N+Y93Q, D57N+Y93A, D57N+S95D, D57N+A97R, D57N+S98P, D57N+S98D, D57N+N100Y, D57N+D104A, D57N+D104G, D57N+E108S, D57N+S111A, D57N+S111K, D57N+S111R, D57N+I114Q, D57N+I114M, D57N+I114W, D57N+K116R, D57N+D118K, D57N+T119R, D57N+S131T, D57N+E133R, D57N+E133Q, D57N+D135P, D57N+A136P, D57N+D139A, D57N+D139R, D57N+K142M, D57N+K142V, D57N+K142S, D57N+K142R, D57N+Q143R, D57N+N150T, D57N+N150R, D57N+N150S, D57N+Q169A, D57N+Q169R, D57N+Q169K, D57N+H172R, D57N+Y174R, D57N+Y174L, D57N+Y174W, D57N+Y174F, D57N+R176Q, D57N+E177S, D57N+E177Y, D57N+N180R, D57N+P183T, D57N+P183G, D57N+Q184E, D57N+Q184K, D57N+R185G, D57N+Y196W, D57N+Y196F, D57N+N200T, D57N+S202R, D57N+Q203T, D57N+R205K, D57N+R210L, D57N+R210G, D57N+R210M, D57N+N213V, D57N+N213D, D57N+T228S, D57N+N229D, D57N+E234F, D57N+E234Y, D57N+A235K, D57N+A235R, D57N+S241C, D57N+Q243K, D57N+Q243E, D57N+R244K, D57N+R244V, D57N+A250G, D57N+K254Y, D57N+G257W, D57N+G257E, D57N+G257A, D57N+W260F, D57E+W260Y, D57E+W260L, D57E+W260T, D57N+Y262F, D57N+S266A, D57N+D268N, D57N+A270D, D57N+N272M, D57N+N272T, D57N+N273E, D57N+N273D, D57N+A276E, D57N+A276W, D57N+A276D, D57N+N279D, D57N+N279E, D57N+T280L, D57N+N283W, D57N+N283H, D57N+Y286W, D57N+Y286F, D57N+L288I, D57N+E290A, D57N+L294P, D57N+L294K, D57N+L294I, D57N+L294R, D57N+L294V, D57N+L294H, D57N+S295K, D57N+S295V, D57N+S295P, D57N+S295L, D57N+S295R, D57N+S295A, D57N+S295N, D57N+S295M, D57N+S295I, D57N+T296S, D57N+F298Y, G59Q+Q60R, G59Q+K63R, G59Q+K63Q, G59Q+D65E, G59Q+R70K, G59Q+N71S, G59Q+S74K, G59Q+E77T, G59Q+E77N, G59Q+D78G, G59Q+H80K, G59Q+V82R, G59Q+V82I, G59Q+V82S, G59Q+A83P, G59Q+A83S, G59Q+Y93Q, G59Q+Y93A, G59Q+S95D, G59Q+A97R, G59Q+S98P, G59Q+S98D, G59Q+N100Y, G59Q+D104A, G59Q+D104G, G59Q+E108S, G59Q+S111A, G59Q+S111K, G59Q+S111R, G59Q+I114Q, G59Q+I114M, G59Q+I114W, G59Q+K116R, G59Q+D118K, G59Q+T119R, G59Q+S131T, G59Q+E133R, G59Q+E133Q, G59Q+D135P, G59Q+A136P, G59Q+D139A, G59Q+D139R, G59Q+K142M, G59Q+K142V, G59Q+K142S, G59Q+K142R, G59Q+Q143R, G59Q+N150T, G59Q+N150R, G59Q+N150S, G59Q+Q169A, G59Q+Q169R, G59Q+Q169K, G59Q+H172R, G59Q+Y174R, G59Q+Y174L, G59Q+Y174W, G59Q+Y174F, G59Q+R176Q, G59Q+E177S, G59Q+E177Y, G59Q+N180R, G59Q+P183T, G59Q+P183G, G59Q+Q184E, G59Q+Q184K, G59Q+R185G, G59Q+Y196W, G59Q+Y196F, G59Q+N200T, G59Q+S202R, G59Q+Q203T, G59Q+R205K, G59Q+R210L, G59Q+R210G, G59Q+R210M, G59Q+N213V, G59Q+N213D, G59Q+T228S, G59Q+N229D, G59Q+E234F, G59Q+E234Y, G59Q+A235K, G59Q+A235R, G59Q+S241C, G59Q+Q243K, G59Q+Q243E, G59Q+R244K, G59Q+R244V, G59Q+A250G, G59Q+K254Y, G59Q+G257W, G59Q+G257E, G59Q+G257A, G59Q+W260F, G59Q+W260Y, G59Q+W260L, G59Q+W260T, G59Q+Y262F, G59Q+S266A, G59Q+D268N, G59Q+A270D, G59Q+N272M, G59Q+N272T, G59Q+N273E, G59Q+N273D, G59Q+A276E, G59Q+A276W, G59Q+A276D, G59Q+N279D, G59Q+N279E, G59Q+T280L, G59Q+N283W, G59Q+N283H, G59Q+Y286W, G59Q+Y286F, G59Q+L288I, G59Q+E290A, G59Q+L294P, G59Q+L294K, G59Q+L294I, G59Q+L294R, G59Q+L294V, G59Q+L294H, G59Q+S295K, G59Q+S295V, G59Q+S295P, G59Q+S295L, G59Q+S295R, G59Q+S295A, G59Q+S295N, G59Q+S295M, G59Q+S295I, G59Q+T296S, G59Q+F298Y, Q60R+K63R, Q60R+K63Q, Q60R+D65E, Q60R+R70K, Q60R+N71S, Q60R+S74K, Q60R+E77T, Q60R+E77N, Q60R+D78G, Q60R+H80K, Q60R+V82R, Q60R+V82I, Q60R+V82S, Q60R+A83P, Q60R+A83S, Q60R+Y93Q, Q60R+Y93A, Q60R+S95D, Q60R+A97R, Q60R+S98P, Q60R+S98D, Q60R+N100Y, Q60R+D104A, Q60R+D104G, Q60R+E108S, Q60R+S111A, Q60R+S111K, Q60R+S111R, Q60R+I114Q, Q60R+I114M, Q60R+I114W, Q60R+K116R, Q60R+D118K, Q60R+T119R, Q60R+S131T, Q60R+E133R, Q60R+E133Q, Q60R+D135P, Q60R+A136P, Q60R+D139A, Q60R+D139R, Q60R+K142M, Q60R+K142V, Q60R+K142S, Q60R+K142R, Q60R+Q143R, Q60R+N150T, Q60R+N150R, Q60R+N150S, Q60R+Q169A, Q60R+Q169R, Q60R+Q169K, Q60R+H172R, Q60R+Y174R, Q60R+Y174L, Q60R+Y174F, Q60R+Y174W, Q60R+R176Q, Q60R+E177S, Q60R+E177Y, Q60R+N180R, Q60R+P183T, Q60R+P183G, Q60R+Q184E, Q60R+Q184K, Q60R+R185G, Q60R+Y196W, Q60R+Y196F, Q60R+N200T, Q60R+S202R, Q60R+Q203T, Q60R+R205K, Q60R+R210L, Q60R+R210G, Q60R+R210M, Q60R+N213V, Q60R+N213D, Q60R+T228S, Q60R+N229D, Q60R+E234F, Q60R+E234Y, Q60R+A235K, Q60R+A235R, Q60R+S241C, Q60R+Q243K, Q60R+Q243E, Q60R+R244K, Q60R+R244V, Q60R+A250G, Q60R+K254Y, Q60R+G257W, Q60R+G257E, Q60R+G257A, Q60R+W260F, Q60R+W260Y, Q60R+W260L, Q60R+W260T, Q60R+Y262F, Q60R+S266A, Q60R+D268N, Q60R+A270D, Q60R+N272M, Q60R+N272T, Q60R+N273E, Q60R+N273D, Q60R+A276E, Q60R+A276W, Q60R+A276D, Q60R+N279D, Q60R+N279E, Q60R+T280L, Q60R+N283W, Q60R+N283H, Q60R+Y286W, Q60R+Y286F, Q60R+L288I, Q60R+E290A, Q60R+L294P, Q60R+L294K, Q60R+L294I, Q60R+L294R, Q60R+L294V, Q60R+L294H, Q60R+S295K, Q60R+S295V, Q60R+S295A, Q60R+S295P, Q60R+S295L, Q60R+S295R, Q60R+S295N, Q60R+S295M, Q60R+S295I, Q60R+T296S, Q60R+F298Y, K63R+D65E, K63R+R70K, K63R+N71S, K63R+S74K, K63R+E77T, K63R+E77N,

K63R+D78G, K63R+H80K, K63R+V82R, K63R+V82I, K63R+V82S, K63R+A83P, K63R+A83S, K63R+Y93Q, K63R+Y93A, K63R+S95D, K63R+A97R, K63R+S98P, K63R+S98D, K63R+N100Y, K63R+D104A, K63R+D104G, K63R+E108S, K63R+S111A, K63R+S111K, K63R+S111R, K63R+I114Q, K63R+I114M, K63R+I114W, K63R+K116R, K63R+D118K, K63R+T119R, K63R+S131T, K63R+E133R, K63R+E133Q, K63R+D135P, K63R+A136P, K63R+D139A, K63R+D139R, K63R+K142M, K63R+K142V, K63R+K142S, K63R+K142R, K63R+Q143R, K63R+N150T, K63R+N150R, K63R+N150S, K63R+Q169A, K63R+Q169R, K63R+Q169K, K63R+H172R, K63R+Y174R, K63R+Y174L, K63R+Y174W, K63R+Y174F, K63R+R176Q, K63R+E177S, K63R+E177Y, K63R+N180R, K63R+P183T, K63R+P183G, K63R+Q184E, K63R+Q184K, K63R+R185G, K63R+Y196W, K63R+Y196F, K63R+N200T, K63R+S202R, K63R+Q203T, K63R+R205K, K63R+R210L, K63R+R210G, K63R+R210M, K63R+N213V, K63R+N213D, K63R+T228S, K63R+N229D, K63R+E234F, K63R+E234Y, K63R+A235K, K63R+A235R, K63R+S241C, K63R+Q243K, K63R+Q243E, K63R+R244K, K63R+R244V, K63R+A250G, K63R+K254Y, K63R+G257W, K63R+G257E, K63R+G257A, K63R+W260F, K63R+W260Y, K63R+W260L, K63R+W260T, K63R+Y262F, K63R+S266A, K63R+D268N, K63R+A270D, K63R+N272M, K63R+N272T, K63R+N273E, K63R+N273D, K63R+A276E, K63R+A276W, K63R+A276D, K63R+N279D, K63R+N279E, K63R+T280L, K63R+N283W, K63R+N283H, K63R+Y286W, K63R+Y286F, K63R+L288I, K63R+E290A, K63R+L294P, K63R+L294K, K63R+L294I, K63R+L294R, K63R+L294V, K63R+L294H, K63R+S295K, K63R+S295V, K63R+S295P, K63R+S295L, K63R+S295R, K63R+S295A, K63R+S295N, K63R+S295M, K63R+S295I, K63R+T296S, K63R+F298Y, K63Q+D65E, K63Q+R70K, K63Q+N71S, K63Q+S74K, K63Q+E77T, K63Q+E77N, K63Q+D78G, K63Q+H80K, K63Q+V82R, K63Q+V82 I, K63Q+V82S, K63Q+A83P, K63Q+A83S, K63Q+Y93Q, K63Q+Y93A, K63Q+S95D, K63Q+A97R, K63Q+S98P, K63Q+S98D, K63Q+N100Y, K63Q+D104A, K63Q+D104G, K63Q+E108S, K63Q+S111A, K63Q+S111K, K63Q+S111R, K63Q+I114Q, K63Q+I114M, K63Q+I114W, K63Q+K116R, K63Q+D118K, K63Q+T119R, K63Q+S131T, K63Q+E133R, K63Q+E133Q, K63Q+D135P, K63Q+A136P, K63Q+D139A, K63Q+D139R, K63Q+K142M, K63Q+K142V, K63Q+K142S, K63Q+K142R, K63Q+Q143R, K63Q+N150T, K63Q+N150R, K63Q+N150S, K63Q+Q169A, K63Q+Q169R, K63Q+Q169K, K63Q+H172R, K63Q+Y174R, K63Q+Y174L, K63Q+Y174W, K63Q+Y174F, K63Q+R176Q, K63Q+E177S, K63Q+E177Y, K63Q+N180R, K63Q+P183T, K63Q+P183G, K63Q+Q184E, K63Q+Q184K, K63Q+R185G, K63Q+Y196W, K63Q+Y196F, K63Q+N200T, K63Q+S202R, K63Q+Q203T, K63Q+R205K, K63Q+R210L, K63Q+R210G, K63Q+R210M, K63Q+N213V, K63Q+N213D, K63Q+T228S, K63Q+N229D, K63Q+E234F, K63Q+E234Y, K63Q+A235K, K63Q+A235R, K63Q+S241C, K63Q+Q243K, K63Q+Q243E, K63Q+R244K, K63Q+R244V, K63Q+A250G, K63Q+K254Y, K63Q+G257W, K63Q+G257E, K63Q+G257A, K63Q+W260F, K63Q+W260Y, K63Q+W260L, K63Q+W260T, K63Q+Y262F, K63Q+S266A, K63Q+D268N, K63Q+A270D, K63Q+N272M, K63Q+N272T, K63Q+N273E, K63Q+N273D, K63Q+A276E, K63Q+A276W, K63Q+A276D, K63Q+N279D, K63Q+N279E, K63Q+T280L, K63Q+N283W, K63Q+N283H, K63Q+Y286W, K63Q+Y286F, K63Q+L288I, K63Q+E290A, K63Q+L294P, K63Q+L294K, K63Q+L294I, K63Q+L294R, K63Q+L294V, K63Q+L294H, K63Q+S295K, K63Q+S295V, K63Q+S295P, K63Q+S295L, K63Q+S295R, K63Q+S295A, K63Q+S295N, K63Q+S295M, K63Q+S295I, K63Q+T296S, K63Q+F298Y, D65E+R70K, D65E+N71S, D65E+S74K, D65E+E77T, D65E+E77N, D65E+D78G, D65E+H80K, D65E+V82R, D65E+V82I, D65E+V82S, D65E+A83P, D65E+A83S, D65E+Y93Q, D65E+Y93A, D65E+S95D, D65E+A97R, D65E+S98P, D65E+S98D, D65E+N100Y, D65E+D104A, D65E+D104G, D65E+E108S, D65E+S111A, D65E+S111K, D65E+S111R, D65E+I114Q, D65E+I114M, D65E+I114W, D65E+K116R, D65E+D118K, D65E+T119R, D65E+S131T, D65E+E133R, D65E+E133Q, D65E+D135P, D65E+A136P, D65E+D139A, D65E+D139R, D65E+K142M, D65E+K142V, D65E+K142S, D65E+K142R, D65E+Q143R, D65E+N150T, D65E+N150R, D65E+N150S, D65E+Q169A, D65E+Q169R, D65E+Q169K, D65E+H172R, D65E+Y174R, D65E+Y174L, D65E+Y174W, D65E+Y174F, D65E+R176Q, D65E+E177S, D65E+E177Y, D65E+N180R, D65E+P183T, D65E+P183G, D65E+Q184E, D65E+Q184K, D65E+R185G, D65E+Y196W, D65E+Y196F, D65E+N200T, D65E+S202R, D65E+Q203T, D65E+R205K, D65E+R210L, D65E+R210G, D65E+R210M, D65E+N213V, D65E+N213D, D65E+T228S, D65E+N229D, D65E+E234F, D65E+E234Y, D65E+A235K, D65E+A235R, D65E+S241C, D65E+Q243K, D65E+Q243E, D65E+R244K, D65E+R244V, D65E+A250G, D65E+K254Y, D65E+G257W, D65E+G257E, D65E+G257A, D65E+W260F, D65E+W260Y, D65E+W260L, D65E+W260T, D65E+Y262F, D65E+S266A, D65E+D268N, D65E+A270D, D65E+N272M, D65E+N272T, D65E+N273E, D65E+N273D, D65E+A276E, D65E+A276W, D65E+A276D, D65E+N279D, D65E+N279E, D65E+T280L, D65E+N283W, D65E+N283H, D65E+Y286W, D65E+Y286F, D65E+L288I, D65E+E290A, D65E+L294P, D65E+L294K, D65E+L294I, D65E+L294R, D65E+L294V, D65E+L294H, D65E+S295K, D65E+S295V, D65E+S295P, D65E+S295L, D65E+S295R, D65E+S295A, D65E+S295N, D65E+S295M, D65E+S295I, D65E+T296S, D65E+F298Y, R70K+N71S, R70K+S74K, R70K+E77T, R70K+E77N, R70K+D78G, R70K+H80K, R70K+V82R, R70K+V82I, R70K+V82S, R70K+A83P, R70K+A83S, R70K+Y93Q, R70K+Y93A, R70K+S95D, R70K+A97R, R70K+S98P, R70K+S98D, R70K+N100Y, R70K+D104A, R70K+D104G, R70K+E108S, R70K+S111A, R70K+S111K, R70K+S111R, R70K+I114Q, R70K+I114M, R70K+I114W, R70K+K116R, R70K+D118K, R70K+T119R, R70K+S131T, R70K+E133R, R70K+E133Q, R70K+D135P, R70K+A136P, R70K+D139A, R70K+D139R, R70K+K142M, R70K+K142V, R70K+K142S, R70K+K142R, R70K+Q143R, R70K+N150T, R70K+N150R, R70K+N150S, R70K+Q169A, R70K+Q169R, R70K+Q169K, R70K+H172R, R70K+Y174R, R70K+Y174L, R70K+Y174W, R70K+Y174F, R70K+R176Q, R70K+E177S, R70K+E177Y, R70K+N180R, R70K+P183T, R70K+P183G, R70K+Q184E, R70K+Q184K, R70K+R185G, R70K+Y196W, R70K+Y196F, R70K+N200T, R70K+S202R, R70K+Q203T, R70K+R205K, R70K+R210L, R70K+R210G, R70K+R210M, R70K+N213V, R70K+N213D, R70K+T228S, R70K+N229D, R70K+E234F, R70K+E234Y, R70K+A235K, R70K+A235R, R70K+S241C, R70K+Q243K, R70K+Q243E, R70K+R244K, R70K+R244V, R70K+A250G, R70K+K254Y, R70K+G257W, R70K+G257E, R70K+G257A, R70K+W260F, R70K+W260Y, R70K+

W260L, R70K+W260T, R70K+Y262F, R70K+S266A, R70K+D268N, R70K+A270D, R70K+N272M, R70K+N272T, R70K+N273E, R70K+N273D, R70K+A276E, R70K+A276W, R70K+A276D, R70K+N279D, R70K+N279E, R70K+T280L, R70K+N283W, R70K+N283H, R70K+Y286W, R70K+Y286F, R70K+L288I, R70K+E290A, R70K+L294P, R70K+L294K, R70K+L294I, R70K+L294R, R70K+L294V, R70K+L294H, R70K+S295K, R70K+S295V, R70K+S295P, R70K+S295L, R70K+S295R, R70K+S295A, R70K+S295N, R70K+S295M, R70K+S295I, R70K+T296S, R70K+F298Y, N71S+S74K, N71S+E77T, N71S+E77N, N71S+D78G, N71S+H80K, N71S+V82R, N71S+V82I, N71S+V82S, N71S+A83P, N71S+A83S, N71S+Y93Q, N71S+Y93A, N71S+S95D, N71S+A97R, N71S+S98P, N71S+S98D, N71S+N100Y, N71S+D104A, N71S+D104G, N71S+E108S, N71S+S111A, N71S+S111K, N71S+S111R, N71S+I114Q, N71S+I114M, N71S+I114W, N71S+K116R, N71S+D118K, N71S+T119R, N71S+S131T, N71S+E133R, N71S+E133Q, N71S+D135P, N71S+A136P, N71S+D139A, N71S+D139R, N71S+K142M, N71S+K142V, N71S+K142S, N71S+K142R, N71S+Q143R, N71S+N150T, N71S+N150R, N71S+N150S, N71S+Q169A, N71S+Q169R, N71S+Q169K, N71S+H172R, N71S+Y174R, N71S+Y174L, N71S+Y174W, N71S+Y174F, N71S+R176Q, N71S+E177S, N71S+E177Y, N71S+N180R, N71S+P183T, N71S+P183G, N71S+Q184E, N71S+Q184K, N71S+R185G, N71S+Y196W, N71S+Y196F, N71S+N200T, N71S+S202R, N71S+Q203T, N71S+R205K, N71S+R210L, N71S+R210G, N71S+R210M, N71S+N213V, N71S+N213D, N71S+T228S, N71S+N229D, N71S+E234F, N71S+E234Y, N71S+A235K, N71S+A235R, N71S+S241C, N71S+Q243K, N71S+Q243E, N71S+R244K, N71S+R244V, N71S+A250G, N71S+K254Y, N71S+G257W, N71S+G257E, N71S+G257A, N71S+W260F, N71S+W260Y, N71S+W260L, N71S+W260T, N71S+Y262F, N71S+S266A, N71S+D268N, N71S+A270D, N71S+N272M, N71S+N272T, N71S+N273E, N71S+N273D, N71S+A276E, N71S+A276W, N71S+A276D, N71S+N279D, N71S+N279E, N71S+T280L, N71S+N283W, N71S+N283H, N71S+Y286W, N71S+Y286F, N71S+L288I, N71S+E290A, N71S+L294P, N71S+L294K, N71S+L294I, N71S+L294R, N71S+L294V, N71S+L294H, N71S+S295K, N71S+S295V, N71S+S295P, N71S+S295L, N71S+S295R, N71S+S295A, N71S+S295N, N71S+S295M, N71S+S295I, N71S+T296S, N71S+F298Y, S74K+E77T, S74K+E77N, S74K+D78G, S74K+H80K, S74K+V82R, S74K+V82I, S74K+V82S, S74K+A83P, S74K+A83S, S74K+Y93Q, S74K+Y93A, S74K+S95D, S74K+A97R, S74K+S98P, S74K+S98D, S74K+N100Y, S74K+D104A, S74K+D104G, S74K+E108S, S74K+S111A, S74K+S111K, S74K+S111R, S74K+I114Q, S74K+I114M, S74K+I114W, S74K+K116R, S74K+D118K, S74K+T119R, S74K+S131T, S74K+E133R, S74K+E133Q, S74K+D135P, S74K+A136P, S74K+D139A, S74K+D139R, S74K+K142M, S74K+K142V, S74K+K142S, S74K+K142R, S74K+Q143R, S74K+N150T, S74K+N150R, S74K+N150S, S74K+Q169A, S74K+Q169R, S74K+Q169K, S74K+H172R, S74K+Y174R, S74K+Y174L, S74K+Y174W, S74K+Y174F, S74K+R176Q, S74K+E177S, S74K+E177Y, S74K+N180R, S74K+P183T, S74K+P183G, S74K+Q184E, S74K+Q184K, S74K+R185G, S74K+Y196W, S74K+Y196F, S74K+N200T, S74K+S202R, S74K+Q203T, S74K+R205K, S74K+R210L, S74K+R210G, S74K+R210M, S74K+N213V, S74K+N213D, S74K+T228S, S74K+N229D, S74K+E234F, S74K+E234Y, S74K+A235K, S74K+A235R, S74K+S241C, S74K+Q243K, S74K+Q243E, S74K+R244K, S74K+R244V, S74K+A250G, S74K+K254Y, S74K+G257W, S74K+G257E, S74K+G257A, S74K+W260F, S74K+W260Y, S74K+W260L, S74K+W260T, S74K+Y262F, S74K+S266A, S74K+D268N, S74K+A270D, S74K+N272M, S74K+N272T, S74K+N273E, S74K+N273D, S74K+A276E, S74K+A276W, S74K+A276D, S74K+N279D, S74K+N279E, S74K+T280L, S74K+N283W, S74K+N283H, S74K+Y286W, S74K+Y286F, S74K+L288I, S74K+E290A, S74K+L294P, S74K+L294K, S74K+L294I, S74K+L294R, S74K+L294V, S74K+L294H, S74K+S295K, S74K+S295V, S74K+S295P, S74K+S295L, S74K+S295R, S74K+S295A, S74K+S295N, S74K+S295M, S74K+S295I, S74K+T296S, S74K+F298Y, E77T+D78G, E77T+H80K, E77T+V82R, E77T+V82I, E77T+V82S, E77T+A83P, E77T+A83S, E77T+Y93Q, E77T+Y93A, E77T+S95D, E77T+A97R, E77T+S98P, E77T+S98D, E77T+N100Y, E77T+D104A, E77T+D104G, E77T+E108S, E77T+S111A, E77T+S111K, E77T+S111R, E77T+I114Q, E77T+I114M, E77T+I114W, E77T+K116R, E77T+D118K, E77T+T119R, E77T+S131T, E77T+E133R, E77T+E133Q, E77T+D135P, E77T+A136P, E77T+D139A, E77T+D139R, E77T+K142M, E77T+K142V, E77T+K142S, E77T+K142R, E77T+Q143R, E77T+N150T, E77T+N150R, E77T+N150S, E77T+Q169A, E77T+Q169R, E77T+Q169K, E77T+H172R, E77T+Y174R, E77T+Y174L, E77T+Y174W, E77T+Y174F, E77T+R176Q, E77T+E177S, E77T+E177Y, E77T+N180R, E77T+P183T, E77T+P183G, E77T+Q184E, E77T+Q184K, E77T+R185G, E77T+Y196W, E77T+Y196F, E77T+N200T, E77T+S202R, E77T+Q203T, E77T+R205K, E77T+R210L, E77T+R210G, E77T+R210M, E77T+N213V, E77T+N213D, E77T+T228S, E77T+N229D, E77T+E234F, E77T+E234Y, E77T+A235K, E77T+A235R, E77T+S241C, E77T+Q243K, E77T+Q243E, E77T+R244K, E77T+R244V, E77T+A250G, E77T+K254Y, E77T+G257W, E77T+G257E, E77T+G257A, E77T+W260F, E77T+W260Y, E77T+W260L, E77T+W260T, E77T+Y262F, E77T+S266A, E77T+D268N, E77T+A270D, E77T+N272M, E77T+N272T, E77T+N273E, E77T+N273D, E77T+A276E, E77T+A276W, E77T+A276D, E77T+N279D, E77T+N279E, E77T+T280L, E77T+N283W, E77T+N283H, E77T+Y286W, E77T+Y286F, E77T+L288I, E77T+E290A, E77T+L294P, E77T+L294K, E77T+L294I, E77T+L294R, E77T+L294V, E77T+L294H, E77T+S295K, E77T+S295V, E77T+S295P, E77T+S295L, E77T+S295R, E77T+S295A, E77T+S295N, E77T+S295M, E77T+S295I, E77T+T296S, E77T+F298Y, E77N+D78G, E77N+H80K, E77N+V82R, E77N+V82I, E77N+V82S, E77N+A83P, E77N+A83S, E77N+Y93Q, E77N+Y93A, E77N+S95D, E77N+A97R, E77N+S98P, E77N+S98D, E77N+N100Y, E77N+D104A, E77N+D104G, E77N+E108S, E77N+S111A, E77N+S111K, E77N+S111R, E77N+I114Q, E77N+I114M, E77N+I114W, E77N+K116R, E77N+D118K, E77N+T119R, E77N+S131T, E77N+E133R, E77N+E133Q, E77N+D135P, E77N+A136P, E77N+D139A, E77N+D139R, E77N+K142M, E77N+K142V, E77N+K142S, E77N+K142R, E77N+Q143R, E77N+N150T, E77N+N150R, E77N+N150S, E77N+Q169A, E77N+Q169R, E77N+Q169K, E77N+H172R, E77N+Y174R, E77N+Y174L, E77N+Y174W, E77N+Y174F, E77N+R176Q, E77N+E177S, E77N+E177Y, E77N+N180R, E77N+P183T, E77N+P183G, E77N+Q184E, E77N+Q184K, E77N+R185G, E77N+Y196W, E77N+Y196F, E77N+N200T, E77N+S202R, E77N+Q203T, E77N+R205K, E77N+R210L, E77N+R210G, E77N+R210M, E77N+N213V, E77N+N213D, E77N+

T228S, E77N+N229D, E77N+E234F, E77N+E234Y, E77N+A235K, E77N+A235R, E77N+S241C, E77N+Q243K, E77N+Q243E, E77N+R244K, E77N+R244V, E77N+A250G, E77N+K254Y, E77N+G257W, E77N+G257E, E77N+G257A, E77N+W260F, E77N+W260Y, E77N+W260L, E77N+W260T, E77N+Y262F, E77N+S266A, E77N+D268N, E77N+A270D, E77N+N272M, E77N+N272T, E77N+N273E, E77N+N273D, E77N+A276E, E77N+A276W, E77N+A276D, E77N+N279D, E77N+N279E, E77N+T280L, E77N+N283W, E77N+N283H, E77N+Y286W, E77N+Y286F, E77N+L288I, E77N+E290A, E77N+L294P, E77N+L294K, E77N+L294I, E77N+L294R, E77N+L294V, E77N+L294H, E77N+S295K, E77N+S295V, E77N+S295P, E77N+S295L, E77N+S295R, E77N+S295A, E77N+S295N, E77N+S295M, E77N+S295I, E77N+T296S, E77N+F298Y, D78G+H80K, D78G+V82R, D78G+V82I, D78G+V82S, D78G+A83P, D78G+A83S, D78G+Y93Q, D78G+Y93A, D78G+S95D, D78G+A97R, D78G+S98P, D78G+S98D, D78G+N100Y, D78G+D104A, D78G+D104G, D78G+E108S, D78G+S111A, D78G+S111K, D78G+S111R, D78G+I114Q, D78G+I114M, D78G+I114W, D78G+K116R, D78G+D118K, D78G+T119R, D78G+S131T, D78G+E133R, D78G+E133Q, D78G+D135P, D78G+A136P, D78G+D139A, D78G+D139R, D78G+K142M, D78G+K142V, D78G+K142S, D78G+K142R, D78G+Q143R, D78G+N150T, D78G+N150R, D78G+N150S, D78G+Q169A, D78G+Q169R, D78G+Q169K, D78G+H172R, D78G+Y174R, D78G+Y174L, D78G+Y174W, D78G+Y174F, D78G+R176Q, D78G+E177S, D78G+E177Y, D78G+N180R, D78G+P183T, D78G+P183G, D78G+Q184E, D78G+Q184K, D78G+R185G, D78G+Y196W, D78G+Y196F, D78G+N200T, D78G+S202R, D78G+Q203T, D78G+R205K, D78G+R210L, D78G+R210G, D78G+R210M, D78G+N213V, D78G+N213D, D78G+T228S, D78G+N229D, D78G+E234F, D78G+E234Y, D78G+A235K, D78G+A235R, D78G+S241C, D78G+Q243K, D78G+Q243E, D78G+R244K, D78G+R244V, D78G+A250G, D78G+K254Y, D78G+G257W, D78G+G257E, D78G+G257A, D78G+W260F, D78G+W260Y, D78G+W260L, D78G+W260T, D78G+Y262F, D78G+S266A, D78G+D268N, D78G+A270D, D78G+N272M, D78G+N272T, D78G+N273E, D78G+N273D, D78G+A276E, D78G+A276W, D78G+A276D, D78G+N279D, D78G+N279E, D78G+T280L, D78G+N283W, D78G+N283H, D78G+Y286W, D78G+Y286F, D78G+L288I, D78G+E290A, D78G+L294P, D78G+L294K, D78G+L294I, D78G+L294R, D78G+L294V, D78G+L294H, D78G+S295K, D78G+S295V, D78G+S295P, D78G+S295L, D78G+S295R, D78G+S295A, D78G+S295N, D78G+S295M, D78G+S295I, D78G+T296S, D78G+F298Y, H80K+V82R, H80K+V82I, H80K+V82S, H80K+A83P, H80K+A83S, H80K+Y93Q, H80K+Y93A, H80K+S95D, H80K+A97R, H80K+S98P, H80K+S98D, H80K+N100Y, H80K+D104A, H80K+D104G, H80K+E108S, H80K+S111A, H80K+S111K, H80K+S111R, H80K+I114Q, H80K+I114M, H80K+I114W, H80K+K116R, H80K+D118K, H80K+T119R, H80K+S131T, H80K+E133R, H80K+E133Q, H80K+D135P, H80K+A136P, H80K+D139A, H80K+D139R, H80K+K142M, H80K+K142V, H80K+K142S, H80K+K142R, H80K+Q143R, H80K+N150T, H80K+N150R, H80K+N150S, H80K+Q169A, H80K+Q169R, H80K+Q169K, H80K+H172R, H80K+Y174R, H80K+Y174L, H80K+Y174W, H80K+Y174F, H80K+R176Q, H80K+E177S, H80K+E177Y, H80K+N180R, H80K+P183T, H80K+P183G, H80K+Q184E, H80K+Q184K, H80K+R185G, H80K+Y196W, H80K+Y196F, H80K+N200T, H80K+S202R, H80K+Q203T, H80K+R205K, H80K+R210L, H80K+R210G, H80K+R210M, H80K+N213V, H80K+N213D, H80K+T228S, H80K+N229D, H80K+E234F, H80K+E234Y, H80K+A235K, H80K+A235R, H80K+S241C, H80K+Q243K, H80K+Q243E, H80K+R244K, H80K+R244V, H80K+A250G, H80K+K254Y, H80K+G257W, H80K+G257E, H80K+G257A, H80K+W260F, H80K+W260Y, H80K+W260L, H80K+W260T, H80K+Y262F, H80K+S266A, H80K+D268N, H80K+A270D, H80K+N272M, H80K+N272T, H80K+N273E, H80K+N273D, H80K+A276E, H80K+A276W, H80K+A276D, H80K+N279D, H80K+N279E, H80K+T280L, H80K+N283W, H80K+N283H, H80K+Y286W, H80K+Y286F, H80K+L288I, H80K+E290A, H80K+L294P, H80K+L294K, H80K+L294I, H80K+L294R, H80K+L294V, H80K+L294H, H80K+S295K, H80K+S295V, H80K+S295P, H80K+S295L, H80K+S295R, H80K+S295A, H80K+S295N, H80K+S295M, H80K+S295I, H80K+T296S, H80K+F298Y, V82R+A83P, V82R+A83S, V82R+Y93Q, V82R+Y93A, V82R+S95D, V82R+A97R, V82R+S98P, V82R+S98D, V82R+N100Y, V82R+D104A, V82R+D104G, V82R+E108S, V82R+S111A, V82R+S111K, V82R+S111R, V82R+I114Q, V82R+I114M, V82R+I114W, V82R+K116R, V82R+D118K, V82R+T119R, V82R+S131T, V82R+E133R, V82R+E133Q, V82R+D135P, V82R+A136P, V82R+D139A, V82R+D139R, V82R+K142M, V82R+K142V, V82R+K142S, V82R+K142R, V82R+Q143R, V82R+N150T, V82R+N150R, V82R+N150S, V82R+Q169A, V82R+Q169R, V82R+Q169K, V82R+H172R, V82R+Y174R, V82R+Y174L, V82R+Y174W, V82R+Y174F, V82R+R176Q, V82R+E177S, V82R+E177Y, V82R+N180R, V82R+P183T, V82R+P183G, V82R+Q184E, V82R+Q184K, V82R+R185G, V82R+Y196W, V82R+Y196F, V82R+N200T, V82R+S202R, V82R+Q203T, V82R+R205K, V82R+R210L, V82R+R210G, V82R+R210M, V82R+N213V, V82R+N213D, V82R+T228S, V82R+N229D, V82R+E234F, V82R+E234Y, V82R+A235K, V82R+A235R, V82R+S241C, V82R+Q243K, V82R+Q243E, V82R+R244K, V82R+R244V, V82R+A250G, V82R+K254Y, V82R+G257W, V82R+G257E, V82R+G257A, V82R+W260F, V82R+W260Y, V82R+W260L, V82R+W260T, V82R+Y262F, V82R+S266A, V82R+D268N, V82R+A270D, V82R+N272M, V82R+N272T, V82R+N273E, V82R+N273D, V82R+A276E, V82R+A276W, V82R+A276D, V82R+N279D, V82R+N279E, V82R+T280L, V82R+N283W, V82R+N283H, V82R+Y286W, V82R+Y286F, V82R+L288I, V82R+E290A, V82R+L294P, V82R+L294K, V82R+L294I, V82R+L294R, V82R+L294V, V82R+L294H, V82R+S295K, V82R+S295V, V82R+S295P, V82R+S295L, V82R+S295R, V82R+S295A, V82R+S295N, V82R+S295M, V82R+S295I, V82R+T296S, V82R+F298Y, V82I+A83P, V82I+A83S, V82I+Y93Q, V82+Y93A, V82I+S95D, V82I+A97R, V82I+S98P, V82I+S98D, V82I+N100Y, V82I+D104A, V82I+D104G, V82I+E108S, V82I+S111A, V82I+S111K, V82I+S111R, V82I+I114Q, V82I+I114M, V82I+I114W, V82I+K116R, V82I+D118K, V82I+T119R, V82I+S131T, V82I+E133R, V82I+E133Q, V82I+D135P, V82I+A136P, V82I+D139A, V82I+D139R, V82I+K142M, V82I+K142V, V82I+K142S, V82I+K142R, V82I+Q143R, V82I+N150T, V82I+N150R, V82I+N150S, V82I+Q169A, V82I+Q169R, V82I+Q169K, V82I+H172R, V82+Y174Q, V82+Y174L, V82+Y174W, V82+Y174F, V82I+R176Q, V82I+E177S, V82I+E177Y, V82I+N180R, V82I+P183T, V82I+P183G, V82I+Q184E, V82I+Q184K, V82I+R185G, V82+Y196W, V82+Y196F, V82I+N200T, V82I+S202R,

V82I+Q203T, V82I+R205K, V82I+R210L, V82I+R210G, V82I+R210M, V82I+N213V, V82I+N213D, V82I+T228S, V82I+N229D, V82I+E234F, V82I+E234Y, V82I+A235K, V82I+A235R, V82I+S241C, V82I+Q243K, V82I+Q243E, V82I+R244K, V82I+R244V, V82I+A250G, V82I+K254Y, V82I+G257W, V82I+G257E, V82I+G257A, V82I+W260F, V82I+W260Y, V82I+W260L, V82I+W260T, V82+Y262F, V82I+S266A, V82I+D268N, V82I+A270D, V82I+N272M, V82I+N272T, V82I+N273E, V82I+N273D, V82I+A276E, V82I+A276W, V82I+A276D, V82I+N279D, V82I+N279E, V82I+T280L, V82I+N283W, V82I+N283H, V82+Y286W, V82+Y286F, V82I+L288I, V82I+E290A, V82I+L294P, V82I+L294K, V82I+L294I, V82I+L294R, V82I+L294V, V82I+L294H, V82I+S295K, V82I+S295V, V82I+S295P, V82I+S295L, V82I+S295R, V82I+S295A, V82I+S295N, V82I+S295M, V82I+S295I, V82I+T296S, V82I+F298Y, V82S+A83P, V82S+A83S, V82S+Y93Q, V82S+Y93A, V82S+S95D, V82S+A97R, V82S+S98P, V82S+S98D, V82S+N100Y, V82S+D104A, V82S+D104G, V82S+E108S, V82S+S111A, V82S+S111K, V82S+S111R, V82S+I114Q, V82S+I114M, V82S+I114W, V82S+K116R, V82S+D118K, V82S+T119R, V82S+S131T, V82S+E133R, V82S+E133Q, V82S+D135P, V82S+A136P, V82S+D139A, V82S+D139R, V82S+K142M, V82S+K142V, V82S+K142S, V82S+K142R, V82S+Q143R, V82S+N150T, V82S+N150R, V82S+N150S, V82S+Q169A, V82S+Q169R, V82S+Q169K, V82S+H172R, V82S+Y174R, V82S+Y174L, V82S+Y174W, V82S+Y174F, V82S+R176Q, V82S+E177S, V82S+E177Y, V82S+N180R, V82S+P183T, V82S+P183G, V82S+Q184E, V82S+Q184K, V82S+R185G, V82S+Y196W, V82S+Y196F, V82S+N200T, V82S+S202R, V82S+Q203T, V82S+R205K, V82S+R210L, V82S+R210G, V82S+R210M, V82S+N213V, V82S+N213D, V82S+T228S, V82S+N229D, V82S+E234F, V82S+E234Y, V82S+A235K, V82S+A235R, V82S+S241C, V82S+Q243K, V82S+Q243E, V82S+R244K, V82S+R244V, V82S+A250G, V82S+K254Y, V82S+G257W, V82S+G257E, V82S+G257A, V82S+W260F, V82S+W260Y, V82S+W260L, V82S+W260T, V82S+Y262F, V82S+S266A, V82S+D268N, V82S+A270D, V82S+N272M, V82S+N272T, V82S+N273E, V82S+N273D, V82S+A276E, V82S+A276W, V82S+A276D, V82S+N279D, V82S+N279E, V82S+T280L, V82S+N283W, V82S+N283H, V82S+Y286W, V82S+Y286F, V82S+L288I, V82S+E290A, V82S+L294P, V82S+L294K, V82S+L294I, V82S+L294R, V82S+L294V, V82S+L294H, V82S+S295K, V82S+S295V, V82S+S295P, V82S+S295L, V82S+S295R, V82S+S295A, V82S+S295N, V82S+S295M, V82S+S295I, V82S+T296S, V82S+F298Y, A83P+Y93Q, A83P+Y93A, A83P+S95D, A83P+A97R, A83P+S98P, A83P+S98D, A83P+N100Y, A83P+D104A, A83P+D104G, A83P+E108S, A83P+S111A, A83P+S111K, A83P+S111R, A83P+I114Q, A83P+I114M, A83P+I114W, A83P+K116R, A83P+D118K, A83P+T119R, A83P+S131T, A83P+E133R, A83P+E133Q, A83P+D135P, A83P+A136P, A83P+D139A, A83P+D139R, A83P+K142M, A83P+K142V, A83P+K142S, A83P+K142R, A83P+Q143R, A83P+N150T, A83P+N150R, A83P+N150S, A83P+Q169A, A83P+Q169R, A83P+Q169K, A83P+H172R, A83P+Y174R, A83P+Y174L, A83P+Y174W, A83P+Y174F, A83P+R176Q, A83P+E177S, A83P+E177Y, A83P+N180R, A83P+P183T, A83P+P183G, A83P+Q184E, A83P+Q184K, A83P+R185G, A83P+Y196W, A83P+Y196F, A83P+N200T, A83P+S202R, A83P+Q203T, A83P+R205K, A83P+R210L, A83P+R210G, A83P+R210M, A83P+N213V, A83P+N213D, A83P+T228S, A83P+N229D, A83P+E234F, A83P+E234Y, A83P+A235K, A83P+A235R, A83P+S241C, A83P+Q243K, A83P+Q243E, A83P+R244K, A83P+R244V, A83P+A250G, A83P+K254Y, A83P+G257W, A83P+G257E, A83P+G257A, A83P+W260F, A83P+W260Y, A83P+W260L, A83P+W260T, A83P+Y262F, A83P+S266A, A83P+D268N, A83P+A270D, A83P+N272M, A83P+N272T, A83P+N273E, A83P+N273D, A83P+A276E, A83P+A276W, A83P+A276D, A83P+N279D, A83P+N279E, A83P+T280L, A83P+N283W, A83P+N283H, A83P+Y286W, A83P+Y286F, A83P+L288I, A83P+E290A, A83P+L294P, A83P+L294K, A83P+L294I, A83P+L294R, A83P+L294V, A83P+L294H, A83P+S295K, A83P+S295V, A83P+S295P, A83P+S295L, A83P+S295R, A83P+S295A, A83P+S295N, A83P+S295M, A83P+S295I, A83P+T296S, A83P+F298Y, A83S+Y93Q, A83S+Y93A, A83S+S95D, A83S+A97R, A83S+S98P, A83S+S98D, A83S+N100Y, A83S+D104A, A83S+D104G, A83S+E108S, A83S+S111A, A83S+S111K, A83S+S111R, A83S+I114Q, A83S+I114M, A83S+I114W, A83S+K116R, A83S+D118K, A83S+T119R, A83S+S131T, A83S+E133R, A83S+E133Q, A83S+D135P, A83S+A136P, A83S+D139A, A83S+D139R, A83S+K142M, A83S+K142V, A83S+K142S, A83S+K142R, A83S+Q143R, A83S+N150T, A83S+N150R, A83S+N150S, A83S+Q169A, A83S+Q169R, A83S+Q169K, A83S+H172R, A83S+Y174R, A83S+Y174L, A83S+Y174W, A83S+Y174F, A83S+R176Q, A83S+E177S, A83S+E177Y, A83S+N180R, A83S+P183T, A83S+P183G, A83S+Q184E, A83S+Q184K, A83S+R185G, A83S+Y196W, A83S+Y196F, A83S+N200T, A83S+S202R, A83S+Q203T, A83S+R205K, A83S+R210L, A83S+R210G, A83S+R210M, A83S+N213V, A83S+N213D, A83S+T228S, A83S+N229D, A83S+E234F, A83S+E234Y, A83S+A235K, A83S+A235R, A83S+S241C, A83S+Q243K, A83S+Q243E, A83S+R244K, A83S+R244V, A83S+A250G, A83S+K254Y, A83S+G257W, A83S+G257E, A83S+G257A, A83S+W260F, A83S+W260Y, A83S+W260L, A83S+W260T, A83S+Y262F, A83S+S266A, A83S+D268N, A83S+A270D, A83S+N272M, A83S+N272T, A83S+N273E, A83S+N273D, A83S+A276E, A83S+A276W, A83S+A276D, A83S+N279D, A83S+N279E, A83S+T280L, A83S+N283W, A83S+N283H, A83S+Y286W, A83S+Y286F, A83S+L288I, A83S+E290A, A83S+L294P, A83S+L294K, A83S+L294I, A83S+L294R, A83S+L294V, A83S+L294H, A83S+S295K, A83S+S295V, A83S+S295P, A83S+S295L, A83S+S295R, A83S+S295A, A83S+S295N, A83S+S295M, A83S+S295I, A83S+T296S, A83S+F298Y, Y93Q+S95D, Y93Q+A97R, Y93Q+S98P, Y93Q+S98D, Y93Q+N100Y, Y93Q+D104A, Y93Q+D104G, Y93Q+E108S, Y93Q+S111A, Y93Q+S111K, Y93Q+S111R, Y93Q+I114Q, Y93Q+I114M, Y93Q+I114W, Y93Q+K116R, Y93Q+D118K, Y93Q+T119R, Y93Q+S131T, Y93Q+E133R, Y93Q+E133Q, Y93Q+D135P, Y93Q+A136P, Y93Q+D139A, Y93Q+D139R, Y93Q+K142M, Y93Q+K142V, Y93Q+K142S, Y93Q+K142R, Y93Q+Q143R, Y93Q+N150T, Y93Q+N150R, Y93Q+N150S, Y93Q+Q169A, Y93Q+Q169R, Y93Q+Q169K, Y93Q+H172R, Y93Q+Y174R, Y93Q+Y174L, Y93Q+Y174W, Y93Q+Y174F, Y93Q+R176Q, Y93Q+E177S, Y93Q+E177Y, Y93Q+N180R, Y93Q+P183T, Y93Q+P183G, Y93Q+Q184E, Y93Q+Q184K, Y93Q+R185G, Y93Q+Y196W, Y93Q+Y196F, Y93Q+N200T, Y93Q+S202R, Y93Q+Q203T, Y93Q+R205K, Y93Q+R210L, Y93Q+R210G, Y93Q+R210M, Y93Q+N213V, Y93Q+N213D, Y93Q+T228S, Y93Q+N229D, Y93Q+E234F, Y93Q+E234Y, Y93Q+A235K, Y93Q+A235R, Y93Q+S241C, Y93Q+Q243K, Y93Q+Q243E, Y93Q+R244K, Y93Q+R244V, Y93Q+A250G, Y93Q+K254Y, Y93Q+G257W, Y93Q+

G257E, Y93Q+G257A, Y93Q+W260F, Y93Q+W260Y, Y93Q+W260L, Y93Q+W260T, Y93Q+Y262F, Y93Q+S266A, Y93Q+D268N, Y93Q+A270D, Y93Q+N272M, Y93Q+N272T, Y93Q+N273E, Y93Q+N273D, Y93Q+A276E, Y93Q+A276W, Y93Q+A276D, Y93Q+N279D, Y93Q+N279E, Y93Q+T280L, Y93Q+N283W, Y93Q+N283H, Y93Q+Y286W, Y93Q+Y286F, Y93Q+L288I, Y93Q+E290A, Y93Q+L294P, Y93Q+L294K, Y93Q+L294I, Y93Q+L294R, Y93Q+L294V, Y93Q+L294H, Y93Q+S295K, Y93Q+S295V, Y93Q+S295P, Y93Q+S295L, Y93Q+S295R, Y93Q+S295A, Y93Q+S295N, Y93Q+S295M, Y93Q+S295I, Y93Q+T296S, Y93Q+F298Y, Y93A+S95D, Y93A+A97R, Y93A+S98P, Y93A+S98D, Y93A+N100Y, Y93A+D104A, Y93A+D104G, Y93A+E108S, Y93A+S111A, Y93A+S111K, Y93A+S111R, Y93A+I114Q, Y93A+I114M, Y93A+I114W, Y93A+K116R, Y93A+D118K, Y93A+T119R, Y93A+S131T, Y93A+E133R, Y93A+E133Q, Y93A+D135P, Y93A+A136P, Y93A+D139A, Y93A+D139R, Y93A+K142M, Y93A+K142V, Y93A+K142S, Y93A+K142R, Y93A+Q143R, Y93A+N150T, Y93A+N150R, Y93A+N150S, Y93A+Q169A, Y93A+Q169R, Y93A+Q169K, Y93A+H172R, Y93A+Y174R, Y93A+Y174L, Y93A+Y174W, Y93A+Y174F, Y93A+R176Q, Y93A+E177S, Y93A+E177Y, Y93A+N180R, Y93A+P183T, Y93A+P183G, Y93A+Q184E, Y93A+Q184K, Y93A+R185G, Y93A+Y196W, Y93A+Y196F, Y93A+N200T, Y93A+S202R, Y93A+Q203T, Y93A+R205K, Y93A+R210L, Y93A+R210G, Y93A+R210M, Y93A+N213V, Y93A+N213D, Y93A+T228S, Y93A+N229D, Y93A+E234F, Y93A+E234Y, Y93A+A235K, Y93A+A235R, Y93A+S241C, Y93A+Q243K, Y93A+Q243E, Y93A+R244K, Y93A+R244V, Y93A+A250G, Y93A+K254Y, Y93A+G257W, Y93A+G257E, Y93A+G257A, Y93A+W260F, Y93A+W260Y, Y93A+W260L, Y93A+W260T, Y93A+Y262F, Y93A+S266A, Y93A+D268N, Y93A+A270D, Y93A+N272M, Y93A+N272T, Y93A+N273E, Y93A+N273D, Y93A+A276E, Y93A+A276W, Y93A+A276D, Y93A+N279D, Y93A+N279E, Y93A+T280L, Y93A+N283W, Y93A+N283H, Y93A+Y286W, Y93A+Y286F, Y93A+L288I, Y93A+E290A, Y93A+L294P, Y93A+L294K, Y93A+L294I, Y93A+L294R, Y93A+L294V, Y93A+L294H, Y93A+S295K, Y93A+S295V, Y93A+S295P, Y93A+S295L, Y93A+S295R, Y93A+S295A, Y93A+S295N, Y93A+S295M, Y93A+S295I, Y93A+T296S, Y93A+F298Y, S95D+A97R, S95D+S98P, S95D+S98D, S95D+N100Y, S95D+D104A, S95D+D104G, S95D+E108S, S95D+S111A, S95D+S111K, S95D+S111R, S95D+I114Q, S95D+I114M, S95D+I114W, S95D+K116R, S95D+D118K, S95D+T119R, S95D+S131T, S95D+E133R, S95D+E133Q, S95D+D135P, S95D+A136P, S95D+D139A, S95D+D139R, S95D+K142M, S95D+K142V, S95D+K142S, S95D+K142R, S95D+Q143R, S95D+N150T, S95D+N150R, S95D+N150S, S95D+Q169A, S95D+Q169R, S95D+Q169K, S95D+H172R, S95D+Y174R, S95D+Y174L, S95D+Y174W, S95D+Y174F, S95D+R176Q, S95D+E177S, S95D+E177Y, S95D+N180R, S95D+P183T, S95D+P183G, S95D+Q184E, S95D+Q184K, S95D+R185G, S95D+Y196W, S95D+Y196F, S95D+N200T, S95D+S202R, S95D+Q203T, S95D+R205K, S95D+R210L, S95D+R210G, S95D+R210M, S95D+N213V, S95D+N213D, S95D+T228S, S95D+N229D, S95D+E234F, S95D+E234Y, S95D+A235K, S95D+A235R, S95D+S241C, S95D+Q243K, S95D+Q243E, S95D+R244K, S95D+R244V, S95D+A250G, S95D+K254Y, S95D+G257W, S95D+G257E, S95D+G257A, S95D+W260F, S95D+W260Y, S95D+W260L, S95D+W260T, S95D+Y262F, S95D+S266A, S95D+D268N, S95D+A270D, S95D+N272M, S95D+N272T, S95D+N273E, S95D+N273D, S95D+A276E, S95D+A276W, S95D+A276D, S95D+N279D, S95D+N279E, S95D+T280L, S95D+N283W, S95D+N283H, S95D+Y286W, S95D+Y286F, S95D+L288I, S95D+E290A, S95D+L294P, S95D+L294K, S95D+L294I, S95D+L294R, S95D+L294V, S95D+L294H, S95D+S295K, S95D+S295V, S95D+S295P, S95D+S295L, S95D+S295R, S95D+S295A, S95D+S295N, S95D+S295M, S95D+S295I, S95D+T296S, S95D+F298Y, A97R+S98P, A97R+S98D, A97R+N100Y, A97R+D104A, A97R+D104G, A97R+E108S, A97R+S111A, A97R+S111K, A97R+S111R, A97R+I114Q, A97R+I114M, A97R+I114W, A97R+K116R, A97R+D118K, A97R+T119R, A97R+S131T, A97R+E133R, A97R+E133Q, A97R+D135P, A97R+A136P, A97R+D139A, A97R+D139R, A97R+K142M, A97R+K142V, A97R+K142S, A97R+K142R, A97R+Q143R, A97R+N150T, A97R+N150R, A97R+N150S, A97R+Q169A, A97R+Q169R, A97R+Q169K, A97R+H172R, A97R+Y174R, A97R+Y174L, A97R+Y174W, A97R+Y174F, A97R+R176Q, A97R+E177S, A97R+E177Y, A97R+N180R, A97R+P183T, A97R+P183G, A97R+Q184E, A97R+Q184K, A97R+R185G, A97R+Y196W, A97R+Y196F, A97R+N200T, A97R+S202R, A97R+Q203T, A97R+R205K, A97R+R210L, A97R+R210G, A97R+R210M, A97R+N213V, A97R+N213D, A97R+T228S, A97R+N229D, A97R+E234F, A97R+E234Y, A97R+A235K, A97R+A235R, A97R+S241C, A97R+Q243K, A97R+Q243E, A97R+R244K, A97R+R244V, A97R+A250G, A97R+K254Y, A97R+G257W, A97R+G257E, A97R+G257A, A97R+W260F, A97R+W260Y, A97R+W260L, A97R+W260T, A97R+Y262F, A97R+S266A, A97R+D268N, A97R+A270D, A97R+N272M, A97R+N272T, A97R+N273E, A97R+N273D, A97R+A276E, A97R+A276W, A97R+A276D, A97R+N279D, A97R+N279E, A97R+T280L, A97R+N283W, A97R+N283H, A97R+Y286W, A97R+Y286F, A97R+L288I, A97R+E290A, A97R+L294P, A97R+L294K, A97R+L294I, A97R+L294R, A97R+L294V, A97R+L294H, A97R+S295K, A97R+S295V, A97R+S295P, A97R+S295L, A97R+S295R, A97R+S295A, A97R+S295N, A97R+S295M, A97R+S295I, A97R+T296S, A97R+F298Y, S98P+N100Y, S98P+D104A, S98P+D104G, S98P+S111A, S98P+S111K, S98P+S111R, S98P+I114Q, S98P+I114M, S98P+I114W, S98P+K116R, S98P+D118K, S98P+T119R, S98P+S131T, S98P+E133R, S98P+E133Q, S98P+D135P, S98P+A136P, S98P+D139A, S98P+D139R, S98P+K142M, S98P+K142V, S98P+K142S, S98P+K142R, S98P+Q143R, S98P+N150T, S98P+N150R, S98P+N150S, S98P+Q169A, S98P+Q169R, S98P+Q169K, S98P+H172R, S98P+Y174R, S98P+Y174L, S98P+Y174W, S98P+Y174F, S98P+R176Q, S98P+E177S, S98P+E177Y, S98P+N180R, S98P+P183T, S98P+P183G, S98P+Q184E, S98P+Q184K, S98P+R185G, S98P+Y196W, S98P+Y196F, S98P+N200T, S98P+S202R, S98P+Q203T, S98P+R205K, S98P+R210L, S98P+R210G, S98P+R210M, S98P+N213V, S98P+N213D, S98P+T228S, S98P+N229D, S98P+E234F, S98P+E234Y, S98P+A235K, S98P+A235R, S98P+S241C, S98P+Q243K, S98P+Q243E, S98P+R244K, S98P+R244V, S98P+A250G, S98P+K254Y, S98P+G257W, S98P+G257E, S98P+G257A, S98P+W260F, S98P+W260Y, S98P+W260L, S98P+W260T, S98P+Y262F, S98P+S266A, S98P+D268N, S98P+A270D, S98P+N272M, S98P+N272T, S98P+N273E, S98P+N273D, S98P+A276E, S98P+A276D, S98P+N279D, S98P+N279E, S98P+T280L, S98P+N283W, S98P+N283H, S98P+Y286W, S98P+Y286F, S98P+L288I, S98P+E290A, S98P+L294P, S98P+

L294K, S98P+L294I, S98P+L294R, S98P+L294V, S98P+ L294H, S98P+S295K, S98P+S295V, S98P+S295P, S98P+ S295L, S98P+S295R, S98P+S295A, S98P+S295N, S98P+ S295M, S98P+S295I, S98P+T296S, S98P+F298Y, S98D+ N100Y, S98D+D104A, S98D+D104G, S98D+E108S, S98D+S111A, S98D+S111K, S98D+S111R, S98D+I114Q, S98D+I114M, S98D+I114W, S98D+K116R, S98D+D118K, S98D+T119R, S98D+S131T, S98D+E133R, S98D+E133Q, S98D+D135P, S98D+A136P, S98D+D139A, S98D+ D139R, S98D+K142M, S98D+K142V, S98D+K142S, S98D+K142R, S98D+Q143R, S98D+N150T, S98D+ N150R, S98D+N150S, S98D+Q169A, S98D+Q169R, S98D+Q169K, S98D+H172R, S98D+Y174R, S98D+ Y174L, S98D+Y174W, S98D+Y174F, S98D+R176Q, S98D+E177S, S98D+E177Y, S98D+N180R, S98D+P183T, S98D+P183G, S98D+Q184E, S98D+Q184K, S98D+ R185G, S98D+Y196W, S98D+Y196F, S98D+N200T, S98D+S202R, S98D+Q203T, S98D+R205K, S98D+ R210L, S98D+R210G, S98D+R210M, S98D+N213V, S98D+N213D, S98D+T228S, S98D+N229D, S98D+ E234F, S98D+E234Y, S98D+A235K, S98D+A235R, S98D+S241C, S98D+Q243K, S98D+Q243E, S98D+ R244K, S98D+R244V, S98D+A250G, S98D+K254Y, S98D+G257W, S98D+G257E, S98D+G257A, S98D+ W260F, S98D+W260Y, S98D+W260L, S98D+W260T, S98D+Y262F, S98D+S266A, S98D+D268N, S98D+ A270D, S98D+N272M, S98D+N272T, S98D+N273E, S98D+N273D, S98D+A276E, S98D+A276W, S98D+ A276D, S98D+N279D, S98D+N279E, S98D+T280L, S98D+N283W, S98D+N283H, S98D+Y286W, S98D+ Y286F, S98D+L288I, S98D+E290A, S98D+L294P, S98D+ L294K, S98D+L294I, S98D+L294R, S98D+L294V, S98D+ L294H, S98D+S295K, S98D+S295V, S98D+S295P, S98D+ S295L, S98D+S295R, S98D+S295A, S98D+S295N, S98D+S295M, S98D+S295I, S98D+T296S, S98D+F298Y, N100Y+D104A, N100Y+D104G, N100Y+E108S, N100Y+ S111A, N100Y+S111K, N100Y+S111R, N100Y+I114Q, N100Y+I114M, N100Y+I114W, N100Y+K116R, N100Y+ D118K, N100Y+T119R, N100Y+S131T, N100Y+E133R, N100Y+E133Q, N100Y+D135P, N100Y+A136P, N100Y+ D139A, N100Y+D139R, N100Y+K142M, N100Y+K142V, N100Y+K142S, N100Y+K142R, N100Y+Q143R, N100Y+ N150T, N100Y+N150R, N100Y+N150S, N100Y+Q169A, N100Y+Q169R, N100Y+Q169K, N100Y+H172R, N100Y+Y174R, N100Y+Y174L, N100Y+Y174W, N100Y+Y174F, N100Y+R176Q, N100Y+E177S, N100Y+ E177Y, N100Y+N180R, N100Y+P183T, N100Y+P183G, N100Y+Q184E, N100Y+Q184K, N100Y+R185G, N100Y+ Y196W, N100Y+Y196F, N100Y+N200T, N100Y+S202R, N100Y+Q203T, N100Y+R205K, N100Y+R210L, N100Y+ R210G, N100Y+R210M, N100Y+N213V, N100Y+N213D, N100Y+T228S, N100Y+N229D, N100Y+E234F, N100Y+ E234Y, N100Y+A235K, N100Y+A235R, N100Y+S241C, N100Y+Q243K, N100Y+Q243E, N100Y+R244K, N100Y+ R244V, N100Y+A250G, N100Y+K254Y, N100Y+G257W, N100Y+G257E, N100Y+G257A, N100Y+W260F, N100Y+W260Y, N100Y+W260L, N100Y+W260T, N100Y+Y262F, N100Y+S266A, N100Y+D268N, N100Y+ A270D, N100Y+N272M, N100Y+N272T, N100Y+N273E, N100Y+N273D, N100Y+A276E, N100Y+A276W, N100Y+A276D, N100Y+N279 D, N100Y+N279E, N100Y+T280L, N100Y+N283W, N100Y+N283H, N100Y+Y286W, N100Y+Y286F, N100Y+L288I, N100Y+ E290A, N100Y+L294P, N100Y+L294K, N100Y+L294I, N100Y+L294R, N100Y+L294V, N100Y+L294H, N100Y+ S295K, N100Y+S295V, N100Y+S295P, N100Y+S295L, N100Y+S295R, N100Y+S295A, N100Y+S295N, N100Y+ S295M, N100Y+S295I, N100Y+T296S, N100Y+F298Y, D104A+E108S, D104A+S111A, D104A+S111K, D104A+ S111R, D104A+I114Q, D104A+I114M, D104A+I114W, D104A+K116R, D104A+D118K, D104A+T119R, D104A+ S131T, D104A+E133R, D104A+E133Q, D104A+D135P, D104A+A136P, D104A+D139A, D104A+D139R, D104A+ K142M, D104A+K142V, D104A+K142S, D104A+K142R, D104A+Q143R, D104A+N150T, D104A+N150R, D104A+ N150S, D104A+Q169A, D104A+Q169R, D104A+Q169K, D104A+H172R, D104A+Y174R, D104A+Y174L, D104A+ Y174W, D104A+Y174F, D104A+R176Q, D104A+E177S, D104A+E177Y, D104A+N180R, D104A+P183T, D104A+ P183G, D104A+Q184E, D104A+Q184K, D104A+R185G, D104A+Y196W, D104A+Y196F, D104A+N200T, D104A+ S202R, D104A+Q203T, D104A+R205K, D104A+R210L, D104A+R210G, D104A+R210M, D104A+N213V, D104A+N213D, D104A+T228S, D104A+N229D, D104A+ E234F, D104A+E234Y, D104A+A235K, D104A+A235R, D104A+S241C, D104A+Q243K, D104A+Q243E, D104A+ R244K, D104A+R244V, D104A+A250G, D104A+K254Y, D104A+G257W, D104A+G257E, D104A+G257A, D104A+W260F, D104A+W260Y, D104A+W260L, D104A+W260T, D104A+Y262F, D104A+S266A, D104A+ D268N, D104A+A270D, D104A+N272M, D104A+N272T, D104A+N273E, D104A+N273D, D104A+A276E, D104A+ A276W, D104A+A276D, D104A+N279D, D104A+N279E, D104A+T280L, D104A+N283W, D104A+N283H, D104A+Y286W, D104A+Y286F, D104A+L288I, D104A+ E290A, D104A+L294P, D104A+L294K, D104A+L294I, D104A+L294R, D104A+L294V, D104A+L294H, D104A+ S295K, D104A+S295V, D104A+S295P, D104A+S295L, D104A+S295R, D104A+S295A, D104A+S295N, D104A+ S295M, D104A+S295I, D104A+T296S, D104A+F298Y, D104G+E108S, D104G+S111A, D104G+S111K, D104G+ S111R, D104G+I114Q, D104G+I114M, D104G+I114W, D104G+K116R, D104G+D118K, D104G+T119R, D104G+ S131T, D104G+E133R, D104G+E133Q, D104G+D135P, D104G+A136P, D104G+D139A, D104G+D139R, D104G+ K142M, D104G+K142V, D104G+K142S, D104G+K142R, D104G+Q143R, D104G+N150T, D104G+N150R, D104G+ N150S, D104G+Q169A, D104G+Q169R, D104G+Q169K, D104G+H172R, D104G+Y174R, D104G+Y174L, D104G+ Y174W, D104G+Y174F, D104G+R176Q, D104G+E177S, D104G+E177Y, D104G+N180R, D104G+P183T, D104G+ P183G, D104G+Q184E, D104G+Q184K, D104G+R185G, D104G+Y196W, D104G+Y196F, D104G+N200T, D104G+ S202R, D104G+Q203T, D104G+R205K, D104G+R210L, D104G+R210G, D104G+R210M, D104G+N213V, D104G+N213D, D104G+T228S, D104G+N229D, D104G+ E234F, D104G+E234Y, D104G+A235K, D104G+A235R, D104G+S241C, D104G+Q243K, D104G+Q243E, D104G+ R244K, D104G+R244V, D104G+A250G, D104G+K254Y, D104G+G257W, D104G+G257E, D104G+G257A, D104G+W260F, D104G+W260Y, D104G+W260L, D104G+W260T, D104G+Y262F, D104G+S266A, D104G+ D268N, D104G+A270D, D104G+N272M, D104G+N272T, D104G+N273E, D104G+N273D, D104G+A276E, D104G+ A276W, D104G+A276D, D104G+N279D, D104G+N279E, D104G+T280L, D104G+N283W, D104G+N283H, D104G+Y286W, D104G+Y286F, D104G+L288I, D104G+ E290A, D104G+L294P, D104G+L294K, D104G+L294I, D104G+L294R, D104G+L294V, D104G+L294H, D104G+ S295K, D104G+S295V, D104G+S295P, D104G+S295L, D104G+S295R, D104G+S295A, D104G+S295N, D104G+ S295M, D104G+S295I, D104G+T296S, D104G+F298Y, E108S+S111A, E108S+S111K, E108S+S111R, E108S+ I114Q, E108S+I114M, E108S+I114W, E108S+K116R,

E108S+D118K, E108S+T119R, E108S+S131T, E108S+ E133R, E108S+E133Q, E108S+D135P, E108S+A136P, E108S+D139A, E108S+D139R, E108S+K142M, E108S+ K142V, E108S+K142S, E108S+K142R, E108S+Q143R, E108S+N150T, E108S+N150R, E108S+N150S, E108S+ Q169A, E108S+Q169R, E108S+Q169K, E108S+H172R, E108S+Y174R, E108S+Y174L, E108S+Y174W, E108S+ Y174F, E108S+R176Q, E108S+E177S, E108S+E177Y, E108S+N180R, E108S+P183T, E108S+P183G, E108S+ Q184E, E108S+Q184K, E108S+R185G, E108S+Y196W, E108S+Y196F, E108S+N200T, E108S+S202R, E108S+ Q203T, E108S+R205K, E108S+R210L, E108S+R210G, E108S+R210M, E108S+N213V, E108S+N213D, E108S+ T228S, E108S+N229D, E108S+E234F, E108S+E234Y, E108S+A235K, E108S+A235R, E108S+S241C, E108S+ Q243K, E108S+Q243E, E108S+R244K, E108S+R244V, E108S+A250G, E108S+K254Y, E108S+G257W, E108S+ G257E, E108S+G257A, E108S+W260F, E108S+W260Y, E108S+W260L, E108S+W260T, E108S+Y262F, E108S+ S266A, E108S+D268N, E108S+A270D, E108S+N272M, E108S+N272T, E108S+N273E, E108S+N273D, E108S+ A276E, E108S+A276W, E108S+A276D, E108S+N279D, E108S+N279E, E108S+T280L, E108S+N283W, E108S+ N283H, E108S+Y286W, E108S+Y286F, E108S+L288I, E108S+E290A, E108S+L294P, E108S+L294K, E108S+ L294I, E108S+L294R, E108S+L294V, E108S+L294H, E108S+S295K, E108S+S295V, E108S+S295P, E108S+ S295L, E108S+S295R, E108S+S295A, E108S+S295N, E108S+S295M, E108S+S295I, E108S+T296S, E108S+ F298Y, S111A+I114Q, S111A+I114M, S111A+I114W, S111A+K116R, S111A+D118K, S111A+T119R, S111A+ S131T, S111A+E133R, S111A+E133Q, S111A+D135P, S111A+A136P, S111A+D139A, S111A+D139R, S111A+ K142M, S111A+K142V, S111A+K142S, S111A+K142R, S111A+Q143R, S111A+N150T, S111A+N150R, S111A+ N150S, S111A+Q169A, S111A+Q169R, S111A+Q169K, S111A+H172R, S111A+Y174R, S111A+Y174L, S111A+ Y174W, S111A+Y174F, S111A+R176Q, S111A+E177S, S111A+E177Y,S111A+N180R,S111A+P183T,S111A+ P183G,S111A+Q184E, S111A+Q184K, S111A+R185G, S111A+Y196W, S111A+Y196F, S111A+N200T, S111A+ S202R, S111A+Q203T, S111A+R205K, S111A+R210L, S111A+R210G, S111A+R210M, S111A+N213V, S111A+ N213D, S111A+T228S, S111A+N229D, S111A+E234F, S111A+E234Y, S111A+A235K, S111A+A235R, S111A+ S241C, S111A+Q243K, S111A+Q243E, S111A+R244K, S111A+R244V, S111A+A250G, S111A+K254Y, S111A+ G257W, S111A+G257E, S111A+G257A, S111A+W260F, S111A+W260Y, S111A+W260L, S111A+W260T, S111A+ Y262F, S111A+S266A, S111A+D268N, S111A+A270D, S111A+N272M, S111A+N272T, S111A+N273E, S111A+ N273D, S111A+A276E, S111A+A276W, S111A+A276D, S111A+N279D, S111A+N279E, S111A+T280L, S111A+ N283W, S111A+N283H, S111A+Y286W, S111A+Y286F, S111A+L288I, S111A+E290A, S111A+L294P, S111A+ L294K, S111A+L294I, S111A+L294R, S111A+L294V, S111A+L294H, S111A+S295K, S111A+S295V, S111A+ S295P, S111A+S295L, S111A+S295R, S111A+S295A, S111A+S295N, S111A+S295M, S111A+S295I, S111A+ T296S, S111A+F298Y, S111K+I114Q, S111K+I114M, S111K+I114W, S111K+K116R, S111K+D118K, S111K+ T119R, S111K+S131T, S111K+E133R, S111K+E133Q, S111K+D135P, S111K+A136P, S111K+D139A, S111K+ D139R, S111K+K142M, S111K+K142V, S111K+K142S, S111K+K142R, S111K+Q143R, S111K+N150T, S111K+ N150R, S111K+N150S, S111K+Q169A, S111K+Q169R, S111K+Q169K, S111K+H172R, S111K+Y174R, S111K+ Y174L, S111K+Y174W, S111K+Y174F, S111K+R176Q, S111K+E177S, S111K+E177Y, S111K+N180R, S111K+ P183T, S111K+P183G, S111K+Q184E, S111K+Q184K, S111K+R185G, S111K+Y196W, S111K+Y196F, S111K+ N200T, S111K+S202R, S111K+Q203T, S111K+R205K, S111K+R210L, S111K+R210G, S111K+R210M, S111K+ N213V, S111K+N213D, S111K+T228S, S111K+N229D, S111K+E234F, S111K+E234Y, S111K+A235K, S111K+ A235R, S111K+S241C, S111K+Q243K, S111K+Q243E, S111K+R244K, S111K+R244V, S111K+A250G, S111K+ K254Y, S111K+G257W, S111K+G257E, S111K+G257A, S111K+W260F, S111K+W260Y, S111K+W260L, S111K+ W260T, S111K+Y262F, S111K+S266A, S111K+D268N, S111K+A270D, S111K+N272M, S111K+N272T, S111K+ N273E, S111K+N273D, S111K+A276E, S111K+A276W, S111K+A276D, S111K+N279D, S111K+N279E, S111K+ T280L, S111K+N283W, S111K+N283H, S111K+Y286W, S111K+Y286F, S111K+L288I, S111K+E290A, S111K+ L294P, S111K+L294K, S111K+L294I, S111K+L294R, S111K+L294V, S111K+L294H, S111K+S295K, S111K+ S295V, S111K+S295P, S111K+S295L, S111K+S295R, S111K+S295A, S111K+S295N, S111K+S295M, S111K+ S295I, S111K+T296S, S111K+F298Y, S111R+I114Q, S111R+I114M, S111R+I114W, S111R+K116R, S111R+ D118K, S111R+T119R, S111R+S131T, S111R+E133R, S111R+E133Q, S111R+D135P, S111R+A136P, S111R+ D139A, S111R+D139R, S111R+K142M, S111R+K142V, S111R+K142S, S111R+K142R, S111R+Q143R, S111R+ N150T, S111R+N150R, S111R+N150S, S111R+Q169A, S111R+Q169R, S111R+Q169K, S111R+H172R, S111R+ Y174R, S111R+Y174L, S111R+Y174W, S111R+Y174F, S111R+R176Q, S111R+E177S, S111R+E177Y, S111R+ N180R, S111R+P183T, S111R+P183G, S111R+Q184E, S111R+Q184K, S111R+R185G, S111R+Y196W, S111R+ Y196F, S111R+N200T, S111R+S202R, S111R+Q203T, S111R+R205K, S111R+R210L, S111R+R210G, S111R+ R210M, S111R+N213V, S111R+N213D, S111R+T228S, S111R+N229D, S111R+E234F, S111R+E234Y, S111R+ A235K, S111R+A235R, S111R+S241C, S111R+Q243K, S111R+Q243E, S111R+R244K, S111R+R244V, S111R+ A250G, S111R+K254Y, S111R+G257W, S111R+G257E, S111R+G257A, S111R+W260F, S111R+W260Y, S111R+ W260L, S111R+W260T, S111R+Y262F, S111R+S266A, S111R+D268N, S111R+A270D, S111R+N272M, S111R+ N272T, S111R+N273E, S111R+N273D, S111R+A276E, S111R+A276W, S111R+A276D, S111R+N279D, S111R+ N279E, S111R+T280L, S111R+N283W, S111R+N283H, S111R+Y286W, S111R+Y286F, S111R+L288I, S111R+ E290A, S111R+L294P, S111R+L294K, S111R+L294I, S111R+L294R, S111R+L294V, S111R+L294H, S111R+ S295K, S111R+S295V, S111R+S295P, S111R+S295L, S111R+S295R, S111R+S295A, S111R+S295N, S111R+ S295M, S111R+S295I, S111R+T296S, S111R+F298Y, I114Q+K116R, I114Q+D118K, I114Q+T119R, I114Q+ S131T, I114Q+E133R, I114Q+E133Q, I114Q+D135P, I114Q+A136P, I114Q+D139A, I114Q+D139R, I114Q+ K142M, I114Q+K142V, I114Q+K142S, I114Q+K142R, I114Q+Q143R, I114Q+N150T, I114Q+N150R, I114Q+ N150S, I114Q+Q169A, I114Q+Q169R, I114Q+Q169K, I114Q+H172R, I114Q+Y174R, I114Q+Y174L, I114Q+ Y174W, I114Q+Y174F, I114Q+R176Q, I114Q+E177S, I114Q+E177Y, I114Q+N180R, I114Q+P183T, I114Q+ P183G, I114Q+Q184E, I114Q+Q184K, I114Q+R185G, I114Q+Y196W, I114Q+Y196F, I114Q+N200T, I114Q+ S202R, I114Q+Q203T, I114Q+R205K, I114Q+R210L, I114Q+R210G, I114Q+R210M, I114Q+N213V, I114Q+ N213D, I114Q+T228S, I114Q+N229D, I114Q+E234F,

I114Q+E234Y, I114Q+A235K, I114Q+A235R, I114Q+ S241C, I114Q+Q243K, I114Q+Q243E, I114Q+R244K, I114Q+R244V, I114Q+A250G, I114Q+K254Y, I114Q+ G257W, I114Q+G257E, I114Q+G257A, I114Q+W260F, I114Q+W260Y, I114Q+W260L, I114Q+W260T, I114Q+ Y262F, I114Q+S266A, I114Q+D268N, I114Q+A270D, I114Q+N272M, I114Q+N272T, I114Q+N273E, I114Q+ N273D, I114Q+A276E, I114Q+A276W, I114Q+A276D, I114Q+N279D, I114Q+N279E, I114Q+T280L, I114Q+ N283W, I114Q+N283H, I114Q+Y286W, I114Q+Y286F, I114Q+L288I, I114Q+E290A, I114Q+L294P, I114Q+ L294K, I114Q+L294I, I114Q+L294R, I114Q+L294V, I114Q+L294H, I114Q+S295K, I114Q+S295V, I114Q+ S295P, I114Q+S295L, I114Q+S295R, I114Q+S295A, I114Q+S295N, I114Q+S295M, I114Q+S295I, I114Q+ T296S, I114Q+F298Y, I114M+K116R, I114M+D118K, I114M+T119R, I114M+S131T, I114M+E133R, I114M+ E133Q, I114M+D135P, I114M+A136P, I114M+D139A, I114M+D139R, I114M+K142M, I114M+K142V, I114M+ K142S, I114M+K142R, I114M+Q143R, I114M+N150T, I114M+N150R, I114M+N150S, I114M+Q169A, I114M+ Q169R, I114M+Q169K, I114M+H172R, I114M+Y174R, I114M+Y174L, I114M+Y174W, I114M+Y174F, I114M+ R176Q, I114M+E177S, I114M+E177Y, I114M+N180R, I114M+P183T, I114M+P183G, I114M+Q184E, I114M+ Q184K, I114M+R185G, I114M+Y196W, I114M+Y196F, I114M+N200T, I114M+S202R, I114M+Q203T, I114M+ R205K, I114M+R210L, I114M+R210G, I114M+R210M, I114M+N213V, I114M+N213D, I114M+T228S, I114M+ N229D, I114M+E234F, I114M+E234Y, I114M+A235K, I114M+A235R, I114M+S241C, I114M+Q243K, I114M+ Q243E, I114M+R244K, I114M+R244V, I114M+A250G, I114M+K254Y, I114M+G257W, I114M+G257E, I114M+ G257A, I114M+W260F, I114M+W260Y, I114M+W260L, I114M+W260T, I114M+Y262F, I114M+S266A, I114M+ D268N, I114M+A270D, I114M+N272M, I114M+N272T, I114M+N273E, I114M+N273D, I114M+A276E, I114M+ A276W, I114M+A276D, I114M+N279D, I114M+N279E, I114M+T280L, I114M+N283W, I114M+N283H, I114M+ Y286W, I114M+Y286F, I114M+L288I, I114M+E290A, I114M+L294P, I114M+L294K, I114M+L294I, I114M+ L294R, I114M+L294V, I114M+L294H, I114M+S295K, I114M+S295V, I114M+S295P, I114M+S295L, I114M+ S295R, I114M+S295A, I114M+S295N, I114M+S295M, I114M+S295I, I114M+T296S, I114M+F298Y, I114W+ K116R, I114W+D118K, I114W+T119R, I114W+S131T, I114W+E133R, I114W+E133Q, I114W+D135P, I114W+ A136P, I114W+D139A, I114W+D139R, I114W+K142M, I114W+K142V, I114W+K142S, I114W+K142R, I114W+ Q143R, I114W+N150T, I114W+N150R, I114W+N150S, I114W+Q169A, I114W+Q169R, I114W+Q169K, I114W+ H172R, I114W+Y174R, I114W+Y174L, I114W+Y174W, I114W+Y174F, I114W+R176Q, I114W+E177S, I114W+ E177Y, I114W+N180R, I114W+P183T, I114W+P183G, I114W+Q184E, I114W+Q184K, I114W+R185G, I114W+ Y196W, I114W+Y196F, I114W+N200T, I114W+S202R, I114W+Q203T, I114W+R205K, I114W+R210L, I114W+ R210G, I114W+R210M, I114W+N213V, I114W+N213D, I114W+T228S, I114W+N229D, I114W+E234F, I114W+ E234Y, I114W+A235K, I114W+A235R, I114W+S241C, I114W+Q243K, I114W+Q243E, I114W+R244K, I114W+ R244V, I114W+A250G, I114W+K254Y, I114W+G257W, I114W+G257E, I114W+G257A, I114W+W260F, I114W+ W260Y, I114W+W260L, I114W+W260T, I114W+Y262F, I114W+S266A, I114W+D268N, I114W+A270D, I114W+ N272M, I114W+N272T, I114W+N273E, I114W+N273D, I114W+A276E, I114W+A276W, I114W+A276D, I114W+ N279D, I114W+N279E, I114W+T280L, I114W+N283W, I114W+N283H, I114W+Y286W, I114W+Y286F, I114W+ L288I, I114W+E290A, I114W+L294P, I114W+L294K, I114W+L294I, I114W+L294R, I114W+L294V, I114W+ L294H, I114W+S295K, I114W+S295V, I114W+S295P, I114W+S295L, I114W+S295R, I114W+S295A, I114W+ S295N, I114W+S295M, I114W+S295I, I114W+T296S, I114W+F298Y, K116R+D118K, K116R+T119R, K116R+ S131T, K116R+E133R, K116R+E133Q, K116R+D135P, K116R+A136P, K116R+D139A, K116R+D139R, K116R+ K142M, K116R+K142V, K116R+K142S, K116R+K142R, K116R+Q143R, K116R+N150T, K116R+N150R, K116R+ N150S, K116R+Q169A, K116R+Q169R, K116R+Q169K, K116R+H172R, K116R+Y174R, K116R+Y174L, K116R+ Y174W, K116R+Y174F, K116R+R176Q, K116R+E177S, K116R+E177Y, K116R+N180R, K116R+P183T, K116R+ P183G, K116R+Q184E, K116R+Q184K, K116R+R185G, K116R+Y196W, K116R+Y196F, K116R+N200T, K116R+ S202R, K116R+Q203T, K116R+R205K, K116R+R210L, K116R+R210G, K116R+R210M, K116R+N213V, K116R+ N213D, K116R+T228S, K116R+N229D, K116R+E234F, K116R+E234Y, K116R+A235K, K116R+A235R, K116R+ S241C, K116R+Q243K, K116R+Q243E, K116R+R244K, K116R+R244V, K116R+A250G, K116R+K254Y, K116R+ G257W, K116R+G257E, K116R+G257A, K116R+W260F, K116R+W260Y, K116R+W260L, K116R+W260T, K116R+Y262F, K116R+S266A, K116R+D268N, K116R+ A270D, K116R+N272M, K116R+N272T, K116R+N273E, K116R+N273D, K116R+A276E, K116R+A276W, K116R+ A276D, K116R+N279D, K116R+N279E, K116R+T280L, K116R+N283W, K116R+N283H, K116R+Y286W, K116R+Y286F, K116R+L288I, K116R+E290A, K116R+ L294P, K116R+L294K, K116R+L294I, K116R+L294R, K116R+L294V, K116R+L294H, K116R+S295K, K116R+ S295V, K116R+S295P, K116R+S295L, K116R+S295R, K116R+S295A, K116R+S295N, K116R+S295M, K116R+ S295I, K116R+T296S, K116R+F298Y, D118K+T119R, D118K+S131T, D118K+E133R, D118K+E133Q, D118K+ D135P, D118K+A136P, D118K+D139A, D118K+D139R, D118K+K142M, D118K+K142V, D118K+K142S, D118K+ K142R, D118K+Q143R, D118K+N150T, D118K+N150R, D118K+N150S, D118K+Q169A, D118K+Q169R, D118K+ Q169K, D118K+H172R, D118K+Y174R, D118K+Y174L, D118K+Y174W, D118K+Y174F, D118K+R176Q, D118K+ E177S, D118K+E177Y, D118K+N180R, D118K+P183T, D118K+P183G, D118K+Q184E, D118K+Q184K, D118K+ R185G, D118K+Y196W, D118K+Y196F, D118K+N200T, D118K+S202R, D118K+Q203T, D118K+R205K, D118K+ R210L, D118K+R210G, D118K+R210M, D118K+N213V, D118K+N213D, D118K+T228S, D118K+N229D, D118K+ E234F, D118K+E234Y, D118K+A235K, D118K+A235R, D118K+S241C, D118K+Q243K, D118K+Q243E, D118K+ R244K, D118K+R244V, D118K+A250G, D118K+K254Y, D118K+G257W, D118K+G257E, D118K+G257A, D118K+W260F, D118K+W260Y, D118K+W260L, D118K+W260T, D118K+Y262F, D118K+S266A, D118K+ D268N, D118K+A270D, D118K+N272M, D118K+N272T, D118K+N273E, D118K+N273D, D118K+A276E, D118K+ A276W, D118K+A276D, D118K+N279D, D118K+N279E, D118K+T280L, D118K+N283W, D118K+N283H, D118K+ Y286W, D118K+Y286F, D118K+L288I, D118K+E290A, D118K+L294P, D118K+L294K, D118K+L294I, D118K+ L294R, D118K+L294V, D118K+L294H, D118K+S295K, D118K+S295V, D118K+S295P, D118K+S295L, D118K+ S295R, D118K+S295A, D118K+S295N, D118K+S295M, D118K+S295I, D118K+T296S, D118K+F298Y, T119R+ S131T, T119R+E133R, T119R+E133Q, T119R+D135P,

T119R+A136P, T119R+D139A, T119R+D139R, T119R+ K142M, T119R+K142V, T119R+K142S, T119R+K142R, T119R+Q143R, T119R+N150T, T119R+N150R, T119R+ N150S, T119R+Q169A, T119R+Q169R, T119R+Q169K, T119R+H172R, T119R+Y174R, T119R+Y174L, T119R+ Y174W, T119R+Y174F, T119R+R176Q, T119R+E177S, T119R+E177Y, T119R+N180R, T119R+P183T, T119R+ P183G, T119R+Q184E, T119R+Q184K, T119R+R185G, T119R+Y196W, T119R+Y196F, T119R+N200T, T119R+ S202R, T119R+Q203T, T119R+R205K, T119R+R210L, T119R+R210G, T119R+R210M, T119R+N213V, T119R+ N213D, T119R+T228S, T119R+N229D, T119R+E234F, T119R+E234Y, T119R+A235K, T119R+A235R, T119R+ S241C, T119R+Q243K, T119R+Q243E, T119R+R244K, T119R+R244V, T119R+A250G, T119R+K254Y, T119R+ G257W, T119R+G257E, T119R+G257A, T119R+W260F, T119R+W260Y, T119R+W260L, T119R+W260T, T119R+ Y262F, T119R+S266A, T119R+D268N, T119R+A270D, T119R+N272M, T119R+N272T, T119R+N273E, T119R+ N273D, T119R+A276E, T119R+A276W, T119R+A276D, T119R+N279D, T119R+N279E, T119R+T280L, T119R+ N283W, T119R+N283H, T119R+Y286W, T119R+Y286F, T119R+L288I, T119R+E290A, T119R+L294P, T119R+ L294K, T119R+L294I, T119R+L294R, T119R+L294V, T119R+L294H, T119R+S295K, T119R+S295V, T119R+ S295P, T119R+S295L, T119R+S295R, T119R+S295A, T119R+S295N, T119R+S295M, T119R+S295I, T119R+ T296S, T119R+F298Y, S131T+E133R, S131T+E133Q, S131T+D135P, S131T+A136P, S131T+D139A, S131T+ D139R, S131T+K142M, S131T+K142V, S131T+K142S, S131T+K142R, S131T+Q143R, S131T+N150T, S131T+ N150R, S131T+N150S, S131T+Q169A, S131T+Q169R, S131T+Q169K, S131T+H172R, S131T+Y174R, S131T+ Y174L, S131T+Y174W, S131T+Y174F, S131T+R176Q, S131T+E177S, S131T+E177Y, S131T+N180R, S131T+ P183T, S131T+P183G, S131T+Q184E, S131T+Q184K, S131T+R185G, S131T+Y196W, S131T+Y196F, S131T+ N200T, S131T+S202R, S131T+Q203T, S131T+R205K, S131T+R210L, S131T+R210G, S131T+R210M, S131T+ N213V, S131T+N213D, S131T+T228S, S131T+N229D, S131T+E234F, S131T+E234Y, S131T+A235K, S131T+ A235R, S131T+S241C, S131T+Q243K, S131T+Q243E, S131T+R244K, S131T+R244V, S131T+A250G, S131T+ K254Y, S131T+G257W, S131T+G257E, S131T+G257A, S131T+W260F, S131T+W260Y, S131T+W260L, S131T+ W260T, S131T+Y262F, S131T+S266A, S131T+D268N, S131T+A270D, S131T+N272M, S131T+N272T, S131T+ N273E, S131T+N273D, S131T+A276E, S131T+A276W, S131T+A276D, S131T+N279D, S131T+N279E, S131T+ T280L, S131T+N283W, S131T+N283H, S131T+Y286W, S131T+Y286F, S131T+L288I, S131T+E290A, S131T+ L294P, S131T+L294K, S131T+L294I, S131T+L294R, S131T+L294V, S131T+L294H, S131T+S295K, S131T+ S295V, S131T+S295P, S131T+S295L, S131T+S295R, S131T+S295A, S131T+S295N, S131T+S295M, S131T+ S295I, S131T+T296S, S131T+F298Y, E133R+D135P, E133R+A136P, E133R+D139A, E133R+D139R, E133R+ K142M, E133R+K142V, E133R+K142S, E133R+K142R, E133R+Q143R, E133R+N150T, E133R+N150R, E133R+ N150S, E133R+Q169A, E133R+Q169R, E133R+Q169K, E133R+H172R, E133R+Y174R, E133R+Y174L, E133R+ Y174W, E133R+Y174F, E133R+R176Q, E133R+E177S, E133R+E177Y, E133R+N180R, E133R+P183T, E133R+ P183G, E133R+Q184E, E133R+Q184K, E133R+R185G, E133R+Y196W, E133R+Y196F, E133R+N200T, E133R+ S202R, E133R+Q203T, E133R+R205K, E133R+R210L, E133R+R210G, E133R+R210M, E133R+N213V, E133R+ N213D, E133R+T228S, E133R+N229D, E133R+E234F, E133R+E234Y, E133R+A235K, E133R+A235R, E133R+ S241C, E133R+Q243K, E133R+Q243E, E133R+R244K, E133R+R244V, E133R+A250G, E133R+K254Y, E133R+ G257W, E133R+G257E, E133R+G257A, E133R+W260F, E133R+W260Y, E133R+W260L, E133R+W260T, E133R+ Y262F, E133R+S266A, E133R+D268N, E133R+A270D, E133R+N272M, E133R+N272T, E133R+N273E, E133R+ N273D, E133R+A276E, E133R+A276W, E133R+A276D, E133R+N279D, E133R+N279E, E133R+T280L, E133R+ N283W, E133R+N283H, E133R+Y286W, E133R+Y286F, E133R+L288I, E133R+E290A, E133R+L294P, E133R+ L294K, E133R+L294I, E133R+L294R, E133R+L294V, E133R+L294H, E133R+S295K, E133R+S295V, E133R+ S295P, E133R+S295L, E133R+S295R, E133R+S295A, E133R+S295N, E133R+S295M, E133R+S295I, E133R+ T296S, E133R+F298Y, E133Q+D135P, E133Q+A136P, E133Q+D139A, E133Q+D139R, E133Q+K142M, E133Q+ K142V, E133Q+K142S, E133Q+K142R, E133Q+Q143R, E133Q+N150T, E133Q+N150R, E133Q+N150S, E133Q+ Q169A, E133Q+Q169R, E133Q+Q169K, E133Q+H172R, E133Q+Y174R, E133Q+Y174L, E133Q+Y174W, E133Q+ Y174F, E133Q+R176Q, E133Q+E177S, E133Q+E177Y, E133Q+N180R, E133Q+P183T, E133Q+P183G, E133Q+ Q184E, E133Q+Q184K, E133Q+R185G, E133Q+Y196W, E133Q+Y196F, E133Q+N200T, E133Q+S202R, E133Q+ Q203T, E133Q+R205K, E133Q+R210L, E133Q+R210G, E133Q+R210M, E133Q+N213V, E133Q+N213D, E133Q+ T228S, E133Q+N229D, E133Q+E234F, E133Q+E234Y, E133Q+A235K, E133Q+A235R, E133Q+S241C, E133Q+ Q243K, E133Q+Q243E, E133Q+R244K, E133Q+R244V, E133Q+A250G, E133Q+K254Y, E133Q+G257W, E133Q+ G257E, E133Q+G257A, E133Q+W260F, E133Q+W260Y, E133Q+W260L, E133Q+W260T, E133Q+Y262F, E133Q+ S266A, E133Q+D268N, E133Q+A270D, E133Q+N272M, E133Q+N272T, E133Q+N273E, E133Q+N273D, E133Q+ A276E, E133Q+A276W, E133Q+A276D, E133Q+N279D, E133Q+N279E, E133Q+T280L, E133Q+N283W, E133Q+ N283H, E133Q+Y286W, E133Q+Y286F, E133Q+L288I, E133Q+E290A, E133Q+L294P, E133Q+L294K, E133Q+ L294I, E133Q+L294R, E133Q+L294V, E133Q+L294H, E133Q+S295K, E133Q+S295V, E133Q+S295P, E133Q+ S295L, E133Q+S295R, E133Q+S295A, E133Q+S295N, E133Q+S295M, E133Q+S295I, E133Q+T296S, E133Q+ F298Y, D135P+A136P, D135P+D139A, D135P+D139R, D135P+K142M, D135P+K142V, D135P+K142S, D135P+ K142R, D135P+Q143R, D135P+N150T, D135P+N150R, D135P+N150S, D135P+Q169A, D135P+Q169R, D135P+ Q169K, D135P+H172R, D135P+Y174R, D135P+Y174L, D135P+Y174W, D135P+Y174F, D135P+R176Q, D135P+ E177S, D135P+E177Y, D135P+N180R, D135P+P183T, D135P+P183G, D135P+Q184E, D135P+Q184K, D135P+ R185G, D135P+Y196W, D135P+Y196F, D135P+N200T, D135P+S202R, D135P+Q203T, D135P+R205K, D135P+ R210L, D135P+R210G, D135P+R210M, D135P+N213V, D135P+N213D, D135P+T228S, D135P+N229D, D135P+ E234F, D135P+E234Y, D135P+A235K, D135P+A235R, D135P+S241C, D135P+Q243K, D135P+Q243E, D135P+ R244K, D135P+R244V, D135P+A250G, D135P+K254Y, D135P+G257W, D135P+G257E, D135P+G257A, D135P+ W260F, D135P+W260Y, D135P+W260L, D135P+W260T, D135P+Y262F, D135P+S266A, D135P+D268N, D135P+ A270D, D135P+N272M, D135P+N272T, D135P+N273E, D135P+N273D, D135P+A276E, D135P+A276W, D135P+ A276D, D135P+N279D, D135P+N279E, D135P+T280L, D135P+N283W, D135P+N283H, D135P+Y286W, D135P+ Y286F, D135P+L288I, D135P+E290A, D135P+L294P,

D135P+L294K, D135P+L294I, D135P+L294R, D135P+L294V, D135P+L294H, D135P+S295K, D135P+S295V, D135P+S295P, D135P+S295L, D135P+S295R, D135P+S295A, D135P+S295N, D135P+S295M, D135P+S295I, D135P+T296S, D135P+F298Y, A136P+D139A, A136P+D139R, A136P+K142M, A136P+K142V, A136P+K142S, A136P+K142R, A136P+Q143R, A136P+N150T, A136P+N150R, A136P+N150S, A136P+Q169A, A136P+Q169R, A136P+Q169K, A136P+H172R, A136P+Y174R, A136P+Y174L, A136P+Y174W, A136P+Y174F, A136P+R176Q, A136P+E177S, A136P+E177Y, A136P+N180R, A136P+P183T, A136P+P183G, A136P+Q184E, A136P+Q184K, A136P+R185G, A136P+Y196W, A136P+Y196F, A136P+N200T, A136P+S202R, A136P+Q203T, A136P+R205K, A136P+R210L, A136P+R210G, A136P+R210M, A136P+N213V, A136P+N213D, A136P+T228S, A136P+N229D, A136P+E234F, A136P+E234Y, A136P+A235K, A136P+A235R, A136P+S241C, A136P+Q243K, A136P+Q243E, A136P+R244K, A136P+R244V, A136P+A250G, A136P+K254Y, A136P+G257W, A136P+G257E, A136P+G257A, A136P+W260F, A136P+W260Y, A136P+W260L, A136P+W260T, A136P+Y262F, A136P+S266A, A136P+D268N, A136P+A270D, A136P+N272M, A136P+N272T, A136P+N273E, A136P+N273D, A136P+A276E, A136P+A276W, A136P+A276D, A136P+N279D, A136P+N279E, A136P+T280L, A136P+N283W, A136P+N283H, A136P+Y286W, A136P+Y286F, A136P+L288I, A136P+E290A, A136P+L294P, A136P+L294K, A136P+L294I, A136P+L294R, A136P+L294V, A136P+L294H, A136P+S295K, A136P+S295V, A136P+S295P, A136P+S295L, A136P+S295R, A136P+S295A, A136P+S295N, A136P+S295M, A136P+S295I, A136P+T296S, A136P+F298Y, D139A+K142M, D139A+K142V, D139A+K142S, D139A+K142R, D139A+Q143R, D139A+N150T, D139A+N150R, D139A+N150S, D139A+Q169A, D139A+Q169R, D139A+Q169K, D139A+H172R, D139A+Y174R, D139A+Y174L, D139A+Y174W, D139A+Y174F, D139A+R176Q, D139A+E177S, D139A+E177Y, D139A+N180R, D139A+P183T, D139A+P183G, D139A+Q184E, D139A+Q184K, D139A+R185G, D139A+Y196W, D139A+Y196F, D139A+N200T, D139A+S202R, D139A+Q203T, D139A+R205K, D139A+R210L, D139A+R210G, D139A+R210M, D139A+N213V, D139A+N213D, D139A+T228S, D139A+N229D, D139A+E234F, D139A+E234Y, D139A+A235K, D139A+A235R, D139A+S241C, D139A+Q243K, D139A+Q243E, D139A+R244K, D139A+R244V, D139A+A250G, D139A+K254Y, D139A+G257W, D139A+G257E, D139A+G257A, D139A+W260F, D139A+W260Y, D139A+W260L, D139A+W260T, D139A+Y262F, D139A+S266A, D139A+D268N, D139A+A270D, D139A+N272M, D139A+N272T, D139A+N273E, D139A+N273D, D139A+A276E, D139A+A276W, D139A+A276D, D139A+N279D, D139A+N279E, D139A+T280L, D139A+N283W, D139A+N283H, D139A+Y286W, D139A+Y286F, D139A+L288I, D139A+E290A, D139A+L294P, D139A+L294K, D139A+L294I, D139A+L294R, D139A+L294V, D139A+L294H, D139A+S295K, D139A+S295V, D139A+S295P, D139A+S295L, D139A+S295R, D139A+S295A, D139A+S295N, D139A+S295M, D139A+S295I, D139A+T296S, D139A+F298Y, D139R+K142M, D139R+K142V, D139R+K142S, D139R+K142R, D139R+Q143R, D139R+N150T, D139R+N150R, D139R+N150S, D139R+Q169A, D139R+Q169R, D139R+Q169K, D139R+H172R, D139R+Y174R, D139R+Y174L, D139R+Y174W, D139R+Y174F, D139R+R176Q, D139R+E177S, D139R+E177Y, D139R+N180R, D139R+P183T, D139R+P183G, D139R+Q184E, D139R+Q184K, D139R+R185G, D139R+Y196W, D139R+Y196F, D139R+N200T, D139R+S202R, D139R+Q203T, D139R+R205K, D139R+R210L, D139R+R210G, D139R+R210M, D139R+N213V, D139R+N213D, D139R+T228S, D139R+N229D, D139R+E234F, D139R+E234Y, D139R+A235K, D139R+A235R, D139R+S241C, D139R+Q243K, D139R+Q243E, D139R+R244K, D139R+R244V, D139R+A250G, D139R+K254Y, D139R+G257W, D139R+G257E, D139R+G257A, D139R+W260F, D139R+W260Y, D139R+W260L, D139R+W260T, D139R+Y262F, D139R+S266A, D139R+D268N, D139R+A270D, D139R+N272M, D139R+N272T, D139R+N273E, D139R+N273D, D139R+A276E, D139R+A276W, D139R+A276D, D139R+N279D, D139R+N279E, D139R+T280L, D139R+N283W, D139R+N283H, D139R+Y286W, D139R+Y286F, D139R+L288I, D139R+E290A, D139R+L294P, D139R+L294K, D139R+L294I, D139R+L294R, D139R+L294V, D139R+L294H, D139R+S295K, D139R+S295V, D139R+S295P, D139R+S295L, D139R+S295R, D139R+S295A, D139R+S295N, D139R+S295M, D139R+S295I, D139R+T296S, D139R+F298Y, K142M+Q143R, K142M+N150T, K142M+N150R, K142M+N150S, K142M+Q169A, K142M+Q169R, K142M+Q169K, K142M+H172R, K142M+Y174R, K142M+Y174L, K142M+Y174W, K142M+Y174F, K142M+R176Q, K142M+E177S, K142M+E177Y, K142M+N180R, K142M+P183T, K142M+P183G, K142M+Q184E, K142M+Q184K, K142M+R185G, K142M+Y196W, K142M+Y196F, K142M+N200T, K142M+S202R, K142M+Q203T, K142M+R205K, K142M+R210L, K142M+R210G, K142M+R210M, K142M+N213V, K142M+N213D, K142M+T228S, K142M+N229D, K142M+E234F, K142M+E234Y, K142M+A235K, K142M+A235R, K142M+S241C, K142M+Q243K, K142M+Q243E, K142M+R244K, K142M+R244V, K142M+A250G, K142M+K254Y, K142M+G257W, K142M+G257E, K142M+G257A, K142M+W260F, K142M+W260Y, K142M+W260L, K142M+W260T, K142M+Y262F, K142M+S266A, K142M+D268N, K142M+A270D, K142M+N272M, K142M+N272T, K142M+N273E, K142M+N273D, K142M+A276E, K142M+A276W, K142M+A276D, K142M+N279D, K142M+N279E, K142M+T280L, K142M+N283W, K142M+N283H, K142M+Y286W, K142M+Y286F, K142M+L288I, K142M+E290A, K142M+L294P, K142M+L294K, K142M+L294I, K142M+L294R, K142M+L294V, K142M+L294H, K142M+S295K, K142M+S295V, K142M+S295P, K142M+S295L, K142M+S295R, K142M+S295A, K142M+S295N, K142M+S295M, K142M+S295I, K142M+T296S, K142M+F298Y, K142V+Q143R, K142V+N150T, K142V+N150R, K142V+N150S, K142V+Q169A, K142V+Q169R, K142V+Q169K, K142V+H172R, K142V+Y174R, K142V+Y174L, K142V+Y174W, K142V+Y174F, K142V+R176Q, K142V+E177S, K142V+E177Y, K142V+N180R, K142V+P183T, K142V+P183G, K142V+Q184E, K142V+Q184K, K142V+R185G, K142V+Y196W, K142V+Y196F, K142V+N200T, K142V+S202R, K142V+Q203T, K142V+R205K, K142V+R210L, K142V+R210G, K142V+R210M, K142V+N213V, K142V+N213D, K142V+T228S, K142V+N229D, K142V+E234F, K142V+E234Y, K142V+A235K, K142V+A235R, K142V+S241C, K142V+Q243K, K142V+Q243E, K142V+R244K, K142V+R244V, K142V+A250G, K142V+K254Y, K142V+G257W, K142V+G257E, K142V+G257A, K142V+W260F, K142V+W260Y, K142V+W260L, K142V+W260T, K142V+Y262F, K142V+S266A, K142V+D268N, K142V+A270D, K142V+N272M, K142V+N272T, K142V+N273E, K142V+N273D, K142V+A276E, K142V+A276W, K142V+A276D, K142V+N279D, K142V+N279E,

K142V+T280L, K142V+N283W, K142V+N283H, K142V+Y286W, K142V+Y286F, K142V+L288I, K142V+E290A, K142V+L294P, K142V+L294K, K142V+L294I, K142V+L294R, K142V+L294V, K142V+L294H, K142V+S295K, K142V+S295V, K142V+S295P, K142V+S295L, K142V+S295R, K142V+S295A, K142V+S295N, K142V+S295M, K142V+S295I, K142V+T296S, K142V+F298Y, K142S+Q143R, K142S+N150T, K142S+N150R, K142S+N150S, K142S+Q169A, K142S+Q169R, K142S+Q169K, K142S+H172R, K142S+Y174R, K142S+Y174L, K142S+Y174W, K142S+Y174F, K142S+R176Q, K142S+E177S, K142S+E177Y, K142S+N180R, K142S+P183T, K142S+P183G, K142S+Q184E, K142S+Q184K, K142S+R185G, K142S+Y196W, K142S+Y196F, K142S+N200T, K142S+S202R, K142S+Q203T, K142S+R205K, K142S+R210L, K142S+R210G, K142S+R210M, K142S+N213V, K142S+N213D, K142S+T228S, K142S+N229D, K142S+E234F, K142S+E234Y, K142S+A235K, K142S+A235R, K142S+S241C, K142S+Q243K, K142S+Q243E, K142S+R244K, K142S+R244V, K142S+A250G, K142S+K254Y, K142S+G257W, K142S+G257E, K142S+G257A, K142S+W260F, K142S+W260Y, K142S+W260L, K142S+W260T, K142S+Y262F, K142S+S266A, K142S+D268N, K142S+A270D, K142S+N272M, K142S+N272T, K142S+N273E, K142S+N273D, K142S+A276E, K142S+A276W, K142S+A276D, K142S+N279D, K142S+N279E, K142S+T280L, K142S+N283W, K142S+N283H, K142S+Y286W, K142S+Y286F, K142S+L288I, K142S+E290A, K142S+L294P, K142S+L294K, K142S+L294I, K142S+L294R, K142S+L294V, K142S+L294H, K142S+S295K, K142S+S295V, K142S+S295P, K142S+S295L, K142S+S295R, K142S+S295A, K142S+S295N, K142S+S295M, K142S+S295I, K142S+T296S, K142S+F298Y, K142R+Q143R, K142R+N150T, K142R+N150R, K142R+N150S, K142R+Q169A, K142R+Q169R, K142R+Q169K, K142R+H172R, K142R+Y174R, K142R+Y174L, K142R+Y174W, K142R+Y174F, K142R+R176Q, K142R+E177S, K142R+E177Y, K142R+N180R, K142R+P183T, K142R+P183G, K142R+Q184E, K142R+Q184K, K142R+R185G, K142R+Y196W, K142R+Y196F, K142R+N200T, K142R+S202R, K142R+Q203T, K142R+R205K, K142R+R210L, K142R+R210G, K142R+R210M, K142R+N213V, K142R+N213D, K142R+T228S, K142R+N229D, K142R+E234F, K142R+E234Y, K142R+A235K, K142R+A235R, K142R+S241C, K142R+Q243K, K142R+Q243E, K142R+R244K, K142R+R244V, K142R+A250G, K142R+K254Y, K142R+G257W, K142R+G257E, K142R+G257A, K142R+W260F, K142R+W260Y, K142R+W260L, K142R+W260T, K142R+Y262F, K142R+S266A, K142R+D268N, K142R+A270D, K142R+N272M, K142R+N272T, K142R+N273E, K142R+N273D, K142R+A276E, K142R+A276W, K142R+A276D, K142R+N279D, K142R+N279E, K142R+T280L, K142R+N283W, K142R+N283H, K142R+Y286W, K142R+Y286F, K142R+L288I, K142R+E290A, K142R+L294P, K142R+L294K, K142R+L294I, K142R+L294R, K142R+L294V, K142R+L294H, K142R+S295K, K142R+S295V, K142R+S295P, K142R+S295L, K142R+S295R, K142R+S295A, K142R+S295N, K142R+S295M, K142R+S295I, K142R+T296S, K142R+F298Y, Q143R+N150T, Q143R+N150R, Q143R+N150S, Q143R+Q169A, Q143R+Q169R, Q143R+Q169K, Q143R+H172R, Q143R+Y174R, Q143R+Y174L, Q143R+Y174W, Q143R+Y174F, Q143R+R176Q, Q143R+E177S, Q143R+E177Y, Q143R+N180R, Q143R+P183T, Q143R+P183G, Q143R+Q184E, Q143R+Q184K, Q143R+R185G, Q143R+Y196W, Q143R+Y196F, Q143R+N200T, Q143R+S202R, Q143R+Q203T, Q143R+R205K, Q143R+R210L, Q143R+R210G, Q143R+R210M, Q143R+N213V, Q143R+N213D, Q143R+T228S, Q143R+N229D, Q143R+E234F, Q143R+E234Y, Q143R+A235K, Q143R+A235R, Q143R+S241C, Q143R+Q243K, Q143R+Q243E, Q143R+R244K, Q143R+R244V, Q143R+A250G, Q143R+K254Y, Q143R+G257W, Q143R+G257E, Q143R+G257A, Q143R+W260F, Q143R+W260Y, Q143R+W260L, Q143R+W260T, Q143R+Y262F, Q143R+S266A, Q143R+D268N, Q143R+A270D, Q143R+N272M, Q143R+N272T, Q143R+N273E, Q143R+N273D, Q143R+A276E, Q143R+A276W, Q143R+A276D, Q143R+N279D, Q143R+N279E, Q143R+T280L, Q143R+N283W, Q143R+N283H, Q143R+Y286W, Q143R+Y286F, Q143R+L288I, Q143R+E290A, Q143R+L294P, Q143R+L294K, Q143R+L294I, Q143R+L294R, Q143R+L294V, Q143R+L294H, Q143R+S295K, Q143R+S295V, Q143R+S295P, Q143R+S295L, Q143R+S295R, Q143R+S295A, Q143R+S295N, Q143R+S295M, Q143R+S295I, Q143R+T296S, Q143R+F298Y, N150T+Q169A, N150T+Q169R, N150T+Q169K, N150T+H172R, N150T+Y174R, N150T+Y174L, N150T+Y174W, N150T+Y174F, N150T+R176Q, N150T+E177S, N150T+E177Y, N150T+N180R, N150T+P183T, N150T+P183G, N150T+Q184E, N150T+Q184K, N150T+R185G, N150T+Y196W, N150T+Y196F, N150T+N200T, N150T+S202R, N150T+Q203T, N150T+R205K, N150T+R210L, N150T+R210G, N150T+R210M, N150T+N213V, N150T+N213D, N150T+T228S, N150T+N229D, N150T+E234F, N150T+E234Y, N150T+A235K, N150T+A235R, N150T+S241C, N150T+Q243K, N150T+Q243E, N150T+R244K, N150T+R244V, N150T+A250G, N150T+K254Y, N150T+G257W, N150T+G257E, N150T+G257A, N150T+W260F, N150T+W260Y, N150T+W260L, N150T+W260T, N150T+Y262F, N150T+S266A, N150T+D268N, N150T+A270D, N150T+N272M, N150T+N272T, N150T+N273E, N150T+N273D, N150T+A276E, N150T+A276W, N150T+A276D, N150T+N279D, N150T+N279E, N150T+T280L, N150T+N283W, N150T+N283H, N150T+Y286W, N150T+Y286F, N150T+L288I, N150T+E290A, N150T+L294P, N150T+L294K, N150T+L294I, N150T+L294R, N150T+L294V, N150T+L294H, N150T+S295K, N150T+S295V, N150T+S295P, N150T+S295L, N150T+S295R, N150T+S295A, N150T+S295N, N150T+S295M, N150T+S295I, N150T+T296S, N150T+F298Y, N150R+Q169A, N150R+Q169R, N150R+Q169K, N150R+H172R, N150R+Y174R, N150R+Y174L, N150R+Y174W, N150R+Y174F, N150R+R176Q, N150R+E177S, N150R+E177Y, N150R+N180R, N150R+P183T, N150R+P183G, N150R+Q184E, N150R+Q184K, N150R+R185G, N150R+Y196W, N150R+Y196F, N150R+N200T, N150R+S202R, N150R+Q203T, N150R+R205K, N150R+R210L, N150R+R210G, N150R+R210M, N150R+N213V, N150R+N213D, N150R+T228S, N150R+N229D, N150R+E234F, N150R+E234Y, N150R+A235K, N150R+A235R, N150R+S241C, N150R+Q243K, N150R+Q243E, N150R+R244K, N150R+R244V, N150R+A250G, N150R+K254Y, N150R+G257W, N150R+G257E, N150R+G257A, N150R+W260F, N150R+W260Y, N150R+W260L, N150R+W260T, N150R+Y262F, N150R+S266A, N150R+D268N, N150R+A270D, N150R+N272M, N150R+N272T, N150R+N273E, N150R+N273D, N150R+A276E, N150R+A276W, N150R+A276D, N150R+N279D, N150R+N279E, N150R+T280L, N150R+N283W, N150R+N283H, N150R+Y286W, N150R+Y286F, N150R+L288I, N150R+E290A, N150R+L294P, N150R+L294K, N150R+L294I, N150R+L294R, N150R+L294V, N150R+L294H, N150R+S295K, N150R+S295V, N150R+S295P, N150R+S295L, N150R+S295R, N150R+S295A, N150R+S295N, N150R+S295M, N150R+S295I, N150R+T296S, N150R+F298Y, N150S+Q169A, N150S+Q169R, N150S+Q169K, N150S+H172R, N150S+Y174R, N150S+Y174L, N150S+Y174W, N150S+

Y174F, N150S+R176Q, N150S+E177S, N150S+E177Y, N150S+N180R, N150S+P183T, N150S+P183G, N150S+Q184E, N150S+Q184K, N150S+R185G, N150S+Y196W, N150S+Y196F, N150S+N200T, N150S+S202R, N150S+Q203T, N150S+R205K, N150S+R210L, N150S+R210G, N150S+R210M, N150S+N213V, N150S+N213D, N150S+T228S, N150S+N229D, N150S+E234F, N150S+E234Y, N150S+A235K, N150S+A235R, N150S+S241C, N150S+Q243K, N150S+Q243E, N150S+R244K, N150S+R244V, N150S+A250G, N150S+K254Y, N150S+G257W, N150S+G257E, N150S+G257A, N150S+W260F, N150S+W260Y, N150S+W260L, N150S+W260T, N150S+Y262F, N150S+S266A, N150S+D268N, N150S+A270D, N150S+N272M, N150S+N272T, N150S+N273E, N150S+N273D, N150S+A276E, N150S+A276W, N150S+A276D, N150S+N279D, N150S+N279E, N150S+T280L, N150S+N283W, N150S+N283H, N150S+Y286W, N150S+Y286F, N150S+L288I, N150S+E290A, N150S+L294P, N150S+L294K, N150S+L294I, N150S+L294R, N150S+L294V, N150S+L294H, N150S+S295K, N150S+S295V, N150S+S295P, N150S+S295L, N150S+S295R, N150S+S295A, N150S+S295N, N150S+S295M, N150S+S295I, N150S+T296S, N150S+F298Y, Q169A+H172R, Q169A+Y174R, Q169A+Y174L, Q169A+Y174W, Q169A+Y174F, Q169A+R176Q, Q169A+E177S, Q169A+E177Y, Q169A+N180R, Q169A+P183T, Q169A+P183G, Q169A+Q184E, Q169A+Q184K, Q169A+R185G, Q169A+Y196W, Q169A+Y196F, Q169A+N200T, Q169A+S202R, Q169A+Q203T, Q169A+R205K, Q169A+R210L, Q169A+R210G, Q169A+R210M, Q169A+N213V, Q169A+N213D, Q169A+T228S, Q169A+N229D, Q169A+E234F, Q169A+E234Y, Q169A+A235K, Q169A+A235R, Q169A+S241C, Q169A+Q243K, Q169A+Q243E, Q169A+R244K, Q169A+R244V, Q169A+A250G, Q169A+K254Y, Q169A+G257W, Q169A+G257E, Q169A+G257A, Q169A+W260F, Q169A+W260Y, Q169A+W260L, Q169A+W260T, Q169A+Y262F, Q169A+S266A, Q169A+D268N, Q169A+A270D, Q169A+N272M, Q169A+N272T, Q169A+N273E, Q169A+N273D, Q169A+A276E, Q169A+A276W, Q169A+A276D, Q169A+N279D, Q169A+N279E, Q169A+T280L, Q169A+N283W, Q169A+N283H, Q169A+Y286W, Q169A+Y286F, Q169A+L288I, Q169A+E290A, Q169A+L294P, Q169A+L294K, Q169A+L294I, Q169A+L294R, Q169A+L294V, Q169A+L294H, Q169A+S295K, Q169A+S295V, Q169A+S295P, Q169A+S295L, Q169A+S295R, Q169A+S295A, Q169A+S295N, Q169A+S295M, Q169A+S295I, Q169A+T296S, Q169A+F298Y, Q169R+H172R, Q169R+Y174R, Q169R+Y174L, Q169R+Y174W, Q169R+Y174F, Q169R+R176Q, Q169R+E177S, Q169R+E177Y, Q169R+N180R, Q169R+P183T, Q169R+P183G, Q169R+Q184E, Q169R+Q184K, Q169R+R185G, Q169R+Y196W, Q169R+Y196F, Q169R+N200T, Q169R+S202R, Q169R+Q203T, Q169R+R205K, Q169R+R210L, Q169R+R210G, Q169R+R210M, Q169R+N213V, Q169R+N213D, Q169R+T228S, Q169R+N229D, Q169R+E234F, Q169R+E234Y, Q169R+A235K, Q169R+A235R, Q169R+S241C, Q169R+Q243K, Q169R+Q243E, Q169R+R244K, Q169R+R244V, Q169R+A250G, Q169R+K254Y, Q169R+G257W, Q169R+G257E, Q169R+G257A, Q169R+W260F, Q169R+W260Y, Q169R+W260L, Q169R+W260T, Q169R+Y262F, Q169R+S266A, Q169R+D268N, Q169R+A270D, Q169R+N272M, Q169R+N272T, Q169R+N273E, Q169R+N273D, Q169R+A276E, Q169R+A276W, Q169R+A276D, Q169R+N279D, Q169R+N279E, Q169R+T280L, Q169R+N283W, Q169R+N283H, Q169R+Y286W, Q169R+Y286F, Q169R+L288I, Q169R+E290A, Q169R+L294P, Q169R+L294K, Q169R+L294I, Q169R+L294R, Q169R+L294V, Q169R+L294H, Q169R+S295K, Q169R+S295V, Q169R+S295P, Q169R+S295L, Q169R+S295R, Q169R+S295A, Q169R+S295N, Q169R+S295M, Q169R+S295I, Q169R+T296S, Q169R+F298Y, Q169K+H172R, Q169K+Y174R, Q169K+Y174L, Q169K+Y174W, Q169K+Y174F, Q169K+R176Q, Q169K+E177S, Q169K+E177Y, Q169K+N180R, Q169K+P183T, Q169K+P183G, Q169K+Q184E, Q169K+Q184K, Q169K+R185G, Q169K+Y196W, Q169K+Y196F, Q169K+N200T, Q169K+S202R, Q169K+Q203T, Q169K+R205K, Q169K+R210L, Q169K+R210G, Q169K+R210M, Q169K+N213V, Q169K+N213D, Q169K+T228S, Q169K+N229D, Q169K+E234F, Q169K+E234Y, Q169K+A235K, Q169K+A235R, Q169K+S241C, Q169K+Q243K, Q169K+Q243E, Q169K+R244K, Q169K+R244V, Q169K+A250G, Q169K+K254Y, Q169K+G257W, Q169K+G257E, Q169K+G257A, Q169K+W260F, Q169K+W260Y, Q169K+W260L, Q169K+W260T, Q169K+Y262F, Q169K+S266A, Q169K+D268N, Q169K+A270D, Q169K+N272M, Q169K+N272T, Q169K+N273E, Q169K+N273D, Q169K+A276E, Q169K+A276W, Q169K+A276D, Q169K+N279D, Q169K+N279E, Q169K+T280L, Q169K+N283W, Q169K+N283H, Q169K+Y286W, Q169K+Y286F, Q169K+L288I, Q169K+E290A, Q169K+L294P, Q169K+L294K, Q169K+L294I, Q169K+L294R, Q169K+L294V, Q169K+L294H, Q169K+S295K, Q169K+S295V, Q169K+S295P, Q169K+S295L, Q169K+S295R, Q169K+S295A, Q169K+S295N, Q169K+S295M, Q169K+S295I, Q169K+T296S, Q169K+F298Y, H172R+Y174R, H172R+Y174L, H172R+Y174W, H172R+Y174F, H172R+R176Q, H172R+E177S, H172R+E177Y, H172R+N180R, H172R+P183T, H172R+P183G, H172R+Q184E, H172R+Q184K, H172R+R185G, H172R+Y196W, H172R+Y196F, H172R+N200T, H172R+S202R, H172R+Q203T, H172R+R205K, H172R+R210L, H172R+R210G, H172R+R210M, H172R+N213V, H172R+N213D, H172R+T228S, H172R+N229D, H172R+E234F, H172R+E234Y, H172R+A235K, H172R+A235R, H172R+S241C, H172R+Q243K, H172R+Q243E, H172R+R244K, H172R+R244V, H172R+A250G, H172R+K254Y, H172R+G257W, H172R+G257E, H172R+G257A, H172R+W260F, H172R+W260Y, H172R+W260L, H172R+W260T, H172R+Y262F, H172R+S266A, H172R+D268N, H172R+A270D, H172R+N272M, H172R+N272T, H172R+N273E, H172R+N273D, H172R+A276E, H172R+A276W, H172R+A276D, H172R+N279D, H172R+N279E, H172R+T280L, H172R+N283W, H172R+N283H, H172R+Y286W, H172R+Y286F, H172R+L288I, H172R+E290A, H172R+L294P, H172R+L294K, H172R+L294I, H172R+L294R, H172R+L294V, H172R+L294H, H172R+S295K, H172R+S295V, H172R+S295P, H172R+S295L, H172R+S295R, H172R+S295A, H172R+S295N, H172R+S295M, H172R+S295I, H172R+T296S, H172R+F298Y, Y174R+R176Q, Y174R+E177S, Y174R+E177Y, Y174R+N180R, Y174R+P183T, Y174R+P183G, Y174R+Q184E, Y174R+Q184K, Y174R+R185G, Y174R+Y196W, Y174R+Y196F, Y174R+N200T, Y174R+S202R, Y174R+Q203T, Y174R+R205K, Y174R+R210L, Y174R+R210G, Y174R+R210M, Y174R+N213V, Y174R+N213D, Y174R+T228S, Y174R+N229D, Y174R+E234F, Y174R+E234Y, Y174R+A235K, Y174R+A235R, Y174R+S241C, Y174R+Q243K, Y174R+Q243E, Y174R+R244K, Y174R+R244V, Y174R+A250G, Y174R+K254Y, Y174R+G257W, Y174R+G257E, Y174R+G257A, Y174R+W260F, Y174R+W260Y, Y174R+W260L, Y174R+W260T, Y174R+Y262F, Y174R+S266A, Y174R+D268N, Y174R+A270D, Y174R+N272M, Y174R+N272T, Y174R+N273E, Y174R+N273D, Y174R+A276E, Y174R+A276W, Y174R+A276D, Y174R+N279D, Y174R+N279E, Y174R+T280L, Y174R+N283W, Y174R+N283H, Y174R+Y286W, Y174R+Y286F, Y174R+L288I,

Y174R+E290A, Y174R+L294P, Y174R+L294K, Y174R+L294I, Y174R+L294R, Y174R+L294V, Y174R+L294H, Y174R+S295K, Y174R+S295V, Y174R+S295P, Y174R+S295L, Y174R+S295R, Y174R+S295A, Y174R+S295N, Y174R+S295M, Y174R+S295I, Y174R+T296S, Y174R+F298Y, Y174L+R176Q, Y174L+E177S, Y174L+E177Y, Y174L+N180R, Y174L+P183T, Y174L+P183G, Y174L+Q184E, Y174L+Q184K, Y174L+R185G, Y174L+Y196W, Y174L+Y196F, Y174L+N200T, Y174L+S202R, Y174L+Q203T, Y174L+R205K, Y174L+R210L, Y174L+R210G, Y174L+R210M, Y174L+N213V, Y174L+N213D, Y174L+T228S, Y174L+N229D, Y174L+E234F, Y174L+E234Y, Y174L+A235K, Y174L+A235R, Y174L+S241C, Y174L+Q243K, Y174L+Q243E, Y174L+R244K, Y174L+R244V, Y174L+A250G, Y174L+K254Y, Y174L+G257W, Y174L+G257E, Y174L+G257A, Y174L+W260F, Y174L+W260Y, Y174L+W260L, Y174L+W260T, Y174L+Y262F, Y174L+S266A, Y174L+D268N, Y174L+A270D, Y174L+N272M, Y174L+N272T, Y174L+N273E, Y174L+N273D, Y174L+A276E, Y174L+A276W, Y174L+A276D, Y174L+N279D, Y174L+N279E, Y174L+T280L, Y174L+N283W, Y174L+N283H, Y174L+Y286W, Y174L+Y286F, Y174L+L288I, Y174L+E290A, Y174L+L294P, Y174L+L294K, Y174L+L294I, Y174L+L294R, Y174L+L294V, Y174L+L294H, Y174L+S295K, Y174L+S295V, Y174L+S295P, Y174L+S295L, Y174L+S295R, Y174L+S295A, Y174L+S295N, Y174L+S295M, Y174L+S295I, Y174L+T296S, Y174L+F298Y, Y174W+R176Q, Y174W+E177S, Y174W+E177Y, Y174W+N180R, Y174W+P183T, Y174W+P183G, Y174W+Q184E, Y174W+Q184K, Y174W+R185G, Y174W+Y196W, Y174W+Y196F, Y174W+N200T, Y174W+S202R, Y174W+Q203T, Y174W+R205K, Y174W+R210L, Y174W+R210G, Y174W+R210M, Y174W+N213V, Y174W+N213D, Y174W+T228S, Y174W+N229D, Y174W+E234F, Y174W+E234Y, Y174W+A235K, Y174W+A235R, Y174W+S241C, Y174W+Q243K, Y174W+Q243E, Y174W+R244K, Y174W+R244V, Y174W+A250G, Y174W+K254Y, Y174W+G257W, Y174W+G257E, Y174W+G257A, Y174W+W260F, Y174W+W260Y, Y174W+W260L, Y174W+W260T, Y174W+Y262F, Y174W+S266A, Y174W+D268N, Y174W+A270D, Y174W+N272M, Y174W+N272T, Y174W+N273E, Y174W+N273D, Y174W+A276E, Y174W+A276W, Y174W+A276D, Y174W+N279D, Y174W+N279E, Y174W+T280L, Y174W+N283W, Y174W+N283H, Y174W+Y286W, Y174W+Y286F, Y174W+L288I, Y174W+E290A, Y174W+L294P, Y174W+L294K, Y174W+L294I, Y174W+L294R, Y174W+L294V, Y174W+L294H, Y174W+S295K, Y174W+S295V, Y174W+S295P, Y174W+S295L, Y174W+S295R, Y174W+S295A, Y174W+S295N, Y174W+S295M, Y174W+S295I, Y174W+T296S, Y174W+F298Y, Y174F+R176Q, Y174F+E177S, Y174F+E177Y, Y174F+N180R, Y174F+P183T, Y174F+P183G, Y174F+Q184E, Y174F+Q184K, Y174F+R185G, Y174F+Y196W, Y174F+Y196F, Y174F+N200T, Y174F+S202R, Y174F+Q203T, Y174F+R205K, Y174F+R210L, Y174F+R210G, Y174F+R210M, Y174F+N213V, Y174F+N213D, Y174F+T228S, Y174F+N229D, Y174F+E234F, Y174F+E234Y, Y174F+A235K, Y174F+A235R, Y174F+S241C, Y174F+Q243K, Y174F+Q243E, Y174F+R244K, Y174F+R244V, Y174F+A250G, Y174F+K254Y, Y174F+G257W, Y174F+G257E, Y174F+G257A, Y174F+W260F, Y174F+W260Y, Y174F+W260L, Y174F+W260T, Y174F+Y262F, Y174F+S266A, Y174F+D268N, Y174F+A270D, Y174F+N272M, Y174F+N272T, Y174F+N273E, Y174F+N273D, Y174F+A276E, Y174F+A276W, Y174F+A276D, Y174F+N279D, Y174F+N279E, Y174F+T280L, Y174F+N283W, Y174F+N283H, Y174F+Y286W, Y174F+Y286F, Y174F+L288I, Y174F+E290A, Y174F+L294P, Y174F+L294K, Y174F+L294I, Y174F+L294R, Y174F+L294V, Y174F+L294H, Y174F+S295K, Y174F+S295V, Y174F+S295P, Y174F+S295L, Y174F+S295R, Y174F+S295A, Y174F+S295N, Y174F+S295M, Y174F+S295I, Y174F+T296S, Y174F+F298Y, R176Q+E177S, R176Q+E177Y, R176Q+N180R, R176Q+P183T, R176Q+P183G, R176Q+Q184E, R176Q+Q184K, R176Q+R185G, R176Q+Y196W, R176Q+Y196F, R176Q+N200T, R176Q+S202R, R176Q+Q203T, R176Q+R205K, R176Q+R210L, R176Q+R210G, R176Q+R210M, R176Q+N213V, R176Q+N213D, R176Q+T228S, R176Q+N229D, R176Q+E234F, R176Q+E234Y, R176Q+A235K, R176Q+A235R, R176Q+S241C, R176Q+Q243K, R176Q+Q243E, R176Q+R244K, R176Q+R244V, R176Q+A250G, R176Q+K254Y, R176Q+G257W, R176Q+G257E, R176Q+G257A, R176Q+W260F, R176Q+W260Y, R176Q+W260L, R176Q+W260T, R176Q+Y262F, R176Q+S266A, R176Q+D268N, R176Q+A270D, R176Q+N272M, R176Q+N272T, R176Q+N273E, R176Q+N273D, R176Q+A276E, R176Q+A276W, R176Q+A276D, R176Q+N279D, R176Q+N279E, R176Q+T280L, R176Q+N283W, R176Q+N283H, R176Q+Y286W, R176Q+Y286F, R176Q+L288I, R176Q+E290A, R176Q+L294P, R176Q+L294K, R176Q+L294I, R176Q+L294R, R176Q+L294V, R176Q+L294H, R176Q+S295K, R176Q+S295V, R176Q+S295P, R176Q+S295L, R176Q+S295R, R176Q+S295A, R176Q+S295N, R176Q+S295M, R176Q+S295I, R176Q+T296S, R176Q+F298Y, E177S+N180R, E177S+P183T, E177S+P183G, E177S+Q184E, E177S+Q184K, E177S+R185G, E177S+Y196W, E177S+Y196F, E177S+N200T, E177S+S202R, E177S+Q203T, E177S+R205K, E177S+R210L, E177S+R210G, E177S+R210M, E177S+N213V, E177S+N213D, E177S+T228S, E177S+N229D, E177S+E234F, E177S+E234Y, E177S+A235K, E177S+A235R, E177S+S241C, E177S+Q243K, E177S+Q243E, E177S+R244K, E177S+R244V, E177S+A250G, E177S+K254Y, E177S+G257W, E177S+G257E, E177S+G257A, E177S+W260F, E177S+W260Y, E177S+W260L, E177S+W260T, E177S+Y262F, E177S+S266A, E177S+D268N, E177S+A270D, E177S+N272M, E177S+N272T, E177S+N273E, E177S+N273D, E177S+A276E, E177S+A276W, E177S+A276D, E177S+N279D, E177S+N279E, E177S+T280L, E177S+N283W, E177S+N283H, E177S+Y286W, E177S+Y286F, E177S+L288I, E177S+E290A, E177S+L294P, E177S+L294K, E177S+L294I, E177S+L294R, E177S+L294V, E177S+L294H, E177S+S295K, E177S+S295V, E177S+S295P, E177S+S295L, E177S+S295R, E177S+S295A, E177S+S295N, E177S+S295M, E177S+S295I, E177S+T296S, E177S+F298Y, E177Y+N180R, E177Y+P183T, E177Y+P183G, E177Y+Q184E, E177Y+Q184K, E177Y+R185G, E177Y+Y196W, E177Y+Y196F, E177Y+N200T, E177Y+S202R, E177Y+Q203T, E177Y+R205K, E177Y+R210L, E177Y+R210G, E177Y+R210M, E177Y+N213V, E177Y+N213D, E177Y+T228S, E177Y+N229D, E177Y+E234F, E177Y+E234Y, E177Y+A235K, E177Y+A235R, E177Y+S241C, E177Y+Q243K, E177Y+Q243E, E177Y+R244K, E177Y+R244V, E177Y+A250G, E177Y+K254Y, E177Y+G257W, E177Y+G257E, E177Y+G257A, E177Y+W260F, E177Y+W260Y, E177Y+W260L, E177Y+W260T, E177Y+Y262F, E177Y+S266A, E177Y+D268N, E177Y+A270D, E177Y+N272M, E177Y+N272T, E177Y+N273E, E177Y+N273D, E177Y+A276E, E177Y+A276D, E177Y+N279D, E177Y+N279E, E177Y+T280L, E177Y+N283W, E177Y+N283H, E177Y+Y286W, E177Y+Y286F, E177Y+L288I, E177Y+E290A, E177Y+L294P, E177Y+L294K, E177Y+L294I,

E177Y+L294R, E177Y+L294V, E177Y+L294H, E177Y+ S295K, E177Y+S295V, E177Y+S295P, E177Y+S295L, E177Y+S295R, E177Y+S295A, E177Y+S295N, E177Y+ S295M, E177Y+S295I, E177Y+T296S, E177Y+F298Y, N180R+P183T, N180R+P183G, N180R+Q184E, N180R+ Q184K, N180R+R185G, N180R+Y196W, N180R+Y196F, N180R+N200T, N180R+S202R, N180R+Q203T, N180R+ R205K, N180R+R210L, N180R+R210G, N180R+R210M, N180R+N213V, N180R+N213D, N180R+T228S, N180R+ N229D, N180R+E234F, N180R+E234Y, N180R+A235K, N180R+A235R, N180R+S241C, N180R+Q243K, N180R+ Q243E, N180R+R244K, N180R+R244V, N180R+A250G, N180R+K254Y, N180R+G257W, N180R+G257E, N180R+ G257A, N180R+W260F, N180R+W260Y, N180R+W260L, N180R+W260T, N180R+Y262F, N180R+S266A, N180R+ D268N, N180R+A270D, N180R+N272M, N180R+N272T, N180R+N273E, N180R+N273D, N180R+A276E, N180R+ A276W, N180R+A276D, N180R+N279D, N180R+N279E, N180R+T280L, N180R+N283W, N180R+N283H, N180R+ Y286W, N180R+Y286F, N180R+L288I, N180R+E290A, N180R+L294P, N180R+L294K, N180R+L294I, N180R+ L294R, N180R+L294V, N180R+L294H, N180R+S295K, N180R+S295V, N180R+S295P, N180R+S295L, N180R+ S295R, N180R+S295A, N180R+S295N, N180R+S295M, N180R+S295I, N180R+T296S, N180R+F298Y, P183T+ Q184E, P183T+Q184K, P183T+R185G, P183T+Y196W, P183T+Y196F, P183T+N200T, P183T+S202R, P183T+ Q203T, P183T+R205K, P183T+R210L, P183T+R210G, P183T+R210M, P183T+N213V, P183T+N213D, P183T+ T228S, P183T+N229D, P183T+E234F, P183T+E234Y, P183T+A235K, P183T+A235R, P183T+S241C, P183T+ Q243K, P183T+Q243E, P183T+R244K, P183T+R244V, P183T+A250G, P183T+K254Y, P183T+G257W, P183T+ G257E, P183T+G257A, P183T+W260F, P183T+W260Y, P183T+W260L, P183T+W260T, P183T+Y262F, P183T+ S266A, P183T+D268N, P183T+A270D, P183T+N272M, P183T+N272T, P183T+N273E, P183T+N273D, P183T+ A276E, P183T+A276W, P183T+A276D, P183T+N279D, P183T+N279E, P183T+T280L, P183T+N283W, P183T+ N283H, P183T+Y286W, P183T+Y286F, P183T+L288I, P183T+E290A, P183T+L294P, P183T+L294K, P183T+ L294I, P183T+L294R, P183T+L294V, P183T+L294H, P183T+S295K, P183T+S295V, P183T+S295P, P183T+ S295L, P183T+S295R, P183T+S295A, P183T+S295N, P183T+S295M, P183T+S295I, P183T+T296S, P183T+ F298Y, P183G+Q184E, P183G+Q184K, P183G+R185G, P183G+Y196W, P183G+Y196F, P183G+N200T, P183G+ S202R, P183G+Q203T, P183G+R205K, P183G+R210L, P183G+R210G, P183G+R210M, P183G+N213V, P183G+ N213D, P183G+T228S, P183G+N229D, P183G+E234F, P183G+E234Y, P183G+A235K, P183G+A235R, P183G+ S241C, P183G+Q243K, P183G+Q243E, P183G+R244K, P183G+R244V, P183G+A250G, P183G+K254Y, P183G+ G257W, P183G+G257E, P183G+G257A, P183G+W260F, P183G+W260Y, P183G+W260L, P183G+W260T, P183G+ Y262F, P183G+S266A, P183G+D268N, P183G+A270D, P183G+N272M, P183G+N272T, P183G+N273E, P183G+ N273D, P183G+A276E, P183G+A276W, P183G+A276D, P183G+N279D, P183G+N279E, P183G+T280L, P183G+ N283W, P183G+N283H, P183G+Y286W, P183G+Y286F, P183G+L288I, P183G+E290A, P183G+L294P, P183G+ L294K, P183G+L294I, P183G+L294R, P183G+L294V, P183G+L294H, P183G+S295K, P183G+S295V, P183G+ S295P, P183G+S295L, P183G+S295R, P183G+S295A, P183G+S295N, P183G+S295M, P183G+S295I, P183G+ T296S, P183G+F298Y, Q184E+R185G, Q184E+Y196W, Q184E+Y196F, Q184E+N200T, Q184E+S202R, Q184E+ Q203T, Q184E+R205K, Q184E+R210L, Q184E+R210G, Q184E+R210M, Q184E+N213V, Q184E+N213D, Q184E+ T228S, Q184E+N229D, Q184E+E234F, Q184E+E234Y, Q184E+A235K, Q184E+A235R, Q184E+S241C, Q184E+ Q243K, Q184E+Q243E, Q184E+R244K, Q184E+R244V, Q184E+A250G, Q184E+K254Y, Q184E+G257W, Q184E+ G257E, Q184E+G257A, Q184E+W260F, Q184E+W260Y, Q184E+W260L, Q184E+W260T, Q184E+Y262F, Q184E+ S266A, Q184E+D268N, Q184E+A270D, Q184E+N272M, Q184E+N272T, Q184E+N273E, Q184E+N273D, Q184E+ A276E, Q184E+A276W, Q184E+A276D, Q184E+N279D, Q184E+N279E, Q184E+T280L, Q184E+N283W, Q184E+ N283H, Q184E+Y286W, Q184E+Y286F, Q184E+L288I, Q184E+E290A, Q184E+L294P, Q184E+L294K, Q184E+ L294I, Q184E+L294R, Q184E+L294V, Q184E+L294H, Q184E+S295K, Q184E+S295V, Q184E+S295P, Q184E+ S295L, Q184E+S295R, Q184E+S295A, Q184E+S295N, Q184E+S295M, Q184E+S295I, Q184E+T296S, Q184E+ F298Y, Q184K+R185G, Q184K+Y196W, Q184K+Y196F, Q184K+N200T, Q184K+S202R, Q184K+Q203T, Q184K+ R205K, Q184K+R210L, Q184K+R210G, Q184K+R210M, Q184K+N213V, Q184K+N213D, Q184K+T228S, Q184K+ N229D, Q184K+E234F, Q184K+E234Y, Q184K+A235K, Q184K+A235R, Q184K+S241C, Q184K+Q243K, Q184K+ Q243E, Q184K+R244K, Q184K+R244V, Q184K+A250G, Q184K+K254Y, Q184K+G257W, Q184K+G257E, Q184K+G257A, Q184K+W260F, Q184K+W260Y, Q184K+W260L, Q184K+W260T, Q184K+Y262F, Q184K+S266A, Q184K+D268N, Q184K+A270D, Q184K+ N272M, Q184K+N272T, Q184K+N273E, Q184K+N273D, Q184K+A276E, Q184K+A276W, Q184K+A276D, Q184K+N279D, Q184K+N279E, Q184K+T280L, Q184K+ N283W, Q184K+N283H, Q184K+Y286W, Q184K+Y286F, Q184K+L288I, Q184K+E290A, Q184K+L294P, Q184K+ L294K, Q184K+L294I, Q184K+L294R, Q184K+L294V, Q184K+L294H, Q184K+S295K, Q184K+S295V, Q184K+ S295P, Q184K+S295L, Q184K+S295R, Q184K+S295A, Q184K+S295N, Q184K+S295M, Q184K+S295I, Q184K+ T296S, Q184K+F298Y, R185G+Y196W, R185G+Y196F, R185G+N200T, R185G+S202R, R185G+Q203T, R185G+ R205K, R185G+R210L, R185G+R210G, R185G+R210M, R185G+N213V, R185G+N213D, R185G+T228S, R185G+ N229D, R185G+E234F, R185G+E234Y, R185G+A235K, R185G+A235R, R185G+S241C, R185G+Q243K, R185G+ Q243E, R185G+R244K, R185G+R244V, R185G+A250G, R185G+K254Y, R185G+G257W, R185G+G257E, R185G+ G257A, R185G+W260F, R185G+W260Y, R185G+W260L, R185G+W260T, R185G+Y262F, R185G+S266A, R185G+ D268N, R185G+A270D, R185G+N272M, R185G+N272T, R185G+N273E, R185G+N273D, R185G+A276E, R185G+ A276W, R185G+A276D, R185G+N279D, R185G+N279E, R185G+T280L, R185G+N283W, R185G+N283H, R185G+ Y286W, R185G+Y286F, R185G+L288I, R185G+E290A, R185G+L294P, R185G+L294K, R185G+L294I, R185G+ L294R, R185G+L294V, R185G+L294H, R185G+S295K, R185G+S295V, R185G+S295P, R185G+S295L, R185G+ S295R, R185G+S295A, R185G+S295N, R185G+S295M, R185G+S295I, R185G+T296S, R185G+F298Y, Y196W+ N200T, Y196W+S202R, Y196W+Q203T, Y196W+R205K, Y196W+R210L, Y196W+R210G, Y196W+R210M, Y196W+N213V, Y196W+N213D, Y196W+T228S, Y196W+N229D, Y196W+E234F, Y196W+E234Y, Y196W+A235K, Y196W+A235R, Y196W+S241C, Y196W+Q243K, Y196W+Q243E, Y196W+R244K, Y196W+R244V, Y196W+A250G, Y196W+K254Y, Y196W+G257W, Y196W+G257E, Y196W+G257A, Y196W+W260F, Y196W+W260Y, Y196W+W260L,

Y196W+W260T, Y196W+Y262F, Y196W+S266A, Y196W+D268N, Y196W+A270D, Y196W+N272M, Y196W+N272T, Y196W+N273E, Y196W+N273D, Y196W+A276E, Y196W+A276W, Y196W+A276D, Y196W+N279D, Y196W+N279E, Y196W+T280L, Y196W+N283W, Y196W+N283H, Y196W+Y286W, Y196W+Y286F, Y196W+L288I, Y196W+E290A, Y196W+L294P, Y196W+L294K, Y196W+L294I, Y196W+L294R, Y196W+L294V, Y196W+L294H, Y196W+S295K, Y196W+S295V, Y196W+S295P, Y196W+S295L, Y196W+S295R, Y196W+S295A, Y196W+S295N, Y196W+S295M, Y196W+S295I, Y196W+T296S, Y196W+F298Y, Y196F+N200T, Y196F+S202R, Y196F+Q203T, Y196F+R205K, Y196F+R210L, Y196F+R210G, Y196F+R210M, Y196F+N213V, Y196F+N213D, Y196F+T228S, Y196F+N229D, Y196F+E234F, Y196F+E234Y, Y196F+A235K, Y196F+A235R, Y196F+S241C, Y196F+Q243K, Y196F+Q243E, Y196F+R244K, Y196F+R244V, Y196F+A250G, Y196F+K254Y, Y196F+G257W, Y196F+G257E, Y196F+G257A, Y196F+W260F, Y196F+W260Y, Y196F+W260L, Y196F+W260T, Y196F+Y262F, Y196F+S266A, Y196F+D268N, Y196F+A270D, Y196F+N272M, Y196F+N272T, Y196F+N273E, Y196F+N273D, Y196F+A276E, Y196F+A276W, Y196F+A276D, Y196F+N279D, Y196F+N279E, Y196F+T280L, Y196F+N283W, Y196F+N283H, Y196F+Y286W, Y196F+Y286F, Y196F+L288I, Y196F+E290A, Y196F+L294P, Y196F+L294K, Y196F+L294I, Y196F+L294R, Y196F+L294V, Y196F+L294H, Y196F+S295K, Y196F+S295V, Y196F+S295P, Y196F+S295L, Y196F+S295R, Y196F+S295A, Y196F+S295N, Y196F+S295M, Y196F+S295I, Y196F+T296S, Y196F+F298Y, N200T+S202R, N200T+Q203T, N200T+R205K, N200T+R210L, N200T+R210G, N200T+R210M, N200T+N213V, N200T+N213D, N200T+T228S, N200T+N229D, N200T+E234F, N200T+E234Y, N200T+A235K, N200T+A235R, N200T+S241C, N200T+Q243K, N200T+Q243E, N200T+R244K, N200T+R244V, N200T+A250G, N200T+K254Y, N200T+G257W, N200T+G257E, N200T+G257A, N200T+W260F, N200T+W260Y, N200T+W260L, N200T+W260T, N200T+Y262F, N200T+S266A, N200T+D268N, N200T+A270D, N200T+N272M, N200T+N272T, N200T+N273E, N200T+N273D, N200T+A276E, N200T+A276W, N200T+A276D, N200T+N279D, N200T+N279E, N200T+T280L, N200T+N283W, N200T+N283H, N200T+Y286W, N200T+Y286F, N200T+L288I, N200T+E290A, N200T+L294P, N200T+L294K, N200T+L294I, N200T+L294R, N200T+L294V, N200T+L294H, N200T+S295K, N200T+S295V, N200T+S295P, N200T+S295L, N200T+S295R, N200T+S295A, N200T+S295N, N200T+S295M, N200T+S295I, N200T+T296S, N200T+F298Y, S202R+Q203T, S202R+R205K, S202R+R210L, S202R+R210G, S202R+R210M, S202R+N213V, S202R+N213D, S202R+T228S, S202R+N229D, S202R+E234F, S202R+E234Y, S202R+A235K, S202R+A235R, S202R+S241C, S202R+Q243K, S202R+Q243E, S202R+R244K, S202R+R244V, S202R+A250G, S202R+K254Y, S202R+G257W, S202R+G257E, S202R+G257A, S202R+W260F, S202R+W260Y, S202R+W260L, S202R+W260T, S202R+Y262F, S202R+S266A, S202R+D268N, S202R+A270D, S202R+N272M, S202R+N272T, S202R+N273E, S202R+N273D, S202R+A276E, S202R+A276W, S202R+A276D, S202R+N279D, S202R+N279E, S202R+T280L, S202R+N283W, S202R+N283H, S202R+Y286W, S202R+Y286F, S202R+L288I, S202R+E290A, S202R+L294P, S202R+L294K, S202R+L294I, S202R+L294R, S202R+L294V, S202R+L294H, S202R+S295K, S202R+S295V, S202R+S295P, S202R+S295L, S202R+S295R, S202R+S295A, S202R+S295N, S202R+S295M, S202R+S295I, S202R+T296S, S202R+F298Y, Q203T+R205K, Q203T+R210L, Q203T+R210G, Q203T+R210M, Q203T+N213V, Q203T+N213D, Q203T+T228S, Q203T+N229D, Q203T+E234F, Q203T+E234Y, Q203T+A235K, Q203T+A235R, Q203T+S241C, Q203T+Q243K, Q203T+Q243E, Q203T+R244K, Q203T+R244V, Q203T+A250G, Q203T+K254Y, Q203T+G257W, Q203T+G257E, Q203T+G257A, Q203T+W260F, Q203T+W260Y, Q203T+W260L, Q203T+W260T, Q203T+Y262F, Q203T+S266A, Q203T+D268N, Q203T+A270D, Q203T+N272M, Q203T+N272T, Q203T+N273E, Q203T+N273D, Q203T+A276E, Q203T+A276W, Q203T+A276D, Q203T+N279D, Q203T+N279E, Q203T+T280L, Q203T+N283W, Q203T+N283H, Q203T+Y286W, Q203T+Y286F, Q203T+L288I, Q203T+E290A, Q203T+L294P, Q203T+L294K, Q203T+L294I, Q203T+L294R, Q203T+L294V, Q203T+L294H, Q203T+S295K, Q203T+S295V, Q203T+S295P, Q203T+S295L, Q203T+S295R, Q203T+S295A, Q203T+S295N, Q203T+S295M, Q203T+S295I, Q203T+T296S, Q203T+F298Y, R205K+R210L, R205K+R210G, R205K+R210M, R205K+N213V, R205K+N213D, R205K+T228S, R205K+N229D, R205K+E234F, R205K+E234Y, R205K+A235K, R205K+A235R, R205K+S241C, R205K+Q243K, R205K+Q243E, R205K+R244K, R205K+R244V, R205K+A250G, R205K+K254Y, R205K+G257W, R205K+G257E, R205K+G257A, R205K+W260F, R205K+W260Y, R205K+W260L, R205K+W260T, R205K+Y262F, R205K+S266A, R205K+D268N, R205K+A270D, R205K+N272M, R205K+N272T, R205K+N273E, R205K+N273D, R205K+A276E, R205K+A276W, R205K+A276D, R205K+N279D, R205K+N279E, R205K+T280L, R205K+N283W, R205K+N283H, R205K+Y286W, R205K+Y286F, R205K+L288I, R205K+E290A, R205K+L294P, R205K+L294K, R205K+L294I, R205K+L294R, R205K+L294V, R205K+L294H, R205K+S295K, R205K+S295V, R205K+S295P, R205K+S295L, R205K+S295R, R205K+S295A, R205K+S295N, R205K+S295M, R205K+S295I, R205K+T296S, R205K+F298Y, R210L+N213V, R210L+N213D, R210L+T228S, R210L+N229D, R210L+E234F, R210L+E234Y, R210L+A235K, R210L+A235R, R210L+S241C, R210L+Q243K, R210L+Q243E, R210L+R244K, R210L+R244V, R210L+A250G, R210L+K254Y, R210L+G257W, R210L+G257E, R210L+G257A, R210L+W260F, R210L+W260Y, R210L+W260 L, R210L+W260T, R210L+Y262F, R210L+S266A, R210L+D268N, R210L+A270D, R210L+N272M, R210L+N272T, R210L+N273E, R210L+N273D, R210L+A276E, R210L+A276W, R210L+A276D, R210L+N279D, R210L+N279E, R210L+T280L, R210L+N283W, R210L+N283H, R210L+Y286W, R210L+Y286F, R210L+L288I, R210L+E290A, R210L+L294P, R210L+L294K, R210L+L294I, R210L+L294R, R210L+L294V, R210L+L294H, R210L+S295K, R210L+S295V, R210L+S295P, R210L+S295L, R210L+S295R, R210L+S295A, R210L+S295N, R210L+S295M, R210L+S295I, R210L+T296S, R210L+F298Y, R210G+N213V, R210G+N213D, R210G+T228S, R210G+N229D, R210G+E234F, R210G+E234Y, R210G+A235K, R210G+A235R, R210G+S241C, R210G+Q243K, R210G+Q243E, R210G+R244K, R210G+R244V, R210G+A250G, R210G+K254Y, R210G+G257W, R210G+G257E, R210G+G257A, R210G+W260F, R210G+W260Y, R210G+W260L, R210G+W260T, R210G+Y262F, R210G+S266A, R210G+D268N, R210G+A270D, R210G+N272M, R210G+N272T, R210G+N273E, R210G+N273D, R210G+A276E, R210G+A276W, R210G+A276D, R210G+N279D, R210G+N279E, R210G+T280L, R210G+N283W, R210G+N283H, R210G+Y286W, R210G+Y286F, R210G+L288I, R210G+E290A, R210G+L294P, R210G+L294K, R210G+L294I, R210G+L294R, R210G+L294V, R210G+L294H,

R210G+S295K, R210G+S295V, R210G+S295P, R210G+S295L, R210G+S295R, R210G+S295A, R210G+S295N, R210G+S295M, R210G+S295I, R210G+T296S, R210G+F298Y, R210M+N213V, R210M+N213D, R210M+T228S, R210M+N229D, R210M+E234F, R210M+E234Y, R210M+A235K, R210M+A235R, R210M+S241C, R210M+Q243K, R210M+Q243E, R210M+R244K, R210M+R244V, R210M+A250G, R210M+K254Y, R210M+G257W, R210M+G257E, R210M+G257A, R210M+W260F, R210M+W260Y, R210M+W260L, R210M+W260T, R210M+Y262F, R210M+S266A, R210M+D268N, R210M+A270D, R210M+N272M, R210M+N272T, R210M+N273E, R210M+N273D, R210M+A276E, R210M+A276W, R210M+A276D, R210M+N279D, R210M+N279E, R210M+T280L, R210M+N283W, R210M+N283H, R210M+Y286W, R210M+Y286F, R210M+L288I, R210M+E290A, R210M+L294P, R210M+L294K, R210M+L294I, R210M+L294R, R210M+L294V, R210M+L294H, R210M+S295K, R210M+S295V, R210M+S295P, R210M+S295L, R210M+S295R, R210M+S295A, R210M+S295N, R210M+S295M, R210M+S295I, R210M+T296S, R210M+F298Y, N213V+T228S, N213V+N229D, N213V+E234F, N213V+E234Y, N213V+A235K, N213V+A235R, N213V+S241C, N213V+Q243K, N213V+Q243E, N213V+R244K, N213V+R244V, N213V+A250G, N213V+K254Y, N213V+G257W, N213V+G257E, N213V+G257A, N213V+W260F, N213V+W260Y, N213V+W260L, N213V+W260T, N213V+Y262F, N213V+S266A, N213V+D268N, N213V+A270D, N213V+N272M, N213V+N272T, N213V+N273E, N213V+N273D, N213V+A276E, N213V+A276W, N213V+A276D, N213V+N279D, N213V+N279E, N213V+T280L, N213V+N283W, N213V+N283H, N213V+Y286W, N213V+Y286F, N213V+L288I, N213V+E290A, N213V+L294P, N213V+L294K, N213V+L294I, N213V+L294R, N213V+L294V, N213V+L294H, N213V+S295K, N213V+S295V, N213V+S295P, N213V+S295L, N213V+S295R, N213V+S295A, N213V+S295N, N213V+S295M, N213V+S295I, N213V+T296S, N213V+F298Y, N213D+T228S, N213D+N229D, N213D+E234F, N213D+E234Y, N213D+A235K, N213D+A235R, N213D+S241C, N213D+Q243K, N213D+Q243E, N213D+R244K, N213D+R244V, N213D+A250G, N213D+K254Y, N213D+G257W, N213D+G257E, N213D+G257A, N213D+W260F, N213D+W260Y, N213D+W260L, N213D+W260T, N213D+Y262F, N213D+S266A, N213D+D268N, N213D+A270D, N213D+N272M, N213D+N272T, N213D+N273E, N213D+N273D, N213D+A276E, N213D+A276W, N213D+A276D, N213D+N279D, N213D+N279E, N213D+T280L, N213D+N283W, N213D+N283H, N213D+Y286W, N213D+Y286F, N213D+L288I, N213D+E290A, N213D+L294P, N213D+L294K, N213D+L294I, N213D+L294R, N213D+L294V, N213D+L294H, N213D+S295K, N213D+S295V, N213D+S295P, N213D+S295L, N213D+S295R, N213D+S295A, N213D+S295N, N213D+S295M, N213D+S295I, N213D+T296S, N213D+F298Y, T228S+N229D, T228S+E234F, T228S+E234Y, T228S+A235K, T228S+A235R, T228S+S241C, T228S+Q243K, T228S+Q243E, T228S+R244K, T228S+R244V, T228S+A250G, T228S+K254Y, T228S+G257W, T228S+G257E, T228S+G257A, T228S+W260F, T228S+W260Y, T228S+W260L, T228S+W260T, T228S+Y262F, T228S+S266A, T228S+D268N, T228S+A270D, T228S+N272M, T228S+N272T, T228S+N273E, T228S+N273D, T228S+A276E, T228S+A276W, T228S+A276D, T228S+N279D, T228S+N279E, T228S+T280L, T228S+N283W, T228S+N283H, T228S+Y286W, T228S+Y286F, T228S+L288I, T228S+E290A, T228S+L294P, T228S+L294K, T228S+L294I, T228S+L294R, T228S+L294V, T228S+L294H, T228S+S295K, T228S+S295V, T228S+S295P, T228S+S295L, T228S+S295R, T228S+S295A, T228S+S295N, T228S+S295M, T228S+S295I, T228S+T296S, T228S+F298Y, N229D+E234F, N229D+E234Y, N229D+A235K, N229D+A235R, N229D+S241C, N229D+Q243K, N229D+Q243E, N229D+R244K, N229D+R244V, N229D+A250G, N229D+K254Y, N229D+G257W, N229D+G257E, N229D+G257A, N229D+W260F, N229D+W260Y, N229D+W260L, N229D+W260T, N229D+Y262F, N229D+S266A, N229D+D268N, N229D+A270D, N229D+N272M, N229D+N272T, N229D+N273E, N229D+N273D, N229D+A276E, N229D+A276W, N229D+A276D, N229D+N279D, N229D+N279E, N229D+T280L, N229D+N283W, N229D+N283H, N229D+Y286W, N229D+Y286F, N229D+L288I, N229D+E290A, N229D+L294P, N229D+L294K, N229D+L294I, N229D+L294R, N229D+L294V, N229D+L294H, N229D+S295K, N229D+S295V, N229D+S295P, N229D+S295L, N229D+S295R, N229D+S295A, N229D+S295N, N229D+S295M, N229D+S295I, N229D+T296S, N229D+F298Y, E234F+A235K, E234F+A235R, E234F+S241C, E234F+Q243K, E234F+Q243E, E234F+R244K, E234F+R244V, E234F+A250G, E234F+K254Y, E234F+G257W, E234F+G257E, E234F+G257A, E234F+W260F, E234F+W260Y, E234F+W260L, E234F+W260T, E234F+Y262F, E234F+S266A, E234F+D268N, E234F+A270D, E234F+N272M, E234F+N272T, E234F+N273E, E234F+N273D, E234F+A276E, E234F+A276W, E234F+A276D, E234F+N279D, E234F+N279E, E234F+T280L, E234F+N283W, E234F+N283H, E234F+Y286W, E234F+Y286F, E234F+L288I, E234F+E290A, E234F+L294P, E234F+L294K, E234F+L294I, E234F+L294R, E234F+L294V, E234F+L294H, E234F+S295K, E234F+S295V, E234F+S295P, E234F+S295L, E234F+S295R, E234F+S295A, E234F+S295N, E234F+S295M, E234F+S295I, E234F+T296S, E234F+F298Y, E234Y+A235K, E234Y+A235R, E234Y+S241C, E234Y+Q243K, E234Y+Q243E, E234Y+R244K, E234Y+R244V, E234Y+A250G, E234Y+K254Y, E234Y+G257W, E234Y+G257E, E234Y+G257A, E234Y+W260F, E234Y+W260Y, E234Y+W260L, E234Y+W260T, E234Y+Y262F, E234Y+S266A, E234Y+D268N, E234Y+A270D, E234Y+N272M, E234Y+N272T, E234Y+N273E, E234Y+N273D, E234Y+A276E, E234Y+A276W, E234Y+A276D, E234Y+N279D, E234Y+N279E, E234Y+T280L, E234Y+N283W, E234Y+N283H, E234Y+Y286W, E234Y+Y286F, E234Y+L288I, E234Y+E290A, E234Y+L294P, E234Y+L294K, E234Y+L294I, E234Y+L294R, E234Y+L294V, E234Y+L294H, E234Y+S295K, E234Y+S295V, E234Y+S295P, E234Y+S295L, E234Y+S295R, E234Y+S295A, E234Y+S295N, E234Y+S295M, E234Y+S295I, E234Y+T296S, E234Y+F298Y, A235K+S241C, A235K+Q243K, A235K+Q243E, A235K+R244K, A235K+R244V, A235K+A250G, A235K+K254Y, A235K+G257W, A235K+G257E, A235K+G257A, A235K+W260F, A235K+W260Y, A235K+W260L, A235K+W260T, A235K+Y262F, A235K+S266A, A235K+D268N, A235K+A270D, A235K+N272M, A235K+N272T, A235K+N273E, A235K+N273D, A235K+A276E, A235K+A276W, A235K+A276D, A235K+N279D, A235K+N279E, A235K+T280L, A235K+N283W, A235K+N283H, A235K+Y286W, A235K+Y286F, A235K+L288I, A235K+E290A, A235K+L294P, A235K+L294K, A235K+L294I, A235K+L294R, A235K+L294V, A235K+L294H, A235K+S295K, A235K+S295V, A235K+S295P, A235K+S295L, A235K+S295R, A235K+S295A, A235K+S295N, A235K+S295M, A235K+S295I, A235K+T296S, A235K+F298Y, A235R+S241C, A235R+Q243K, A235R+Q243E, A235R+R244K,

A235R+R244V, A235R+A250G, A235R+K254Y, A235R+ G257W, A235R+G257E, A235R+G257A, A235R+W260F, A235R+W260L, A235R+W260Y, A235R+W260T, A235R+Y262F, A235R+S266A, A235R+D268N, A235R+ A270D, A235R+N272M, A235R+N272T, A235R+N273E, A235R+N273D, A235R+A276E, A235R+A276W, A235R+ A276D, A235R+N279D, A235R+N279E, A235R+T280L, A235R+N283W, A235R+N283H, A235R+Y286W, A235R+Y286F, A235R+L288I, A235R+E290A, A235R+ L294P, A235R+L294K, A235R+L294I, A235R+L294R, A235R+L294V, A235R+L294H, A235R+S295K, A235R+ S295V, A235R+S295P, A235R+S295L, A235R+S295R, A235R+S295A, A235R+S295N, A235R+S295M, A235R+ S295I, A235R+T296S, A235R+F298Y, S241C+Q243K, S241C+Q243E, S241C+R244K, S241C+R244V, S241C+ A250G, S241C+K254Y, S241C+G257W, S241C+G257E, S241C+G257A, S241C+W260F, S241C+W260Y, S241C+ W260L, S241C+W260T, S241C+Y262F, S241C+S266A, S241C+D268N, S241C+A270D, S241C+N272M, S241C+ N272T, S241C+N273E, S241C+N273D, S241C+A276E, S241C+A276W, S241C+A276D, S241C+N279D, S241C+ N279E, S241C+T280L, S241C+N283W, S241C+N283H, S241C+Y286W, S241C+Y286F, S241C+L288I, S241C+ E290A, S241C+L294P, S241C+L294K, S241C+L294I, S241C+L294R, S241C+L294V, S241C+L294H, S241C+ S295K, S241C+S295V, S241C+S295P, S241C+S295L, S241C+S295R, S241C+S295A, S241C+S295N, S241C+ S295M, S241C+S295I, S241C+T296S, S241C+F298Y, Q243K+R244K, Q243K+R244V, Q243K+A250G, Q243K+ K254Y, Q243K+G257W, Q243K+G257E, Q243K+G257A, Q243K+W260F, Q243K+W260Y, Q243K+W260L, Q243K+W260T, Q243K+Y262F, Q243K+S266A, Q243K+ D268N, Q243K+A270D, Q243K+N272M, Q243K+N272T, Q243K+N273E, Q243K+N273D, Q243K+A276E, Q243K+ A276W, Q243K+A276D, Q243K+N279D, Q243K+N279E, Q243K+T280L, Q243K+N283W, Q243K+N283H, Q243K+Y286W, Q243K+Y286F, Q243K+L288I, Q243K+ E290A, Q243K+L294P, Q243K+L294K, Q243K+L294I, Q243K+L294R, Q243K+L294V, Q243K+L294H, Q243K+ S295K, Q243K+S295V, Q243K+S295P, Q243K+S295L, Q243K+S295R, Q243K+S295A, Q243K+S295N, Q243K+ S295M, Q243K+S295I, Q243K+T296S, Q243K+F298Y, Q243E+R244K, Q243E+R244V, Q243E+A250G, Q243E+ K254Y, Q243E+G257W, Q243E+G257E, Q243E+G257A, Q243E+W260F, Q243E+W260Y, Q243E+W260L, Q243E+ W260T, Q243E+Y262F, Q243E+S266A, Q243E+D268N, Q243E+A270D, Q243E+N272M, Q243E+N272T, Q243E+ N273E, Q243E+N273D, Q243E+A276E, Q243E+A276W, Q243E+A276D, Q243E+N279D, Q243E+N279E, Q243E+ T280L, Q243E+N283W, Q243E+N283H, Q243E+Y286W, Q243E+Y286F, Q243E+L288I, Q243E+E290A, Q243E+ L294P, Q243E+L294K, Q243E+L294I, Q243E+L294R, Q243E+L294V, Q243E+L294H, Q243E+S295K, Q243E+ S295V, Q243E+S295P, Q243E+S295L, Q243E+S295R, Q243E+S295A, Q243E+S295N, Q243E+S295M, Q243E+ S295I, Q243E+T296S, Q243E+F298Y, R244K+A250G, R244K+K254Y, R244K+G257W, R244K+G257E, R244K+ G257A, R244K+W260F, R244K+W260Y, R244K+W260L, R244K+W260T, R244K+Y262F, R244K+S266A, R244K+ D268N, R244K+A270D, R244K+N272M, R244K+N272T, R244K+N273E, R244K+N273D, R244K+A276E, R244K+ A276W, R244K+A276D, R244K+N279D, R244K+N279E, R244K+T280L, R244K+N283W, R244K+N283H, R244K+ Y286W, R244K+Y286F, R244K+L288I, R244K+E290A, R244K+L294P, R244K+L294K, R244K+L294I, R244K+ L294R, R244K+L294V, R244K+L294H, R244K+S295K, R244K+S295V, R244K+S295P, R244K+S295L, R244K+ S295R, R244K+S295A, R244K+S295N, R244K+S295M, R244K+S295I, R244K+T296S, R244K+F298Y, R244V+ A250G, R244V+K254Y, R244V+G257W, R244V+G257E, R244V+G257A, R244V+W260F, R244V+W260Y, R244V+W260L, R244V+W260T, R244V+Y262F, R244V+ S266A, R244V+D268N, R244V+A270D, R244V+N272M, R244V+N272T, R244V+N273E, R244V+N273D, R244V+ A276E, R244V+A276W, R244V+A276D, R244V+N279D, R244V+N279E, R244V+T280L, R244V+N283W, R244V+ N283H, R244V+Y286W, R244V+Y286F, R244V+L288I, R244V+E290A, R244V+L294P, R244V+L294K, R244V+ L294I, R244V+L294R, R244V+L294V, R244V+L294H, R244V+S295K, R244V+S295V, R244V+S295P, R244V+ S295L, R244V+S295R, R244V+S295A, R244V+S295N, R244V+S295M, R244V+S295I, R244V+T296S, R244V+ F298Y, A250G+K254Y, A250G+G257W, A250G+G257E, A250G+G257A, A250G+W260F, A250G+W260Y, A250G+W260L, A250G+W260T, A250G+Y262F, A250G+ S266A, A250G+D268N, A250G+A270D, A250G+N272M, A250G+N272T, A250G+N273E, A250G+N273D, A250G+ A276E, A250G+A276W, A250G+A276D, A250G+N279D, A250G+N279E, A250G+T280L, A250G+N283W, A250G+ N283H, A250G+Y286W, A250G+Y286F, A250G+L288I, A250G+E290A, A250G+L294P, A250G+L294K, A250G+ L294I, A250G+L294R, A250G+L294V, A250G+L294H, A250G+S295K, A250G+S295V, A250G+S295P, A250G+ S295L, A250G+S295R, A250G+S295A, A250G+S295N, A250G+S295M, A250G+S295I, A250G+T296S, A250G+ F298Y, K254Y+G257W, K254Y+G257E, K254Y+G257A, K254Y+W260F, A250G+W260Y, A250G+W260L, A250G+W260T, K254Y+Y262F, K254Y+S266A, K254Y+ D268N, K254Y+A270D, K254Y+N272M, K254Y+N272T, K254Y+N273E, K254Y+N273D, K254Y+A276E, K254Y+ A276W, K254Y+A276D, K254Y+N279D, K254Y+N279E, K254Y+T280L, K254Y+N283W, K254Y+N283H, K254Y+Y286W, K254Y+Y286F, K254Y+L288I, K254Y+ E290A, K254Y+L294P, K254Y+L294K, K254Y+L294I, K254Y+L294R, K254Y+L294V, K254Y+L294H, K254Y+ S295K, K254Y+S295V, K254Y+S295P, K254Y+S295L, K254Y+S295R, K254Y+S295A, K254Y+S295N, K254Y+ S295M, K254Y+S295I, K254Y+T296S, K254Y+F298Y, G257W+W260F, G257W+W260Y, G257W+W260L, G257W+W260T, G257W+Y262F, G257W+S266A, G257W+D268N, G257W+A270D, G257W+N272M, G257W+N272T, G257W+N273E, G257W+N273D, G257W+A276E, G257W+A276W, G257W+A276D, G257W+N279D, G257W+N279E, G257W+T280L, G257W+N283W, G257W+N283H, G257W+Y286W, G257W+Y286F, G257W+L288I, G257W+E290A, G257W+L294P, G257W+L294K, G257W+L294I, G257W+L294R, G257W+L294V, G257W+L294H, G257W+S295K, G257W+S295V, G257W+S295P, G257W+S295L, G257W+S295R, G257W+S295A, G257W+S295N, G257W+S295M, G257W+S295I, G257W+T296S, G257W+F298Y, G257E+W260F, G257E+ W260Y, G257E+W260L, G257E+W260T, G257E+Y262F, G257E+S266A, G257E+D268N, G257E+A270D, G257E+ N272M, G257E+N272T, G257E+N273E, G257E+N273D, G257E+A276E, G257E+A276W, G257E+A276D, G257E+ N279D, G257E+N279E, G257E+T280L, G257E+N283W, G257E+N283H, G257E+Y286W, G257E+Y286F, G257E+ L288I, G257E+E290A, G257E+L294P, G257E+L294K, G257E+L294I, G257E+L294R, G257E+L294V, G257E+ L294H, G257E+S295K, G257E+S295V, G257E+S295P, G257E+S295L, G257E+S295R, G257E+S295A, G257E+ S295N, G257E+S295M, G257E+S295I, G257E+T296S, G257E+F298Y, G257A+W260F, G257A+W260Y, G257A+

W260L, G257A+W260T, G257A+Y262F, G257A+S266A, G257A+D268N, G257A+A270D, G257A+N272M, G257A+N272T, G257A+N273E, G257A+N273D, G257A+A276E, G257A+A276W, G257A+A276D, G257A+N279D, G257A+N279E, G257A+T280L, G257A+N283W, G257A+N283H, G257A+Y286W, G257A+Y286F, G257A+L288I, G257A+E290A, G257A+L294P, G257A+L294K, G257A+L294I, G257A+L294R, G257A+L294V, G257A+L294H, G257A+S295K, G257A+S295V, G257A+S295P, G257A+S295L, G257A+S295R, G257A+S295A, G257A+S295N, G257A+S295M, G257A+S295I, G257A+T296S, G257A+F298Y, W260F+Y262F, W260F+S266A, W260F+D268N, W260F+A270D, W260F+N272M, W260F+N272T, W260F+N273E, W260F+N273D, W260F+A276E, W260F+A276W, W260F+A276D, W260F+N279D, W260F+N279E, W260F+T280L, W260F+N283W, W260F+N283H, W260F+Y286W, W260F+Y286F, W260F+L288I, W260F+E290A, W260F+L294P, W260F+L294K, W260F+L294I, W260F+L294R, W260F+L294V, W260F+L294H, W260F+S295K, W260F+S295V, W260F+S295P, W260F+S295L, W260F+S295R, W260F+S295A, W260F+S295N, W260F+S295M, W260F+S295I, W260F+T296S, W260F+F298Y, W260Y+Y262F, W260L+Y262F, W260T+Y262F, Y262F+S266A, Y262F+D268N, Y262F+A270D, Y262F+N272M, Y262F+N272T, Y262F+N273E, Y262F+N273D, Y262F+A276E, Y262F+A276W, Y262F+A276D, Y262F+N279D, Y262F+N279E, Y262F+T280L, Y262F+N283W, Y262F+N283H, Y262F+Y286W, Y262F+Y286F, Y262F+L288I, Y262F+E290A, Y262F+L294P, Y262F+L294K, Y262F+L294I, Y262F+L294R, Y262F+L294V, Y262F+L294H, Y262F+S295K, Y262F+S295V, Y262F+S295P, Y262F+S295L, Y262F+S295R, Y262F+S295A, Y262F+S295N, Y262F+S295M, Y262F+S295I, Y262F+T296S, Y262F+F298Y, W260Y+S266A, W260L+S266A, W260T+S266A, S266A+D268N, S266A+A270D, S266A+N272M, S266A+N272T, S266A+N273E, S266A+N273D, S266A+A276E, S266A+A276W, S266A+A276D, S266A+N279D, S266A+N279E, S266A+T280L, S266A+N283W, S266A+N283H, S266A+Y286W, S266A+Y286F, S266A+L288I, S266A+E290A, S266A+L294P, S266A+L294K, S266A+L294I, S266A+L294R, S266A+L294V, S266A+L294H, S266A+S295K, S266A+S295V, S266A+S295P, S266A+S295L, S266A+S295R, S266A+S295A, S266A+S295N, S266A+S295M, S266A+S295I, S266A+T296S, S266A+F298Y, W260Y+D268N, W260L+D268N, W260T+D268N, D268N+A270D, D268N+N272M, D268N+N272T, D268N+N273E, D268N+N273D, D268N+A276E, D268N+A276W, D268N+A276D, D268N+N279D, D268N+N279E, D268N+T280L, D268N+N283W, D268N+N283H, D268N+Y286W, D268N+Y286F, D268N+L288I, D268N+E290A, D268N+L294P, D268N+L294K, D268N+L294I, D268N+L294R, D268N+L294V, D268N+L294H, D268N+S295K, D268N+S295V, D268N+S295P, D268N+S295L, D268N+S295R, D268N+S295A, D268N+S295N, D268N+S295M, D268N+S295I, D268N+T296S, D268N+F298Y, W260Y+A270D, W260L+A270D, W260T+A270D, A270D+N272M, A270D+N272T, A270D+N273E, A270D+N273D, A270D+A276E, A270D+A276W, A270D+A276D, A270D+N279D, A270D+N279E, A270D+T280L, A270D+N283W, A270D+N283H, A270D+Y286W, A270D+Y286F, A270D+L288I, A270D+E290A, A270D+L294P, A270D+L294K, A270D+L294I, A270D+L294R, A270D+L294V, A270D+L294H, A270D+S295K, A270D+S295V, A270D+S295P, A270D+S295L, A270D+S295R, A270D+S295A, A270D+S295N, A270D+S295M, A270D+S295I, A270D+T296S, A270D+F298Y, W260Y+N272M, W260L+N272M, W260T+N272M, N272M+N273E, N272M+N273D, N272M+A276E, N272M+A276W, N272M+A276D, N272M+N279D, N272M+N279E, N272M+T280L, N272M+N283W, N272M+N283H, N272M+Y286W, N272M+Y286F, N272M+L288I, N272M+E290A, N272M+L294P, N272M+L294K, N272M+L294I, N272M+L294R, N272M+L294V, N272M+L294H, N272M+S295K, N272M+S295V, N272M+S295P, N272M+S295L, N272M+S295R, N272M+S295A, N272M+S295N, N272M+S295M, N272M+S295I, N272M+T296S, N272M+F298Y, W260Y+N272T, W260L+N272T, W260T+N272T, N272T+N273E, N272T+N273D, N272T+A276E, N272T+A276W, N272T+A276D, N272T+N279D, N272T+N279E, N272T+T280L, N272T+N283W, N272T+N283H, N272T+Y286W, N272T+Y286F, N272T+L288I, N272T+E290A, N272T+L294P, N272T+L294K, N272T+L294I, N272T+L294R, N272T+L294V, N272T+L294H, N272T+S295K, N272T+S295V, N272T+S295P, N272T+S295L, N272T+S295R, N272T+S295A, N272T+S295N, N272T+S295M, N272T+S295I, N272T+T296S, N272T+F298Y, W260Y+N273E, W260L+N273E, W260T+N273E, N273E+A276E, N273E+A276W, N273E+A276D, N273E+N279D, N273E+N279E, N273E+T280L, N273E+N283W, N273E+N283H, N273E+Y286W, N273E+Y286F, N273E+L288I, N273E+E290A, N273E+L294P, N273E+L294K, N273E+L294I, N273E+L294R, N273E+L294V, N273E+L294H, N273E+S295K, N273E+S295V, N273E+S295P, N273E+S295L, N273E+S295R, N273E+S295A, N273E+S295N, N273E+S295M, N273E+S295I, N273E+T296S, N273E+F298Y, W260Y+N273D, W260L+N273D, W260T+N273D, N273D+A276E, N273D+A276W, N273D+A276D, N273D+N279D, N273D+N279E, N273D+T280L, N273D+N283W, N273D+N283H, N273D+Y286W, N273D+Y286F, N273D+L288I, N273D+E290A, N273D+L294P, N273D+L294K, N273D+L294I, N273D+L294R, N273D+L294V, N273D+L294H, N273D+S295K, N273D+S295V, N273D+S295P, N273D+S295L, N273D+S295R, N273D+S295A, N273D+S295N, N273D+S295M, N273D+S295I, N273D+T296S, N273D+F298Y, W260Y+A276E, W260L+A276E, W260T+A276E, A276E+N279D, A276E+N279E, A276E+T280L, A276E+N283W, A276E+N283H, A276E+Y286W, A276E+Y286F, A276E+L288I, A276E+E290A, A276E+L294P, A276E+L294K, A276E+L294I, A276E+L294R, A276E+L294V, A276E+L294H, A276E+S295K, A276E+S295V, A276E+S295P, A276E+S295L, A276E+S295R, A276E+S295A, A276E+S295N, A276E+S295M, A276E+S295I, A276E+T296S, W260Y+A276W, W260L+A276W, W260T+A276W, A276E+F298Y, A276W+N279D, A276W+N279E, A276W+T280L, A276W+N283W, A276W+N283H, A276W+Y286W, A276W+Y286F, A276W+L288I, A276W+E290A, A276W+L294P, A276W+L294K, A276W+L294I, A276W+L294R, A276W+L294V, A276W+L294H, A276W+S295K, A276W+S295V, A276W+S295P, A276W+S295L, A276W+S295R, A276W+S295A, A276W+S295N, A276W+S295M, A276W+S295I, A276W+T296S, A276W+F298Y, W260Y+A276D, W260L+A276D, W260T+A276D, A276D+N279D, A276D+N279E, A276D+T280L, A276D+N283W, A276D+N283H, A276D+Y286W, A276D+Y286F, A276D+L288I, A276D+E290A, A276D+L294P, A276D+L294K, A276D+L294I, A276D+L294R, A276D+L294V, A276D+L294H, A276D+S295K, A276D+S295V, A276D+S295P, A276D+S295L, A276D+S295R, A276D+S295A, A276D+S295N, A276D+S295M, A276D+S295I, A276D+T296S, A276D+F298Y, W260Y+N279D, W260L+N279D, W260T+N279D, N279D+T280L, N279D+N283W, N279D+N283H, N279D+Y286W, N279D+Y286F, N279D+L288I, N279D+E290A, N279D+L294P, N279D+L294K, N279D+L294I,

N279D+L294R, N279D+L294V, N279D+L294H, N279D+ S295K, N279D+S295V, N279D+S295P, N279D+S295L, N279D+S295R, N279D+S295A, N279D+S295N, N279D+ S295M, N279D+S295I, N279D+T296S, N279D+F298Y, W260Y+N279E, W260L+N279E, W260T+N279E, N279E+T280L, N279E+N283W, N279E+N283H, N279E+ Y286W, N279E+Y286F, N279E+L288I, N279E+E290A, N279E+L294P, N279E+L294K, N279E+L294I, N279E+ L294R, N279E+L294V, N279E+L294H, N279E+S295K, N279E+S295V, N279E+S295P, N279E+S295L, N279E+ S295R, N279E+S295A, N279E+S295N, N279E+S295M, N279E+S295I, N279E+T296S, N279E+F298Y, W260Y+ T280L, W260L+T280L, W260T+T280L, T280L+N283W, T280L+N283H, T280L+Y286W, T280L+Y286F, T280L+ L288I, T280L+E290A, T280L+L294P, T280L+L294K, T280L+L294I, T280L+L294R, T280L+L294V, T280L+ L294H, T280L+S295K, T280L+S295V, T280L+S295P, T280L+S295L, T280L+S295R, T280L+S295A, T280L+ S295N, T280L+S295M, T280L+S295I, T280L+T296S, T280L+F298Y, W260Y+N283W, W260L+N283W, W260T+N283W, N283W+Y286W, N283W+Y286F, N283W+L288I, N283W+E290A, N283W+L294P, N283W+L294K, N283W+L294I, N283W+L294R, N283W+L294V, N283W+L294H, N283W+S295K, N283W+S295V, N283W+S295P, N283W+S295L, N283W+S295R, N283W+S295A, N283W+S295N, N283W+S295M, N283W+S295I, N283W+T296S, N283W+F298Y, W260Y+N283H, W260L+N283H, W260T+N283H, N283H+Y286W, N283H+Y286F, N283H+L288I, N283H+E290A, N283H+L294P, N283H+ L294K, N283H+L294I, N283H+L294R, N283H+L294V, N283H+L294H, N283H+S295K, N283H+S295V, N283H+ S295P, N283H+S295L, N283H+S295R, N283H+S295A, N283H+S295N, N283H+S295M, N283H+S295I, N283H+ T296S, W260Y+Y286W, W260L+Y286W, W260T+ Y286W, Y286W+L288I, Y286W+E290A, Y286W+L294P, Y286W+L294K, Y286W+L294I, Y286W+L294R, Y286W+L294V, Y286W+L294H, Y286W+S295K, Y286W+S295V, Y286W+S295P, Y286W+S295L, Y286W+ S295R, Y286W+S295A, Y286W+S295N, Y286W+S295M, Y286W+S295I, Y286W+T296S, Y286W+F298Y, W260Y+ Y286F, W260L+Y286F, W260T+Y286F, Y286F+L288I, Y286F+E290A, Y286F+L294P, Y286F+L294K, Y286F8+ L294I, Y286F+L294R, Y286F+L294V, Y286F+L294H, Y286F+S295K, Y286F+S295V, Y286F+S295P, Y286F+ S295L, Y286F+S295R, Y286F+S295A, Y286F+S295N, Y286F+S295M, Y286F+S295I, Y286F+T296S, Y286F+ F298Y, W260Y+L288I, W260L+L288I, W260T+L288I, L288I+E290A, L288I+L294P, L288I+L294K, L288I+ L294I, L288I+L294R, L288I+L294V, L288I+L294H, L288I+S295K, L288I+S295V, L288I+S295P, L288I+ S295L, L288I+S295R, L288I+S295A, L288I+S295N, L288I+S295M, L288I+S295I, L288I+T296S, L288I+ F298Y, W260Y+E290A, W260L+E290A, W260T+E290A, E290A+L294P, E290A+L294K, E290A+L294I, E290A+ L294R, E290A+L294V, E290A+L294H, E290A+S295K, E290A+S295V, E290A+S295P, E290A+S295L, E290A+ S295R, E290A+S295A, E290A+S295N, E290A+S295M, E290A+S295I, E290A+T296S, E290A+F298Y, W260Y+ S294P, W260L+S294P, W260T+S294P, L294P+S295K, L294P+S295V, L294P+S295P, L294P+S295L, L294P+ S295R, L294P+S295A, L294P+S295N, L294P+S295M, L294P+S295I, L294P+T296S, L294P+F298Y, W260Y+ L294K, W260L+L294K, W260T+L294K, L294K+S295K, L294K+S295V, L294K+S295P, L294K+S295L, L294K+ S295R, L294K+S295A, L294K+S295N, L294K+S295M, L294K+S295I, L294K+T296S, L294K+F298Y, W260Y+ L294I, W260L+L294I, W260T+L294I, L294I+S295K, L294I+S295V, L294I+S295P, L294I+S295L, L294I+ S295R, L294I+S295A, L294I+S295N, L294I+S295M, L294I+S295I, L294I+T296S, L294I+F298Y, W260Y+ L294R, W260L+L294R, W260T+L294R, L294R+S295K, L294R+S295V, L294R+S295P, L294R+S295L, L294R+ S295R, L294R+S295A, L294R+S295N, L294R+S295M, L294R+S295I, L294R+T296S, L294R+F298Y, W260Y+ L294V, W260L+L294V, W260T+L294V, L294V+S295K, L294V+S295V, L294V+S295P, L294V+S295L, L294V+ S295R, L294V+S295A, L294V+S295N, L294V+S295M, L294V+S295I, L294V+T296S, L294V+F298Y, W260Y+ L294H, W260L+L294H, W260T+L294H, L294H+S295K, L294H+S295V, L294H+S295P, L294H+S295L, L294H+ S295R, L294H+S295A, L294H+S295N, L294H+S295M, L294H+S295I, L294H+T296S, L294H+F298Y, W260Y+ S295K, W260L+S295K, W260T+S295K, S295K+T296S, S295K+F298Y, W260Y+S295V, W260L+S295V, W260T+ S295V, S295V+T296S, S295V+F298Y, W260Y+S295P, W260L+S295P, W260T+S295P, S295P+T296S, S295P+ F298Y, W260Y+S295L, W260L+S295L, W260T+S295L, S295L+T296S, S295L+F298Y, W260Y+S295R, W260L+ S295R, W260T+S295R, S295R+T296S, S295R+F298Y, W260Y+S295A, W260L+S295A, W260T+S295A, S295A+ T296S, S295A+F298Y, W260Y+S295N, W260L+S295N, W260T+S295N, S295N+T296S, S295N+F298Y, W260Y+ S295M, W260L+S295M, W260T+S295M, S295M+T296S, S295M+F298Y, W260Y+S295I, W260L+S295I, W260T+ S295I, S295I+T296S, S295I+F298Y, W260Y+T296S, W260L+T296S, W260T+T296S, T296S+F298Y, W260Y+ F298Y, W260L+F298Y, and W260T+F298Y.

In an embodiment, the variant has sequence identity of at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent mannanase.

In another embodiment, the variant has at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

As described above the stability, such as the in-detergent stability or thermostability, may be determined as described in the Examples.

Thus, in one embodiment, the variant of the present invention has an improved stability when measured at pH 9.0, 10.5, and/or 10.8. In particular, the stability may be determined at a pH of 9.0.

Accordingly, in one embodiment, the variant is selected from the list of variants shown in the Examples.

Stability may not only be measured at pH 9.0 but may also be measured at either more alcaline or acidic pH. The pH that stability is measured at may vary depending on the detergent composition the variant (or enzyme) needs to be stable in. Thus, the present invention also encompass stability at other pH, such as pH 10.8. Thus, in one embodiment, the variant of the present invention has an improved stability when measured at pH 10.8.

In one embodiment, the improved stability of the variant of the present invention is measured either at pH 9.0 or 10.8, or the improved stability is seen at both pHs, i.e. pH 9.0 and pH 10.8. Thus in one embodiment, the variant has an improved stability compared to the parent mannanase, when the stability is measured at pH 9.0 and/or pH 10.8.

In one embodiment, the variant has an Improvement Factor of at least 3.0 for a measure of stability at pH 9.0, pH 10.5, and/or pH 10.8.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuNal, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

In another embodiment, the variant comprises a substitution in the position corresponding to position 260 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of W260F, W260L, W260Y, and W260T.

In another embodiment, the variant comprises a substitution in the position corresponding to position 288 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is L288I.

In another embodiment, the variant comprises a substitution in the position corresponding to position 294 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of L294P, L294K, L294I, L294R, L294V, and L294H.

In another embodiment, the variant comprises a substitution in the position corresponding to position 295 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of S295K, S295V, S295P, S295L, S295R, S295A, S295N, S295M, and S295I.

In another embodiment, the second substitution is a substitution in the position corresponding to position 1 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of A1G and A1V.

In another embodiment, the second substitution is a substitution in the position corresponding to position 2 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N2E.

In another embodiment, the second substitution is a substitution in the position corresponding to position 3 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S3P.

In another embodiment, the second substitution is a substitution in the position corresponding to position 4 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is G4D.

In another embodiment, the second substitution is a substitution in the position corresponding to position 5 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is F5H.

In another embodiment, the second substitution is a substitution in the position corresponding to position 6 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Y6H, Y6M, Y6F, Y6W, and Y6H.

In another embodiment, the second substitution is a substitution in the position corresponding to position 8 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of S8T, S8P, and S8R.

In another embodiment, the second substitution is a substitution in the position corresponding to position 11 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of T11K, and T11R.

In another embodiment, the second substitution is a substitution in the position corresponding to position 13 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is Y13F.

In another embodiment, the second substitution is a substitution in the position corresponding to position 14 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of D14S and D14K.

In another embodiment, the variant comprises or consists of a substitution in the position corresponding to position 18 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N18V and N18R.

In another embodiment, the second substitution is a substitution in the position corresponding to position 30 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is A30T.

In another embodiment, the second substitution is a substitution in the position corresponding to position 32 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Y32F and Y32W.

In another embodiment, the second substitution is a substitution in the position corresponding to position 33 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is K33Q.

In another embodiment, the second substitution is a substitution in the position corresponding to position 34 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D34G.

In another embodiment, the second substitution is a substitution in the position corresponding to position 35 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is Q35L.

In another embodiment, the second substitution is a substitution in the position corresponding to position 37 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is T37P.

In another embodiment, the second substitution is a substitution in the position corresponding to position 41 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of E41V and E41N.

In another embodiment, the second substitution is a substitution in the position corresponding to position 45 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N45G.

In another embodiment, the second substitution is a substitution in the position corresponding to position 47 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of G47S and G47A.

In another embodiment, the second substitution is a substitution in the position corresponding to position 57 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D57N.

In another embodiment, the second substitution is a substitution in the position corresponding to position 59 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is G59Q.

In another embodiment, the second substitution is a substitution in the position corresponding to position 60 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is Q60R.

In another embodiment, the second substitution is a substitution in the position corresponding to position 63 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of K63R and K63Q.

In another embodiment, the second substitution is a substitution in the position corresponding to position 65 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D65E.

In another embodiment, the second substitution is a substitution in the position corresponding to position 70 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is R70K.

In another embodiment, the second substitution is a substitution in the position corresponding to position 71 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N71S.

In another embodiment, the second substitution is a substitution in the position corresponding to position 74 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S74K.

In another embodiment, the second substitution is a substitution in the position corresponding to position 77 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of E77T and E77N.

In another embodiment, the second substitution is a substitution in the position corresponding to position 78 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D78G.

In another embodiment, the second substitution is a substitution in the position corresponding to position 80 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is H80K.

In another embodiment, the second substitution is a substitution in the position corresponding to position 82 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of V82R, V82I and V82S.

In another embodiment, the second substitution is a substitution in the position corresponding to position 83 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of A83P and A83S.

In another embodiment, the second substitution is a substitution in the position corresponding to position 93 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Y93Q and Y93A.

In another embodiment, the second substitution is a substitution in the position corresponding to position 95 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S95D.

In another embodiment, the second substitution is a substitution in the position corresponding to position 97 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is A97R.

In another embodiment, the second substitution is a substitution in the position corresponding to position 98 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S98D.

In another embodiment, the second substitution is a substitution in the position corresponding to position 100 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N100Y.

In another embodiment, the second substitution is a substitution in the position corresponding to position 104 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of D104A and D104G.

In another embodiment, the second substitution is a substitution in the position corresponding to position 108 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is E108S.

In another embodiment, the second substitution is a substitution in the position corresponding to position 111 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of S111A, S111K, and S111R.

In another embodiment, the second substitution is a substitution in the position corresponding to position 114 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of I114Q, I114M, and I114W.

In another embodiment, the second substitution is a substitution in the position corresponding to position 116 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is K116R.

In another embodiment, the second substitution is a substitution in the position corresponding to position 118 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D118K.

In another embodiment, the second substitution is a substitution in the position corresponding to position 119 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is T119R.

In another embodiment, the second substitution is a substitution in the position corresponding to position 131 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S131T.

In another embodiment, the second substitution is a substitution in the position corresponding to position 133 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of E133R and E133Q.

In another embodiment, the second substitution is a substitution in the position corresponding to position 135 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D135P.

In another embodiment, the second substitution is a substitution in the position corresponding to position 136 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is A136P.

In another embodiment, the second substitution is a substitution in the position corresponding to position 139 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of D139R and D139A.

In another embodiment, the second substitution is a substitution in the position corresponding to position 142 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of K142R, K142M, K142S, and K142V.

In another embodiment, the second substitution is a substitution in the position corresponding to position 143 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is Q143R.

In another embodiment, the second substitution is a substitution in the position corresponding to position 150 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N150R, N150T, and N150S.

In another embodiment, the second substitution is a substitution in the position corresponding to position 169 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Q169A, Q169R, and Q169K.

In another embodiment, the second substitution is a substitution in the position corresponding to position 172 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is H172R.

In another embodiment, the second substitution is a substitution in the position corresponding to position 174 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Y174R, Y174L, Y174W, and Y174F.

In another embodiment, the second substitution is a substitution in the position corresponding to position 176 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is R176Q.

In another embodiment, the second substitution is a substitution in the position corresponding to position 177 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of E177S and E177Y.

In another embodiment, the second substitution is a substitution in the position corresponding to position 180 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N180R.

In another embodiment, the second substitution is a substitution in the position corresponding to position 183 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of P183T and P183G.

In another embodiment, the second substitution is a substitution in the position corresponding to position 184 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Q184E and Q184K.

In another embodiment, the second substitution is a substitution in the position corresponding to position 185 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is R185G.

In another embodiment, the second substitution is a substitution in the position corresponding to position 196 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Y196W or Y196F.

In another embodiment, the second substitution is a substitution in the position corresponding to position 200 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N200T.

In another embodiment, the second substitution is a substitution in the position corresponding to position 202 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S202R.

In another embodiment, the second substitution is a substitution in the position corresponding to position 203 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is Q203T.

In another embodiment, the second substitution is a substitution in the position corresponding to position 205 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is R205K.

In another embodiment, the second substitution is a substitution in the position corresponding to position 210 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of R210M, R210G, and R210L.

In another embodiment, the second substitution is a substitution in the position corresponding to position 213 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N213V and N213D.

In another embodiment, the second substitution is a substitution in the position corresponding to position 228 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is T228S.

In another embodiment, the second substitution is a substitution in the position corresponding to position 229 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is N229D.

In another embodiment, the second substitution is a substitution in the position corresponding to position 234 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of E234F and E234Y.

In another embodiment, the second substitution is a substitution in the position corresponding to position 235 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of A235R and A235K.

In another embodiment, the second substitution is a substitution in the position corresponding to position 241 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S241C.

In another embodiment, the second substitution is a substitution in the position corresponding to position 243 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Q243E and Q243K.

In another embodiment, the second substitution is a substitution in the position corresponding to position 244 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of R244K and R244V.

In another embodiment, the second substitution is a substitution in the position corresponding to position 250 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is A250G.

In another embodiment, the second substitution is a substitution in the position corresponding to position 254 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is K254Y.

In another embodiment, the second substitution is a substitution in the position corresponding to position 257 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of G257W, G257E, G257A, and G257G.

In another embodiment, the second substitution is a substitution in the position corresponding to position 260 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is W260F.

In another embodiment, the second substitution is a substitution in the position corresponding to position 262 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is Y262F.

In another embodiment, the second substitution is a substitution in the position corresponding to position 266 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is S266A.

In another embodiment, the second substitution is a substitution in the position corresponding to position 268 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is D268N.

In another embodiment, the second substitution is a substitution in the position corresponding to position 270 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is A270D.

In another embodiment, the second substitution is a substitution in the position corresponding to position 184 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N272M and N272T.

In another embodiment, the second substitution is a substitution in the position corresponding to position 273 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N273E and N273D.

In another embodiment, the second substitution is a substitution in the position corresponding to position 276 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of A276E, A276D, and A276W.

In another embodiment, the second substitution is a substitution in the position corresponding to position 279 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N279D and N279E.

In another embodiment, the second substitution is a substitution in the position corresponding to position 280 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is T280L.

In another embodiment, the second substitution is a substitution in the position corresponding to position 283 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of N283H and N283W.

In another embodiment, the second substitution is a substitution in the position corresponding to position 286 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of Y286W and Y286F.

In another embodiment, the second substitution is a substitution in the position corresponding to position 288 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is L288I.

In another embodiment, the second substitution is a substitution in the position corresponding to position 290 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is E290A.

In another embodiment, the second substitution is a substitution in the position corresponding to position 294 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of L294R, L294V, L294P, L294H, L294K, and L294I.

In another embodiment, the second substitution is a substitution in the position corresponding to position 295 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is selected from the group of S295I, S295K, S295A, S295M, S295N, S295V, S295P, S295L, and S295R.

In another embodiment, the second substitution is a substitution in the position corresponding to position 296 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is T296S.

In another embodiment, the second substitution is a substitution in the position corresponding to position 298 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improveds stability compared to the mannanase of SEQ ID NO: 2. In one embodiment, the substitution is F298Y.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for mannanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of 250 to 300, e.g., 260 to 300, 270 to 300, 285 to 300 amino acids.

In an embodiment, the variant has improved specific activity compared to the parent enzyme.

In an embodiment, the variant has improved stability under storage conditions compared to the parent enzyme.

In an embodiment, the variant has improved thermal activity compared to the parent enzyme.

In an embodiment, the variant has improved thermostability compared to the parent enzyme.

In an alternative aspect, the present invention relates to an isolated mannanase variant of a parent mannannase, wherein the variant comprises at least two substitutions in any two or more positions corresponding to positions selected from the group of 3, 37, 47, 77, 82, 83, 93, 98, 116, 135, 136, 241, 257, and 258, wherein numbering is according to SEQ ID NO: 2, said variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

In one specific embodiment, the variant comprises at least two of the substitutions selected from the group of: S3P, T37P, G47A, G47S, E77T, V82I, V82R, A83P, Y93Q, Y93C, Y93A, Y93F, Y93I, Y93R, S98P, K116R, D135P, A136P, S241C, G257W, G257E, G257L, G257A, G257S, G257Y, G257F, and P258Q.

Such alternative variants have been shown to have an improved stability as compared to the parent mannanase.

Parent Mannanases

The parent mannanase may be (a) a polypeptide having at least 58%, such as at least 65% sequence identity to the mature polypeptide of SEQ ID NO: 1; (b) a polypeptide encoded by a polynucleotide that hybridizes under low stringency conditions with (i) the mature polypeptide coding sequence of SEQ ID NO: 3, (ii) the full-length complement of (i); or (c) a polypeptide encoded by a polynucleotide having at least 58%, such as at least 65% sequence identity to the mature polypeptide coding sequence of SEQ ID NO: 3.

In an aspect, the parent mannanase has a sequence identity to the mature polypeptide of SEQ ID NO: 1 of at least 58%, such as at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has mannanase activity. In one aspect, the amino acid sequence of the parent mannanase differs by up to 20 amino acids, e.g., 1, 2, 3, 4, 5, 6, 7, 8, 9, 10, 11, 12, 13, 14, 15, 16, 17, 18, 19, or 20 from the mature polypeptide of SEQ ID NO: 1.

In an aspect, the parent mannanase has a sequence identity to the polypeptide of SEQ ID NO: 2 of at least 58%, such as at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has mannanase activity. In one aspect, the amino acid sequence of the parent mannanase differs by up to 20 amino acids, e.g., 1, 2, 3, 4, 5, 6, 7, 8, 9, 10, 11, 12, 13, 14, 15, 16, 17, 18, 19, or 20 from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 1.

In another aspect, the parent is a fragment of the polypeptide of SEQ ID NO: 2 containing at least 250 amino acid residues, e.g., at least 270 and at least 290 amino acid residues.

In another embodiment, the parent is an allelic variant of the polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 3, or (ii) the full-length complement of (i) or (ii) (Sambrook et al., 1989, *Molecular Cloning, A Laboratory Manual,* 2d edition, Cold Spring Harbor, New York).

The polynucleotide of SEQ ID NO: 3 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 3; (ii) the mature polypeptide coding sequence of SEQ ID NO: 3; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 3. In another aspect, the nucleic acid probe is a polynucleotide that encodes the polypeptide of SEQ ID NO: 1; the mature polypeptide thereof; or a fragment thereof. In another aspect, the nucleic acid probe is SEQ ID NO: 3.

In another embodiment, the parent is encoded by a polynucleotide having a sequence identity to the mature polypeptide coding sequence of SEQ ID NO: 3 of at least 58%, such as at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial mannanase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* mannanase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* mannanase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* mannanase.

In another aspect, the parent is a *Streptococcus equisimilis, Streptococcus pyogenes, Streptococcus uberis*, or *Streptococcus equi* subsp. *Zooepidemicus* mannanase.

In another aspect, the parent is a *Streptomyces achromogenes, Streptomyces avermitilis, Streptomyces coelicolor, Streptomyces griseus*, or *Streptomyces lividans* mannanase.

In another aspect, the parent is a *Bacillus bogoriensis* mannanase, e.g., the mannanase of SEQ ID NO: 1 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having mannanase activity, comprising: (a) introducing into a parent mannanase at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, wherein the variant has mannanase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention. Thus, in one aspect, the present invention relates to a polynucleotide encoding a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in one aspect, the present invention relates to a polynucleotide encoding a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. Thus, in one aspect, the present invention relates to recombinant expression vectors comprising a polynucleotide encoding a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, a promoter, and transcriptional and translational stop signals.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. Thus, in one aspect, the present invention relates to recombinant host cells, comprising a polynucleotide encoding a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direc the production of a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO:

2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a Strepto-myces cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant. Thus, in one aspect, the present invention relates to methods of producing a variant, comprising the steps of (a) cultivating a host cell comprising a polynucleotide encoding a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direc the production of a variant under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants, such as a mannanase enzyme assay as described in Example 2. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Methods or Uses

Methods for Improving the Nutritional Value of Animal Feed

The present invention further relates to a method for improving the nutritional value of an animal feed comprising plant based material, comprising adding to the feed a mannanase variant.

The term improving the nutritional value of an animal feed means improving the availability of nutrients in the feed. The nutritional values refers in particular to improving the solubilization and degradation of the arabinoxylan-containing fraction (e.g., such as hemicellulose) of the feed, thereby leading to increased release of nutrients from cells in the endosperm that have cell walls composed of highly recalcitrant hemicellulose. Consequently, an increased release of arabinoxylan oligomers indicates a disruption of the cell walls and as a result the nutritional value of the feed is improved resulting in increased growth rate and/or weight gain and/or feed conversion (i.e., the weight of ingested feed relative to weight gain). In addition the arabinoxylan oligomer release may result in improved utilization of these components per se either directly or by bacterial fermentation in the hind gut thereby resulting in a production of short chain fatty acids that may be readily absorbed in the hind and utilised in the energy metabolism.

Compositions of the Invention

The present invention also relates to compositions comprising a polypeptide variant of the present invention. Accordingly, the present invention relates to compositions comprising a variant comprising at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2. Preferably, the compositions are enriched in such a variant. The term "enriched" means that the alpha-amylase activity of the composition has been increased, e.g., with an enrichment factor of 1.1.

In one embodiment, the present invention relates to a composition comprising a variant comprising at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, and a protease, such as a protease of SEQ ID NO: 4 or a variant thereof. The protease variant may be a variant of SEQ ID NO: 4 or any protease having at least 70% sequence identity thereto comprising one or more substitutions selected from the group of substitutions: Y161A, R164S, and A188P, or a variant comprising one or more substitutions selected from the group: S9E, N42R, N74D, V199I, Q200L, Y203W, S253D, N255W, and L256E.

The composition may comprise a polypeptide variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger,* or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatutn, Fusarium roseum, Fusarium sambucinum, Fusarium sarcochroum, Fusarium sulphureum, Fusarium toruloseum, Fusarium trichothecioides,* or *Fusarium venenatum; Humicola,* e.g., *Humicola insolens* or *Humicola lanuginosa;* or *Trichoderma,* e.g., *Trichoderma harzianum,*

*Trichoderma koningii, Trichoderma longibrachiatum, Trichoderma reesei,* or *Trichoderma viride.*

The compositions may be prepared in accordance with methods known in the art and may be in the form of a liquid or a dry composition. For instance, the composition may be in the form of a granulate or a microgranulate. The polypeptide variant may be stabilized in accordance with methods known in the art.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries. Thus, the present invention also relates to a detergent additive comprising a variant of the invention, optionally in the form of a non-dusting granulate, stabilized liquid, or protected enzyme. Accordingly, the present invention relates to a detergent additive comprising variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, optionally, wherein the detergent additive is in the form of a non-dusting granulate, stabilized liquid, or protected enzyme.

In one aspect, the present invention relates to detergent compositions comprising a polypeptide variant of the present invention in combination with one or more additional cleaning composition components. Accordingly, the present invention relates to a detergent composition comprising variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, in combination with one or more additional cleaning composition component.

The choice of additional components is within the skill of the artisan and includes conventional ingredients, including the exemplary non-limiting components set forth below.

The choice of components may include, for textile care, such as laundry, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Accordingly, the present invention also relates to a composition which is a cleaning composition.

A composition according to the present invention may further comprise a detergent component, such as a surfactant, a bleach, a dispersant polymer such as a sulfonated polymer, a complexing agent, a bleach catalyst such as a manganese bleach catalyst, a crystal growth inhibitor, and/or fabric hueing agents.

In one embodiment, the composition is a phosphate free composition.

The detergent composition of the invention may for example be directed to an ADW (Automatic Dish Wash) composition comprising an enzyme of the present invention in combination with one or more additional ADW composition components. The choice of additional components is within the skill of the artisan and includes conventional ingredients, including the exemplary non-limiting components set forth below. Accordingly, in one aspect, the invention relates to a manual or automatic dishwashing detergent composition comprising a variant of the invention, and optionally a surfactant.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. Accordingly, in one aspect, the present invention relates to a manual or automatic laundry detergent composition comprising a variant according to the invention.

In a specific aspect, the invention provides a detergent concentrate/additive comprising the polypeptide of the invention. The detergent additive, as well as the detergent composition, may comprise one or more other enzymes such as an amylase, protease, a lipase, a peroxidase, another amylolytic enzyme, e.g., alpha-amylase, glucoamylase, maltogenic amylase, CGTase and/or a cellulase, another mannanase, pectinase, pectine lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE®, SAVINASE® (SEQ ID NO: 3), PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3®, FN4® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), *Biochemica et Biophysica Acta*, 1131:253-360), *B. stearothermophilus* (JP 64/744992) or *B. pumilus* (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE<™> and LIPOLASE ULTRA<™> (Novozymes A/S).

Amylases: Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful alpha-amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available alpha-amylases are DURAMYL<™>, LIQUEZYME™, TERMAMYL<™>, NATALASE<™>, FUNGAMYL<™> and BAN<™> (Novozymes A/S), Preferenz S100, Preferenz S110, Preferenz S1000 (SEQ ID NO: 11), Excellenz S110, Excellenz S1000, Excellenz S2000, RAPIDASE<™> and PURASTAR<™> (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes A/S).

Lechinases/Beta-glucanases: Suitable Lechinases include those of bacterial or fungal origin. They may be chemically modified or protein engineered. Examples of useful beta-glucanases include those described in WO 2015/144824 (Novozymes A/S) and WO 99/06516 (Henkel KGAA).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually comprise from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually comprise from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid mono-ethanol-amide, polyhydroxy alkyl fatty acid amide, or N-acyl N-alkyl derivatives of glucosamine ("glucamides").

The detergent may comprise 0-65% of a detergent builder or complexing agent such as MGDA, GLDA, zeolite, diphosphate, tripho-sphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as sulfonated polymers, polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as bleach catalysts, e.g. Mn-based or Co-based, tetraacetylethylenediamine or nonanoyloxybenzenesul-fonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent composition may comprise about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry/ADW/hard surface cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent may comprise 0-30% by weight, such as about 1% to about 20%, of a bleaching system. Any bleaching system known in the art for use in laundry/ADW/hard surface cleaning detergents may be utilized. Suitable bleaching system components include bleaching catalysts, photo-bleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

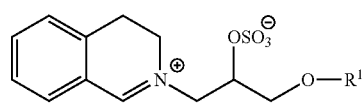

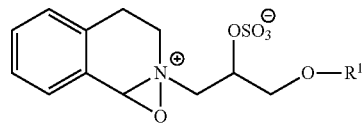

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

The detergent may comprise 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The detergent compositions of the present invention may also comprise fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

It is at present contemplated that in the detergent compositions any enzyme, in particular the alpha amylase polypeptides of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The alpha amylase polypeptides of the invention may additionally be incorporated in the detergent formulations disclosed in WO 2006/002643, which is hereby incorporated as reference.

Uses

The present invention is also directed to methods for using a polypeptide variant of the invention. The use may be in detergents, in particular laundry detergent compositions and dishwashing detergent compositions. Accordingly, the present invention relates to use of a variant comprises at least two substitutions, wherein (a) said first substitution is in an amino acid position selected from the positions 260, 288, 294, or 295, and (b) said at least second substitution is selected from any other position in said variant, wherein numbering is according to SEQ ID NO: 2, said variant has mannanase activity and has at least 58%, such as at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

Thus, the invention provides the use of a polypeptide variant of a parent polypeptide or composition of the invention, in a domestic or industrial cleaning process. In particular, the invention relates to use of a polypeptide variant according to the invention in laundry, dishwash; such as automatic or manual dishwash, hard surface cleaning, industrial and institutional cleaning, textile desizing, starch modification, starch liquefaction, saccharification, feed, baking, or brewing.

In one embodiment, the use is cleaning of fabric, for example laundry.

In another embodiment, the use is cleaning of ceramic, plastic or glass material, for example dishwashing.

Accordingly, the polypeptide variants of the invention are applicable as a component in washing, dishwashing, and hard surface cleaning detergent compositions (in either a domestic or industrial setting).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1: Site-Saturation Library Generation

The gene of Mannanase (SEQ ID NO: 3) was cloned into the *Bacillus subtilis* expression cassette and transformed in a derivative of the expression host, *Bacillus subtilis* 168, deficient in alkaline protease, neutral protease, alpha-amylase and pectate lyase. Site-saturation libraries were generated by the method known as "Mega PCR" approach in each mentioned position in the Mannanase gene with NNS doping in the forward mutagenic primer. NNS is a well-known method, where the "N" designates any of the four nucleotide bases and "S" designates the nulceotides "C" and "G".

Two PCR reactions were performed, wherein 1) was generation of C-terminal fragment with the flanking C-terminal reverse primer and the forward mutagenic primer, and 2) was generation of Mega PCR product using the C-terminal fragment as the reverse mega-primer and the flanking N-terminal forward primer to give the full-length cassette. The Mega PCR product was then transformed in to the *Bacillus* host, where site-specific homologous recombination in the *Bacillus* chromosome took place.

After 18-20 hours of growth in LB agar media with chloramphinecol for antibiotic selection, the transformed colonies were picked and inoculated in to the aqueous growth media, i.e. TB-Gly media. After 3 days of growth, culture PCR was carried out by initial heat lysis of cells, followed by PCR. The sequence of the PCR products were confirmed by sanger sequencing and the resulting variants were tested in screening assays. The polymerase used for the PCR reaction was Phusion DNA polymerase (obtained from ThermoScientific, Cat. No.: F530L).

Example 2: Variant Generation by Site-Directed Mutagenesis

The gene of Mannanase (SEQ ID NO: 3) was cloned into the *Bacillus subtilis* expression cassette and transformed in the expression host, *Bacillus subtilis* as described in Example 1. A Mega PCR-based site-directed mutagenesis (SDM) was carried out to generate variants of the Mannanase gene by introducing mutations at specific sites (as described in Example 1). SDM was carried out using a single mutagenic primer of 20-30 base pairs with the desired amino acid change (substitution/deletion/insertion) lying in the middle of the oligonucleotide with sufficient flanking residues (9-15 base pairs). Two PCR reactions were involved 1) generation of C-terminal fragment with the flanking C-terminal reverse primer and the forward mutagenic primer 2) generation of Mega PCR product using the C-terminal fragment as the reverse mega-primer and the flanking N-terminal forward primer to give the full-length cassette. The Mega PCR product was then transformed in to the *Bacillus* host, where site-specific homologous recombination in the *Bacillus* chromosome takes place.

After 18-20 hours of growth in LB agar media with appropriate antibiotic, the transformed colonies were picked and inoculated in to the aqueous expression media and given for screening assays. The hits from the screening assays were subjected to culture PCR and sent for sequence confirmation. The polymerase used for the PCR reaction was Phusion DNA polymerase (obtained from ThermoScientific, Cat. No.: F530L).

Example 3: Detergent Stability Determination

Variants of the present invention and generated as described in Example 1 and 2, were tested for detergent stability at pH 9.0 and pH 10.5-10.8. Stability test was performed by incubating the variants in detergent for different length of time and temperature (given in the tables below) depending on the stability of wild-type (WT) or backbone and comparing the activity against control plate which was incubated at 4° C. for the same duration. The stability test was performed in two different detergents (Model O detergent described in Table 1, and commercially available detergent Arms & Hammer (listed as A&H)).

To the Model O detergent was added a protease, and for the A&H detergent a protease and protease inhibitor are already present in the detergent.

The residual activity was measured by using the Mannanase enzyme assay using insoluble Azo-carob-galactomannan substrate from Megazyme. Substrate was incubated with enzyme for 20 min at 25° C. for 20 min, shaking at 800 rpm. The reaction mixture was kept static for 10 min to allow insoluble substrate to settle. Enzyme activity was measured by reading the optical density of supernatant at 590 nm. The residual activity was calculated by taking the ratio of Stress response to Un-stress response and expressing in terms of % RA.

TABLE 1

| Model O detergent | |
|---|---|
| Compound | Content of compound (% w/w) |
| Na-LAS (linear alkylbenzene sulphonate) | 5.3 |
| AEOS (Alkylethoxy sulphate) | 10.7 |
| Soyfatty acid | 1.0 |
| AEO (Alcohol polyethoxylated) | 5.3 |
| TEA (Trietanolamine) | 0.4 |
| Sodium citrate | 2.0 |
| $CaCl_2$ | 0.02 |
| Water | 75.3 |

Water hardness adjusted to 12° dH by addition of $CaCl_2$, $MgCl_2$, and $NaHCO_3$ ($Ca^{2+}:Mg^{2+}:HCO^{3-}=2:1:4.5$) to the test system. After washing the textiles were flushed in tap water and dried.

Table 2 and Table 3 below show the stability results obtained from Example 3.

TABLE 2

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| S3P G47S E77T Y93Q K116R A136P G257W L288I L294P S295K | 9 | Model O | 40 C. | 24 hr | 81.2 | 3.0 |
| S3P G47S E77T Y93Q K116R A136P W260F L288I L294P S295K | 9 | Model O | 40 C. | 24 hr | 83.7 | 10.9 |
| W260F L288I L294P S295L | 9 | Model O | 40 C. | 24 hr | 88.4 | 16.9 |
| W260F L288I L294P S295V | 9 | Model O | 40 C. | 24 hr | 86.1 | 13.5 |
| W260F L288I L294P S295P | 9 | Model O | 40 C. | 24 hr | 83.7 | 11.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| L288I L294P S295V | 9 | Model O | 40 C. | 24 hr | 80.1 | 6.2 |
| L288I L294P S295K | 9 | Model O | 40 C. | 24 hr | 77.5 | 7.1 |
| L288I L294P S295L | 9 | Model O | 40 C. | 24 hr | 76.0 | 5.9 |
| L288I L294P S295K G47A | 9 | Model O | 45 C. | 16 hr | 59.6 | 6.3 |
| L288I L294P S295K K116R | 9 | Model O | 45 C. | 16 hr | 53.0 | 4.6 |
| L288I L294P S295K G47S | 9 | Model O | 45 C. | 16 hr | 53.8 | 5.1 |
| L288I L294P S295K Y93Q | 9 | Model O | 45 C. | 16 hr | 66.7 | 7.5 |
| L288I L294P S295K T37P | 9 | Model O | 45 C. | 16 hr | 53.9 | 4.6 |
| L288I L294P S295K A136P | 9 | Model O | 45 C. | 16 hr | 69.3 | 8.1 |
| W260F L288I L294P S295V G47A | 9 | Model O | 45 C. | 16 hr | 90.4 | 38.8 |
| W260F L288I L294P S295V G47S | 9 | Model O | 45 C. | 16 hr | 87.8 | 28.9 |
| W260F L288I L294P S295V K116R | 9 | Model O | 45 C. | 16 hr | 87.6 | 40.9 |
| W260F L288I L294P S295V Y93Q | 9 | Model O | 45 C. | 16 hr | 80.2 | 16.4 |
| W260F L288I L294P S295V T37P | 9 | Model O | 45 C. | 16 hr | 82.5 | 14.6 |
| W260F L288I L294P S295V E77T | 9 | Model O | 45 C. | 16 hr | 75.6 | 9.7 |
| W260F L288I L294P S295V A136P | 9 | Model O | 45 C. | 16 hr | 87.9 | 23.8 |
| L288I L294P S295P | 9 | Model O | 45 C. | 16 hr | 63.3 | 7.2 |
| S3P G47S Y93Q K116R A136P W260F L288I L294P S295K | 9 | Model O | 50 C. | 16 hr | 60.3 | 13.8 |
| S3P G47S E77T K116R A136P W260F L288I L294P S295K | 9 | Model O | 50 C. | 16 hr | 35.7 | 6.6 |
| S3P G47S E77T Y93Q A136P W260F L288I L294P S295K | 9 | Model O | 50 C. | 16 hr | 52.5 | 10.5 |
| S3P G47S E77T Y93Q K116R A136P L288I L294P S295K | 9 | Model O | 50 C. | 16 hr | 28.2 | 5.3 |
| W260F L288I L294P S295V Y93A | 9 | Model O | 50 C. | 24 hr | 73.4 | 36.1 |
| W260F L288I L294P S295V Y93I | 9 | Model O | 50 C. | 24 hr | 73.8 | 36.1 |
| W260F L288I L294P S295V Y93F | 9 | Model O | 50 C. | 24 hr | 68.7 | 30.1 |
| W260F L288I L294P S295V Y93R | 9 | Model O | 50 C. | 24 hr | 66.1 | 31.5 |
| W260F L288I L294P S295V A83P | 9 | Model O | 50 C. | 24 hr | 63.6 | 22.0 |
| W260F L288I L294P S295V V82I | 9 | Model O | 50 C. | 24 hr | 63.3 | 26.6 |
| W260F L288I L294P S295V L81R | 9 | Model O | 50 C. | 24 hr | 37.1 | 10.9 |
| W260F L288I L294P S295V E77N | 9 | Model O | 50 C. | 24 hr | 57.1 | 19.7 |
| W260F L288I L294P S295V A83S | 9 | Model O | 50 C. | 24 hr | 57.1 | 21.3 |
| W260F L288I L294P S295V S202R | 9 | Model O | 50 C. | 24 hr | 82.5 | 36.1 |
| W260F L288I L294P S295V G47K | 9 | Model O | 50 C. | 24 hr | 53.4 | 17.8 |
| W260F L288I L294P S295V G47T | 9 | Model O | 50 C. | 24 hr | 61.8 | 24.7 |
| W260F L288I L294P S295V H80K | 9 | Model O | 50 C. | 24 hr | 58.8 | 20.6 |
| W260F L288I L294P S295V D135P | 9 | Model O | 50 C. | 24 hr | 58.4 | 18.0 |
| W260F L288I L294P S295V I96A | 9 | Model O | 50 C. | 24 hr | 20.2 | 6.8 |
| W260L L288I L294P S295V | 9 | Model O | 50 C. | 24 hr | 65.6 | 21.3 |
| W260F L288I L294R S295V | 9 | Model O | 50 C. | 24 hr | 51.9 | 16.4 |
| W260F L288I L294P S295V | 9 | Model O | 50 C. | 24 hr | 54.1 | 16.0 |
| W260F L288I L294P S295V G47R | 9 | Model O | 50 C. | 40 hr | 34.6 | 16.6 |
| W260F L288I L294K S295V | 9 | Model O | 50 C. | 40 hr | 23.0 | 12.1 |
| W260F L288I L294P S295V G47Y | 9 | Model O | 50 C. | 40 hr | 25.8 | 13.2 |
| W260F L288I L294P S295V H80R | 9 | Model O | 50 C. | 40 hr | 34.3 | 15.8 |
| W260F L288I L294P S295V D118K | 9 | Model O | 50 C. | 40 hr | 28.2 | 13.7 |
| W260F L288I L294P S295V T119R | 9 | Model O | 50 C. | 40 hr | 27.3 | 12.7 |
| W260F L288I L294P S295V S202E | 9 | Model O | 50 C. | 40 hr | 59.6 | 31.5 |
| W260F L288I L294P S295V G257E | 9 | Model O | 50 C. | 40 hr | 36.7 | 16.4 |
| W260F L288I L294P S295V A136P D14A | 9 | Model O | 50 C. | 40 hr | 22.2 | 11.6 |
| W260F L288I L294P S295V A136P T37P | 9 | Model O | 50 C. | 40 hr | 55.5 | 27.6 |
| W260F L288I L294P S295V A136P G47A | 9 | Model O | 50 C. | 40 hr | 54.9 | 29.8 |
| W260F L288I L294P S295V A136P G47K | 9 | Model O | 50 C. | 40 hr | 46.6 | 23.4 |
| W260F L288I L294P S295V A136P G47R | 9 | Model O | 50 C. | 40 hr | 44.8 | 21.5 |
| W260F L288I L294P S295V A136P G47S | 9 | Model O | 50 C. | 40 hr | 51.8 | 27.1 |
| W260F L288I L294P S295V A136P G47Y | 9 | Model O | 50 C. | 40 hr | 40.9 | 19.6 |
| W260F L288I L294P S295V A136P E77T | 9 | Model O | 50 C. | 40 hr | 47.3 | 26.0 |
| W260F L288I L294P S295V A136P H80R | 9 | Model O | 50 C. | 40 hr | 59.4 | 29.9 |
| W260F L288I L294P S295V A136P L81R | 9 | Model O | 50 C. | 40 hr | 60.6 | 35.6 |
| W260F L288I L294P S295V A136P V82I | 9 | Model O | 50 C. | 40 hr | 57.7 | 31.5 |
| W260F L288I L294P S295V A136P A83P | 9 | Model O | 50 C. | 40 hr | 49.7 | 23.4 |
| W260F L288I L294P S295V A136P A83S | 9 | Model O | 50 C. | 40 hr | 52.4 | 26.7 |
| W260F L288I L294P S295V A136P Y93A | 9 | Model O | 50 C. | 40 hr | 48.1 | 23.2 |
| W260F L288I L294P S295V A136P Y93Q | 9 | Model O | 50 C. | 40 hr | 60.6 | 36.7 |
| W260F L288I L294P S295V A136P K116R | 9 | Model O | 50 C. | 40 hr | 54.6 | 26.7 |
| W260F L288I L294P S295V A136P D118K | 9 | Model O | 50 C. | 40 hr | 57.8 | 31.6 |
| W260F L288I L294P S295V A136P T119R | 9 | Model O | 50 C. | 40 hr | 58.9 | 15.5 |
| W260F L288I L294P S295V A136P | 9 | Model O | 50 C. | 40 hr | 51.7 | 26.9 |
| W260F L288I L294P S295V A136P S202E | 9 | Model O | 50 C. | 40 hr | 52.2 | 26.3 |
| W260F L288I L294P S295V A136P S202R | 9 | Model O | 50 C. | 40 hr | 74.7 | 59.3 |
| W260F L288I L294P S295V A136P G257E | 9 | Model O | 50 C. | 40 hr | 56.9 | 32.1 |
| S3P G47S E77T Y93Q K116R A136P W260F L288I L294P S295V | 9 | Model O | 50 C. | 40 hr | 52.9 | 23.8 |
| W260F L288I L294P S295V S202R S8T | 9 | Model O | 50 C. | 65 hr | 48.7 | 37.7 |
| W260F L288I L294P S295V S202R T37P | 9 | Model O | 50 C. | 65 hr | 40.2 | 27.5 |
| W260F L288I L294P S295V S202R E41V | 9 | Model O | 50 C. | 65 hr | 55.5 | 37.3 |
| W260F L288I L294P S295V S202R G47A | 9 | Model O | 50 C. | 65 hr | 38.3 | 28.6 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| W260F L288I L294P S295V S202R G47K | 9 | Model O | 50 C. | 65 hr | 33.7 | 24.6 |
| W260F L288I L294P S295V S202R G47R | 9 | Model O | 50 C. | 65 hr | 33.7 | 24.1 |
| W260F L288I L294P S295V S202R G47S | 9 | Model O | 50 C. | 65 hr | 34.5 | 25.0 |
| W260F L288I L294P S295V S202R G47Y | 9 | Model O | 50 C. | 65 hr | 27.0 | 20.6 |
| W260F L288I L294P S295V S202R E77T | 9 | Model O | 50 C. | 65 hr | 38.6 | 28.6 |
| W260F L288I L294P S295V S202R D78G | 9 | Model O | 50 C. | 65 hr | 42.7 | 29.9 |
| W260F L288I L294P S295V S202R H80K | 9 | Model O | 50 C. | 65 hr | 44.6 | 33.0 |
| W260F L288I L294P S295V S202R A83P | 9 | Model O | 50 C. | 65 hr | 35.0 | 25.8 |
| W260F L288I L294P S295V S202R A83S | 9 | Model O | 50 C. | 65 hr | 35.4 | 25.5 |
| W260F L288I L294P S295V S202R Y93A | 9 | Model O | 50 C. | 65 hr | 41.0 | 28.5 |
| W260F L288I L294P S295V S202R Y93Q | 9 | Model O | 50 C. | 65 hr | 57.8 | 47.6 |
| W260F L288I L294P S295V S202R S98P | 9 | Model O | 50 C. | 65 hr | 49.4 | 38.6 |
| W260F L288I L294P S295V S202R K116R | 9 | Model O | 50 C. | 65 hr | 33.9 | 25.1 |
| W260F L288I L294P S295V S202R D118K | 9 | Model O | 50 C. | 65 hr | 39.9 | 28.8 |
| W260F L288I L294P S295V S202R T119R | 9 | Model O | 50 C. | 65 hr | 41.3 | 31.1 |
| W260F L288I L294P S295V S202R A136P | 9 | Model O | 50 C. | 65 hr | 55.5 | 45.1 |
| W260F L288I L294P S295V S202R | 9 | Model O | 50 C. | 65 hr | 43.2 | 30.8 |
| W260F L288I L294P S295V S202R G257E | 9 | Model O | 50 C. | 65 hr | 48.9 | 37.4 |
| W260F L288I L294P S295V S202R T299P | 9 | Model O | 50 C. | 65 hr | 38.6 | 28.3 |
| W260L L288I L294P S295V S202R | 9 | Model O | 50 C. | 65 hr | 62.4 | 51.2 |
| S8T A136P S202R W260F L288I L294P S295V | 9 | Model O | 50 C. | 65 hr | 73.9 | 90.7 |
| D14A A136P S202R W260F L288I L294P S295V | 9 | Model O | 50 C. | 65 hr | 20.0 | 17.3 |
| D14S A136P S202R W260F L288I L294P S295V | 9 | Model O | 50 C. | 65 hr | 39.6 | 30.2 |
| T37P A136P S202R W260F L288I L294P S295V | 9 | Model O | 50 C. | 65 hr | 60.5 | 54.9 |
| E41V A136P S202R W260F L288I L294P S295V | 9 | Model O | 50 C. | 65 hr | 66.0 | 64.6 |
| G47A A136P S202R W260F L288I L294P S295V | 9 | Model O | 50 C. | 65 hr | 59.4 | 52.2 |
| G47K A136P S202R W260F L288I L294P S295V | 9 | Model O | 50 C. | 65 hr | 64.1 | 62.9 |
| G47R A136P S202R W260F L288I L294P S295V | 9 | Model O | 50 C. | 65 hr | 58.8 | 51.1 |
| G47S A136P S202R W260F L288I L294P S295V | 9 | Model O | 50 C. | 65 hr | 60.9 | 51.7 |
| G47Y A136P S202R W260F L288I L294P S295V | 9 | Model O | 50 C. | 65 hr | 55.8 | 45.3 |
| E77N A136P S202R W260F L288I L294P S295V | 9 | Model O | 50 C. | 65 hr | 63.6 | 54.3 |
| E77T A136P S202R W260F L288I L294P S295V | 9 | Model O | 50 C. | 65 hr | 60.8 | 55.3 |
| D78G A136P S202R W260F L288I L294P S295V | 9 | Model O | 50 C. | 65 hr | 66.8 | 70.6 |
| H80K A136P S202R W260F L288I L294P S295V | 9 | Model O | 50 C. | 65 hr | 67.0 | 69.1 |
| H80R A136P S202R W260F L288I L294P S295V | 9 | Model O | 50 C. | 65 hr | 66.1 | 67.7 |
| L81R A136P S202R W260F L288I L294P S295V | 9 | Model O | 50 C. | 65 hr | 36.6 | 27.3 |
| V82I A136P S202R W260F L288I L294P S295V | 9 | Model O | 50 C. | 65 hr | 68.5 | 79.1 |
| A83P A136P S202R W260F L288I L294P S295V | 9 | Model O | 50 C. | 65 hr | 61.5 | 54.1 |
| A83S A136P S202R W260F L288I L294P S295V | 9 | Model O | 50 C. | 65 hr | 62.6 | 58.2 |
| A83T A136P S202R W260F L288I L294P S295V | 9 | Model O | 50 C. | 65 hr | 54.1 | 44.7 |
| Y93A A136P S202R W260F L288I L294P S295V | 9 | Model O | 50 C. | 65 hr | 59.9 | 53.7 |
| Y93F A136P S202R W260F L288I L294P S295V | 9 | Model O | 50 C. | 65 hr | 66.0 | 63.6 |
| Y93I A136P S202R W260F L288I L294P S295V | 9 | Model O | 50 C. | 65 hr | 65.7 | 62.9 |
| Y93Q A136P S202R W260F L288I L294P S295V | 9 | Model O | 50 C. | 65 hr | 73.9 | 96.4 |
| Y93R A136P S202R W260F L288I L294P S295V | 9 | Model O | 50 C. | 65 hr | 62.7 | 54.9 |
| S98P A136P S202R W260F L288I L294P S295V | 9 | Model O | 50 C. | 65 hr | 73.3 | 85.6 |
| K116R A136P S202R W260F L288I L294P S295V | 9 | Model O | 50 C. | 65 hr | 63.9 | 61.0 |
| D118K A136P S202R W260F L288I L294P S295V | 9 | Model O | 50 C. | 65 hr | 67.2 | 68.5 |
| T119R A136P S202R W260F L288I L294P S295V | 9 | Model O | 50 C. | 65 hr | 64.1 | 66.1 |
| A136P S202R G257A W260F L288I L294P S295V | 9 | Model O | 50 C. | 65 hr | 67.9 | 69.6 |
| A136P S202R G257E W260F L288I L294P S295V | 9 | Model O | 50 C. | 65 hr | 71.0 | 80.5 |
| A136P S202R W260L L288I L294P S295V | 9 | Model O | 50 C. | 65 hr | 79.0 | 96.4 |
| A136P S202R W260F L288I L294P S295V T299P | 9 | Model O | 50 C. | 65 hr | 62.9 | 60.8 |
| S3P A136P S202R W260F L288I L294P S295V | 9 | Model O | 50 C. | 65 hr | 68.6 | 89.7 |
| A136P S202R W260F L288I L294P S295I | 9 | Model O | 50 C. | 65 hr | 51.6 | 42.0 |
| A136P S202R W260F L288I L294P S295P | 9 | Model O | 50 C. | 65 hr | 46.7 | 35.2 |
| G47Q A136P S202R W260F L288I L294P S295V | 9 | Model O | 50 C. | 65 hr | 65.6 | 59.8 |
| G47T A136P S202R W260F L288I L294P S295V | 9 | Model O | 50 C. | 65 hr | 63.6 | 65.2 |
| A136P S202R W260F L288I L294P S295V | 9 | Model O | 50 C. | 114 hr | 45.1 | 62.2 |
| E41V Y93F S202R W260F L288I L294P S295V | 9 | Model O | 50 C. | 138 hr | 24.5 | 42.6 |
| E41V Y93I S202R W260F L288I L294P S295V | 9 | Model O | 50 C. | 138 hr | 28.3 | 41.0 |
| E41V Y93Q S202R W260F L288I L294P S295V | 9 | Model O | 50 C. | 138 hr | 30.8 | 50.8 |
| E41V Y93R S202R W260F L288I L294P S295V | 9 | Model O | 50 C. | 138 hr | 22.5 | 36.2 |
| E41V S98P S202R W260F L288I L294P S295V | 9 | Model O | 50 C. | 138 hr | 29.8 | 49.5 |
| E41V D118K S202R W260F L288I L294P S295V | 9 | Model O | 50 C. | 138 hr | 23.2 | 37.0 |
| E41V T119R S202R W260F L288I L294P S295V | 9 | Model O | 50 C. | 138 hr | 27.7 | 42.1 |
| E41V S202R G257E W260F L288I L294P S295V | 9 | Model O | 50 C. | 138 hr | 25.8 | 45.2 |
| S8T Y93Q S202R W260F L288I L294P S295V | 9 | Model O | 50 C. | 138 hr | 36.4 | 58.2 |
| G47A Y93Q S202R W260F L288I L294P S295V | 9 | Model O | 50 C. | 138 hr | 21.0 | 36.6 |
| G47K Y93Q S202R W260F L288I L294P S295V | 9 | Model O | 50 C. | 138 hr | 24.4 | 41.3 |
| G47Q Y93Q S202R W260F L288I L294P S295V | 9 | Model O | 50 C. | 138 hr | 33.7 | 53.5 |
| G47R Y93Q S202R W260F L288I L294P S295V | 9 | Model O | 50 C. | 138 hr | 23.6 | 41.6 |
| G47S Y93Q S202R W260F L288I L294P S295V | 9 | Model O | 50 C. | 138 hr | 25.7 | 42.5 |
| G47T Y93Q S202R W260F L288I L294P S295V | 9 | Model O | 50 C. | 138 hr | 28.3 | 46.1 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| E77N Y93Q S202R W260F L288I L294P S295V | 9 | Model O | 50 C. | 138 hr | 29.3 | 47.7 |
| E77T Y93Q S202R W260F L288I L294P S295V | 9 | Model O | 50 C. | 138 hr | 25.7 | 44.1 |
| D78G Y93Q S202R W260F L288I L294P S295V | 9 | Model O | 50 C. | 138 hr | 29.6 | 49.9 |
| H80K Y93Q S202R W260F L288I L294P S295V | 9 | Model O | 50 C. | 138 hr | 28.0 | 48.1 |
| H80R Y93Q S202R W260F L288I L294P S295V | 9 | Model O | 50 C. | 138 hr | 31.6 | 51.2 |
| A83T Y93Q S202R W260F L288I L294P S295V | 9 | Model O | 50 C. | 138 hr | 21.2 | 37.6 |
| Y93Q S98P S202R W260F L288I L294P S295V | 9 | Model O | 50 C. | 138 hr | 35.5 | 59.3 |
| Y93Q K116R S202R W260F L288I L294P S295V | 9 | Model O | 50 C. | 138 hr | 27.0 | 46.2 |
| Y93Q D118K S202R W260F L288I L294P S295V | 9 | Model O | 50 C. | 138 hr | 30.3 | 50.4 |
| Y93Q T119R S202R W260F L288I L294P S295V | 9 | Model O | 50 C. | 138 hr | 28.6 | 49.8 |
| Y93Q S202R G257E W260F L288I L294P S295V | 9 | Model O | 50 C. | 138 hr | 32.3 | 53.1 |
| T37P G47K A136P S202R W260F L288I L294P S295V | 9 | Model O | 50 C. | 138 hr | 30.0 | 49.1 |
| G47K E77N A136P S202R W260F L288I L294P S295V | 9 | Model O | 50 C. | 138 hr | 28.4 | 47.7 |
| G47K E77T A136P S202R W260F L288I L294P S295V | 9 | Model O | 50 C. | 138 hr | 25.4 | 42.7 |
| G47K H80R A136P S202R W260F L288I L294P S295V | 9 | Model O | 50 C. | 138 hr | 34.1 | 54.7 |
| G47K V82I A136P S202R W260F L288I L294P S295V | 9 | Model O | 50 C. | 138 hr | 34.5 | 56.6 |
| G47K A83S A136P S202R W260F L288I L294P S295V | 9 | Model O | 50 C. | 138 hr | 30.9 | 51.3 |
| G47K Y93Q A136P S202R W260F L288I L294P S295V | 9 | Model O | 50 C. | 138 hr | 41.6 | 66.9 |
| G47K D118K A136P S202R W260F L288I L294P S295V | 9 | Model O | 50 C. | 138 hr | 30.6 | 48.1 |
| G47K T119R A136P S202R W260F L288I L294P S295V | 9 | Model O | 50 C. | 138 hr | 28.6 | 46.9 |
| G47K A136P S202R G257A W260F L288I L294P S295V | 9 | Model O | 50 C. | 138 hr | 34.5 | 56.5 |
| G47K A136P S202R G257E W260F L288I L294P S295V | 9 | Model O | 50 C. | 138 hr | 36.1 | 61.2 |
| G47Q E77T A136P S202R W260F L288I L294P S295V | 9 | Model O | 50 C. | 138 hr | 30.5 | 50.2 |
| G47R E77N A136P S202R W260F L288I L294P S295V | 9 | Model O | 50 C. | 138 hr | 29.5 | 48.5 |
| G47R H80K A136P S202R W260F L288I L294P S295V | 9 | Model O | 50 C. | 138 hr | 29.9 | 53.1 |
| G47R A83S A136P S202R W260F L288I L294P S295V | 9 | Model O | 50 C. | 138 hr | 24.9 | 43.7 |
| G47R A136P S202R G257A W260F L288I L294P S295V | 9 | Model O | 50 C. | 138 hr | 30.0 | 49.6 |
| G47S H80R A136P S202R W260F L288I L294P S295V | 9 | Model O | 50 C. | 138 hr | 32.7 | 53.6 |
| G47T E77T A136P S202R W260F L288I L294P S295V | 9 | Model O | 50 C. | 138 hr | 29.0 | 48.3 |
| G47Y E77T A136P S202R W260F L288I L294P S295V | 9 | Model O | 50 C. | 138 hr | 20.2 | 37.8 |
| G47Y S98P A136P S202R W260F L288I L294P S295V | 9 | Model O | 50 C. | 138 hr | 27.6 | 44.6 |
| G47Y T119R A136P S202R W260F L288I L294P S295V | 9 | Model O | 50 C. | 138 hr | 21.7 | 40.3 |
| L81R S98P A136P S202R W260F L288I L294P S295V | 9 | Model O | 50 C. | 138 hr | 20.0 | 36.2 |
| L81R A136P S202R G257E W260F L288I L294P S295V | 9 | Model O | 50 C. | 138 hr | 26.6 | 43.8 |
| V82I Y93Q S202R W260F L288I L294P S295V | 9 | Model O | 50 C. | 138 hr | 36.8 | 58.1 |
| A83P Y93Q S202R W260F L288I L294P S295V | 9 | Model O | 50 C. | 138 hr | 21.5 | 39.8 |
| A83S Y93Q S202R W260F L288I L294P S295V | 9 | Model O | 50 C. | 138 hr | 21.6 | 38.4 |
| Y93Q S202R G257A W260F L288I L294P S295V | 9 | Model O | 50 C. | 138 hr | 26.7 | 42.8 |
| G47K H80K A136P S202R W260F L288I L294P S295V | 9 | Model O | 50 C. | 138 hr | 27.0 | 47.4 |
| G47K A83T A136P S202R W260F L288I L294P S295V | 9 | Model O | 50 C. | 138 hr | 23.5 | 40.4 |
| G47K S98P A136P S202R W260F L288I L294P S295V | 9 | Model O | 50 C. | 138 hr | 35.6 | 57.3 |
| G47K K116R A136P S202R W260F L288I L294P S295V | 9 | Model O | 50 C. | 138 hr | 21.8 | 36.4 |
| G47K A136P S202R W260F L288I L294P S295V T299P | 9 | Model O | 50 C. | 138 hr | 21.1 | 38.5 |
| G47R H80R A136P S202R W260F L288I L294P S295V | 9 | Model O | 50 C. | 138 hr | 35.9 | 58.9 |
| G47R S98P A136P S202R W260F L288I L294P S295V | 9 | Model O | 50 C. | 138 hr | 29.3 | 47.5 |
| G47R A136P S202R G257E W260F L288I L294P S295V | 9 | Model O | 50 C. | 138 hr | 31.6 | 49.7 |
| G47S T119R A136P S202R W260F L288I L294P S295V | 9 | Model O | 50 C. | 138 hr | 20.8 | 36.3 |
| S8T Y93Q A136P S202R W260F L288I L294P S295V | 9 | Model O | 50 C. | 138 hr | 27.4 | 48.6 |
| T37P Y93Q A136P S202R W260F L288I L294P S295V | 9 | Model O | 50 C. | 138 hr | 33.2 | 50.5 |
| A83P Y93Q A136P S202R W260F L288I L294P S295V | 9 | Model O | 50 C. | 138 hr | 31.7 | 52.0 |
| A83T Y93Q A136P S202R W260F L288I L294P S295V | 9 | Model O | 50 C. | 138 hr | 28.8 | 48.2 |
| Y93Q K116R A136P S202R W260F L288I L294P S295V | 9 | Model O | 50 C. | 138 hr | 27.3 | 46.3 |
| Y93Q D118K A136P S202R W260F L288I L294P S295V | 9 | Model O | 50 C. | 138 hr | 47.6 | 77.9 |
| G47A A136P S202R W260L L288I L294P S295V | 9 | Model O | 50 C. | 138 hr | 48.8 | 86.8 |
| A136P S202R G257E W260L L288I L294P S295V | 9 | Model O | 50 C. | 138 hr | 41.0 | 76.5 |
| S8T E41V A136P S202R W260F L288I L294P S295V | 9 | Model O | 50 C. | 138 hr | 30.3 | 46.2 |
| S8T G47K A136P S202R W260F L288I L294P S295V | 9 | Model O | 50 C. | 138 hr | 28.2 | 43.5 |
| S8T G47Q A136P S202R W260F L288I L294P S295V | 9 | Model O | 50 C. | 138 hr | 26.3 | 44.9 |
| S8T E77T A136P S202R W260F L288I L294P S295V | 9 | Model O | 50 C. | 138 hr | 22.9 | 40.7 |
| S8T D78G A136P S202R W260F L288I L294P S295V | 9 | Model O | 50 C. | 138 hr | 30.8 | 55.0 |
| S8T V82I A136P S202R W260F L288I L294P S295V | 9 | Model O | 50 C. | 138 hr | 33.0 | 53.1 |
| S8T Y93A A136P S202R W260F L288I L294P S295V | 9 | Model O | 50 C. | 138 hr | 33.0 | 54.8 |
| S8T T119R A136P S202R W260F L288I L294P S295V | 9 | Model O | 50 C. | 138 hr | 29.9 | 50.7 |
| S8T A136P S202R G257E W260F L288I L294P S295V | 9 | Model O | 50 C. | 138 hr | 39.5 | 65.5 |
| S3P D78G A136P S202R W260F L288I L294P S295V | 9 | Model O | 50 C. | 138 hr | 25.7 | 43.9 |
| S3P Y93I A136P S202R W260F L288I L294P S295V | 9 | Model O | 50 C. | 138 hr | 29.5 | 47.9 |
| S3P T119R A136P S202R W260F L288I L294P S295V | 9 | Model O | 50 C. | 138 hr | 29.6 | 49.4 |
| S3P A136P S202R G257E W260F L288I L294P S295V | 9 | Model O | 50 C. | 138 hr | 33.8 | 56.3 |
| G47Q S98P A136P S202R W260F L288I L294P S295V | 9 | Model O | 50 C. | 138 hr | 35.1 | 57.2 |
| E77N S98P A136P S202R W260F L288I L294P S295V | 9 | Model O | 50 C. | 138 hr | 31.1 | 53.4 |
| E77T S98P A136P S202R W260F L288I L294P S295V | 9 | Model O | 50 C. | 138 hr | 29.8 | 49.5 |
| D78G S98P A136P S202R W260F L288I L294P S295V | 9 | Model O | 50 C. | 138 hr | 31.8 | 52.7 |
| H80G S98P A136P S202R W260F L288I L294P S295V | 9 | Model O | 50 C. | 138 hr | 47.2 | 82.4 |
| Y93A S98P A136P S202R W260F L288I L294P S295V | 9 | Model O | 50 C. | 138 hr | 23.7 | 40.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93F S98P A136P S202R W260F L288I L294P S295V | 9 | Model O | 50 C. | 138 hr | 38.2 | 64.4 |
| S98P K116R A136P S202R W260F L288I L294P S295V | 9 | Model O | 50 C. | 138 hr | 37.4 | 62.2 |
| S98P A136P S202R G257A W260F L288I L294P S295V | 9 | Model O | 50 C. | 138 hr | 48.9 | 87.7 |
| S98P A136P S202R G257E W260F L288I L294P S295V | 9 | Model O | 50 C. | 138 hr | 40.9 | 63.5 |
| E41V A136P S202R G257E W260F L288I L294P S295V | 9 | Model O | 50 C. | 138 hr | 40.9 | 68.8 |
| G47Q A136P S202R G257E W260F L288I L294P S295V | 9 | Model O | 50 C. | 138 hr | 35.9 | 58.0 |
| G47T A136P S202R G257E W260F L288I L294P S295V | 9 | Model O | 50 C. | 138 hr | 32.4 | 53.3 |
| Y93A A136P S202R G257E W260F L288I L294P S295V | 9 | Model O | 50 C. | 138 hr | 33.5 | 52.8 |
| K116R A136P S202R G257E W260F L288I L294P S295V | 9 | Model O | 50 C. | 138 hr | 37.3 | 69.4 |
| D118K A136P S202R G257E W260F L288I L294P S295V | 9 | Model O | 50 C. | 138 hr | 41.8 | 67.3 |
| T119R A136P S202R G257E W260F L288I L294P S295V | 9 | Model O | 50 C. | 138 hr | 46.6 | 70.5 |
| E41V V82I A136P S202R W260F L288I L294P S295V | 9 | Model O | 50 C. | 138 hr | 33.9 | 53.1 |
| G47A V82I A136P S202R W260F L288I L294P S295V | 9 | Model O | 50 C. | 138 hr | 27.4 | 45.3 |
| G47R V82I A136P S202R W260F L288I L294P S295V | 9 | Model O | 50 C. | 138 hr | 27.7 | 46.6 |
| G47S V82I A136P S202R W260F L288I L294P S295V | 9 | Model O | 50 C. | 138 hr | 38.0 | 59.0 |
| G47Y V82I A136P S202R W260F L288I L294P S295V | 9 | Model O | 50 C. | 138 hr | 21.4 | 36.9 |
| E77T V82I A136P S202R W260F L288I L294P S295V | 9 | Model O | 50 C. | 138 hr | 34.9 | 54.5 |
| H80R V82I A136P S202R W260F L288I L294P S295V | 9 | Model O | 50 C. | 138 hr | 38.1 | 58.6 |
| V82I Y93I A136P S202R W260F L288I L294P S295V | 9 | Model O | 50 C. | 138 hr | 31.7 | 54.6 |
| V82I K116R A136P S202R W260F L288I L294P S295V | 9 | Model O | 50 C. | 138 hr | 27.8 | 43.7 |
| Y93Q S202R W260F L288I L294P S295V | 9 | Model O | 50 C. | 138 hr | 23.4 | 41.0 |
| S98P S202E W260F L288I L294P S295V | 9 | Model O | 50 C. | 138 hr | 27.0 | 48.2 |
| G47R Y93Q A136P S202R W260F L288I L294P S295V | 10.5 | A & H | 40 C. | 65 hr | 25.6 | 84.4 |
| G47S Y93Q A136P S202R W260F L288I L294P S295V | 10.5 | A & H | 40 C. | 65 hr | 43.7 | 91.0 |
| G47Y Y93Q A136P S202R W260F L288I L294P S295V | 10.5 | A & H | 40 C. | 65 hr | 27.7 | 60.6 |
| D78G Y93Q A136P S202R W260F L288I L294P S295V | 10.5 | A & H | 40 C. | 65 hr | 49.7 | 110.5 |
| H80K Y93Q A136P S202R W260F L288I L294P S295V | 10.5 | A & H | 40 C. | 65 hr | 59.0 | 141.8 |
| H80R Y93Q A136P S202R W260F L288I L294P S295V | 10.5 | A & H | 40 C. | 65 hr | 53.0 | 125.2 |
| A83S Y93Q A136P S202R W260F L288I L294P S295V | 10.5 | A & H | 40 C. | 65 hr | 43.7 | 98.1 |
| Y93Q S98P A136P S202R W260F L288I L294P S295V | 10.5 | A & H | 40 C. | 65 hr | 47.3 | 100.6 |
| Y93Q T119R A136P S202R W260F L288I L294P S295V | 10.5 | A & H | 40 C. | 65 hr | 49.4 | 117.4 |
| Y93I A136P S202R W260L L288I L294P S295V | 10.5 | A & H | 40 C. | 65 hr | 32.3 | 70.4 |
| S8T A136P S202R G257A W260F L288I L294P S295V | 10.5 | A & H | 40 C. | 65 hr | 20.1 | 47.7 |
| S3P S98P A136P S202R W260F L288I L294P S295V | 10.5 | A & H | 40 C. | 65 hr | 30.0 | 63.8 |
| E41V S98P A136P S202R W260F L288I L294P S295V | 10.5 | A & H | 40 C. | 65 hr | 33.4 | 71.0 |
| G47A S98P A136P S202R W260F L288I L294P S295V | 10.5 | A & H | 40 C. | 65 hr | 28.3 | 63.7 |
| G47S S98P A136P S202R W260F L288I L294P S295V | 10.5 | A & H | 40 C. | 65 hr | 27.9 | 64.4 |
| A83S S98P A136P S202R W260F L288I L294P S295V | 10.5 | A & H | 40 C. | 65 hr | 36.0 | 80.0 |
| S98P D118K A136P S202R W260F L288I L294P S295V | 10.5 | A & H | 40 C. | 65 hr | 40.5 | 79.7 |
| S98P T119R A136P S202R W260F L288I L294P S295V | 10.5 | A & H | 40 C. | 65 hr | 26.8 | 60.8 |
| T37P A136P S202R G257E W260F L288I L294P S295V | 10.5 | A & H | 40 C. | 65 hr | 25.9 | 61.0 |
| G47A A136P S202R G257E W260F L288I L294P S295V | 10.5 | A & H | 40 C. | 65 hr | 24.9 | 58.3 |
| G47Y A136P S202R G257E W260F L288I L294P S295V | 10.5 | A & H | 40 C. | 65 hr | 22.3 | 45.1 |
| E77N A136P S202R G257E W260F L288I L294P S295V | 10.5 | A & H | 40 C. | 65 hr | 29.5 | 60.2 |
| A83S A136P S202R G257E W260F L288I L294P S295V | 10.5 | A & H | 40 C. | 65 hr | 20.4 | 68.7 |
| V82I Y93F A136P S202R W260F L288I L294P S295V | 10.5 | A & H | 40 C. | 65 hr | 24.2 | 55.7 |
| V82I Y93R A136P S202R W260F L288I L294P S295V | 10.5 | A & H | 40 C. | 65 hr | 20.4 | 49.3 |
| Y93Q S95D A136P S202R W260F L288I L294P S295V | 10.5 | A & H | 40 C. | 65 hr | 55.2 | 104.1 |
| Y93Q A97R A136P S202R W260F L288I L294P S295V | 10.5 | A & H | 40 C. | 65 hr | 24.3 | 54.1 |
| Y93Q A97S A136P S202R W260F L288I L294P S295V | 10.5 | A & H | 40 C. | 65 hr | 36.3 | 72.2 |
| Y93Q D104A A136P S202R W260F L288I L294P S295V | 10.5 | A & H | 40 C. | 65 hr | 39.8 | 86.8 |
| Y93Q D104G A136P S202R W260F L288I L294P S295V | 10.5 | A & H | 40 C. | 65 hr | 35.6 | 66.8 |
| Y93Q D104Q A136P S202R W260F L288I L294P S295V | 10.5 | A & H | 40 C. | 65 hr | 25.1 | 56.5 |
| Y93Q S111A A136P S202R W260F L288I L294P S295V | 10.5 | A & H | 40 C. | 65 hr | 47.2 | 95.2 |
| Y93Q S111K A136P S202R W260F L288I L294P S295V | 10.5 | A & H | 40 C. | 65 hr | 41.0 | 89.7 |
| Y93Q S111R A136P S202R W260F L288I L294P S295V | 10.5 | A & H | 40 C. | 65 hr | 38.7 | 83.6 |
| Y93Q I114Q A136P S202R W260F L288I L294P S295V | 10.5 | A & H | 40 C. | 65 hr | 45.5 | 97.8 |
| Y93Q I114W A136P S202R W260F L288I L294P S295V | 10.5 | A & H | 40 C. | 65 hr | 28.7 | 81.3 |
| Y93Q A136P D139A S202R W260F L288I L294P S295V | 10.5 | A & H | 40 C. | 65 hr | 67.2 | 188.0 |
| Y93Q A136P D139G S202R W260F L288I L294P S295V | 10.5 | A & H | 40 C. | 65 hr | 30.7 | 69.8 |
| Y93Q A136P D139R S202R W260F L288I L294P S295V | 10.5 | A & H | 40 C. | 65 hr | 60.7 | 147.1 |
| Y93Q A136P K142M S202R W260F L288I L294P S295V | 10.5 | A & H | 40 C. | 65 hr | 38.5 | 85.8 |
| Y93Q A136P K142S S202R W260F L288I L294P S295V | 10.5 | A & H | 40 C. | 65 hr | 20.0 | 46.5 |
| Y93Q A136P K142V S202R W260F L288I L294P S295V | 10.5 | A & H | 40 C. | 65 hr | 37.4 | 75.9 |
| S8T A136P D139A S202R W260F L288I L294P S295V | 10.5 | A & H | 40 C. | 65 hr | 25.1 | 57.2 |
| S8T A136P D139R S202R W260F L288I L294P S295V | 10.5 | A & H | 40 C. | 65 hr | 41.7 | 95.8 |
| S3P A136P D139A S202R W260F L288I L294P S295V | 10.5 | A & H | 40 C. | 65 hr | 20.6 | 47.0 |
| S3P A136P D139R S202R W260F L288I L294P S295V | 10.5 | A & H | 40 C. | 65 hr | 26.7 | 59.2 |
| S95D S98P A136P S202R W260F L288I L294P S295V | 10.5 | A & H | 40 C. | 65 hr | 42.7 | 93.0 |
| S98P S111A A136P S202R W260F L288I L294P S295V | 10.5 | A & H | 40 C. | 65 hr | 27.9 | 66.8 |
| S98P I114M A136P S202R W260F L288I L294P S295V | 10.5 | A & H | 40 C. | 65 hr | 27.1 | 57.4 |
| S98P I114W A136P S202R W260F L288I L294P S295V | 10.5 | A & H | 40 C. | 65 hr | 21.6 | 49.9 |
| S98P A136P D139A S202R W260F L288I L294P S295V | 10.5 | A & H | 40 C. | 65 hr | 43.6 | 88.3 |
| S98P A136P D139R S202R W260F L288I L294P S295V | 10.5 | A & H | 40 C. | 65 hr | 50.4 | 95.4 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| S98P A136P D139V S202R W260F L288I L294P S295V | 10.5 | A & H | 40 C. | 65 hr | 28.6 | 62.8 |
| S98P A136P D139W S202R W260F L288I L294P S295V | 10.5 | A & H | 40 C. | 65 hr | 22.4 | 55.2 |
| S98P A136P K142M S202R W260F L288I L294P S295V | 10.5 | A & H | 40 C. | 65 hr | 25.4 | 55.9 |
| E41V Y93Q A136P S202R W260F L288I L294P S295V | 10.5 | A & H | 42C | 16 hr | 51.4 | 171.4 |
| G47A Y93Q A136P S202R W260F L288I L294P S295V | 10.5 | A & H | 42 C. | 16 hr | 30.3 | 91.4 |
| G47Q Y93Q A136P S202R W260F L288I L294P S295V | 10.5 | A & H | 42 C. | 16 hr | 44.2 | 129.2 |
| G47T Y93Q A136P S202R W260F L288I L294P S295V | 10.5 | A & H | 42 C. | 16 hr | 41.8 | 118.6 |
| E77Y Y93Q A136P S202R W260F L288I L294P S295V | 10.5 | A & H | 42 C. | 16 hr | 34.2 | 99.2 |
| Y93Q A136P S202R G257A W260F L288I L294P S295V | 10.5 | A & H | 42 C. | 16 hr | 32.7 | 96.3 |
| Y93Q A136P S202R G257E W260F L288I L294P S295V | 10.5 | A & H | 42 C. | 16 hr | 59.1 | 194.5 |
| T37R Y93Q A136P S202R W260F L288I L294P S295V | 10.5 | A & H | 42 C. | 16 hr | 41.3 | 119.8 |
| R70K Y93Q A136P S202R W260F L288I L294P S295V | 10.5 | A & H | 42 C. | 16 hr | 36.5 | 106.5 |
| N45G Y93Q A136P S202R W260F L288I L294P S295V | 10.5 | A & H | 42 C. | 16 hr | 34.5 | 105.9 |
| Q35L Y93Q A136P S202R W260F L288I L294P S295V | 10.5 | A & H | 42 C. | 16 hr | 21.8 | 74.2 |
| N18V Y93Q A136P S202R W260F L288I L294P S295V | 10.5 | A & H | 42 C. | 16 hr | 43.8 | 133.8 |
| N18R Y93Q A136P S202R W260F L288I L294P S295V | 10.5 | A & H | 42 C. | 16 hr | 38.4 | 114.6 |
| N71S Y93Q A136P S202R W260F L288I L294P S295V | 10.5 | A & H | 42 C. | 16 hr | 28.2 | 83.9 |
| S74K Y93Q A136P S202R W260F L288I L294P S295V | 10.5 | A & H | 42 C. | 16 hr | 39.1 | 109.4 |
| Y93Q A136P Y174R S202R W260F L288I L294P S295V | 10.5 | A & H | 42 C. | 16 hr | 23.3 | 75.3 |
| Y93Q A136P Q143R S202R W260F L288I L294P S295V | 10.5 | A & H | 42 C. | 16 hr | 27.5 | 87.5 |
| Y93Q A136P N180R S202R W260F L288I L294P S295V | 10.5 | A & H | 42 C. | 16 hr | 36.5 | 105.0 |
| Y93Q A136P Q169A S202R W260F L288I L294P S295V | 10.5 | A & H | 42 C. | 16 hr | 33.8 | 99.0 |
| Y93Q A136P Q169R S202R W260F L288I L294P S295V | 10.5 | A & H | 42 C. | 16 hr | 30.6 | 85.5 |
| Y93Q A136P Q169K S202R W260F L288I L294P S295V | 10.5 | A & H | 42 C. | 16 hr | 30.8 | 89.6 |
| Y93Q A136P E177S S202R W260F L288I L294P S295V | 10.5 | A & H | 42 C. | 16 hr | 36.1 | 105.2 |
| Y93Q A136P E177Y S202R W260F L288I L294P S295V | 10.5 | A & H | 42 C. | 16 hr | 33.1 | 101.1 |
| Y93Q A136P N150T S202R W260F L288I L294P S295V | 10.5 | A & H | 42 C. | 16 hr | 37.9 | 110.6 |
| Y93Q A136P N150R S202R W260F L288I L294P S295V | 10.5 | A & H | 42 C. | 16 hr | 38.0 | 108.6 |
| Y93Q A136P Q184E S202R W260F L288I L294P S295V | 10.5 | A & H | 42 C. | 16 hr | 34.7 | 103.1 |
| Y93Q A136P Q184K S202R W260F L288I L294P S295V | 10.5 | A & H | 42 C. | 16 hr | 34.6 | 101.9 |
| Y93Q A136P Q184S S202R W260F L288I L294P S295V | 10.5 | A & H | 42 C. | 16 hr | 28.9 | 90.3 |
| Y93Q A136P R185G S202R W260F L288I L294P S295V | 10.5 | A & H | 42 C. | 16 hr | 33.4 | 99.7 |
| Y93R A136P S202R W260L L288I L294P S295V | 10.5 | A & H | 42 C. | 16 hr | 35.9 | 107.1 |
| V82I A136P D139A S202R W260F L288I L294P S295V | 10.5 | A & H | 42 C. | 16 hr | 22.4 | 74.0 |
| V82I A136P D139R S202R W260F L288I L294P S295V | 10.5 | A & H | 42 C. | 16 hr | 33.3 | 96.8 |
| S95D A136P S202R W260F L288I L294P S295V | 10.5 | A & H | 42 C. | 16 hr | 71.6 | 380.7 |
| A136P D139A S202R W260F L288I L294P S295V | 10.5 | A & H | 42 C. | 16 hr | 21.3 | 70.1 |
| A136P D139R S202R W260F L288I L294P S295V | 10.5 | A & H | 42 C. | 16 hr | 35.9 | 114.4 |
| D65E S98P A136P S202R W260F L288I L294P S295V | 10.5 | A & H | 42 C. | 16 hr | 21.4 | 69.3 |
| T37R S98P A136P S202R W260F L288I L294P S295V | 10.5 | A & H | 42 C. | 16 hr | 39.0 | 116.3 |
| R70K S98P A136P S202R W260F L288I L294P S295V | 10.5 | A & H | 42 C. | 16 hr | 39.1 | 114.7 |
| N45G S98P A136P S202R W260F L288I L294P S295V | 10.5 | A & H | 42 C. | 16 hr | 29.8 | 93.4 |
| N71S S98P A136P S202R W260F L288I L294P S295V | 10.5 | A & H | 42 C. | 16 hr | 26.0 | 83.7 |
| S74K S98P A136P S202R W260F L288I L294P S295V | 10.5 | A & H | 42 C. | 16 hr | 40.1 | 118.0 |
| S98P A136P Y174R S202R W260F L288I L294P S295V | 10.5 | A & H | 42 C. | 16 hr | 21.9 | 73.8 |
| S98P A136P Y174L S202R W260F L288I L294P S295V | 10.5 | A & H | 42 C. | 16 hr | 26.6 | 89.4 |
| S98P A136P Q143R S202R W260F L288I L294P S295V | 10.5 | A & H | 42 C. | 16 hr | 20.9 | 66.9 |
| S98P A136P N180R S202R W260F L288I L294P S295V | 10.5 | A & H | 42 C. | 16 hr | 37.8 | 113.1 |
| S98P A136P Q169A S202R W260F L288I L294P S295V | 10.5 | A & H | 42 C. | 16 hr | 35.4 | 106.6 |
| S98P A136P Q169K S202R W260F L288I L294P S295V | 10.5 | A & H | 42 C. | 16 hr | 31.2 | 95.7 |
| S98P A136P E177S S202R W260F L288I L294P S295V | 10.5 | A & H | 42 C. | 16 hr | 32.5 | 108.0 |
| S98P A136P E177Y S202R W260F L288I L294P S295V | 10.5 | A & H | 42 C. | 16 hr | 38.1 | 102.1 |
| S98P A136P N150T S202R W260F L288I L294P S295V | 10.5 | A & H | 42 C. | 16 hr | 34.1 | 101.8 |
| S98P A136P N150S S202R W260F L288I L294P S295V | 10.5 | A & H | 42 C. | 16 hr | 34.7 | 108.7 |
| S98P A136P N150R S202R W260F L288I L294P S295V | 10.5 | A & H | 42 C. | 16 hr | 42.0 | 128.3 |
| S98P A136P Q184E S202R W260F L288I L294P S295V | 10.5 | A & H | 42 C. | 16 hr | 25.1 | 79.2 |
| S98P A136P Q184K S202R W260F L288I L294P S295V | 10.5 | A & H | 42 C. | 16 hr | 36.1 | 111.9 |
| S98P A136P Q184S S202R W260F L288I L294P S295V | 10.5 | A & H | 42 C. | 16 hr | 26.3 | 86.1 |
| S98P A136P R185G S202R W260F L288I L294P S295V | 10.5 | A & H | 42 C. | 16 hr | 29.4 | 94.3 |
| N18V H80K S98P A136P S202R W260F L288I L294P S295V | 10.5 | A & H | 42 C. | 40 hr | 21.1 | 175.2 |
| H80K S95D S98P A136P S202R W260F L288I L294P S295V | 10.5 | A & H | 42 C. | 40 hr | 37.4 | 273.2 |
| H80K S98P A136P D139A S202R W260F L288I L294P S295V | 10.5 | A & H | 42 C. | 40 hr | 23.9 | 197.5 |
| H80K S98P A136P D139R S202R W260F L288I L294P S295V | 10.5 | A & H | 42 C. | 40 hr | 28.5 | 217.1 |
| H80K S98P A136P S202R R210G W260F L288I L294P S295V | 10.5 | A & H | 42 C. | 40 hr | 24.6 | 196.4 |
| S3P S98P A136P S202R G257A W260F L288I L294P S295V | 10.5 | A & H | 42 C. | 40 hr | 23.2 | 187.3 |
| S8T S98P A136P S202R G257A W260F L288I L294P S295V | 10.5 | A & H | 42 C. | 40 hr | 26.0 | 202.8 |
| N18V S98P A136P S202R G257A W260F L288I L294P S295V | 10.5 | A & H | 42 C. | 40 hr | 26.6 | 210.5 |
| T37R S98P A136P S202R G257A W260F L288I L294P S295V | 10.5 | A & H | 42 C. | 40 hr | 22.4 | 181.6 |
| E41V S98P A136P S202R G257A W260F L288I L294P S295V | 10.5 | A & H | 42 C. | 40 hr | 20.3 | 172.2 |
| R70K S98P A136P S202R G257A W260F L288I L294P S295V | 10.5 | A & H | 42 C. | 40 hr | 22.2 | 187.0 |
| D78G S98P A136P S202R G257A W260F L288I L294P S295V | 10.5 | A & H | 42 C. | 40 hr | 29.6 | 214.7 |
| A83S S98P A136P S202R G257A W260F L288I L294P S295V | 10.5 | A & H | 42 C. | 40 hr | 22.9 | 175.7 |
| Y93F S98P A136P S202R G257A W260F L288I L294P S295V | 10.5 | A & H | 42 C. | 40 hr | 28.3 | 211.2 |
| Y93Q S98P A136P S202R G257A W260F L288I L294P S295V | 10.5 | A & H | 42 C. | 40 hr | 34.9 | 247.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| S98P I114Q A136P S202R G257A W260F L288I L294P S295V | 10.5 | A & H | 42 C. | 40 hr | 21.8 | 182.5 |
| S98P D118K A136P S202R G257A W260F L288I L294P S295V | 10.5 | A & H | 42 C. | 40 hr | 25.6 | 197.7 |
| S98P T119R A136P S202R G257A W260F L288I L294P S295V | 10.5 | A & H | 42 C. | 40 hr | 22.3 | 167.0 |
| S98P A136P N150T S202R G257A W260F L288I L294P S295V | 10.5 | A & H | 42 C. | 40 hr | 21.8 | 182.5 |
| S98P A136P N150S S202R G257A W260F L288I L294P S295V | 10.5 | A & H | 42 C. | 40 hr | 21.2 | 177.1 |
| S98P A136P E177S S202R G257A W260F L288I L294P S295V | 10.5 | A & H | 42 C. | 40 hr | 21.7 | 175.1 |
| S98P A136P E177Y S202R G257A W260F L288I L294P S295V | 10.5 | A & H | 42 C. | 40 hr | 20.4 | 167.9 |
| S98P A136P Q184K S202R G257A W260F L288I L294P S295V | 10.5 | A & H | 42 C. | 40 hr | 20.3 | 178.2 |
| S95D S98P A136P S202R G257A W260F L288I L294P S295V | 10.5 | A & H | 42 C. | 40 hr | 42.2 | 346.1 |
| S95E S98P A136P S202R G257A W260F L288I L294P S295V | 10.5 | A & H | 42 C. | 40 hr | 28.8 | 226.2 |
| S98P A136P D139A S202R G257A W260F L288I L294P S295V | 10.5 | A & H | 42 C. | 40 hr | 33.5 | 249.4 |
| S98P A136P N200T S202R G257A W260F L288I L294P S295V | 10.5 | A & H | 42 C. | 40 hr | 26.9 | 216.6 |
| S98P A136P S202R R210L G257A W260F L288I L294P S295V | 10.5 | A & H | 42 C. | 40 hr | 20.9 | 167.8 |
| S98P A136P S202R R210G G257A W260F L288I L294P S295V | 10.5 | A & H | 42 C. | 40 hr | 31.7 | 244.5 |
| S98P A136P S202R E234Y G257A W260F L288I L294P S295V | 10.5 | A & H | 42 C. | 40 hr | 33.4 | 255.0 |
| S8T Y93Q D118K A136P S202R W260F L288I L294P S295V | 10.5 | A & H | 42 C. | 40 hr | 31.4 | 240.1 |
| N18V Y93Q D118K A136P S202R W260F L288I L294P S295V | 10.5 | A & H | 42 C. | 40 hr | 34.2 | 239.6 |
| T37P Y93Q D118K A136P S202R W260F L288I L294P S295V | 10.5 | A & H | 42 C. | 40 hr | 28.1 | 204.1 |
| E41V Y93Q D118K A136P S202R W260F L288I L294P S295V | 10.5 | A & H | 42 C. | 40 hr | 26.9 | 198.6 |
| S74K Y93Q D118K A136P S202R W260F L288I L294P S295V | 10.5 | A & H | 42 C. | 40 hr | 20.8 | 179.9 |
| D78G Y93Q D118K A136P S202R W260F L288I L294P S295V | 10.5 | A & H | 42 C. | 40 hr | 21.9 | 180.8 |
| H80K Y93Q D118K A136P S202R W260F L288I L294P S295V | 10.5 | A & H | 42 C. | 40 hr | 22.9 | 181.3 |
| H80R Y93Q D118K A136P S202R W260F L288I L294P S295V | 10.5 | A & H | 42 C. | 40 hr | 22.2 | 170.8 |
| A83S Y93Q D118K A136P S202R W260F L288I L294P S295V | 10.5 | A & H | 42 C. | 40 hr | 22.6 | 178.5 |
| Y93Q S98P D118K A136P S202R W260F L288I L294P S295V | 10.5 | A & H | 42 C. | 40 hr | 29.3 | 216.7 |
| Y93Q S111A D118K A136P S202R W260F L288I L294P S295V | 10.5 | A & H | 42 C. | 40 hr | 21.4 | 181.7 |
| Y93Q S111K D118K A136P S202R W260F L288I L294P S295V | 10.5 | A & H | 42 C. | 40 hr | 22.0 | 175.9 |
| Y93Q D118K A136P N150T S202R W260F L288I L294P S295V | 10.5 | A & H | 42 C. | 40 hr | 20.0 | 168.3 |
| Y93Q D118K A136P N150S S202R W260F L288I L294P S295V | 10.5 | A & H | 42 C. | 40 hr | 21.0 | 173.2 |
| Y93Q D118K A136P N150R S202R W260F L288I L294P S295V | 10.5 | A & H | 42 C. | 40 hr | 21.9 | 183.7 |
| Y93Q D118K A136P E177S S202R W260F L288I L294P S295V | 10.5 | A & H | 42 C. | 40 hr | 20.8 | 174.5 |
| Y93Q S95D D118K A136P S202R W260F L288I L294P S295V | 10.5 | A & H | 42 C. | 40 hr | 53.6 | 424.5 |
| Y93Q S95E D118K A136P S202R W260F L288I L294P S295V | 10.5 | A & H | 42 C. | 40 hr | 31.0 | 232.1 |
| Y93Q D118K A136P D139A S202R W260F L288I L294P S295V | 10.5 | A & H | 42 C. | 40 hr | 37.5 | 259.4 |
| Y93Q D118K A136P D139R S202R W260F L288I L294P S295V | 10.5 | A & H | 42 C. | 40 hr | 49.2 | 388.6 |
| Y93Q D118K A136P D139V S202R W260F L288I L294P S295V | 10.5 | A & H | 42 C. | 40 hr | 26.7 | 191.0 |
| Y93Q D118K A136P D139W S202R W260F L288I L294P S295V | 10.5 | A & H | 42 C. | 40 hr | 27.2 | 208.7 |
| Y93Q D118K A136P N200T S202R W260F L288I L294P S295V | 10.5 | A & H | 42 C. | 40 hr | 26.0 | 188.9 |
| Y93Q D118K A136P S202R R210L W260F L288I L294P S295V | 10.5 | A & H | 42 C. | 40 hr | 23.8 | 182.2 |
| Y93Q D118K A136P S202R R210M W260F L288I L294P S295V | 10.5 | A & H | 42 C. | 40 hr | 32.6 | 226.4 |
| Y93Q D118K A136P S202R R210G W260F L288I L294P S295V | 10.5 | A & H | 42 C. | 40 hr | 33.2 | 229.7 |
| Y93Q D118K A136P S202R E234Y W260F L288I L294P S295V | 10.5 | A & H | 42 C. | 40 hr | 35.5 | 256.8 |
| T37P S98P A136P S202R W260F L288I L294P S295V | 10.5 | A & H | 42 C. | 16 hr | 33.5 | 98.9 |
| H80R S98P A136P S202R W260F L288I L294P S295V | 10.5 | A & H | 42 C. | 16 hr | 36.1 | 103.3 |
| V82I S98P A136P S202R W260F L288I L294P S295V | 10.5 | A & H | 42 C. | 16 hr | 39.2 | 118.0 |
| V82I A83P A136P S202R W260F L288I L294P S295V | 10.5 | A & H | 42 C. | 16 hr | 24.0 | 77.5 |
| Y93Q A136P D139A S202R W260F L288I L294P S295V S3P | 10.5 | A & H | 44 C. | 16 hr | 22.1 | 182.3 |
| Y93Q A136P D139A S202R W260F L288I L294P S295V N18V | 10.5 | A & H | 44 C. | 16 hr | 24.1 | 193.8 |
| Y93Q A136P D139A S202R W260F L288I L294P S295V E41V | 10.5 | A & H | 44 C. | 16 hr | 25.2 | 193.7 |
| Y93Q A136P D139A S202R W260F L288I L294P S295V V82I | 10.5 | A & H | 44 C. | 16 hr | 21.3 | 174.0 |
| Y93Q A136P D139A S202R W260F L288I L294P S295V S95D | 10.5 | A & H | 44 C. | 16 hr | 48.6 | 378.5 |
| Y93Q A136P D139A S202R W260F L288I L294P S295V S98P | 10.5 | A & H | 44 C. | 16 hr | 22.4 | 176.3 |
| Y93Q A136P D139A S202R W260F L288I L294P S295V R210M | 10.5 | A & H | 44 C. | 16 hr | 25.9 | 198.6 |
| Y93Q A136P D139A S202R W260F L288I L294P S295V R210G | 10.5 | A & H | 44 C. | 16 hr | 35.4 | 255.2 |
| Y93Q A136P D139A S202R W260F L288I L294P S295V E234Y | 10.5 | A & H | 44 C. | 16 hr | 27.3 | 209.1 |
| Y93Q A136P D139A S202R W260F L288I L294P S295V N273D | 10.5 | A & H | 44 C. | 16 hr | 20.0 | 174.6 |
| Y93Q A136P D139A S202R W260F L288I L294P S295V N213V | 10.5 | A & H | 44 C. | 16 hr | 21.8 | 182.4 |
| Y93Q A136P D139A S202R W260F L288I L294P S295V N213D | 10.5 | A & H | 44 C. | 16 hr | 21.2 | 165.1 |
| H80K Y93Q A136P S202R W260F L288I L294P S295V S95D | 10.5 | A & H | 44 C. | 16 hr | 32.9 | 251.1 |
| H80K Y93Q A136P S202R W260F L288I L294P S295V D139R | 10.5 | A & H | 44 C. | 16 hr | 25.2 | 192.5 |
| H80K Y93Q A136P S202R W260F L288I L294P S295V E234Y | 10.5 | A & H | 44 C. | 16 hr | 20.7 | 157.9 |
| Y93Q A136P D139A S202R W260F L288I L294P S295V P183G | 10.5 | A & H | 44 C. | 16 hr | 25.6 | 191.3 |
| Y93Q A136P D139A S202R W260F L288I L294P S295V P183T | 10.5 | A & H | 44 C. | 16 hr | 24.3 | 184.8 |
| Y93Q A136P D139A S202R W260F L288I L294P S295V Q243E | 10.5 | A & H | 44 C. | 16 hr | 21.9 | 175.9 |
| Y93Q A136P D139A S202R W260F L288I L294P S295V N283W | 10.5 | A & H | 44 C. | 16 hr | 30.8 | 237.5 |
| Y93Q A136P D139A S202R W260F L288I L294P S295V N283H | 10.5 | A & H | 44 C. | 16 hr | 26.2 | 188.6 |
| Y93Q A136P D139A S202R W260F L288I L294P S295V A276W | 10.5 | A & H | 44 C. | 16 hr | 20.5 | 164.3 |
| Y93Q A136P D139A S202R W260F L288I L294P S295V A276D | 10.5 | A & H | 44 C. | 16 hr | 26.6 | 193.6 |
| Y93Q S95D D118K A136P S202R W260F N279D L288I L294P S295V | 10.5 | A & H | 44 C. | 40 hr | 38.2 | 676.4 |
| Y93Q S95D D118K A136P S202R W260F N279E L288I L294P S295V | 10.5 | A & H | 44 C. | 40 hr | 43.3 | 778.8 |
| Y93Q S95D N100Y D118K A136P S202R W260F L288I L294P S295V | 10.5 | A & H | 44 C. | 40 hr | 23.0 | 442.9 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D D118K A136P S202R W260F N273E L288I L294P S295V | 10.5 | A & H | 44 C. | 40 hr | 30.7 | 551.0 |
| Y6H Y93Q S95D D118K A136P S202R W260F L288I L294P S295V | 10.5 | A & H | 44 C. | 40 hr | 24.2 | 458.1 |
| Y6M Y93Q S95D D118K A136P S202R W260F L288I L294P S295V | 10.5 | A & H | 44 C. | 40 hr | 25.7 | 479.1 |
| Y93Q S95D D118K A136P S202R N213V W260F L288I L294P S295V | 10.5 | A & H | 44 C. | 40 hr | 33.4 | 593.1 |
| Y93Q S95D D118K A136P S202R N213D W260F L288I L294P S295V | 10.5 | A & H | 44 C. | 40 hr | 34.2 | 608.0 |
| Y93Q S95D D118K A136P P183T S202R W260F L288I L294P S295V | 10.5 | A & H | 44 C. | 40 hr | 33.2 | 591.7 |
| Y93Q S95D D118K A136P S202R W260F N272M L288I L294P S295V | 10.5 | A & H | 44 C. | 40 hr | 25.1 | 452.9 |
| Y93Q S95D D118K A136P S202R W260F N272T L288I L294P S295V | 10.5 | A & H | 44 C. | 40 hr | 36.1 | 639.9 |
| Y93Q S95D D118K A136P S202R Q243K W260F L288I L294P S295V | 10.5 | A & H | 44 C. | 40 hr | 33.1 | 587.7 |
| Y93Q S95D D118K A136P S202R Q243E W260F L288I L294P S295V | 10.5 | A & H | 44 C. | 40 hr | 33.8 | 599.7 |
| Y93Q S95D D118K A136P S202R W260F N283W L288I L294P S295V | 10.5 | A & H | 44 C. | 40 hr | 39.6 | 702.9 |
| Y93Q S95D D118K A136P S202R W260F N283H L288I L294P S295V | 10.5 | A & H | 44 C. | 40 hr | 42.6 | 764.9 |
| Y93Q S95D D118K A136P S202R W260F A276E L288I L294P S295V | 10.5 | A & H | 44 C. | 40 hr | 38.4 | 681.8 |
| Y93Q S95D D118K A136P S202R W260F A276W L288I L294P S295V | 10.5 | A & H | 44 C. | 40 hr | 30.5 | 547.3 |
| Y93Q S95D D118K A136P S202R W260F A276D L288I L294P S295V | 10.5 | A & H | 44 C. | 40 hr | 34.9 | 617.1 |
| Y93Q S95D D118K A136P S202R W260F T280L L288I L294P S295V | 10.5 | A & H | 44 C. | 40 hr | 31.3 | 560.5 |
| S8T Y93Q S95D D118K A136P S202R W260F L288I L294P S295V | 10.5 | A & H | 44 C. | 40 hr | 33.3 | 592.3 |
| N18V Y93Q S95D D118K A136P S202R W260F L288I L294P S295V | 10.5 | A & H | 44 C. | 40 hr | 37.3 | 659.4 |
| N18R Y93Q S95D D118K A136P S202R W260F L288I L294P S295V | 10.5 | A & H | 44 C. | 40 hr | 23.4 | 447.7 |
| T37P Y93Q S95D D118K A136P S202R W260F L288I L294P S295V | 10.5 | A & H | 44 C. | 40 hr | 26.7 | 492.9 |
| T37R Y93Q S95D D118K A136P S202R W260F L288I L294P S295V | 10.5 | A & H | 44 C. | 40 hr | 32.5 | 576.4 |
| N45G Y93Q S95D D118K A136P S202R W260F L288I L294P S295V | 10.5 | A & H | 44 C. | 40 hr | 23.2 | 444.8 |
| G47A Y93Q S95D D118K A136P S202R W260F L288I L294P S295V | 10.5 | A & H | 44 C. | 40 hr | 21.7 | 425.5 |
| G47K Y93Q S95D D118K A136P S202R W260F L288I L294P S295V | 10.5 | A & H | 44 C. | 40 hr | 26.7 | 500.1 |
| G47S Y93Q S95D D118K A136P S202R W260F L288I L294P S295V | 10.5 | A & H | 44 C. | 40 hr | 27.4 | 484.9 |
| D65E Y93Q S95D D118K A136P S202R W260F L288I L294P S295V | 10.5 | A & H | 44 C. | 40 hr | 21.2 | 404.5 |
| R70K Y93Q S95D D118K A136P S202R W260F L288I L294P S295V | 10.5 | A & H | 44 C. | 40 hr | 30.9 | 559.7 |
| N71S Y93Q S95D D118K A136P S202R W260F L288I L294P S295V | 10.5 | A & H | 44 C. | 40 hr | 24.2 | 456.4 |
| S74K Y93Q S95D D118K A136P S202R W260F L288I L294P S295V | 10.5 | A & H | 44 C. | 40 hr | 27.8 | 508.2 |
| Y93Q S95D S111A D118K A136P S202R W260F L288I L294P S295V | 10.5 | A & H | 44 C. | 40 hr | 23.8 | 452.6 |
| Y93Q S95D S111K D118K A136P S202R W260F L288I L294P S295V | 10.5 | A & H | 44 C. | 40 hr | 24.6 | 472.5 |
| Y93Q S95D S111R D118K A136P S202R W260F L288I L294P S295V | 10.5 | A & H | 44 C. | 40 hr | 22.6 | 437.8 |
| Y93Q S95D I114M D118K A136P S202R W260F L288I L294P S295V | 10.5 | A & H | 44 C. | 40 hr | 28.8 | 496.3 |
| Y93Q S95D I114W D118K A136P S202R W260F L288I L294P S295V | 10.5 | A & H | 44 C. | 40 hr | 25.8 | 461.9 |
| Y93Q S95D K116R D118K A136P S202R W260F L288I L294P S295V | 10.5 | A & H | 44 C. | 40 hr | 22.8 | 466.1 |
| Y93Q S95D D118K T119R A136P S202R W260F L288I L294P S295V | 10.5 | A & H | 44 C. | 40 hr | 25.5 | 476.3 |
| Y93Q S95D D118K A136P K142M S202R W260F L288I L294P S295V | 10.5 | A & H | 44 C. | 40 hr | 21.1 | 390.1 |
| Y93Q S95D D118K A136P K142V S202R W260F L288I L294P S295V | 10.5 | A & H | 44 C. | 40 hr | 23.7 | 451.4 |
| Y93Q S95D D118K A136P Q143R S202R W260F L288I L294P S295V | 10.5 | A & H | 44 C. | 40 hr | 22.0 | 390.7 |
| Y93Q S95D D118K A136P N150T S202R W260F L288I L294P S295V | 10.5 | A & H | 44 C. | 40 hr | 25.9 | 481.7 |
| Y93Q S95D D118K A136P N150S S202R W260F L288I L294P S295V | 10.5 | A & H | 44 C. | 40 hr | 26.2 | 485.1 |
| Y93Q S95D D118K A136P N150R S202R W260F L288I L294P S295V | 10.5 | A & H | 44 C. | 40 hr | 26.2 | 474.2 |
| Y93Q S95D D118K A136P Q169A S202R W260F L288I L294P S295V | 10.5 | A & H | 44 C. | 40 hr | 28.3 | 516.6 |
| Y93Q S95D D118K A136P Q169R S202R W260F L288I L294P S295V | 10.5 | A & H | 44 C. | 40 hr | 21.3 | 420.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D D118K A136P Q169K S202R W260F L288I L294P S295V | 10.5 | A & H | 44 C. | 40 hr | 28.0 | 508.1 |
| Y93Q S95D D118K A136P Y174R S202R W260F L288I L294P S295V | 10.5 | A & H | 44 C. | 40 hr | 26.1 | 465.7 |
| Y93Q S95D D118K A136P Y174L S202R W260F L288I L294P S295V | 10.5 | A & H | 44 C. | 40 hr | 25.1 | 449.6 |
| Y93Q S95D D118K A136P E177Y S202R W260F L288I L294P S295V | 10.5 | A & H | 44 C. | 40 hr | 28.6 | 492.2 |
| Y93Q S95D D118K A136P N180R S202R W260F L288I L294P S295V | 10.5 | A & H | 44 C. | 40 hr | 26.7 | 478.1 |
| Y93Q S95D D118K A136P Q184E S202R W260F L288I L294P S295V | 10.5 | A & H | 44 C. | 40 hr | 28.0 | 512.0 |
| Y93Q S95D D118K A136P Q184K S202R W260F L288I L294P S295V | 10.5 | A & H | 44 C. | 40 hr | 28.7 | 520.9 |
| Y93Q S95D D118K A136P Q184S S202R W260F L288I L294P S295V | 10.5 | A & H | 44 C. | 40 hr | 23.0 | 443.8 |
| Y93Q S95D D118K A136P R185G S202R W260F L288I L294P S295V | 10.5 | A & H | 44 C. | 40 hr | 28.1 | 509.8 |
| Y93Q S95D D118K A136P S202R R210L W260F L288I L294P S295V | 10.5 | A & H | 44 C. | 40 hr | 34.5 | 611.4 |
| Y93Q S95D D118K A136P S202R R210M W260F L288I L294P S295V | 10.5 | A & H | 44 C. | 40 hr | 38.6 | 683.3 |
| Y93Q S95D D118K A136P S202R E234F W260F L288I L294P S295V | 10.5 | A & H | 44 C. | 40 hr | 20.9 | 406.6 |
| Y93Q S95D D118K A136P S202R E234Y W260F L288I L294P S295V | 10.5 | A & H | 44 C. | 40 hr | 36.2 | 641.7 |
| Y93Q S95D D118K A136P S202R A235R W260F L288I L294P S295V | 10.5 | A & H | 44 C. | 40 hr | 27.4 | 452.8 |
| Y93Q S95D D118K A136P S202R A235K W260F L288I L294P S295V | 10.5 | A & H | 44 C. | 40 hr | 25.6 | 457.9 |
| Y93Q S95D D118K A136P S202R R244K W260F L288I L294P S295V | 10.5 | A & H | 44 C. | 40 hr | 27.4 | 519.1 |
| E77N Y93Q S95D D118K A136P S202R W260F L288I L294P S295V | 10.5 | A & H | 44 C. | 40 hr | 24.9 | 452.4 |
| E77T Y93Q S95D D118K A136P S202R W260F L288I L294P S295V | 10.5 | A & H | 44 C. | 40 hr | 23.1 | 418.0 |
| D78G Y93Q S95D D118K A136P S202R W260F L288I L294P S295V | 10.5 | A & H | 44 C. | 40 hr | 34.5 | 574.4 |
| V82I Y93Q S95D D118K A136P S202R W260F L288I L294P S295V | 10.5 | A & H | 44 C. | 40 hr | 28.4 | 518.0 |
| Y6H Y93Q D118K A136P D139R S202R W260F L288I L294P S295V | 10.5 | A & H | 44 C. | 24 hr | 31.4 | 353.0 |
| Y6M Y93Q D118K A136P D139R S202R W260F L288I L294P S295V | 10.5 | A & H | 44 C. | 24 hr | 36.1 | 407.9 |
| Y93Q D118K A136P D139R S202R N213V W260F L288I L294P S295V | 10.5 | A & H | 44 C. | 24 hr | 40.2 | 440.2 |
| Y93Q D118K A136P D139R S202R W260F N272T L288I L294P S295V | 10.5 | A & H | 44 C. | 24 hr | 47.5 | 609.1 |
| Y93Q D118K A136P D139R S202R W260F T280L L288I L294P S295V | 10.5 | A & H | 44 C. | 24 hr | 46.3 | 564.3 |
| N18V Y93Q D118K A136P D139R S202R W260F L288I L294P S295V | 10.5 | A & H | 44 C. | 24 hr | 38.9 | 458.3 |
| N18R Y93Q D118K A136P D139R S202R W260F L288I L294P S295V | 10.5 | A & H | 44 C. | 24 hr | 25.4 | 310.5 |
| T37R Y93Q D118K A136P D139R S202R W260F L288I L294P S295V | 10.5 | A & H | 44 C. | 24 hr | 34.6 | 408.0 |
| E41V Y93Q D118K A136P D139R S202R W260F L288I L294P S295V | 10.5 | A & H | 44 C. | 24 hr | 37.5 | 449.7 |
| N45G Y93Q D118K A136P D139R S202R W260F L288I L294P S295V | 10.5 | A & H | 44 C. | 24 hr | 31.6 | 345.5 |
| G47A Y93Q D118K A136P D139R S202R W260F L288I L294P S295V | 10.5 | A & H | 44 C. | 24 hr | 27.3 | 324.2 |
| G47K Y93Q D118K A136P D139R S202R W260F L288I L294P S295V | 10.5 | A & H | 44 C. | 24 hr | 24.5 | 294.3 |
| G47S Y93Q D118K A136P D139R S202R W260F L288I L294P S295V | 10.5 | A & H | 44 C. | 24 hr | 29.1 | 338.4 |
| R70K Y93Q D118K A136P D139R S202R W260F L288I L294P S295V | 10.5 | A & H | 44 C. | 24 hr | 30.3 | 355.8 |
| N71S Y93Q D118K A136P D139R S202R W260F L288I L294P S295V | 10.5 | A & H | 44 C. | 24 hr | 22.1 | 278.1 |
| S74K Y93Q D118K A136P D139R S202R W260F L288I L294P S295V | 10.5 | A & H | 44 C. | 24 hr | 36.5 | 424.5 |
| Y93Q S111A D118K A136P D139R S202R W260F L288I L294P S295V | 10.5 | A & H | 44 C. | 24 hr | 27.5 | 330.0 |
| Y93Q S111K D118K A136P D139R S202R W260F L288I L294P S295V | 10.5 | A & H | 44 C. | 24 hr | 26.5 | 306.8 |
| Y93Q S111R D118K A136P D139R S202R W260F L288I L294P S295V | 10.5 | A & H | 44 C. | 24 hr | 24.8 | 303.1 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q I114Q D118K A136P D139R S202R W260F L288I L294P S295V | 10.5 | A & H | 44 C. | 24 hr | 27.6 | 331.8 |
| Y93Q I114W D118K A136P D139R S202R W260F L288I L294P S295V | 10.5 | A & H | 44 C. | 24 hr | 28.1 | 316.5 |
| Y93Q K116R D118K A136P D139R S202R W260F L288I L294P S295V | 10.5 | A & H | 44 C. | 24 hr | 22.3 | 276.9 |
| Y93Q D118K T119R A136P D139R S202R W260F L288I L294P S295V | 10.5 | A & H | 44 C. | 24 hr | 23.6 | 277.4 |
| Y93Q D118K A136P D139R K142M S202R W260F L288I L294P S295V | 10.5 | A & H | 44 C. | 24 hr | 32.1 | 367.8 |
| Y93Q D118K A136P D139R N150R S202R W260F L288I L294P S295V | 10.5 | A & H | 44 C. | 24 hr | 33.2 | 375.8 |
| Y93Q D118K A136P D139R Q169A S202R W260F L288I L294P S295V | 10.5 | A & H | 44 C. | 24 hr | 24.2 | 289.5 |
| Y93Q D118K A136P D139R Q169R S202R W260F L288I L294P S295V | 10.5 | A & H | 44 C. | 24 hr | 31.3 | 341.2 |
| Y93Q D118K A136P D139R Q169K S202R W260F L288I L294P S295V | 10.5 | A & H | 44 C. | 24 hr | 27.1 | 316.2 |
| Y93Q D118K A136P D139R E177Y S202R W260F L288I L294P S295V | 10.5 | A & H | 44 C. | 24 hr | 35.7 | 412.0 |
| Y93Q D118K A136P D139R Q184E S202R W260F L288I L294P S295V | 10.5 | A & H | 44 C. | 24 hr | 29.0 | 335.0 |
| Y93Q D118K A136P D139R Q184K S202R W260F L288I L294P S295V | 10.5 | A & H | 44 C. | 24 hr | 28.9 | 335.7 |
| Y93Q D118K A136P D139R Q184S S202R W260F L288I L294P S295V | 10.5 | A & H | 44 C. | 24 hr | 26.1 | 316.2 |
| Y93Q D118K A136P D139R S202R R210G W260F L288I L294P S295V | 10.5 | A & H | 44 C. | 24 hr | 57.2 | 742.1 |
| Y93Q D118K A136P D139R S202R E234Y W260F L288I L294P S295V | 10.5 | A & H | 44 C. | 24 hr | 53.3 | 666.5 |
| Y93Q D118K A136P D139R S202R A235K W260F L288I L294P S295V | 10.5 | A & H | 44 C. | 24 hr | 28.9 | 340.3 |
| E77T Y93Q D118K A136P D139R S202R W260F L288I L294P S295V | 10.5 | A & H | 44 C. | 24 hr | 20.5 | 282.8 |
| D78G Y93Q D118K A136P D139R S202R W260F L288I L294P S295V | 10.5 | A & H | 44 C. | 24 hr | 32.2 | 368.4 |
| V82I Y93Q D118K A136P D139R S202R W260F L288I L294P S295V | 10.5 | A & H | 44 C. | 24 hr | 33.5 | 372.5 |
| S95D S98P A136P S202R N213V G257A W260F L288I L294P S295V | 10.5 | A & H | 44 C. | 24 hr | 32.0 | 360.2 |
| S95D S98P A136P S202R G257A W260F N272M L288I L294P S295V | 10.5 | A & H | 44 C. | 24 hr | 23.8 | 267.3 |
| S95D S98P A136P S202R G257A W260F N272T L288I L294P S295V | 10.5 | A & H | 44 C. | 24 hr | 34.3 | 383.6 |
| S95D S98P A136P S202R Q243K G257A W260F L288I L294P S295V | 10.5 | A & H | 44 C. | 24 hr | 36.1 | 408.4 |
| S95D S98P A136P S202R G257A W260F N283W L288I L294P S295V | 10.5 | A & H | 44 C. | 24 hr | 36.0 | 401.9 |
| S95D S98P A136P S202R G257A W260F A276E L288I L294P S295V | 10.5 | A & H | 44 C. | 24 hr | 37.1 | 399.6 |
| S95D S98P A136P S202R G257A W260F A276W L288I L294P S295V | 10.5 | A & H | 44 C. | 24 hr | 30.4 | 344.8 |
| S95D S98P A136P S202R G257A W260F A276D L288I L294P S295V | 10.5 | A & H | 44 C. | 24 hr | 33.1 | 385.6 |
| S8T S95D S98P A136P S202R G257A W260F L288I L294P S295V | 10.5 | A & H | 44 C. | 24 hr | 25.6 | 305.4 |
| N18V S95D S98P A136P S202R G257A W260F L288I L294P S295V | 10.5 | A & H | 44 C. | 24 hr | 31.2 | 366.4 |
| N18R S95D S98P A136P S202R G257A W260F L288I L294P S295V | 10.5 | A & H | 44 C. | 24 hr | 21.4 | 257.3 |
| T37R S95D S98P A136P S202R G257A W260F L288I L294P S295V | 10.5 | A & H | 44 C. | 24 hr | 31.3 | 341.3 |
| E41V S95D S98P A136P S202R G257A W260F L288I L294P S295V | 10.5 | A & H | 44 C. | 24 hr | 32.2 | 360.2 |
| N45G S95D S98P A136P S202R G257A W260F L288I L294P S295V | 10.5 | A & H | 44 C. | 24 hr | 24.6 | 289.4 |
| G47A S95D S98P A136P S202R G257A W260F L288I L294P S295V | 10.5 | A & H | 44 C. | 24 hr | 21.6 | 268.8 |
| G47K S95D S98P A136P S202R G257A W260F L288I L294P S295V | 10.5 | A & H | 44 C. | 24 hr | 24.9 | 304.0 |
| G47S S95D S98P A136P S202R G257A W260F L288I L294P S295V | 10.5 | A & H | 44 C. | 24 hr | 25.2 | 285.1 |
| R70K S95D S98P A136P S202R G257A W260F L288I L294P S295V | 10.5 | A & H | 44 C. | 24 hr | 28.5 | 330.1 |
| S74K S95D S98P A136P S202R G257A W260F L288I L294P S295V | 10.5 | A & H | 44 C. | 24 hr | 25.2 | 302.9 |
| S95D S98P S111A A136P S202R G257A W260F L288I L294P S295V | 10.5 | A & H | 44 C. | 24 hr | 21.1 | 274.4 |
| S95D S98P S111R A136P S202R G257A W260F L288I L294P S295V | 10.5 | A & H | 44 C. | 24 hr | 24.6 | 297.3 |
| S95D S98P I114M A136P S202R G257A W260F L288I L294P S295V | 10.5 | A & H | 44 C. | 24 hr | 20.4 | 269.4 |
| S95D S98P K116R A136P S202R G257A W260F L288I L294P S295V | 10.5 | A & H | 44 C. | 24 hr | 22.3 | 274.5 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| S95D S98P D118K A136P S202R G257A W260F L288I L294P S295V | 10.5 | A & H | 44 C. | 24 hr | 26.6 | 332.0 |
| S95D S98P T119R A136P S202R G257A W260F L288I L294P S295V | 10.5 | A & H | 44 C. | 24 hr | 24.7 | 300.0 |
| S95D S98P A136P K142M S202R G257A W260F L288I L294P S295V | 10.5 | A & H | 44 C. | 24 hr | 20.7 | 267.0 |
| S95D S98P A136P N150S S202R G257A W260F L288I L294P S295V | 10.5 | A & H | 44 C. | 24 hr | 24.8 | 300.9 |
| S95D S98P A136P N150R S202R G257A W260F L288I L294P S295V | 10.5 | A & H | 44 C. | 24 hr | 24.6 | 294.2 |
| S95D S98P A136P Q169A S202R G257A W260F L288I L294P S295V | 10.5 | A & H | 44 C. | 24 hr | 20.2 | 266.7 |
| S95D S98P A136P Y174R S202R G257A W260F L288I L294P S295V | 10.5 | A & H | 44 C. | 24 hr | 24.3 | 283.3 |
| S95D S98P A136P Y174L S202R G257A W260F L288I L294P S295V | 10.5 | A & H | 44 C. | 24 hr | 21.2 | 268.9 |
| S95D S98P A136P E177Y S202R G257A W260F L288I L294P S295V | 10.5 | A & H | 44 C. | 24 hr | 25.0 | 313.8 |
| S95D S98P A136P N180R S202R G257A W260F L288I L294P S295V | 10.5 | A & H | 44 C. | 24 hr | 22.4 | 268.3 |
| S95D S98P A136P Q184K S202R G257A W260F L288I L294P S295V | 10.5 | A & H | 44 C. | 24 hr | 22.4 | 273.5 |
| S95D S98P A136P S202R E234F G257A W260F L288I L294P S295V | 10.5 | A & H | 44 C. | 24 hr | 24.5 | 300.8 |
| S95D S98P A136P S202R E234Y G257A W260F L288I L294P S295V | 10.5 | A & H | 44 C. | 24 hr | 43.5 | 501.3 |
| E77T S95D S98P A136P S202R G257A W260F L288I L294P S295V | 10.5 | A & H | 44 C. | 24 hr | 28.0 | 315.7 |
| D78G S95D S98P A136P S202R G257A W260F L288I L294P S295V | 10.5 | A & H | 44 C. | 24 hr | 25.0 | 311.5 |
| V82I S95D S98P A136P S202R G257A W260F L288I L294P S295V | 10.5 | A & H | 44 C. | 24 hr | 29.8 | 338.1 |
| H80K S95D S98P A136P S202R W260F N279E L288I L294P S295V | 10.5 | A & H | 44 C. | 16 hr | 28.6 | 204.7 |
| H80K S95D S98P A136P S202R W260F N273D L288I L294P S295V | 10.5 | A & H | 44 C. | 16 hr | 22.5 | 165.5 |
| H80K S95D S98P A136P S202R W260F N273E L288I L294P S295V | 10.5 | A & H | 44 C. | 16 hr | 20.8 | 164.5 |
| H80K S95D S98P A136P S202R N213V W260F L288I L294P S295V | 10.5 | A & H | 44 C. | 16 hr | 23.5 | 183.7 |
| H80K S95D S98P A136P P183T S202R W260F L288I L294P S295V | 10.5 | A & H | 44 C. | 16 hr | 29.4 | 216.7 |
| H80K S95D S98P A136P S202R Q243K W260F L288I L294P S295V | 10.5 | A & H | 44 C. | 16 hr | 25.1 | 185.6 |
| H80K S95D S98P A136P S202R W260F N283W L288I L294P S295V | 10.5 | A & H | 44 C. | 16 hr | 30.1 | 221.8 |
| H80K S95D S98P A136P S202R W260F N283H L288I L294P S295V | 10.5 | A & H | 44 C. | 16 hr | 29.2 | 208.4 |
| H80K S95D S98P A136P S202R W260F A276E L288I L294P S295V | 10.5 | A & H | 44 C. | 16 hr | 25.4 | 188.3 |
| H80K S95D S98P A136P S202R W260F A276D L288I L294P S295V | 10.5 | A & H | 44 C. | 16 hr | 24.8 | 191.2 |
| H80K S95D S98P A136P S202R W260F T280L L288I L294P S295V | 10.5 | A & H | 44 C. | 16 hr | 20.0 | 158.9 |
| N18V H80K S95D S98P A136P S202R W260F L288I L294P S295V | 10.5 | A & H | 44 C. | 16 hr | 24.0 | 185.2 |
| T37P H80K S95D S98P A136P S202R W260F L288I L294P S295V | 10.5 | A & H | 44 C. | 16 hr | 21.7 | 169.8 |
| T37R H80K S95D S98P A136P S202R W260F L288I L294P S295V | 10.5 | A & H | 44 C. | 16 hr | 21.1 | 178.8 |
| E41V H80K S95D S98P A136P S202R W260F L288I L294P S295V | 10.5 | A & H | 44 C. | 16 hr | 23.0 | 174.4 |
| H80K S95D S98P D118K A136P S202R W260F L288I L294P S295V | 10.5 | A & H | 44 C. | 16 hr | 21.8 | 180.1 |
| H80K S95D S98P A136P N150R S202R W260F L288I L294P S295V | 10.5 | A & H | 44 C. | 16 hr | 20.1 | 155.3 |
| H80K S95D S98P A136P S202R R210L W260F L288I L294P S295V | 10.5 | A & H | 44 C. | 16 hr | 26.5 | 197.2 |
| H80K S95D S98P A136P S202R R210M W260F L288I L294P S295V | 10.5 | A & H | 44 C. | 16 hr | 33.4 | 242.3 |
| H80K S95D S98P A136P S202R R210G W260F L288I L294P S295V | 10.5 | A & H | 44 C. | 16 hr | 32.7 | 221.3 |
| H80K S95D S98P A136P S202R E234Y W260F L288I L294P S295V | 10.5 | A & H | 44 C. | 16 hr | 34.7 | 233.6 |
| H80K S95D S98P A136P D139A S202R W260F L288I L294P S295V | 10.5 | A & H | 44 C. | 16 hr | 37.0 | 254.3 |
| S95D S98P A136P D139A S202R G257A W260F L288I L294P S295V | 10.5 | A & H | 44 C. | 16 hr | 42.6 | 268.1 |
| A1G H80K Y93Q S95D A136P S202R W260F L288I L294P S295V | 10.5 | A & H | 44 C. | 40 hr | 25.1 | 486.8 |
| H80K Y93Q S95D A136P S202R Q243K W260F L288I L294P S295V | 10.5 | A & H | 44 C. | 40 hr | 30.6 | 573.7 |
| S3P H80K Y93Q S95D A136P S202R W260F L288I L294P S295V | 10.5 | A & H | 44 C. | 40 hr | 21.3 | 447.3 |
| T37P H80K Y93Q S95D A136P S202R W260F L288I L294P S295V | 10.5 | A & H | 44 C. | 40 hr | 22.4 | 474.6 |
| G47A H80K Y93Q S95D A136P S202R W260F L288I L294P S295V | 10.5 | A & H | 44 C. | 40 hr | 35.9 | 694.5 |
| S8T H80K Y93Q S95D A136P S202R W260F L288I L294P S295V | 10.5 | A & H | 44 C. | 40 hr | 26.6 | 510.9 |
| H80K Y93Q S95D A136P S202R W260F A276E L288I L294P S295V | 10.5 | A & H | 44 C. | 40 hr | 29.1 | 540.3 |
| H80K Y93Q S95D T119R A136P S202R W260F L288I L294P S295V | 10.5 | A & H | 44 C. | 40 hr | 23.4 | 467.2 |
| H80K Y93Q S95D D118K A136P S202R W260F L288I L294P S295V | 10.5 | A & H | 44 C. | 40 hr | 36.8 | 661.6 |
| E41V H80K Y93Q S95D A136P S202R W260F L288I L294P S295V | 10.5 | A & H | 44 C. | 40 hr | 27.6 | 523.6 |
| T37R H80K Y93Q S95D A136P S202R W260F L288I L294P S295V | 10.5 | A & H | 44 C. | 40 hr | 21.1 | 441.1 |
| R70K H80K Y93Q S95D A136P S202R W260F L288I L294P S295V | 10.5 | A & H | 44 C. | 40 hr | 20.4 | 447.2 |
| N18V H80K Y93Q S95D A136P S202R W260F L288I L294P S295V | 10.5 | A & H | 44 C. | 40 hr | 26.0 | 492.0 |
| S74K H80K Y93Q S95D A136P S202R W260F L288I L294P S295V | 10.5 | A & H | 44 C. | 40 hr | 22.5 | 440.5 |
| H80K Y93Q S95D A136P N150T S202R W260F L288I L294P S295V | 10.5 | A & H | 44 C. | 40 hr | 20.5 | 437.8 |
| H80K Y93Q S95D A136P N150R S202R W260F L288I L294P S295V | 10.5 | A & H | 44 C. | 40 hr | 24.4 | 458.1 |
| H80K Y93Q S95D A136P Q184E S202R W260F L288I L294P S295V | 10.5 | A & H | 44 C. | 40 hr | 20.2 | 430.9 |
| H80K Y93Q S95D A136P S202R R210L W260F L288I L294P S295V | 10.5 | A & H | 44 C. | 40 hr | 27.1 | 522.3 |
| H80K Y93Q S95D A136P S202R R210M W260F L288I L294P S295V | 10.5 | A & H | 44 C. | 40 hr | 31.1 | 590.9 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| H80K Y93Q S95D A136P S202R R210G W260F L288I L294P S295V | 10.5 | A & H | 44 C. | 40 hr | 33.9 | 627.4 |
| H80K Y93Q S95D A136P D139W S202R W260F L288I L294P S295V | 10.5 | A & H | 44 C. | 40 hr | 21.6 | 432.4 |
| H80K Y93Q S95D A136P N200T S202R W260F L288I L294P S295V | 10.5 | A & H | 44 C. | 40 hr | 27.7 | 499.4 |
| D78G H80K Y93Q S95D A136P S202R W260F L288I L294P S295V | 10.5 | A & H | 44 C. | 40 hr | 22.2 | 463.6 |
| H80K V82I Y93Q S95D A136P S202R W260F L288I L294P S295V | 10.5 | A & H | 44 C. | 40 hr | 24.8 | 488.1 |
| H80K Y93Q S95D A136P S202R W260F N279D L288I L294P S295V | 10.5 | A & H | 44 C. | 40 hr | 27.7 | 535.0 |
| H80K Y93Q S95D A136P S202R W260F N279E L288I L294P S295V | 10.5 | A & H | 44 C. | 40 hr | 37.6 | 678.9 |
| H80K Y93Q S95D A136P S202R W260F N273D L288I L294P S295V | 10.5 | A & H | 44 C. | 40 hr | 24.8 | 494.0 |
| Y6H H80K Y93Q S95D A136P S202R W260F L288I L294P S295V | 10.5 | A & H | 44 C. | 40 hr | 20.6 | 431.0 |
| Y6M H80K Y93Q S95D A136P S202R W260F L288I L294P S295V | 10.5 | A & H | 44 C. | 40 hr | 21.3 | 428.5 |
| H80K Y93Q S95D A136P S202R N213V W260F L288I L294P S295V | 10.5 | A & H | 44 C. | 40 hr | 24.6 | 486.5 |
| H80K Y93Q S95D A136P S202R N213D W260F L288I L294P S295V | 10.5 | A & H | 44 C. | 40 hr | 28.6 | 551.5 |
| H80K Y93Q S95D A136P P183G S202R W260F L288I L294P S295V | 10.5 | A & H | 44 C. | 40 hr | 29.8 | 575.6 |
| H80K Y93Q S95D A136P P183T S202R W260F L288I L294P S295V | 10.5 | A & H | 44 C. | 40 hr | 31.1 | 610.2 |
| H80K Y93Q S95D A136P S202R W260F L288I L294P S295V | 10.5 | A & H | 44 C. | 40 hr | 23.1 | 467.4 |
| S95D A136P S202R Q243E W260F L288I L294P S295V | 10.5 | A & H | 44 C. | 16 hr | 22.1 | 181.9 |
| S95D A136P S202R Q243K W260F L288I L294P S295V | 10.5 | A & H | 44 C. | 16 hr | 28.1 | 204.7 |
| T37P S95D A136P S202R W260F L288I L294P S295V | 10.5 | A & H | 44 C. | 16 hr | 21.8 | 173.3 |
| G47S S95D A136P S202R W260F L288I L294P S295V | 10.5 | A & H | 44 C. | 16 hr | 20.1 | 166.9 |
| H80K S95D A136P S202R W260F L288I L294P S295V | 10.5 | A & H | 44 C. | 16 hr | 20.9 | 175.8 |
| G47K S95D A136P S202R W260F L288I L294P S295V | 10.5 | A & H | 44 C. | 16 hr | 20.0 | 162.7 |
| S95D T119R A136P S202R W260F L288I L294P S295V | 10.5 | A & H | 44 C. | 16 hr | 21.5 | 174.9 |
| H80R S95D A136P S202R W260F L288I L294P S295V | 10.5 | A & H | 44 C. | 16 hr | 20.2 | 163.9 |
| S95D D118K A136P S202R W260F L288I L294P S295V | 10.5 | A & H | 44 C. | 16 hr | 21.8 | 173.5 |
| D78G S95D A136P S202R W260F L288I L294P S295V | 10.5 | A & H | 44 C. | 16 hr | 22.6 | 174.5 |
| S95D I114Q A136P S202R W260F L288I L294P S295V | 10.5 | A & H | 44 C. | 16 hr | 24.7 | 175.2 |
| S95D I114W A136P S202R W260F L288I L294P S295V | 10.5 | A & H | 44 C. | 16 hr | 27.8 | 203.6 |
| T37S S95D A136P S202R W260F L288I L294P S295V | 10.5 | A & H | 44 C. | 16 hr | 23.2 | 184.6 |
| R70K S95D A136P S202R W260F L288I L294P S295V | 10.5 | A & H | 44 C. | 16 hr | 25.6 | 186.9 |
| N18V S95D A136P S202R W260F L288I L294P S295V | 10.5 | A & H | 44 C. | 16 hr | 33.8 | 210.9 |
| S74K S95D A136P S202R W260F L288I L294P S295V | 10.5 | A & H | 44 C. | 16 hr | 20.8 | 167.1 |
| S95D A136P Q169A S202R W260F L288I L294P S295V | 10.5 | A & H | 44 C. | 16 hr | 21.9 | 163.1 |
| S95D A136P Q169K S202R W260F L288I L294P S295V | 10.5 | A & H | 44 C. | 16 hr | 21.2 | 147.5 |
| S95D A136P E177Y S202R W260F L288I L294P S295V | 10.5 | A & H | 44 C. | 16 hr | 21.2 | 171.3 |
| S95D A136P N150T S202R W260F L288I L294P S295V | 10.5 | A & H | 44 C. | 16 hr | 24.2 | 209.2 |
| S95D A136P N150S S202R W260F L288I L294P S295V | 10.5 | A & H | 44 C. | 16 hr | 22.0 | 168.1 |
| S95D A136P N150R S202R W260F L288I L294P S295V | 10.5 | A & H | 44 C. | 16 hr | 23.9 | 187.2 |
| S95D A136P Q184E S202R W260F L288I L294P S295V | 10.5 | A & H | 44 C. | 16 hr | 23.9 | 204.2 |
| S95D A136P S202R R210L W260F L288I L294P S295V | 10.5 | A & H | 44 C. | 16 hr | 23.7 | 188.1 |
| S95D A136P S202R R210M W260F L288I L294P S295V | 10.5 | A & H | 44 C. | 16 hr | 33.0 | 246.3 |
| S95D A136P D139V S202R W260F L288I L294P S295V | 10.5 | A & H | 44 C. | 16 hr | 24.0 | 196.0 |
| S95D A136P N200T S202R W260F L288I L294P S295V | 10.5 | A & H | 44 C. | 16 hr | 29.1 | 207.9 |
| S95D A136P S202R W260F N273D L288I L294P S295V | 10.5 | A & H | 44 C. | 16 hr | 25.4 | 200.8 |
| Y6M S95D A136P S202R W260F L288I L294P S295V | 10.5 | A & H | 44 C. | 16 hr | 21.9 | 181.7 |
| S95D A136P P183G S202R W260F L288I L294P S295V | 10.5 | A & H | 44 C. | 16 hr | 33.3 | 243.1 |
| S95D A136P P183T S202R W260F L288I L294P S295V | 10.5 | A & H | 44 C. | 16 hr | 30.5 | 236.4 |
| S95D A136P S202R W260F T280L L288I L294P S295V | 10.5 | A & H | 44 C. | 16 hr | 33.0 | 200.0 |
| H80K Y93Q S95D A136P S202R W260F N272M L288I L294P S295V | 10.5 | A & H | 44 C. | 16 hr | 41.1 | 286.1 |
| H80K Y93Q S95D A136P S202R W260F N272T L288I L294P S295V | 10.5 | A & H | 44 C. | 16 hr | 52.7 | 352.7 |
| H80K Y93Q S95D A136P S202R W260F N283W L288I L294P S295V | 10.5 | A & H | 44 C. | 16 hr | 59.1 | 451.0 |
| H80K Y93Q S95D A136P S202R W260F N283H L288I L294P S295V | 10.5 | A & H | 44 C. | 16 hr | 57.9 | 416.0 |
| H80K Y93Q S95D A136P S202R W260F A276D L288I L294P S295V | 10.5 | A & H | 44 C. | 16 hr | 58.0 | 413.6 |
| S95D E133R A136P S202R W260F L288I L294P S295V | 10.5 | A & H | 44 C. | 16 hr | 21.7 | 178.3 |
| H80K Y93Q S95D A136P S202R W260F T280L L288I L294P S295V | 10.5 | A & H | 44 C. | 16 hr | 53.0 | 453.0 |
| H80K Y93Q D118K A136P D139R S202R W260F L288I L294P S295V | 10.5 | A & H | 44 C. | 16 hr | 39.1 | 279.1 |
| Y93Q S95D D118K A136P D139R S202R W260F L288I L294P S295V | 10.5 | A & H | 44 C. | 16 hr | 44.9 | 351.9 |
| A1G Y93Q S95D A136P D139A S202R W260F L288I L294P S295V | 10.5 | A & H | 44 C. | 40 hr | 28.8 | 574.9 |
| Y93Q S95D A136P D139A S202R Q243E W260F L288I L294P S295V | 10.5 | A & H | 44 C. | 40 hr | 28.9 | 548.1 |
| Y93Q S95D A136P D139A S202R Q243K W260F L288I L294P S295V | 10.5 | A & H | 44 C. | 40 hr | 32.0 | 570.1 |
| Y93Q S95D K116R A136P D139A S202R W260F L288I L294P S295V | 10.5 | A & H | 44 C. | 40 hr | 21.7 | 423.3 |
| S3P Y93Q S95D A136P D139A S202R W260F L288I L294P S295V | 10.5 | A & H | 44 C. | 40 hr | 24.0 | 444.5 |
| T37P Y93Q S95D A136P D139A S202R W260F L288I L294P S295V | 10.5 | A & H | 44 C. | 40 hr | 20.9 | 450.2 |
| H80K Y93Q S95D A136P D139A S202R W260F L288I L294P S295V | 10.5 | A & H | 44 C. | 40 hr | 21.3 | 435.4 |
| Y93Q S95D A136P D139A S202R W260F A276E L288I L294P S295V | 10.5 | A & H | 44 C. | 40 hr | 30.2 | 571.6 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D A136P D139A S202R G257A W260F L288I L294P S295V | 10.5 | A & H | 44 C. | 40 hr | 34.0 | 615.0 |
| Y93Q S95D T119R A136P D139A S202R W260F L288I L294P S295V | 10.5 | A & H | 44 C. | 40 hr | 20.4 | 449.5 |
| D78G Y93Q S95D A136P D139A S202R W260F L288I L294P S295V | 10.5 | A & H | 44 C. | 40 hr | 25.5 | 497.1 |
| E41V Y93Q S95D A136P D139A S202R W260F L288I L294P S295V | 10.5 | A & H | 44 C. | 40 hr | 35.4 | 643.8 |
| Y93Q S95D S111A A136P D139A S202R W260F L288I L294P S295V | 10.5 | A & H | 44 C. | 40 hr | 20.7 | 442.1 |
| Y93Q S95D A136P D139R S202R W260F L288I L294P S295V | 10.5 | A & H | 44 C. | 40 hr | 25.6 | 476.8 |
| R70K Y93Q S95D A136P D139A S202R W260F L288I L294P S295V | 10.5 | A & H | 44 C. | 40 hr | 21.1 | 428.8 |
| N18V Y93Q S95D A136P D139A S202R W260F L288I L294P S295V | 10.5 | A & H | 44 C. | 40 hr | 27.8 | 559.0 |
| S74K Y93Q S95D A136P D139A S202R W260F L288I L294P S295V | 10.5 | A & H | 44 C. | 40 hr | 22.8 | 454.1 |
| Y93Q S95D A136P D139A E177Y S202R W260F L288I L294P S295V | 10.5 | A & H | 44 C. | 40 hr | 24.4 | 479.1 |
| Y93Q S95D A136P D139A N150S S202R W260F L288I L294P S295V | 10.5 | A & H | 44 C. | 40 hr | 22.6 | 491.3 |
| Y93Q S95D A136P D139A N150R S202R W260F L288I L294P S295V | 10.5 | A & H | 44 C. | 40 hr | 21.2 | 458.7 |
| Y93Q S95D A136P D139A R185G S202R W260F L288I L294P S295V | 10.5 | A & H | 44 C. | 40 hr | 22.0 | 445.1 |
| Y93Q S95D A136P D139A S202R R210M W260F L288I L294P S295V | 10.5 | A & H | 44 C. | 40 hr | 26.8 | 504.2 |
| Y93Q S95D A136P D139A S202R R210G W260F L288I L294P S295V | 10.5 | A & H | 44 C. | 40 hr | 28.7 | 536.7 |
| Y93Q S95D A136P D139A N200T S202R W260F L288I L294P S295V | 10.5 | A & H | 44 C. | 40 hr | 20.2 | 424.6 |
| Y93Q S95D A136P D139A S202R W260F N279E L288I L294P S295V | 10.5 | A & H | 44 C. | 40 hr | 34.0 | 565.9 |
| Y93Q S95D A136P D139A S202R N213V W260F L288I L294P S295V | 10.5 | A & H | 44 C. | 40 hr | 24.2 | 467.1 |
| Y93Q S95D A136P D139A S202R N213D W260F L288I L294P S295V | 10.5 | A & H | 44 C. | 40 hr | 24.0 | 440.2 |
| Y93Q S95D A136P D139A P183G S202R W260F L288I L294P S295V | 10.5 | A & H | 44 C. | 40 hr | 25.3 | 474.1 |
| Y93Q S95D A136P D139A P183T S202R W260F L288I L294P S295V | 10.5 | A & H | 44 C. | 40 hr | 27.6 | 481.6 |
| Y93Q S95D A136P D139A S202R W260F N272M L288I L294P S295V | 10.5 | A & H | 44 C. | 40 hr | 23.0 | 488.3 |
| Y93Q S95D A136P D139A S202R W260F N272T L288I L294P S295V | 10.5 | A & H | 44 C. | 40 hr | 27.2 | 500.7 |
| Y93Q S95D A136P D139A S202R W260F N283W L288I L294P S295V | 10.5 | A & H | 44 C. | 40 hr | 30.0 | 570.6 |
| Y93Q S95D A136P D139A S202R W260F N283H L288I L294P S295V | 10.5 | A & H | 44 C. | 40 hr | 30.2 | 531.6 |
| Y93Q S95D A136P D139A S202R W260F A276W L288I L294P S295V | 10.5 | A & H | 44 C. | 40 hr | 24.1 | 477.8 |
| Y93Q S95D A136P D139A S202R W260F A276D L288I L294P S295V | 10.5 | A & H | 44 C. | 40 hr | 25.7 | 517.0 |
| Y93Q S95D A136P D139A S202R W260F T280L L288I L294P S295V | 10.5 | A & H | 44 C. | 40 hr | 27.3 | 488.8 |
| Y93Q S95D A136P D139A S202R W260F L288I L294P S295V | 10.5 | A & H | 44 C. | 40 hr | 27.6 | 531.3 |
| A1V Y93Q D118K A136P D139R S202R R210G G257A W260F A276D L288I L294P S295V | 10.5 | A & H | 44 C. | 40 hr | 52.2 | 1118.4 |
| Y93Q D118K A136P D139R S202R R210G Q243K W260F L288I L294P S295V | 10.5 | A & H | 44 C. | 40 hr | 31.8 | 621.3 |
| S3P Y93Q D118K A136P D139R S202R R210G W260F L288I L294P S295V | 10.5 | A & H | 44 C. | 40 hr | 30.8 | 593.5 |
| T37P Y93Q D118K A136P D139R S202R R210G W260F L288I L294P S295V | 10.5 | A & H | 44 C. | 40 hr | 24.9 | 492.9 |
| S8T Y93Q D118K A136P D139R S202R R210G W260F L288I L294P S295V | 10.5 | A & H | 44 C. | 40 hr | 27.7 | 530.8 |
| G47S Y93Q D118K A136P D139R S202R R210G W260F L288I L294P S295V | 10.5 | A & H | 44 C. | 40 hr | 28.0 | 528.3 |
| H80K Y93Q D118K A136P D139R S202R R210G W260F L288I L294P S295V | 10.5 | A & H | 44 C. | 40 hr | 25.2 | 496.3 |
| Y93Q D118K A136P D139R S202R R210G W260F A276E L288I L294P S295V | 10.5 | A & H | 44 C. | 40 hr | 32.1 | 629.1 |
| E77N Y93Q D118K A136P D139R S202R R210G W260F L288I L294P S295V | 10.5 | A & H | 44 C. | 40 hr | 23.8 | 482.1 |
| G47K S95D S98P D118K A136P D139R S202R R210G W260F L288I L294P S295V | 10.5 | A & H | 44 C. | 40 hr | 42.2 | 806.1 |
| E41V Y93Q D118K A136P D139R S202R R210G W260F L288I L294P S295V | 10.5 | A & H | 44 C. | 40 hr | 29.1 | 541.9 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| T37R Y93Q D118K A136P D139R S202R R210G W260F L288I L294P S295V | 10.5 | A & H | 44 C. | 40 hr | 23.8 | 471.7 |
| R70K Y93Q D118K A136P D139R S202R R210G W260F L288I L294P S295V | 10.5 | A & H | 44 C. | 40 hr | 31.8 | 617.8 |
| N45G Y93Q D118K A136P D139R S202R R210G W260F L288I L294P S295V | 10.5 | A & H | 44 C. | 40 hr | 37.9 | 719.5 |
| N18V Y93Q D118K A136P D139R S202R R210G W260F L288I L294P S295V | 10.5 | A & H | 44 C. | 40 hr | 36.8 | 678.6 |
| Y93Q D118K A136P D139R N180R S202R R210G W260F L288I L294P S295V | 10.5 | A & H | 44 C. | 40 hr | 27.6 | 511.2 |
| Y93Q D118K A136P D139R E177S S202R R210G W260F L288I L294P S295V | 10.5 | A & H | 44 C. | 40 hr | 25.3 | 483.6 |
| Y93Q D118K A136P D139R E177Y S202R R210G W260F L288I L294P S295V | 10.5 | A & H | 44 C. | 40 hr | 35.6 | 689.9 |
| Y93Q D118K A136P D139R N150T S202R R210G W260F L288I L294P S295V | 10.5 | A & H | 44 C. | 40 hr | 25.8 | 491.2 |
| Y93Q D118K A136P D139R N150S S202R R210G W260F L288I L294P S295V | 10.5 | A & H | 44 C. | 40 hr | 24.9 | 513.3 |
| Y93Q D118K A136P D139R S202R R210G E234F G257A W260F A276D L288I L294P S295V | 10.5 | A & H | 44 C. | 40 hr | 42.1 | 810.5 |
| Y93Q D118K A136P D139R S202R R210G E234Y W260F L288I L294P S295V | 10.5 | A & H | 44 C. | 40 hr | 42.0 | 768.5 |
| Y93Q D118K A136P D139R S202R R210G A235K W260F L288I L294P S295V | 10.5 | A & H | 44 C. | 40 hr | 35.6 | 625.3 |
| Y93Q D118K A136P D139R S202R R210G R244K G257A W260F A276D L288I L294P S295V | 10.5 | A & H | 44 C. | 40 hr | 50.2 | 973.3 |
| Y93Q S95D D118K A136P D139R S202R R210G W260F L288I L294P S295V | 10.5 | A & H | 44 C. | 40 hr | 58.7 | 1181.5 |
| Y93Q A97S D118K A136P D139R S202R R210G G257A W260F A276D L288I L294P S295V | 10.5 | A & H | 44 C. | 40 hr | 43.7 | 865.9 |
| Y93Q D118K A136P D139R N200T S202R R210G W260F L288I L294P S295V | 10.5 | A & H | 44 C. | 40 hr | 23.1 | 477.4 |
| G47A Y93Q S95D D118K A136P S202R W260F N279E L288I L294P S295V | 10.5 | A & H | 46 C. | 18 hr | 27.3 | 415.2 |
| G47S Y93Q S95D D118K A136P S202R W260F N279E L288I L294P S295V | 10.5 | A & H | 46 C. | 18 hr | 28.2 | 427.4 |
| V82I Y93Q S95D D118K A136P S202R W260F N279E L288I L294P S295V | 10.5 | A & H | 46 C. | 18 hr | 36.9 | 559.0 |
| E77N Y93Q S95D D118K A136P S202R W260F N279E L288I L294P S295V | 10.5 | A & H | 46 C. | 18 hr | 24.9 | 392.9 |
| H80R Y93Q S95D D118K A136P S202R W260F N279E L288I L294P S295V | 10.5 | A & H | 46 C. | 18 hr | 38.7 | 564.9 |
| D78G Y93Q S95D D118K A136P S202R W260F N279E L288I L294P S295V | 10.5 | A & H | 46 C. | 18 hr | 39.6 | 575.2 |
| E41V Y93Q S95D D118K A136P S202R W260F N279E L288I L294P S295V | 10.5 | A & H | 46 C. | 18 hr | 38.2 | 605.8 |
| Y93Q S95D D104G D118K A136P S202R W260F N279E L288I L294P S295V | 10.5 | A & H | 46 C. | 18 hr | 22.5 | 351.1 |
| Y93Q S95D S111A D118K A136P S202R W260F N279E L288I L294P S295V | 10.5 | A & H | 46 C. | 18 hr | 32.2 | 489.6 |
| Y93Q S95D S111R D118K A136P S202R W260F N279E L288I L294P S295V | 10.5 | A & H | 46 C. | 18 hr | 26.7 | 411.3 |
| Y93Q S95D S111K D118K A136P S202R W260F N279E L288I L294P S295V | 10.5 | A & H | 46 C. | 18 hr | 27.9 | 435.8 |
| D65E Y93Q S95D D118K A136P S202R W260F N279E L288I L294P S295V | 10.5 | A & H | 46 C. | 18 hr | 33.9 | 512.7 |
| R70K Y93Q S95D D118K A136P S202R W260F N279E L288I L294P S295V | 10.5 | A & H | 46 C. | 18 hr | 34.2 | 550.2 |
| N18V Y93Q S95D D118K A136P S202R W260F N279E L288I L294P S295V | 10.5 | A & H | 46 C. | 18 hr | 37.6 | 537.4 |
| S74K Y93Q S95D D118K A136P S202R W260F N279E L288I L294P S295V | 10.5 | A & H | 46 C. | 18 hr | 33.0 | 486.7 |
| Y93Q S95D D118K A136P Y174R S202R W260F N279E L288I L294P S295V | 10.5 | A & H | 46 C. | 18 hr | 28.8 | 418.6 |
| Y93Q S95D D118K A136P Q169A S202R W260F N279E L288I L294P S295V | 10.5 | A & H | 46 C. | 18 hr | 33.7 | 500.9 |
| Y93Q S95D D118K A136P E177S S202R W260F N279E L288I L294P S295V | 10.5 | A & H | 46 C. | 18 hr | 30.0 | 466.4 |
| Y93Q S95D D118K A136P E177Y S202R W260F N279E L288I L294P S295V | 10.5 | A & H | 46 C. | 18 hr | 32.0 | 505.7 |
| Y93Q S95D D118K T119R A136P S202R W260F N279E L288I L294P S295V | 10.5 | A & H | 46 C. | 18 hr | 22.1 | 348.7 |
| Y93Q S95D D118K A136P P183T S202R W260F N279E L288I L294P S295V | 10.5 | A & H | 46 C. | 18 hr | 39.4 | 564.8 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| V82I Y93Q S95D D118K A136P S202R W260F N283H L288I L294P S295V | 10.5 | A & H | 46 C. | 18 hr | 36.8 | 588.0 |
| Y93Q S95D A136P D139A S202R E234Y Q243E W260F A276E N279E L288I L294P S295V | 10.5 | A & H | 46 C. | 18 hr | 64.3 | 1328.1 |
| Y93Q S95D D118K A136P D139A S202R E234Y A235K Q243E W260F A276E N279E N283W L288I L294P S295V | 10.5 | A & H | 46 C. | 18 hr | 70.7 | 1454.5 |
| Y93Q S95D A136P D139A S202R E234Y A235K Q243E W260F A276E N279E L288I L294P S295V | 10.5 | A & H | 46 C. | 18 hr | 65.9 | 1454.5 |
| A1G Y93Q S95D D118K A136P S202R W260F N279E L288I L294P S295V | 10.5 | A & H | 46 C. | 16 hr | 25.9 | 687.7 |
| A1V Y93Q S95D D118K A136P S202R W260F N279E L288I L294P S295V | 10.5 | A & H | 46 C. | 16 hr | 22.6 | 663.8 |
| Y93Q S95D D118K A136P S202R Q243Y W260F N279E L288I L294P S295V | 10.5 | A & H | 46 C. | 16 hr | 32.4 | 851.1 |
| Y93Q S95D D118K A136P S202R Q243E W260F N279E L288I L294P S295V | 10.5 | A & H | 46 C. | 16 hr | 27.8 | 720.9 |
| Y93Q S95D D118K A136P S202R Q243K W260F N279E L288I L294P S295V | 10.5 | A & H | 46 C. | 16 hr | 31.3 | 823.0 |
| Y93Q S95D D118K A136P S202R Q243H W260F N279E L288I L294P S295V | 10.5 | A & H | 46 C. | 16 hr | 20.1 | 537.2 |
| S3P Y93Q S95D D118K A136P S202R W260F N279E L288I L294P S295V | 10.5 | A & H | 46 C. | 16 hr | 27.8 | 719.7 |
| T37P Y93Q S95D D118K A136P S202R W260F N279E L288I L294P S295V | 10.5 | A & H | 46 C. | 16 hr | 23.2 | 622.9 |
| S8T Y93Q S95D D118K A136P S202R W260F N279E L288I L294P S295V | 10.5 | A & H | 46 C. | 16 hr | 21.3 | 616.8 |
| Y93Q S95D D118K A136P S202R G257A W260F N279E L288I L294P S295V | 10.5 | A & H | 46 C. | 16 hr | 26.3 | 690.4 |
| N45G Y93Q S95D D118K A136P S202R W260F N279E L288I L294P S295V | 10.5 | A & H | 46 C. | 16 hr | 22.4 | 527.1 |
| Y93Q S95D D118K A136P S202R R244K W260F N279E L288I L294P S295V | 10.5 | A & H | 46 C. | 16 hr | 40.8 | 465.4 |
| Y93Q S95D D118K A136P P183G S202R W260F N279E L288I L294P S295V | 10.5 | A & H | 46 C. | 16 hr | 24.7 | 597.3 |
| Y93Q S95D D118K E133R A136P S202R W260F N279E L288I L294P S295V | 10.5 | A & H | 46 C. | 16 hr | 23.3 | 729.6 |
| Y93Q S95D S98P D118K A136P S202R W260F N279E L288I L294P S295V | 10.5 | A & H | 46 C. | 16 hr | 27.1 | 332.1 |
| Y93Q S95D I114Q D118K A136P S202R W260F N279E L288I L294P S295V | 10.5 | A & H | 46 C. | 16 hr | 33.0 | 497.5 |
| Y93Q S95D I114W D118K A136P S202R W260F N279E L288I L294P S295V | 10.5 | A & H | 46 C. | 16 hr | 26.6 | 585.4 |
| Y93Q S95D D118K A136P S202R W260F A276D N279E L288I L294P S295V | 10.5 | A & H | 46 C. | 16 hr | 28.2 | 637.9 |
| Y93Q S95D D118K A136P S202R W260F N279E N283W L288I L294P S295V | 10.5 | A & H | 46 C. | 16 hr | 26.4 | 619.5 |
| D57N Y93Q S95D D118K A136P S202R W260F N279E L288I L294P S295V | 10.5 | A & H | 46 C. | 16 hr | 20.7 | 364.0 |
| Q60R Y93Q S95D D118K A136P S202R W260F N279E L288I L294P S295V | 10.5 | A & H | 46 C. | 16 hr | 24.2 | 1054.9 |
| E77K Y93Q S95D D118K A136P S202R W260F N279E L288I L294P S295V | 10.5 | A & H | 46 C. | 16 hr | 23.5 | 448.5 |
| Y93Q S95D D118K A136P H172R S202R W260F N279E L288I L294P S295V | 10.5 | A & H | 46 C. | 16 hr | 22.5 | 212.8 |
| Y93Q S95D D118K A136P S202R A250G W260F N279E L288I L294P S295V | 10.5 | A & H | 46 C. | 16 hr | 28.7 | 148.3 |
| Y93Q S95D D118K A136P S202R W260F N279E L288I L294K S295G | 10.5 | A & H | 46 C. | 16 hr | 41.6 | 379.1 |
| A1V E77N Y93Q D118K A136P D139R S202R R210G W260F L288I L294P S295V | 10.5 | A & H | 46 C. | 18 hr | 30.5 | 606.4 |
| A1V G47K Y93Q D118K A136P D139R S202R R210G W260F L288I L294P S295V | 10.5 | A & H | 46 C. | 18 hr | 31.3 | 696.8 |
| A1V D78G Y93Q D118K A136P D139R S202R R210G W260F L288I L294P S295V | 10.5 | A & H | 46 C. | 18 hr | 37.4 | 731.9 |
| A1V Y93Q D104G D118K A136P D139R S202R R210G W260F L288I L294P S295V | 10.5 | A & H | 46 C. | 18 hr | 28.7 | 698.1 |
| A1V Y93Q S111A D118K A136P D139R S202R R210G W260F L288I L294P S295V | 10.5 | A & H | 46 C. | 18 hr | 30.8 | 750.5 |
| A1V Y93Q S111R D118K A136P D139R S202R R210G W260F L288I L294P S295V | 10.5 | A & H | 46 C. | 18 hr | 27.5 | 720.2 |
| A1V Y93Q D118K A136P D139R K142V S202R R210G W260F L288I L294P S295V | 10.5 | A & H | 46 C. | 18 hr | 37.6 | 783.8 |
| A1V R70K Y93Q D118K A136P D139R S202R R210G W260F L288I L294P S295V | 10.5 | A & H | 46 C. | 18 hr | 28.1 | 721.1 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| A1V N18V Y93Q D118K A136P D139R S202R R210G W260F L288I L294P S295V | 10.5 | A & H | 46 C. | 18 hr | 27.8 | 866.2 |
| A1V N18R Y93Q D118K A136P D139R S202R R210G W260F L288I L294P S295V | 10.5 | A & H | 46 C. | 18 hr | 32.7 | 555.3 |
| A1V Y93Q D118K A136P D139R Y174R S202R R210G W260F L288I L294P S295V | 10.5 | A & H | 46 C. | 18 hr | 37.1 | 347.8 |
| A1V Y93Q D118K A136P D139R Q169R S202R R210G W260F L288I L294P S295V | 10.5 | A & H | 46 C. | 18 hr | 30.4 | 783.5 |
| A1V Y93Q D118K A136P D139R E177Y S202R R210G W260F L288I L294P S295V | 10.5 | A & H | 46 C. | 18 hr | 30.3 | 808.2 |
| A1V Y93Q D118K A136P D139R N150R S202R R210G W260F L288I L294P S295V | 10.5 | A & H | 46 C. | 18 hr | 22.1 | 981.4 |
| A1V Y93Q D118K A136P D139R R185G S202R R210G W260F L288I L294P S295V | 10.5 | A & H | 46 C. | 18 hr | 30.6 | 723.8 |
| A1V Y93Q D118K A136P D139R S202R R210G E234F W260F L288I L294P S295V | 10.5 | A & H | 46 C. | 18 hr | 32.2 | 803.1 |
| A1V Y93Q D118K A136P D139R S202R R210G A235R W260F L288I L294P S295V | 10.5 | A & H | 46 C. | 18 hr | 34.0 | 703.5 |
| A1V Y93Q D118K A136P D139R S202R R210G A235K W260F L288I L294P S295V | 10.5 | A & H | 46 C. | 18 hr | 20.5 | 659.2 |
| A1V Y93Q S95D D118K A136P D139R S202R R210G W260F L288I L294P S295V | 10.5 | A & H | 46 C. | 18 hr | 29.8 | 359.5 |
| A1V Y93Q A97R D118K A136P D139R S202R R210G W260F L288I L294P S295V | 10.5 | A & H | 46 C. | 18 hr | 29.5 | 451.3 |
| A1V Y93Q A97S D118K A136P D139R S202R R210G W260F L288I L294P S295V | 10.5 | A & H | 46 C. | 18 hr | 29.1 | 602.0 |
| A1V Y93Q D118K T119R A136P D139R S202R R210G W260F L288I L294P S295V | 10.5 | A & H | 46 C. | 18 hr | 23.5 | 560.5 |
| A1V Y93Q D118K A136P D139R N200T S202R R210G W260F L288I L294P S295V | 10.5 | A & H | 46 C. | 18 hr | 25.8 | 855.3 |
| A1V Y93Q N100Y D118K A136P D139R S202R R210G W260F L288I L294P S295V | 10.5 | A & H | 46 C. | 18 hr | 27.0 | 560.6 |
| A1V Y93Q N100H D118K A136P D139R S202R R210G W260F L288I L294P S295V | 10.5 | A & H | 46 C. | 18 hr | 28.4 | 573.3 |
| A1V Y93Q D118K A136P D139R S202R R210G W260F N273D L288I L294P S295V | 10.5 | A & H | 46 C. | 18 hr | 30.2 | 632.7 |
| A1V Y93Q D118K A136P D139R S202R R210G W260F N273E L288I L294P S295V | 10.5 | A & H | 46 C. | 18 hr | 25.7 | 676.5 |
| A1V Y6H Y93Q D118K A136P D139R S202R R210G W260F L288I L294P S295V | 10.5 | A & H | 46 C. | 18 hr | 21.3 | 613.7 |
| A1V Y6M Y93Q D118K A136P D139R S202R R210G W260F L288I L294P S295V | 10.5 | A & H | 46 C. | 18 hr | 36.2 | 739.7 |
| A1V Y93Q D118K A136P D139R P183T S202R R210G W260F L288I L294P S295V | 10.5 | A & H | 46 C. | 18 hr | 32.7 | 1021.9 |
| A1V Y93Q D118K A136P D139R S202R R210G W260F N272M L288I L294P S295V | 10.5 | A & H | 46 C. | 18 hr | 35.9 | 603.2 |
| A1V Y93Q D118K A136P D139R S202R R210G W260F N272T L288I L294P S295V | 10.5 | A & H | 46 C. | 18 hr | 34.5 | 896.9 |
| A1V Y93Q D118K A136P D139R S202R R210G W260F N283H L288I L294P S295V | 10.5 | A & H | 46 C. | 18 hr | 33.2 | 919.7 |
| A1V Y93Q D118K A136P D139R S202R R210G W260F A276W L288I L294P S295V | 10.5 | A & H | 46 C. | 18 hr | 29.5 | 669.4 |
| A1V T11K Y93Q D118K A136P D139R S202R R210G W260F L288I L294P S295V | 10.5 | A & H | 46 C. | 18 hr | 31.6 | 686.3 |
| A1V T11R Y93Q D118K A136P D139R S202R R210G W260F L288I L294P S295V | 10.5 | A & H | 46 C. | 18 hr | 26.5 | 592.8 |
| A1V A30T Y93Q D118K A136P D139R S202R R210G G257A W260F A276D L288I L294P S295V | 10.5 | A & H | 46 C. | 18 hr | 24.3 | 1569.3 |
| A1V D34G Y93Q D118K A136P D139R S202R R210G W260F L288I L294P S295V | 10.5 | A & H | 46 C. | 18 hr | 28.4 | 243.5 |
| A1V Y93Q D118K A136P D139R S202R R210G W260F L288I L294P S295V | 10.5 | A & H | 46 C. | 18 hr | 23.1 | 754.0 |
| Y93Q S95D D118K A136P D139R S202R R210G Q243Y W260F L288I L294P S295V | 10.5 | A & H | 46 C. | 18 hr | 36.0 | 1188.3 |
| Y93Q S95D D118K A136P D139R S202R R210G Q243K W260F L288I L294P S295V | 10.5 | A & H | 46 C. | 18 hr | 26.7 | 1413.3 |
| Y93Q S95D D118K A136P D139R S202R R210G Q243H W260F L288I L294P S295V | 10.5 | A & H | 46 C. | 18 hr | 27.1 | 942.0 |
| S3P Y93Q S95D D118K A136P D139R S202R R210G W260F L288I L294P S295V | 10.5 | A & H | 46 C. | 18 hr | 30.4 | 979.8 |
| G47A Y93Q S95D D118K A136P D139R S202R R210G W260F L288I L294P S295V | 10.5 | A & H | 46 C. | 18 hr | 27.2 | 727.1 |
| E77T Y93Q S95D D118K A136P D139R S202R R210G W260F L288I L294P S295V | 10.5 | A & H | 46 C. | 18 hr | 25.5 | 745.6 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| G47S Y93Q S95D D118K A136P D139R S202R R210G W260F L288I L294P S295V | 10.5 | A & H | 46 C. | 18 hr | 26.1 | 688.9 |
| H80Y Y93Q S95D D118K A136P D139R S202R R210G W260F L288I L294P S295V | 10.5 | A & H | 46 C. | 18 hr | 27.8 | 959.2 |
| Y93Q S95D D118K A136P D139R S202R R210G W260F A276E L288I L294P S295V | 10.5 | A & H | 46 C. | 18 hr | 45.0 | 1602.2 |
| G59Q Y93Q S95D D118K A136P D139R S202R R210G W260F L288I L294P S295V | 10.5 | A & H | 46 C. | 18 hr | 28.0 | 450.6 |
| Y93Q S95D D118K A136P D139R S202R R210G G257A W260F L288I L294P S295V | 10.5 | A & H | 46 C. | 18 hr | 39.4 | 1331.9 |
| A83S Y93Q S95D D118K A136P D139R S202R R210G W260F L288I L294P S295V | 10.5 | A & H | 46 C. | 18 hr | 42.0 | 940.2 |
| E77N Y93Q S95D D118K A136P D139R S202R R210G W260F L288I L294P S295V | 10.5 | A & H | 46 C. | 18 hr | 41.0 | 884.5 |
| G47K Y93Q S95D D118K A136P D139R S202R R210G W260F L288I L294P S295V | 10.5 | A & H | 46 C. | 18 hr | 27.0 | 888.5 |
| H80R Y93Q S95D D118K A136P D139R S202R R210G W260F L288I L294P S295V | 10.5 | A & H | 46 C. | 18 hr | 41.6 | 1061.2 |
| D78G Y93Q S95D D118K A136P D139R S202R R210G W260F L288I L294P S295V | 10.5 | A & H | 46 C. | 18 hr | 27.4 | 1119.2 |
| E41V Y93Q S95D D118K A136P D139R S202R R210G W260F L288I L294P S295V | 10.5 | A & H | 46 C. | 18 hr | 21.1 | 1062.5 |
| Y93Q S95D D104A D118K A136P D139R S202R R210G W260F L288I L294P S295V | 10.5 | A & H | 46 C. | 18 hr | 54.4 | 765.2 |
| Y93Q S95D S111K D118K A136P D139R S202R R210G W260F L288I L294P S295V | 10.5 | A & H | 46 C. | 18 hr | 34.2 | 847.6 |
| Y93Q S95D D118K A136P D139R K142M S202R R210G W260F L288I L294P S295V | 10.5 | A & H | 46 C. | 18 hr | 32.2 | 1104.7 |
| Y93Q S95D D118K A136P D139R K142V S202R R210G W260F L288I L294P S295V | 10.5 | A & H | 46 C. | 18 hr | 49.3 | 1107.1 |
| D65E Y93Q S95D D118K A136P D139R S202R R210G W260F L288I L294P S295V | 10.5 | A & H | 46 C. | 18 hr | 48.0 | 730.8 |
| R70K Y93Q S95D D118K A136P D139R S202R R210G W260F L288I L294P S295V | 10.5 | A & H | 46 C. | 18 hr | 50.3 | 959.4 |
| N45G Y93Q S95D D118K A136P D139R S202R R210G W260F L288I L294P S295V | 10.5 | A & H | 46 C. | 18 hr | 36.8 | 889.8 |
| Q35L Y93Q S95D D118K A136P D139R S202R R210G W260F L288I L294P S295V | 10.5 | A & H | 46 C. | 18 hr | 35.8 | 638.2 |
| N18V Y93Q S95D D118K A136P D139R S202R R210G W260F L288I L294P S295V | 10.5 | A & H | 46 C. | 18 hr | 42.6 | 1161.8 |
| N18R Y93Q S95D D118K A136P D139R S202R R210G W260F L288I L294P S295V | 10.5 | A & H | 46 C. | 18 hr | 27.1 | 805.5 |
| N71S Y93Q S95D D118K A136P D139R S202R R210G W260F L288I L294P S295V | 10.5 | A & H | 46 C. | 18 hr | 24.8 | 758.3 |
| Y93Q S95D D118K A136P D139R Y174R S202R R210G W260F L288I L294P S295V | 10.5 | A & H | 46 C. | 18 hr | 28.6 | 549.1 |
| Y93Q S95D D118K A136P D139R Y174L S202R R210G W260F L288I L294P S295V | 10.5 | A & H | 46 C. | 18 hr | 26.5 | 733.0 |
| Y93Q S95D D118K A136P D139R Q143R S202R R210G W260F L288I L294P S295V | 10.5 | A & H | 46 C. | 18 hr | 37.1 | 650.0 |
| Y93Q S95D D118K A136P D139R N180R S202R R210G W260F L288I L294P S295V | 10.5 | A & H | 46 C. | 18 hr | 31.9 | 917.9 |
| Y93Q S95D D118K A136P D139R Q169A S202R R210G W260F L288I L294P S295V | 10.5 | A & H | 46 C. | 18 hr | 58.2 | 1004.4 |
| Y93Q S95D D118K A136P D139R Q169K S202R R210G W260F L288I L294P S295V | 10.5 | A & H | 46 C. | 18 hr | 47.2 | 184.0 |
| Y93Q S95D D118K A136P D139R E177S S202R R210G W260F L288I L294P S295V | 10.5 | A & H | 46 C. | 18 hr | 33.9 | 1050.2 |
| Y93Q S95D D118K A136P D139R E177Y S202R R210G W260F L288I L294P S295V | 10.5 | A & H | 46 C. | 18 hr | 35.0 | 1054.1 |
| Y93Q S95D D118K A136P D139R N150T S202R R210G W260F L288I L294P S295V | 10.5 | A & H | 46 C. | 18 hr | 34.0 | 1347.2 |
| Y93Q S95D D118K A136P D139R N150S S202R R210G W260F L288I L294P S295V | 10.5 | A & H | 46 C. | 18 hr | 42.6 | 218.8 |
| Y93Q S95D D118K A136P D139R N150R S202R R210G W260F L288I L294P S295V | 10.5 | A & H | 46 C. | 18 hr | 41.6 | 973.6 |
| Y93Q S95D D118K A136P D139R Q184K S202R R210G W260F L288I L294P S295V | 10.5 | A & H | 46 C. | 18 hr | 42.4 | 1003.1 |
| Y93Q S95D D118K A136P D139R Q184S S202R R210G W260F L288I L294P S295V | 10.5 | A & H | 46 C. | 18 hr | 30.0 | 780.7 |
| Y93Q S95D D118K A136P D139R R185G S202R R210G W260F L288I L294P S295V | 10.5 | A & H | 46 C. | 18 hr | 29.0 | 863.4 |
| Y93Q S95D D118K A136P D139R S202R R210G E234F W260F L288I L294P S295V | 10.5 | A & H | 46 C. | 18 hr | 38.3 | 1148.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D D118K A136P D139R S202R R210G A235R W260F L288I L294P S295V | 10.5 | A & H | 46 C. | 18 hr | 33.8 | 784.6 |
| Y93Q S95D D118K A136P D139R S202R R210G R244K W260F L288I L294P S295V | 10.5 | A & H | 46 C. | 18 hr | 35.6 | 958.0 |
| Y93Q S95D K116R D118K A136P D139R S202R R210G W260F L288I L294P S295V | 10.5 | A & H | 46 C. | 18 hr | 41.9 | 837.9 |
| Y93Q S95D D118K T119R A136P D139R S202R R210G W260F L288I L294P S295V | 10.5 | A & H | 46 C. | 18 hr | 40.1 | 725.0 |
| Y93Q S95D D118K A136P D139R N200T S202R R210G W260F L288I L294P S295V | 10.5 | A & H | 46 C. | 18 hr | 23.5 | 1089.3 |
| Y93Q S95D D118K A136P D139R S202R R205K R210G W260F L288I L294P S295V | 10.5 | A & H | 46 C. | 18 hr | 29.5 | 786.2 |
| Y93Q S95D D118K A136P D139R S202R R210G W260F N279D L288I L294P S295V | 10.5 | A & H | 46 C. | 18 hr | 39.1 | 1109.3 |
| Y93Q S95D N100Y D118K A136P D139R S202R R210G W260F L288I L294P S295V | 10.5 | A & H | 46 C. | 18 hr | 33.7 | 816.5 |
| Y93Q S95D N100H D118K A136P D139R S202R R210G W260F L288I L294P S295V | 10.5 | A & H | 46 C. | 18 hr | 26.7 | 694.8 |
| Y93Q S95D D118K A136P D139R S202R R210G W260F N273E L288I L294P S295V | 10.5 | A & H | 46 C. | 18 hr | 45.1 | 1174.7 |
| Y6H Y93Q S95D D118K A136P D139R S202R R210G W260F L288I L294P S295V | 10.5 | A & H | 46 C. | 18 hr | 31.7 | 865.6 |
| Y6M Y93Q S95D D118K A136P D139R S202R R210G W260F L288I L294P S295V | 10.5 | A & H | 46 C. | 18 hr | 28.1 | 848.4 |
| Y93Q S95D D118K A136P D139R S202R R210G W260F N272M L288I L294P S295V | 10.5 | A & H | 46 C. | 18 hr | 33.2 | 761.8 |
| Y93Q S95D D118K A136P D139R S202R R210G W260F N272T L288I L294P S295V | 10.5 | A & H | 46 C. | 18 hr | 22.0 | 1159.9 |
| Y93Q S95D D118K A136P D139R S202R R210G W260F N283W L288I L294P S295V | 10.5 | A & H | 46 C. | 18 hr | 27.0 | 992.9 |
| Y93Q S95D D118K A136P D139R S202R R210G W260F N283H L288I L294P S295V | 10.5 | A & H | 46 C. | 18 hr | 25.2 | 1452.7 |
| Y93Q S95D D118K A136P D139R S202R R210G W260F A276W L288I L294P S295V | 10.5 | A & H | 46 C. | 18 hr | 36.9 | 947.9 |
| Y93Q S95D D118K A136P D139R S202R R210G W260F A276D L288I L294P S295V | 10.5 | A & H | 46 C. | 18 hr | 38.7 | 1210.6 |
| Y93Q S95D D118K A136P D139R S202R R210G W260F T280L L288I L294P S295V | 10.5 | A & H | 46 C. | 18 hr | 36.3 | 1151.7 |
| A30T Y93Q S95D D118K A136P D139R S202R R210G W260F L288I L294P S295V | 10.5 | A & H | 46 C. | 18 hr | 42.0 | 2171.5 |
| D34G Y93Q S95D D118K A136P D139R S202R R210G W260F L288I L294P S295V | 10.5 | A & H | 46 C. | 18 hr | 43.5 | 279.2 |
| D57N Y93Q S95D D118K A136P D139R S202R R210G W260F L288I L294P S295V | 10.5 | A & H | 46 C. | 18 hr | 48.8 | 715.2 |
| E77K Y93Q S95D D118K A136P D139R S202R R210G W260F L288I L294P S295V | 10.5 | A & H | 46 C. | 18 hr | 38.1 | 676.6 |
| Y93Q S95D E108S D118K A136P D139R S202R R210G W260F L288I L294P S295V | 10.5 | A & H | 46 C. | 18 hr | 39.5 | 496.7 |
| Y93Q S95D D118K A136P D139R H172R S202R R210G W260F L288I L294P S295V | 10.5 | A & H | 46 C. | 18 hr | 31.3 | 638.6 |
| Y93Q S95D D118K A136P D139R S202R R210G T228S W260F L288I L294P S295V | 10.5 | A & H | 46 C. | 18 hr | 35.8 | 610.2 |
| A1V Q60R Y93Q D118K A136P D139R S202R R210G W260F L288I L294P S295V | 10.5 | A & H | 46 C. | 18 hr | 25.3 | 1039.2 |
| A1V Y93Q S98T D118K A136P D139R S202R R210G W260F L288I L294P S295V | 10.5 | A & H | 46 C. | 18 hr | 35.3 | 487.6 |
| A1V Y93Q D118K A136P D139R H172R S202R R210G W260F L288I L294P S295V | 10.5 | A & H | 46 C. | 18 hr | 29.0 | 356.2 |
| A1V Y93Q D118K A136P D139R S202R R210G W260F L288I L294G S295R | 10.5 | A & H | 46 C. | 18 hr | 44.6 | 222.0 |
| A1V Y93Q I114M D118K A136P D139R S202R R210G W260F L288I L294P S295V | 10.5 | A & H | 46 C. | 18 hr | 33.3 | 625.0 |
| A1V Y93Q I114W D118K A136P D139R S202R R210G W260F L288I L294P S295V | 10.5 | A & H | 46 C. | 18 hr | 43.1 | 655.4 |
| Y93Q S95D D118K A136P D139R S202R R210G A250G W260F L288I L294P S295V | 10.5 | A & H | 46 C. | 18 hr | 32.2 | 155.0 |
| Y93Q S95D D118K A136P D139R S202R R210G K254Y W260F L288I L294P S295V | 10.5 | A & H | 46 C. | 18 hr | 35.2 | 424.1 |
| Y93Q S95D D118K A136P D139R S202R R210G W260F D268N L288I L294P S295V | 10.5 | A & H | 46 C. | 18 hr | 31.2 | 214.9 |
| Y93Q S95D D118K A136P D139R S202R R210G W260F A270D L288I L294P S295V | 10.5 | A & H | 46 C. | 18 hr | 48.4 | 487.5 |
| Y93Q S95D D118K A136P D139R S202R R210G W260F A270N L288I L294P S295V | 10.5 | A & H | 46 C. | 18 hr | 42.2 | 482.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D D118K A136P D139R S202R R210G W260F L288I L294P S295G | 10.5 | A & H | 46 C. | 18 hr | 50.4 | 479.8 |
| Y93Q S95D A97R D118K A136P D139R S202R R210G W260F L288I L294P S295V | 10.5 | A & H | 46 C. | 18 hr | 39.3 | 544.0 |
| Y93Q S95D A97S D118K A136P D139R S202R R210G W260F L288I L294P S295V | 10.5 | A & H | 46 C. | 18 hr | 46.2 | 583.9 |
| Y93Q S95D I114M D118K A136P D139R S202R R210G W260F L288I L294P S295V | 10.5 | A & H | 46 C. | 18 hr | 46.3 | 895.9 |
| Y93Q S95D S98T D118K A136P D139R S202R R210G W260F L288I L294P S295V | 10.5 | A & H | 46 C. | 18 hr | 27.5 | 632.9 |
| Y93Q S95D S98D D118K A136P D139R S202R R210G W260F L288I L294P S295V | 10.5 | A & H | 46 C. | 18 hr | 64.5 | 814.6 |
| Y93Q S95D D118K A136P D139R S202R R210G W260F L288I E290A L294P S295V | 10.5 | A & H | 46 C. | 18 hr | 31.5 | 609.5 |
| Y93Q S95D D118K A136P D139R S202R R210G W260F L288I L294P S295V T296S | 10.5 | A & H | 46 C. | 18 hr | 61.1 | 771.7 |
| Y93Q S95D D118K A136P D139R S202R R210G W260F L288I L294P S295V F298Y | 10.5 | A & H | 46 C. | 18 hr | 24.3 | 1215.3 |
| A1V H80K Y93Q S95D A136P D139A S202R E234Y Q243E W260F A276E N279E L288I L294P S295V | 10.5 | A & H | 46 C. | 18 hr | 39.0 | 1860.9 |
| H80K Y93Q S95D A136P D139A S202R E234Y Q243E W260F A276E N279E L288I L294P S295V | 10.5 | A & H | 46 C. | 18 hr | 39.2 | 1938.3 |
| H80K Y93Q S95D D118K A136P D139A S202R R210G E234Y Q243E W260F A276E N279E N283W L288I L294P S295V | 10.5 | A & H | 46 C. | 18 hr | 41.2 | 1391.5 |
| V82I Y93Q S95D A136P D139A S202R E234Y A235K Q243E W260F A276E N279E L288I L294P S295V | 10.5 | A & H | 46 C. | 36 hr | 24.1 | 1931.1 |
| G47K Y93Q S95D A136P D139A S202R E234Y A235K Q243E W260F A276E N279E L288I L294P S295V | 10.5 | A & H | 46 C. | 36 hr | 30.0 | 1650.9 |
| Y93Q S95D A136P D139A S202R N213D E234Y A235K Q243E W260F A276E N279E L288I L294P S295V | 10.5 | A & H | 46 C. | 36 hr | 29.5 | 2751.4 |
| Y93Q S95D D118K A136P D139A S202R E234Y A235K Q243E W260F A276E N279E L288I L294P S295V | 10.5 | A & H | 46 C. | 36 hr | 25.5 | 2411.7 |
| D14S Y93Q S95D A136P D139A S202R E234Y A235K Q243E W260F A276E N279E L288I L294P S295V | 10.5 | A & H | 46 C. | 36 hr | 28.3 | 669.1 |
| Y93Q S95D I114W A136P D139A S202R E234Y A235K Q243E W260F A276E N279E L288I L294P S295V | 10.5 | A & H | 46 C. | 36 hr | 20.3 | 2132.1 |
| D65E Y93Q S95D A136P D139A S202R E234Y A235K Q243E W260F A276E N279E L288I L294P S295V | 10.5 | A & H | 46 C. | 36 hr | 22.6 | 1787.1 |
| R70K Y93Q S95D A136P D139A S202R E234Y A235K Q243E W260F A276E N279E L288I L294P S295V | 10.5 | A & H | 46 C. | 36 hr | 37.7 | 2373.2 |
| N45G Y93Q S95D A136P D139A S202R E234Y A235K Q243E W260F A276E N279E L288I L294P S295V | 10.5 | A & H | 46 C. | 36 hr | 35.3 | 1986.2 |
| Q35L Y93Q S95D A136P D139A S202R E234Y A235K Q243E W260F A276E N279E L288I L294P S295V | 10.5 | A & H | 46 C. | 36 hr | 23.5 | 1624.7 |
| N71S Y93Q S95D A136P D139A S202R E234Y A235K Q243E W260F A276E N279E L288I L294P S295V | 10.5 | A & H | 46 C. | 36 hr | 35.1 | 2048.6 |
| Y93Q S95D A136P D139A Y174R S202R E234Y A235K Q243E W260F A276E N279E L288I L294P S295V | 10.5 | A & H | 46 C. | 36 hr | 25.5 | 1920.2 |
| Y93Q S95D A136P D139A Y174L S202R E234Y A235K Q243E W260F A276E N279E L288I L294P S295V | 10.5 | A & H | 46 C. | 36 hr | 34.6 | 1930.2 |
| Y93Q S95D A136P D139A Q169A S202R E234Y A235K Q243E W260F A276E N279E L288I L294P S295V | 10.5 | A & H | 46 C. | 36 hr | 22.6 | 2268.5 |
| Y93Q S95D A136P D139A Q169R S202R E234Y A235K Q243E W260F A276E N279E L288I L294P S295V | 10.5 | A & H | 46 C. | 36 hr | 34.6 | 2362.8 |
| Y93Q S95D A136P D139A E177Y S202R E234Y A235K Q243E W260F A276E N279E L288I L294P S295V | 10.5 | A & H | 46 C. | 36 hr | 45.0 | 1496.0 |
| Y93Q S95D A136P D139A N150T S202R E234Y A235K Q243E W260F A276E N279E L288I L294P S295V | 10.5 | A & H | 46 C. | 36 hr | 29.1 | 2514.6 |
| Y93Q S95D A136P D139A Q184S S202R E234Y A235K Q243E W260F A276E N279E L288I L294P S295V | 10.5 | A & H | 46 C. | 36 hr | 33.3 | 2098.2 |
| Y93Q S95D A136P D139A R185G S202R E234Y A235K Q243E W260F A276E N279E L288I L294P S295V | 10.5 | A & H | 46 C. | 36 hr | 32.7 | 2208.0 |
| Y93Q S95D A136P D139A S202R R210G E234Y A235K Q243E W260F A276E N279E L288I L294P S295V | 10.5 | A & H | 46 C. | 36 hr | 61.3 | 2662.8 |
| Y93Q S95D A136P D139A N200T S202R E234Y A235K Q243E W260F A276E N279E L288I L294P S295V | 10.5 | A & H | 46 C. | 36 hr | 64.5 | 2804.2 |
| Y93Q S95D N100Y A136P D139A S202R E234Y A235K Q243E W260F A276E N279E L288I L294P S295V | 10.5 | A & H | 46 C. | 36 hr | 53.9 | 1806.1 |
| Y93Q S95D A136P D139A S202R N213V E234Y A235K Q243E W260F A276E N279E L288I L294P S295V | 10.5 | A & H | 46 C. | 36 hr | 41.0 | 2449.3 |
| Y93Q S95D A136P D139A P183G S202R E234Y A235K Q243E W260F A276E N279E L288I L294P S295V | 10.5 | A & H | 46 C. | 36 hr | 37.7 | 2389.4 |
| T11K Y93Q S95D A136P D139A S202R E234Y A235K Q243E W260F A276E N279E L288I L294P S295V | 10.5 | A & H | 46 C. | 36 hr | 29.1 | 1731.3 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| T11R Y93Q S95D A136P D139A S202R E234Y A235K Q243E W260F A276E N279E L288I L294P S295V | 10.5 | A & H | 46 C. | 36 hr | 30.5 | 1712.3 |
| A30T Y93Q S95D A136P D139A S202R E234Y A235K Q243E W260F A276E N279E L288I L294P S295V | 10.5 | A & H | 46 C. | 36 hr | 59.1 | 3980.4 |
| E77K Y93Q S95D A136P D139A S202R E234Y A235K Q243E W260F A276E N279E L288I L294P S295V | 10.5 | A & H | 46 C. | 36 hr | 27.8 | 1673.3 |
| Y93Q S95D A136P D139A S202R T228S E234Y A235K Q243E W260F A276E N279E L288I L294P S295V | 10.5 | A & H | 46 C. | 36 hr | 26.0 | 1497.7 |
| Y93Q S95D A136P D139A S202R N229D E234Y A235K Q243E W260F A276E N279E L288I L294P S295V | 10.5 | A & H | 46 C. | 36 hr | 34.5 | 2063.4 |
| Y93Q S95D A136P D139A S202R E234Y A235K Q243E W260F S266A A276E N279E L288I L294P S295V | 10.5 | A & H | 46 C. | 36 hr | 34.4 | 2040.6 |
| Y93Q S95D A136P D139A S202R E234Y A235K Q243E W260F A276E N279E L288I L294P S295V F298Y | 10.5 | A & H | 46 C. | 36 hr | 36.6 | 1865.5 |
| Y93Q S95D A97R A136P D139A S202R E234Y A235K Q243E W260F A276E N279E L288I L294P S295V | 10.5 | A & H | 46 C. | 36 hr | 23.2 | 1482.5 |
| Y93Q S95D S98D A136P D139A S202R E234Y A235K Q243E W260F A276E N279E L288I L294P S295V | 10.5 | A & H | 46 C. | 36 hr | 34.2 | 1951.9 |
| Y93Q S95D A136P D139A S202R Q203T E234Y A235K Q243E W260F A276E N279E L288I L294P S295V | 10.5 | A & H | 46 C. | 36 hr | 38.0 | 2071.4 |
| Y93Q S95D A136P D139A S202R E234Y A235K Q243E W260F A276E N279E L288I L294R S295V | 10.5 | A & H | 46 C. | 36 hr | 31.3 | 1784.6 |
| Y93Q S95D K116R D118K A136P D139A S202R E234Y A235K Q243E W260F A276E N279E N283W L288I L294P S295V | 10.5 | A & H | 46 C. | 36 hr | 25.4 | 1518.6 |
| H80K Y93Q S95D D118K A136P D139A S202R E234Y A235K Q243E W260F A276E N279E N283W L288I L294P S295V | 10.5 | A & H | 46 C. | 36 hr | 35.7 | 1975.4 |
| A1G Y93Q S95D D118K A136P D139A S202R E234Y A235K Q243E W260F A276E N279E N283W L288I L294P S295V | 10.5 | A & H | 46 C. | 36 hr | 43.0 | 2568.6 |
| S3P Y93Q S95D D118K A136P D139A S202R E234Y A235K Q243E W260F A276E N279E N283W L288I L294P S295V | 10.5 | A & H | 46 C. | 36 hr | 42.2 | 2368.1 |
| T37P Y93Q S95D D118K A136P D139A S202R E234Y A235K Q243E W260F A276E N279E N283W L288I L294P S295V | 10.5 | A & H | 46 C. | 36 hr | 38.3 | 2099.4 |
| G47A Y93Q S95D D118K A136P D139A S202R E234Y A235K Q243E W260F A276E N279E N283W L288I L294P S295V | 10.5 | A & H | 46 C. | 36 hr | 26.8 | 1571.6 |
| V82I Y93Q S95D D118K A136P D139A S202R E234Y A235K Q243E W260F A276E N279E N283W L288I L294P S295V | 10.5 | A & H | 46 C. | 36 hr | 37.1 | 2108.7 |
| Y93Q S95D D118K A136P D139A S202R E234Y A235K Q243E G257A W260F A276E N279E N283W L288I L294P S295V | 10.5 | A & H | 46 C. | 36 hr | 48.6 | 3017.4 |
| A83S Y93Q S95D D118K A136P D139A S202R E234Y A235K Q243E W260F A276E N279E N283W L288I L294P S295V | 10.5 | A & H | 46 C. | 36 hr | 46.3 | 2758.1 |
| E77N Y93Q S95D D118K A136P D139A S202R E234Y A235K Q243E W260F A276E N279E N283W L288I L294P S295V | 10.5 | A & H | 46 C. | 36 hr | 41.1 | 2325.3 |
| G47K Y93Q S95D D118K A136P D139A S202R E234Y A235K Q243E W260F A276E N279E N283W L288I L294P S295V | 10.5 | A & H | 46 C. | 36 hr | 30.2 | 1708.9 |
| E41V Y93Q S95D D118K A136P D139A S202R E234Y A235K Q243E W260F A276E N279E N283W L288I L294P S295V | 10.5 | A & H | 46 C. | 36 hr | 44.3 | 2548.3 |
| Y93Q S95D D104A D118K A136P D139A S202R E234Y A235K Q243E W260F A276E N279E N283W L288I L294P S295V | 10.5 | A & H | 46 C. | 36 hr | 35.5 | 2170.8 |
| Y93Q S95D S111A D118K A136P D139A S202R E234Y A235K Q243E W260F A276E N279E N283W L288I L294P S295V | 10.5 | A & H | 46 C. | 36 hr | 37.9 | 2086.0 |
| Y93Q S95D S111R D118K A136P D139A S202R E234Y A235K Q243E W260F A276E N279E N283W L288I L294P S295V | 10.5 | A & H | 46 C. | 36 hr | 31.3 | 1743.2 |
| Y93Q S95D S111K D118K A136P D139A S202R E234Y A235K Q243E W260F A276E N279E N283W L288I L294P S295V | 10.5 | A & H | 46 C. | 36 hr | 44.7 | 2515.3 |
| Y93Q S95D I114M D118K A136P D139A S202R E234Y A235K Q243E W260F A276E N279E N283W L288I L294P S295V | 10.5 | A & H | 46 C. | 36 hr | 43.0 | 2592.0 |
| D65E Y93Q S95D D118K A136P D139A S202R E234Y A235K Q243E W260F A276E N279E N283W L288I L294P S295V | 10.5 | A & H | 46 C. | 36 hr | 29.2 | 1714.4 |
| T37R Y93Q S95D D118K A136P D139A S202R E234Y A235K Q243E W260F A276E N279E N283W L288I L294P S295V | 10.5 | A & H | 46 C. | 36 hr | 45.4 | 2640.3 |
| N45G Y93Q S95D D118K A136P D139A S202R E234Y A235K Q243E W260F A276E N279E N283W L288I L294P S295V | 10.5 | A & H | 46 C. | 36 hr | 34.0 | 1949.0 |
| Q35L Y93Q S95D D118K A136P D139A S202R E234Y A235K Q243E W260F A276E N279E N283W L288I L294P S295V | 10.5 | A & H | 46 C. | 36 hr | 24.0 | 1446.6 |
| N18V Y93Q S95D D118K A136P D139A S202R E234Y A235K Q243E W260F A276E N279E N283W L288I L294P S295V | 10.5 | A & H | 46 C. | 36 hr | 35.6 | 1914.8 |
| S74K Y93Q S95D D118K A136P D139A S202R E234Y A235K Q243E W260F A276E N279E N283W L288I L294P S295V | 10.5 | A & H | 46 C. | 36 hr | 41.7 | 2273.1 |
| Y93Q S95D D118K A136P D139A Y174L S202R E234Y A235K Q243E W260F A276E N279E N283W L288I L294P S295V | 10.5 | A & H | 46 C. | 36 hr | 39.2 | 2131.7 |
| Y93Q S95D D118K A136P D139A N180R S202R E234Y A235K Q243E W260F A276E N279E N283W L288I L294P S295V | 10.5 | A & H | 46 C. | 36 hr | 32.0 | 1824.0 |
| Y93Q S95D D118K A136P D139A Q169R S202R E234Y A235K Q243E W260F A276E N279E N283W L288I L294P S295V | 10.5 | A & H | 46 C. | 36 hr | 47.3 | 2666.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D D118K A136P D139A Q169K S202R E234Y A235K Q243E W260F A276E N279E N283W L288I L294P S295V | 10.5 | A & H | 46 C. | 36 hr | 40.1 | 2342.9 |
| Y93Q S95D D118K A136P D139A E177S S202R E234Y A235K Q243E W260F A276E N279E N283W L288I L294P S295V | 10.5 | A & H | 46 C. | 36 hr | 40.1 | 2020.2 |
| Y93Q S95D D118K A136P D139A E177Y S202R E234Y A235K Q243E W260F A276E N279E N283W L288I L294P S295V | 10.5 | A & H | 46 C. | 36 hr | 37.3 | 2129.8 |
| Y93Q S95D D118K A136P D139A N150S S202R E234Y A235K Q243E W260F A276E N279E N283W L288I L294P S295V | 10.5 | A & H | 46 C. | 36 hr | 43.0 | 2479.7 |
| Y93Q S95D D118K A136P D139A N150R S202R E234Y A235K Q243E W260F A276E N279E N283W L288I L294P S295V | 10.5 | A & H | 46 C. | 36 hr | 43.4 | 2668.9 |
| Y93Q S95D D118K A136P D139A Q184E S202R E234Y A235K Q243E W260F A276E N279E N283W L288I L294P S295V | 10.5 | A & H | 46 C. | 36 hr | 37.2 | 2182.6 |
| Y93Q S95D D118K A136P D139A Q184K S202R E234Y A235K Q243E W260F A276E N279E N283W L288I L294P S295V | 10.5 | A & H | 46 C. | 36 hr | 33.7 | 1892.4 |
| Y93Q S95D D118K A136P D139A Q184S S202R E234Y A235K Q243E W260F A276E N279E N283W L288I L294P S295V | 10.5 | A & H | 46 C. | 36 hr | 35.5 | 1914.8 |
| Y93Q S95D D118K A136P D139A R185G S202R E234Y A235K Q243E W260F A276E N279E N283W L288I L294P S295V | 10.5 | A & H | 46 C. | 36 hr | 45.4 | 2639.1 |
| Y93Q S95D D118K A136P D139A S202R R210L E234Y A235K Q243E W260F A276E N279E N283W L288I L294P S295V | 10.5 | A & H | 46 C. | 36 hr | 38.1 | 2115.9 |
| Y93Q S95D D118K A136P D139A S202R R210M E234Y A235K Q243E W260F A276E N279E N283W L288I L294P S295V | 10.5 | A & H | 46 C. | 36 hr | 44.0 | 2577.8 |
| Y93Q S95D D118K A136P D139A S202R R210G E234Y A235K Q243E W260F A276E N279E N283W L288I L294P S295V | 10.5 | A & H | 46 C. | 36 hr | 63.6 | 4032.0 |
| Y93Q S95D D118K A136P D139A N200T S202R E234Y A235K Q243E W260F A276E N279E N283W L288I L294P S295V | 10.5 | A & H | 46 C. | 36 hr | 54.8 | 3483.1 |
| Y93Q S95D D118K A136P D139A S202R R205K E234Y A235K Q243E W260F A276E N279E N283W L288I L294P S295V | 10.5 | A & H | 46 C. | 36 hr | 32.6 | 1696.3 |
| Y93Q S95D N100Y D118K A136P D139A S202R E234Y A235K Q243E W260F A276E N279E N283W L288I L294P S295V | 10.5 | A & H | 46 C. | 36 hr | 38.2 | 1933.7 |
| Y93Q S95D N100H D118K A136P D139A S202R E234Y A235K Q243E W260F A276E N279E N283W L288I L294P S295V | 10.5 | A & H | 46 C. | 36 hr | 33.3 | 1741.8 |
| Y6H Y93Q S95D D118K A136P D139A S202R E234Y A235K Q243E W260F A276E N279E N283W L288I L294P S295V | 10.5 | A & H | 46 C. | 36 hr | 32.4 | 1833.1 |
| Y6M Y93Q S95D D118K A136P D139A S202R E234Y A235K Q243E W260F A276E N279E N283W L288I L294P S295V | 10.5 | A & H | 46 C. | 36 hr | 35.6 | 2033.1 |
| Y93Q S95D D118K A136P D139A S202R N213V E234Y A235K Q243E W260F A276E N279E N283W L288I L294P S295V | 10.5 | A & H | 46 C. | 36 hr | 41.8 | 2503.0 |
| Y93Q S95D D118K A136P D139A P183T S202R E234Y A235K Q243E W260F A276E N279E N283W L288I L294P S295V | 10.5 | A & H | 46 C. | 36 hr | 44.1 | 2828.0 |
| T11K Y93Q S95D D118K A136P D139A S202R E234Y A235K Q243E W260F A276E N279E N283W L288I L294P S295V | 10.5 | A & H | 46 C. | 36 hr | 34.5 | 1937.8 |
| T11R Y93Q S95D D118K A136P D139A S202R E234Y A235K Q243E W260F A276E N279E N283W L288I L294P S295V | 10.5 | A & H | 46 C. | 36 hr | 33.2 | 1914.8 |
| Y6H A30T Y93Q S95D D118K A136P D139A S202R E234Y A235K Q243E W260F A276E N279E N283W L288I L294P S295V | 10.5 | A & H | 46 C. | 36 hr | 63.7 | 4543.9 |
| D57N Y93Q S95D D118K A136P D139A S202R E234Y A235K Q243E W260F A276E N279E N283W L288I L294P S295V | 10.5 | A & H | 46 C. | 36 hr | 32.5 | 1888.6 |
| Q60R Y93Q S95D D118K A136P D139A S202R E234Y A235K Q243E W260F A276E N279E N283W L288I L294P S295V | 10.5 | A & H | 46 C. | 36 hr | 47.7 | 2569.7 |
| Y93Q S95D D118K A136P D139A S202R N229D E234Y A235K Q243E W260F A276E N279E N283W L288I L294P S295V | 10.5 | A & H | 46 C. | 36 hr | 33.8 | 1809.9 |
| Y93Q S95D D118K A136P D139A S202R E234Y A235K Q243E W260F S266A A276E N279E N283W L288I L294P S295V | 10.5 | A & H | 46 C. | 36 hr | 37.6 | 2133.1 |
| Y93Q S95D D118K A136P D139A S202R E234Y A235K Q243E W260F A270D A276E N279E N283W L288I L294P S295V | 10.5 | A & H | 46 C. | 36 hr | 24.1 | 1452.5 |
| Y93Q S95D A97R D118K A136P D139A S202R E234Y A235K Q243E W260F A276E N279E N283W L288I L294P S295V | 10.5 | A & H | 46 C. | 36 hr | 21.9 | 1278.8 |
| Y93Q S95D A97S D118K A136P D139A S202R E234Y A235K Q243E W260F A276E N279E N283W L288I L294P S295V | 10.5 | A & H | 46 C. | 36 hr | 28.4 | 1665.3 |
| Y93Q S95D S98D D118K A136P D139A S202R E234Y A235K Q243E W260F A276E N279E N283W L288I L294P S295V | 10.5 | A & H | 46 C. | 36 hr | 42.7 | 2393.8 |
| Y93Q S95D D118K A136P D139A S202R Q203T E234Y A235K Q243E W260F A276E N279E N283W L288I L294P S295V | 10.5 | A & H | 46 C. | 36 hr | 45.5 | 2633.5 |
| A30T Y93Q S95D D118K A136P D139R S202R R210G W260F L288I L294P S295V A1V | 10.8 | A & H | 44 C. | 44 hr | 59.1 | 2064.6 |
| A30T Y93Q S95D D118K A136P D139R S202R R210G W260F L288I L294P S295V Q243E | 10.8 | A & H | 44 C. | 44 hr | 58.8 | 2003.6 |
| A30T Y93Q S95D D118K A136P D139R S202R R210G W260F L288I L294P S295V Q243K | 10.8 | A & H | 44 C. | 44 hr | 58.1 | 1994.0 |
| A30T Y93Q S95D D118K A136P D139R S202R R210G W260F L288I L294P S295V Q243H | 10.8 | A & H | 44 C. | 44 hr | 55.7 | 2105.9 |
| A30T Y93Q S95D D118K A136P D139R S202R R210G W260F L288I L294P S295V S3P | 10.8 | A & H | 44 C. | 44 hr | 56.1 | 1714.3 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R S202R R210G W260F L288I L294P S295V G47A | 10.8 | A & H | 44 C. | 44 hr | 58.5 | 1947.0 |
| A30T Y93Q S95D D118K A136P D139R S202R R210G W260F L288I L294P S295V S8T | 10.8 | A & H | 44 C. | 44 hr | 61.0 | 1945.9 |
| A30T Y93Q S95D D118K A136P D139R S202R R210G W260F L288I L294P S295V E77T | 10.8 | A & H | 44 C. | 44 hr | 37.9 | 664.6 |
| A30T Y93Q S95D D118K A136P D139R S202R R210G W260F L288I L294P S295V G47S | 10.8 | A & H | 44 C. | 44 hr | 49.5 | 1107.5 |
| A30T Y93Q S95D D118K A136P D139R S202R R210G W260F L288I L294P S295V H80K | 10.8 | A & H | 44 C. | 44 hr | 57.9 | 1704.2 |
| A30T Y93Q S95D D118K A136P D139R S202R R210G W260F L288I L294P S295V S131T | 10.8 | A & H | 44 C. | 44 hr | 54.9 | 1515.8 |
| A30T Y93Q S95D D118K A136P D139R S202R R210G W260F L288I L294P S295V A276E | 10.8 | A & H | 44 C. | 44 hr | 66.6 | 1851.9 |
| A30T Y93Q S95D D118K A136P D139R S202R R210G W260F L288I L294P S295V G257A | 10.8 | A & H | 44 C. | 44 hr | 64.4 | 2237.5 |
| A30T Y93Q S95D D118K A136P D139R S202R R210G W260F L288I L294P S295V A83S | 10.8 | A & H | 44 C. | 44 hr | 57.4 | 1945.9 |
| A30T Y93Q S95D D118K A136P D139R S202R R210G W260F L288I L294P S295V D14K | 10.8 | A & H | 44 C. | 44 hr | 21.2 | 664.6 |
| A30T Y93Q S95D D118K A136P D139R S202R R210G W260F L288I L294P S295V E77N | 10.8 | A & H | 44 C. | 44 hr | 52.0 | 1107.5 |
| A30T Y93Q S95D D118K A136P D139R S202R R210G W260F L288I L294P S295V G47K | 10.8 | A & H | 44 C. | 44 hr | 52.4 | 1704.2 |
| A30T Y93Q S95D D118K A136P D139R S202R R210G W260F L288I L294P S295V D14A | 10.8 | A & H | 44 C. | 44 hr | 27.2 | 1515.8 |
| A30T Y93Q S95D D118K A136P D139R S202R R210G W260F L288I L294P S295V D14S | 10.8 | A & H | 44 C. | 44 hr | 32.3 | 1107.5 |
| A30T Y93Q S95D D118K A136P D139R S202R R210G W260F L288I L294P S295V E41V | 10.8 | A & H | 44 C. | 44 hr | 56.8 | 1704.2 |
| A30T Y93Q S95D D118K A136P D139R S202R R210G W260F L288I L294P S295V D104A | 10.8 | A & H | 44 C. | 44 hr | 50.4 | 1515.8 |
| A30T Y93Q S95D D118K A136P D139R S202R R210G W260F L288I L294P S295V S111R | 10.8 | A & H | 44 C. | 44 hr | 49.6 | 1851.9 |
| A30T Y93Q S95D D118K A136P D139R S202R R210G W260F L288I L294P S295V S111K | 10.8 | A & H | 44 C. | 44 hr | 52.8 | 1851.9 |
| A30T Y93Q S95D D118K A136P D139R S202R R210G W260F L288I L294P S295V T37R | 10.8 | A & H | 44 C. | 44 hr | 61.7 | 2237.5 |
| A30T Y93Q S95D D118K A136P D139R S202R R210G W260F L288I L294P S295V R70K | 10.8 | A & H | 44 C. | 44 hr | 56.0 | 1702.9 |
| A30T Y93Q S95D D118K A136P D139R S202R R210G W260F L288I L294P S295V N45G | 10.8 | A & H | 44 C. | 44 hr | 53.4 | 1784.0 |
| A30T Y93Q S95D D118K A136P D139R S202R R210G W260F L288I L294P S295V N18R | 10.8 | A & H | 44 C. | 44 hr | 50.5 | 1663.0 |
| A30T Y93Q S95D D118K A136P D139R S202R R210G W260F L288I L294P S295V Y174R | 10.8 | A & H | 44 C. | 44 hr | 47.7 | 1778.2 |
| A30T Y93Q S95D D118K A136P D139R S202R R210G W260F L288I L294P S295V N180R | 10.8 | A & H | 44 C. | 44 hr | 54.7 | 1784.0 |
| A30T Y93Q S95D D118K A136P D139R S202R R210G W260F L288I L294P S295V Q169R | 10.8 | A & H | 44 C. | 44 hr | 61.4 | 1784.0 |
| A30T Y93Q S95D D118K A136P D139R S202R R210G W260F L288I L294P S295V Q169A | 10.8 | A & H | 44 C. | 44 hr | 55.1 | 1663.0 |
| A30T Y93Q S95D D118K A136P D139R S202R R210G W260F L288I L294P S295V Q169K | 10.8 | A & H | 44 C. | 44 hr | 56.7 | 1778.3 |
| A30T Y93Q S95D D118K A136P D139R S202R R210G W260F L288I L294P S295V E177Y | 10.8 | A & H | 44 C. | 44 hr | 57.6 | 1809.0 |
| A30T Y93Q S95D D118K A136P D139R S202R R210G W260F L288I L294P S295V N150T | 10.8 | A & H | 44 C. | 44 hr | 57.0 | 1274.4 |
| A30T Y93Q S95D D118K A136P D139R S202R R210G W260F L288I L294P S295V N150S | 10.8 | A & H | 44 C. | 44 hr | 55.8 | 1778.3 |
| A30T Y93Q S95D D118K A136P D139R S202R R210G W260F L288I L294P S295V N150R | 10.8 | A & H | 44 C. | 44 hr | 57.8 | 2126.9 |
| A30T Y93Q S95D D118K A136P D139R S202R R210G W260F L288I L294P S295V Q184K | 10.8 | A & H | 44 C. | 44 hr | 55.0 | 2200.6 |
| A30T Y93Q S95D D118K A136P D139R S202R R210G W260F L288I L294P S295V Q184S | 10.8 | A & H | 44 C. | 44 hr | 57.6 | 1809.0 |
| A30T Y93Q S95D D118K A136P D139R S202R R210G W260F L288I L294P S295V E234F | 10.8 | A & H | 44 C. | 44 hr | 41.6 | 1274.4 |
| A30T Y93Q S95D D118K A136P D139R S202R R210G W260F L288I L294P S295V E234Y | 10.8 | A & H | 44 C. | 44 hr | 55.7 | 2023.2 |
| A30T Y93Q S95D D118K A136P D139R S202R R210G W260F L288I L294P S295V A235R | 10.8 | A & H | 44 C. | 44 hr | 33.7 | 2273.7 |
| A30T Y93Q S95D D118K A136P D139R S202R R210G W260F L288I L294P S295V R244K | 10.8 | A & H | 44 C. | 44 hr | 53.9 | 1769.2 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R S202R R210G W260F L288I L294P S295V K116R | 10.8 | A & H | 44 C. | 44 hr | 56.8 | 2300.4 |
| A30T Y93Q S95D D118K A136P D139R S202R R210G W260F L288I L294P S295V T119R | 10.8 | A & H | 44 C. | 44 hr | 40.7 | 1744.8 |
| A30T Y93Q S95D D118K A136P D139R S202R R210G W260F L288I L294P S295V N200T | 10.8 | A & H | 44 C. | 44 hr | 64.1 | 1312.4 |
| A30T Y93Q S95D D118K A136P D139R S202R R210G W260F L288I L294P S295V N279D | 10.8 | A & H | 44 C. | 44 hr | 58.6 | 2126.9 |
| A30T Y93Q S95D D118K A136P D139R S202R R210G W260F L288I L294P S295V N279E | 10.8 | A & H | 44 C. | 44 hr | 61.2 | 2200.6 |
| A30T Y93Q S95D D118K A136P D139R S202R R210G W260F L288I L294P S295V N100Y | 10.8 | A & H | 44 C. | 44 hr | 47.8 | 2029.9 |
| A30T Y93Q S95D D118K A136P D139R S202R R210G W260F L288I L294P S295V N100H | 10.8 | A & H | 44 C. | 44 hr | 50.0 | 2067.1 |
| A30T Y93Q S95D D118K A136P D139R S202R R210G W260F L288I L294P S295V N273E | 10.8 | A & H | 44 C. | 44 hr | 59.8 | 1951.1 |
| A30T Y93Q S95D D118K A136P D139R S202R R210G W260F L288I L294P S295V Y6H | 10.8 | A & H | 44 C. | 44 hr | 57.5 | 2029.9 |
| A30T Y93Q S95D D118K A136P D139R S202R R210G W260F L288I L294P S295V P183T | 10.8 | A & H | 44 C. | 44 hr | 56.8 | 2067.1 |
| A30T Y93Q S95D D118K A136P D139R S202R R210G W260F L288I L294P S295V N283W | 10.8 | A & H | 44 C. | 44 hr | 57.8 | 1847.9 |
| A30T Y93Q S95D D118K A136P D139R S202R R210G W260F L288I L294P S295V N283H | 10.8 | A & H | 44 C. | 44 hr | 57.9 | 1951.1 |
| A30T Y93Q S95D D118K A136P D139R S202R R210G W260F L288I L294P S295V A276D | 10.8 | A & H | 44 C. | 44 hr | 62.3 | 2273.7 |
| A30T Y93Q S95D D118K A136P D139R S202R R210G W260F L288I L294P S295V T280L | 10.8 | A & H | 44 C. | 44 hr | 55.6 | 1756.0 |
| A30T Y93Q S95D D118K A136P D139R S202R R210G W260F L288I L294P S295V T11R | 10.8 | A & H | 44 C. | 44 hr | 44.6 | 1434.8 |
| A30T Y93Q S95D D118K A136P D139R S202R R210G W260F L288I L294P S295V D57N | 10.8 | A & H | 44 C. | 44 hr | 48.5 | 1921.8 |
| A30T Y93Q S95D D118K A136P D139R S202R R210G W260F L288I L294P S295V Q60R | 10.8 | A & H | 44 C. | 44 hr | 56.3 | 1769.2 |
| A30T Y93Q S95D D118K A136P D139R S202R R210G W260F L288I L294P S295V E108S | 10.8 | A & H | 44 C. | 44 hr | 42.0 | 1258.4 |
| A30T Y93Q S95D D118K A136P D139R S202R R210G W260F L288I L294P S295V H172R | 10.8 | A & H | 44 C. | 44 hr | 43.6 | 1274.4 |
| A30T Y93Q S95D D118K A136P D139R S202R R210G W260F L288I L294P S295V T228S | 10.8 | A & H | 44 C. | 44 hr | 39.0 | 1309.3 |
| A30T Y93Q S95D D118K A136P D139R S202R R210G W260F L288I L294P S295V N229D | 10.8 | A & H | 44 C. | 44 hr | 58.1 | 2145.4 |
| A30T Y93Q S95D D118K A136P D139R S202R R210G W260F L288I L294P S295V N213V | 10.8 | A & H | 44 C. | 44 hr | 55.8 | 1753.3 |
| A30T Y93Q S95D D118K A136P D139R S202R R210G W260F L288I L294P S295V N213D | 10.8 | A & H | 44 C. | 44 hr | 57.6 | 2050.3 |
| A30T Y93Q S95D D118K A136P D139R S202R R210G W260F L288I L294R S295V | 10.8 | A & H | 44 C. | 44 hr | 50.9 | 1597.7 |
| Q60R Y93Q S95D D118K A136P D139R S202R R210G W260F L288I L294P S295V E177Y | 10.8 | A & H | 44 C. | 40 hr | 31.2 | 1994.0 |
| Q60R Y93Q S95D D118K A136P D139R S202R R210G W260F L288I L294P S295V E234F | 10.8 | A & H | 44 C. | 40 hr | 23.3 | 2105.9 |
| Q60R Y93Q S95D D118K A136P D139R S202R R210G W260F L288I L294P S295V R205K | 10.8 | A & H | 44 C. | 40 hr | 25.1 | 1714.3 |
| Q60R Y93Q S95D D118K A136P D139R S202R R210G W260F L288I L294P S295V Y6M | 10.8 | A & H | 44 C. | 40 hr | 21.7 | 375.7 |
| Q60R Y93Q S95D D118K A136P D139R S202R R210G W260F L288I L294P S295V A1V | 10.8 | A & H | 44 C. | 40 hr | 31.5 | 1947.0 |
| Q60R Y93Q S95D D118K A136P D139R S202R R210G W260F L288I L294P S295V Q243Y | 10.8 | A & H | 44 C. | 40 hr | 36.2 | 2127.8 |
| Q60R Y93Q S95D D118K A136P D139R S202R R210G W260F L288I L294P S295V Q243K | 10.8 | A & H | 44 C. | 40 hr | 40.3 | 1474.4 |
| Q60R Y93Q S95D D118K A136P D139R S202R R210G W260F L288I L294P S295V S3P | 10.8 | A & H | 44 C. | 40 hr | 36.9 | 2176.5 |
| Q60R Y93Q S95D D118K A136P D139R S202R R210G W260F L288I L294P S295V S8T | 10.8 | A & H | 44 C. | 40 hr | 38.8 | 2457.5 |
| Q60R Y93Q S95D D118K A136P D139R S202R R210G W260F L288I L294P S295V E77T | 10.8 | A & H | 44 C. | 40 hr | 28.8 | 2517.3 |
| Q60R Y93Q S95D D118K A136P D139R S202R R210G W260F L288I L294P S295V H80K | 10.8 | A & H | 44 C. | 40 hr | 31.8 | 664.6 |
| Q60R Y93Q S95D D118K A136P D139R S202R R210G W260F L288I L294P S295V S131T | 10.8 | A & H | 44 C. | 40 hr | 25.3 | 439.9 |
| Q60R Y93Q S95D D118K A136P D139R S202R R210G W260F L288I L294P S295V A276E | 10.8 | A & H | 44 C. | 40 hr | 42.8 | 1767.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Q60R Y93Q S95D D118K A136P D139R S202R R210G W260F L288I L294P S295V V82I | 10.8 | A & H | 44 C. | 40 hr | 26.0 | 1679.2 |
| Q60R Y93Q S95D D118K A136P D139R S202R R210G W260F L288I L294P S295V G257A | 10.8 | A & H | 44 C. | 40 hr | 41.7 | 808.2 |
| Q60R Y93Q S95D D118K A136P D139R S202R R210G W260F L288I L294P S295V A83S | 10.8 | A & H | 44 C. | 40 hr | 35.6 | 573.8 |
| Q60R Y93Q S95D D118K A136P D139R S202R R210G W260F L288I L294P S295V E77N | 10.8 | A & H | 44 C. | 40 hr | 34.0 | 1515.8 |
| Q60R Y93Q S95D D118K A136P D139R S202R R210G W260F L288I L294P S295V H80R | 10.8 | A & H | 44 C. | 40 hr | 34.8 | 570.3 |
| Q60R Y93Q S95D D118K A136P D139R S202R R210G W260F L288I L294P S295V E41V | 10.8 | A & H | 44 C. | 40 hr | 32.6 | 1586.9 |
| Q60R Y93Q S95D D118K A136P D139R S202R R210G W260F L288I L294P S295V S111A | 10.8 | A & H | 44 C. | 40 hr | 26.8 | 1534.8 |
| Q60R Y93Q S95D D118K A136P D139R S202R R210G W260F L288I L294P S295V S111R | 10.8 | A & H | 44 C. | 40 hr | 24.3 | 424.8 |
| Q60R Y93Q S95D D118K A136P D139R S202R R210G W260F L288I L294P S295V S111K | 10.8 | A & H | 44 C. | 40 hr | 28.4 | 1784.0 |
| Q60R Y93Q S95D D118K A136P D139R S202R R210G W260F L288I L294P S295V D65E | 10.8 | A & H | 44 C. | 40 hr | 23.4 | 2248.8 |
| Q60R Y93Q S95D D118K A136P D139R S202R R210G W260F L288I L294P S295V R70K | 10.8 | A & H | 44 C. | 40 hr | 32.4 | 1663.0 |
| Q60R Y93Q S95D D118K A136P D139R S202R R210G W260F L288I L294P S295V N45G | 10.8 | A & H | 44 C. | 40 hr | 27.3 | 1788.6 |
| Q60R Y93Q S95D D118K A136P D139R S202R R210G W260F L288I L294P S295V N18V | 10.8 | A & H | 44 C. | 40 hr | 39.1 | 2188.3 |
| Q60R Y93Q S95D D118K A136P D139R S202R R210G W260F L288I L294P S295V N18R | 10.8 | A & H | 44 C. | 40 hr | 21.6 | 1778.2 |
| Q60R Y93Q S95D D118K A136P D139R S202R R210G W260F L288I L294P S295V N71S | 10.8 | A & H | 44 C. | 40 hr | 25.8 | 2056.9 |
| Q60R Y93Q S95D D118K A136P D139R S202R R210G W260F L288I L294P S295V Y174L | 10.8 | A & H | 44 C. | 40 hr | 22.2 | 1861.3 |
| Q60R Y93Q S95D D118K A136P D139R S202R R210G W260F L288I L294P S295V Q169A | 10.8 | A & H | 44 C. | 40 hr | 26.0 | 1274.4 |
| Q60R Y93Q S95D D118K A136P D139R S202R R210G W260F L288I L294P S295V Q169R | 10.8 | A & H | 44 C. | 40 hr | 28.3 | 2023.2 |
| Q60R Y93Q S95D D118K A136P D139R S202R R210G W260F L288I L294P S295V Q169K | 10.8 | A & H | 44 C. | 40 hr | 28.1 | 989.2 |
| Q60R Y93Q S95D D118K A136P D139R S202R R210G W260F L288I L294P S295V E177S | 10.8 | A & H | 44 C. | 40 hr | 32.9 | 1919.7 |
| Q60R Y93Q S95D D118K A136P D139R S202R R210G W260F L288I L294P S295V N150T | 10.8 | A & H | 44 C. | 40 hr | 32.2 | 1930.8 |
| Q60R Y93Q S95D D118K A136P D139R S202R R210G W260F L288I L294P S295V N150S | 10.8 | A & H | 44 C. | 40 hr | 35.3 | 1248.0 |
| Q60R Y93Q S95D D118K A136P D139R S202R R210G W260F L288I L294P S295V N150R | 10.8 | A & H | 44 C. | 40 hr | 29.1 | 2374.4 |
| Q60R Y93Q S95D D118K A136P D139R S202R R210G W260F L288I L294P S295V Q184E | 10.8 | A & H | 44 C. | 40 hr | 29.9 | 504.8 |
| Q60R Y93Q S95D D118K A136P D139R S202R R210G W260F L288I L294P S295V Q184K | 10.8 | A & H | 44 C. | 40 hr | 29.7 | 2126.9 |
| Q60R Y93Q S95D D118K A136P D139R S202R R210G W260F L288I L294P S295V Q184S | 10.8 | A & H | 44 C. | 40 hr | 27.1 | 2200.6 |
| Q60R Y93Q S95D D118K A136P D139R S202R R210G W260F L288I L294P S295V R185G | 10.8 | A & H | 44 C. | 40 hr | 26.8 | 1393.9 |
| Q60R Y93Q S95D D118K A136P D139R S202R R210G W260F L288I L294P S295V A235R | 10.8 | A & H | 44 C. | 40 hr | 24.4 | 431.2 |
| Q60R Y93Q S95D D118K A136P D139R S202R R210G W260F L288I L294P S295V A235K | 10.8 | A & H | 44 C. | 40 hr | 27.6 | 2274.2 |
| Q60R Y93Q S95D D118K A136P D139R S202R R210G W260F L288I L294P S295V R244K | 10.8 | A & H | 44 C. | 40 hr | 25.2 | 2029.9 |
| Q60R Y93Q S95D D118K A136P D139R S202R R210G W260F L288I L294P S295V K116R | 10.8 | A & H | 44 C. | 40 hr | 22.7 | 388.9 |
| Q60R Y93Q S95D D118K A136P D139R S202R R210G W260F L288I L294P S295V N200T | 10.8 | A & H | 44 C. | 40 hr | 36.0 | 2067.1 |
| Q60R Y93Q S95D D118K A136P D139R S202R R210G W260F L288I L294P S295V N279D | 10.8 | A & H | 44 C. | 40 hr | 35.7 | 1992.7 |
| Q60R Y93Q S95D D118K A136P D139R S202R R210G W260F L288I L294P S295V N279E | 10.8 | A & H | 44 C. | 40 hr | 48.6 | 1951.1 |
| Q60R Y93Q S95D D118K A136P D139R S202R R210G W260F L288I L294P S295V N100Y | 10.8 | A & H | 44 C. | 40 hr | 24.1 | 2273.7 |
| Q60R Y93Q S95D D118K A136P D139R S202R R210G W260F L288I L294P S295V N100H | 10.8 | A & H | 44 C. | 40 hr | 21.2 | 1894.3 |
| Q60R Y93Q S95D D118K A136P D139R S202R R210G W260F L288I L294P S295V N273D | 10.8 | A & H | 44 C. | 40 hr | 37.7 | 586.6 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| Q60R Y93Q S95D D118K A136P D139R S202R R210G W260F L288I L294P S295V N273E | 10.8 | A & H | 44 C. | 40 hr | 32.8 | 1393.3 |
| Q60R Y93Q S95D D118K A136P D139R S202R R210G W260F L288I L294P S295V Y6H | 10.8 | A & H | 44 C. | 40 hr | 23.8 | 1585.1 |
| Q60R Y93Q S95D D118K A136P D139R S202R R210G W260F L288I L294P S295V P183T | 10.8 | A & H | 44 C. | 40 hr | 32.4 | 533.9 |
| Q60R Y93Q S95D D118K A136P D139R S202R R210G W260F L288I L294P S295V N272T | 10.8 | A & H | 44 C. | 40 hr | 37.1 | 1311.4 |
| Q60R Y93Q S95D D118K A136P D139R S202R R210G W260F L288I L294P S295V N283H | 10.8 | A & H | 44 C. | 40 hr | 38.5 | 1189.7 |
| Q60R Y93Q S95D D118K A136P D139R S202R R210G W260F L288I L294P S295V A276D | 10.8 | A & H | 44 C. | 40 hr | 38.7 | 619.7 |
| Q60R Y93Q S95D D118K A136P D139R S202R R210G W260F L288I L294P S295V T280L | 10.8 | A & H | 44 C. | 40 hr | 34.1 | 1768.9 |
| Q60R Y93Q S95D D118K A136P D139R S202R R210G W260F L288I L294P S295V A30T | 10.8 | A & H | 44 C. | 40 hr | 56.9 | 922.9 |
| Q60R Y93Q S95D D118K A136P D139R S202R R210G W260F L288I L294P S295V | 10.8 | A & H | 44 C. | 40 hr | 30.0 | 500.7 |
| Y93Q S95D D118K A136P D139A K142S S202R E234Y A235K Q243E W260F A276E N279E N283W L288I L294P S295V | 10.8 | A & H | 44 C. | 40 hr | 34.9 | 375.7 |
| Y93Q S95D D118K A136P D139A S202R E234Y A235K Q243E R244K W260F A276E N279E N283W L288I L294P S295V | 10.8 | A & H | 44 C. | 40 hr | 42.4 | 516.8 |
| Y93Q S95D D118K A136P D139A S202R E234Y A235K Q243E W260F N272T A276E N279E N283W L288I L294P S295V | 10.8 | A & H | 44 C. | 40 hr | 41.0 | 1091.1 |
| Y93Q S95D D118K A136P D139A S202R E234Y A235K Q243E W260F N273D A276E N279E N283W L288I L294P S295V | 10.8 | A & H | 44 C. | 40 hr | 42.0 | 665.9 |
| Y93Q S95D D118K A136P D139A S202R E234Y A235K Q243E W260F N273E A276E N279E N283W L288I L294P S295V | 10.8 | A & H | 44 C. | 40 hr | 42.5 | 599.1 |
| Y93Q S95D D118K A136P D139A S202R E234Y A235K Q243E W260F A276E N279E T280L N283W L288I L294P S295V | 10.8 | A & H | 44 C. | 40 hr | 29.6 | 311.8 |
| S95D D118K A136P D139A S202R E234Y A235K Q243E W260F A276E N279E N283W L288I L294P S295V | 10.8 | A & H | 44 C. | 40 hr | 24.9 | 603.0 |
| H80K Y93Q S95D D118K A136P D139A S202R R210G A235K Q243E W260F A276E N279E N283W L288I L294P S295V | 10.8 | A & H | 44 C. | 40 hr | 47.4 | 372.4 |
| A1V H80K Y93Q S95D D118K A136P D139A S202R E234Y Q243E W260F A276E N279E N283W L288I L294P S295V | 10.8 | A & H | 44 C. | 40 hr | 36.1 | 448.8 |
| A1V H80K Y93Q S95D D118K A136P D139R S202R R210G E234Y Q243E W260F A276E N279E N283W L288I L294P S295V | 10.8 | A & H | 44 C. | 40 hr | 32.5 | 424.8 |
| Q60R Y93Q S95D D118K A136P D139R S202R R210G W260F L288I L294P S295V S266A | 10.8 | A & H | 44 C. | 44 hr | 25.4 | 492.3 |
| Q60R Y93Q S95D D118K A136P D139R S202R R210G W260F L288I L294P S295V A97R | 10.8 | A & H | 44 C. | 44 hr | 20.9 | 395.9 |
| Q60R Y93Q S95D D118K A136P D139R S202R R210G W260F L288I L294P S295V A97S | 10.8 | A & H | 44 C. | 44 hr | 21.5 | 394.3 |
| Q60R Y93Q S95D D118K A136P D139R S202R R210G W260F L288I L294P S295V S98P | 10.8 | A & H | 44 C. | 44 hr | 28.4 | 350.8 |
| Q60R Y93Q S95D D118K A136P D139R S202R R210G W260F L288I L294P S295V I114M | 10.8 | A & H | 44 C. | 44 hr | 26.0 | 453.9 |
| Q60R Y93Q S95D D118K A136P D139R S202R R210G W260F L288I L294P S295V I114Q | 10.8 | A & H | 44 C. | 44 hr | 29.1 | 479.5 |
| Q60R Y93Q S95D D118K A136P D139R S202R R210G W260F L288I L294P S295V I114W | 10.8 | A & H | 44 C. | 44 hr | 30.6 | 482.6 |
| Q60R Y93Q S95D D118K A136P D139R S202R R210G W260F L288I L294P S295V S98D | 10.8 | A & H | 44 C. | 44 hr | 27.7 | 522.1 |
| Q60R Y93Q S95D D118K A136P D139R S202R R210G W260F L288I L294P S295V N200D | 10.8 | A & H | 44 C. | 44 hr | 20.7 | 525.6 |
| Q60R Y93Q S95D D118K A136P D139R S202R R210G W260F L288I L294P S295V Q203T | 10.8 | A & H | 44 C. | 44 hr | 27.7 | 506.6 |
| Q60R Y93Q S95D D118K A136P D139R S202R R210G W260F L288I L294P S295V T296S | 10.8 | A & H | 44 C. | 44 hr | 22.1 | 461.1 |
| Q60R Y93Q S95D D118K A136P D139R S202R R210G W260F L288I L294P S295V F298Y | 10.8 | A & H | 44 C. | 44 hr | 27.8 | 459.5 |
| Q60R Y93Q S95D D118K A136P D139R S202R R210G W260F L288I L294P S295V N213V | 10.8 | A & H | 44 C. | 44 hr | 30.3 | 502.4 |
| Q60R Y93Q S95D D118K A136P D139R S202R R210G W260F L288I L294P S295V N213D | 10.8 | A & H | 44 C. | 44 hr | 36.8 | 431.2 |
| Q60R Y93Q S95D D118K A136P D139R S202R R210G W260F L288I L294R S295V | 10.8 | A & H | 44 C. | 44 hr | 24.8 | 451.4 |
| A30T Y93Q S95D D118K A136P D139R S202R R210G W260F L288I L294P S295V S266A | 10.8 | A & H | 44 C. | 44 hr | 51.8 | 826.4 |
| A30T Y93Q S95D D118K A136P D139R S202R R210G W260F L288I L294P S295V A270D | 10.8 | A & H | 44 C. | 44 hr | 41.0 | 586.6 |
| A30T Y93Q S95D D118K A136P D139R S202R R210G W260F L288I L294P S295V A270N | 10.8 | A & H | 44 C. | 44 hr | 27.5 | 563.3 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R S202R R210G W260F L288I L294P S295G | 10.8 | A & H | 44 C. | 44 hr | 31.9 | 424.1 |
| A30T Y93Q S95D D118K A136P D139R S202R R210G W260F L288I L294K S295G | 10.8 | A & H | 44 C. | 44 hr | 31.3 | 533.9 |
| A30T Y93Q S95D D118K A136P D139R S202R R210G W260F L288I L294P S295V A97R | 10.8 | A & H | 44 C. | 44 hr | 41.9 | 1165.6 |
| A30T Y93Q S95D D118K A136P D139R S202R R210G W260F L288I L294P S295V A97S | 10.8 | A & H | 44 C. | 44 hr | 45.9 | 636.4 |
| A30T Y93Q S95D D118K A136P D139R S202R R210G W260F L288I L294P S295V S98P | 10.8 | A & H | 44 C. | 44 hr | 55.2 | 625.0 |
| A30T Y93Q S95D D118K A136P D139R S202R R210G W260F L288I L294P S295V I114M | 10.8 | A & H | 44 C. | 44 hr | 59.3 | 1824.3 |
| A30T Y93Q S95D D118K A136P D139R S202R R210G W260F L288I L294P S295V I114Q | 10.8 | A & H | 44 C. | 44 hr | 56.8 | 619.7 |
| A30T Y93Q S95D D118K A136P D139R S202R R210G W260F L288I L294P S295V S98T | 10.8 | A & H | 44 C. | 44 hr | 50.0 | 360.0 |
| A30T Y93Q S95D D118K A136P D139R S202R R210G W260F L288I L294P S295V S98D | 10.8 | A & H | 44 C. | 44 hr | 54.5 | 360.7 |
| A30T Y93Q S95D D118K A136P D139R S202R R210G W260F L288I L294P S295V N200D | 10.8 | A & H | 44 C. | 44 hr | 52.5 | 1035.5 |
| A30T Y93Q S95D D118K A136P D139R S202R R210G W260F L288I L294P S295V Q203T | 10.8 | A & H | 44 C. | 44 hr | 51.1 | 129.4 |
| A30T Y93Q S95D D118K A136P D139R S202R R210G W260F L288I L294P S295V E290A | 10.8 | A & H | 44 C. | 44 hr | 49.0 | 1710.6 |
| A30T Y93Q S95D D118K A136P D139R S202R R210G W260F L288I L294P S295V T296S | 10.8 | A & H | 44 C. | 44 hr | 54.1 | 1908.7 |
| A30T Y93Q S95D D118K A136P D139R S202R R210G W260F L288I L294P S295V F298Y | 10.8 | A & H | 44 C. | 44 hr | 60.9 | 365.6 |
| T37R Y93Q S95D D118K A136P D139R S202R R210G W260F A276E L288I L294P S295V | 10.8 | A & H | 44 C. | 40 hr | 78.6 | 524.4 |
| Y93Q S95D D118K A136P D139R S202R R210G Q243K W260F N279E L288I L294P S295V | 10.8 | A & H | 44 C. | 40 hr | 66.4 | 1026.7 |
| E41V Y93Q S95D D118K A136P D139R S202R R210G W260F A276E L288I L294P S295V | 10.8 | A & H | 44 C. | 40 hr | 64.4 | 327.4 |
| A30T Y93Q S95D D118K A136P D139R S202R R210G W260F A276E L288I L294P S295V | 10.8 | A & H | 44 C. | 40 hr | 65.2 | 275.0 |
| E77T Y93Q S95D D118K A136P D139R S202R R210G Q243K W260F L288I L294P S295V | 10.8 | A & H | 44 C. | 40 hr | 38.1 | 244.4 |
| Y6H Y93Q S95D D118K A136P D139R S202R R210G W260F A276E L288I L294P S295V | 10.8 | A & H | 44 C. | 40 hr | 61.8 | 184.4 |
| H80K Y93Q S95D D118K A136P D139R S202R R210G Q243K W260F L288I L294P S295V | 10.8 | A & H | 44 C. | 40 hr | 71.3 | 285.5 |
| S3P Y93Q S95D D118K A136P D139R S202R R210G W260F A276E L288I L294P S295V | 10.8 | A & H | 44 C. | 40 hr | 54.2 | 439.8 |
| Y93Q S95D D118K A136P D139R N150T S202R R210G W260F A276E L288I L294P S295V | 10.8 | A & H | 44 C. | 40 hr | 59.3 | 509.2 |
| Y93Q S95D D118K A136P D139R S202R R210G Q243K W260F A276E L288I L294P S295V | 10.8 | A & H | 44 C. | 40 hr | 58.7 | 502.7 |
| A30T Y93Q S95D D118K A136P D139R S202R R210G Q243K W260F L288I L294P S295V | 10.8 | A & H | 44 C. | 40 hr | 59.2 | 503.6 |
| Y93Q S95D D118K A136P D139R S202R R210G E234Y Q243K W260F L288I L294P S295V | 10.8 | A & H | 44 C. | 40 hr | 52.1 | 783.5 |
| Y93Q S95D I114Q D118K A136P D139R S202R R210G W260F A276E L288I L294P S295V | 10.8 | A & H | 44 C. | 40 hr | 42.7 | 507.7 |
| Y93Q S95D D118K A136P D139R S202R R210G E234Y W260F A276E L288I L294P S295V | 10.8 | A & H | 44 C. | 40 hr | 58.0 | 450.0 |
| E77N Y93Q S95D D118K A136P D139R S202R R210G W260F A276E L288I L294P S295V | 10.8 | A & H | 44 C. | 40 hr | 51.6 | 468.1 |
| Y93Q S95D D118K A136P D139R Y174R S202R R210G W260F A276E L288I L294P S295V | 10.8 | A & H | 44 C. | 40 hr | 46.9 | 502.4 |
| Y93Q S95D D118K A136P D139R S202R R210G Q243E W260F A276E L288I L294P S295V | 10.8 | A & H | 44 C. | 40 hr | 50.5 | 662.6 |
| Y93Q S95D D118K A136P D139R S202R R210G Q243H W260F A276E L288I L294P S295V | 10.8 | A & H | 44 C. | 40 hr | 50.0 | 442.6 |
| Y93Q S95D D118K A136P D139R S202R R210G Q243Y W260F A276E L288I L294P S295V | 10.8 | A & H | 44 C. | 40 hr | 52.7 | 475.0 |
| Q60R Y93Q S95D D118K A136P D139R S202R R210G Q243K W260F L288I L294P S295V | 10.8 | A & H | 44 C. | 40 hr | 49.3 | 478.4 |
| S8T Y93Q S95D D118K A136P D139R S202R R210G Q243K W260F L288I L294P S295V | 10.8 | A & H | 44 C. | 40 hr | 47.1 | 2245.4 |
| Y93Q S95D D118K A136P D139R N150T S202R R210G Q243K W260F L288I L294P S295V | 10.8 | A & H | 44 C. | 40 hr | 48.9 | 597.5 |
| H80R Y93Q S95D D118K A136P D139R S202R R210G W260F A276E L288I L294P S295V | 10.8 | A & H | 44 C. | 40 hr | 44.0 | 589.9 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93Q S95D D118K A136P D139R S202R R210G Q243K W260F N279D L288I L294P S295V | 10.8 | A & H | 44 C. | 40 hr | 46.5 | 2235.5 |
| A1G Y93Q S95D D118K A136P D139R S202R R210G W260F A276E L288I L294P S295V | 10.8 | A & H | 44 C. | 40 hr | 44.6 | 1312.9 |
| Y93Q S95D I114M D118K A136P D139R S202R R210G W260F A276E L288I L294P S295V | 10.8 | A & H | 44 C. | 40 hr | 33.3 | 1305.9 |
| Y93Q S95D D118K S131T A136P D139R S202R R210G W260F A276E L288I L294P S295V | 10.8 | A & H | 44 C. | 40 hr | 47.2 | 1690.0 |
| Y93Q S95D D118K A136P D139R S202R R210G W260F A276E N283H L288I L294P S295V | 10.8 | A & H | 44 C. | 40 hr | 47.8 | 223.9 |
| Y93Q S95D D118K A136P D139R S202R R210G W260F A276E L288I L294P S295V T296S | 10.8 | A & H | 44 C. | 40 hr | 32.9 | 915.7 |
| Y93Q S95D D118K A136P D139R S202R R210G W260F A276E N283W L288I L294P S295V | 10.8 | A & H | 44 C. | 40 hr | 46.6 | 2326.7 |
| V82I Y93Q S95D D118K A136P D139R S202R R210G W260F A276E L288I L294P S295V | 10.8 | A & H | 44 C. | 40 hr | 39.3 | 561.1 |
| Y93Q S95D D118K A136P D139R S202R R210G Q243K W260F T280L L288I L294P S295V | 10.8 | A & H | 44 C. | 40 hr | 49.7 | 554.6 |
| Y93Q S95D D118K A136P D139R N150R S202R R210G Q243K W260F L288I L294P S295V | 10.8 | A & H | 44 C. | 40 hr | 81.4 | 1181.8 |
| R70K Y93Q S95D D118K A136P D139R S202R R210G W260F A276E L288I L294P S295V | 10.8 | A & H | 44 C. | 40 hr | 49.5 | 765.9 |
| Y93Q S95D D118K A136P D139R S202R R210G Q243K W260F A276D L288I L294P S295V | 10.8 | A & H | 44 C. | 40 hr | 43.2 | 1839.5 |
| Y93Q S95D D118K A136P D139R N150S S202R R210G W260F A276E L288I L294P S295V | 10.8 | A & H | 44 C. | 40 hr | 46.8 | 1681.3 |
| A83S Y93Q S95D D118K A136P D139R S202R R210G W260F A276E L288I L294P S295V | 10.8 | A & H | 44 C. | 40 hr | 45.4 | 538.1 |
| Y93Q S95D D118K A136P D139R S202R R210G W260F A276E N279E L288I L294P S295V | 10.8 | A & H | 44 C. | 40 hr | 44.4 | 529.1 |
| Y93Q S95D D118K A136P D139R S202R R210G Q243K W260F N283H L288I L294P S295V | 10.8 | A & H | 44 C. | 40 hr | 41.3 | 528.9 |
| S74Y Y93Q S95D D118K A136P D139R S202R R210G W260F A276E L288I L294P S295V | 10.8 | A & H | 44 C. | 40 hr | 43.0 | 1607.3 |
| Y93Q S95D D118K A136P D139R S202R R210G A235R W260F A276E L288I L294P S295V | 10.8 | A & H | 44 C. | 40 hr | 44.2 | 2481.6 |
| Y93Q S95D D118K A136P D139R Q169R S202R R210G W260F A276E L288I L294P S295V | 10.8 | A & H | 44 C. | 40 hr | 39.1 | 509.0 |
| Y93Q S95D D118K A136P D139R S202R R210G W260F A276E L288I L294R S295V | 10.8 | A & H | 44 C. | 40 hr | 28.1 | 1943.2 |
| H80K Y93Q S95D D118K A136P D139R S202R R210G W260F A276E L288I L294P S295V | 10.8 | A & H | 44 C. | 40 hr | 41.8 | 501.7 |
| Y93Q S95D D118K A136P D139R P183T S202R R210G Q243K W260F L288I L294P S295V | 10.8 | A & H | 44 C. | 40 hr | 44.8 | 498.4 |
| G47K Y93Q S95D D118K A136P D139R S202R R210G W260F A276E L288I L294P S295V | 10.8 | A & H | 44 C. | 40 hr | 38.2 | 1768.4 |
| Y93Q S95D D118K A136P D139R N180R S202R R210G W260F A276E L288I L294P S295V | 10.8 | A & H | 44 C. | 40 hr | 39.2 | 2087.6 |
| A83S Y93Q S95D D118K A136P D139R S202R R210G Q243K W260F L288I L294P S295V | 10.8 | A & H | 44 C. | 40 hr | 39.7 | 489.0 |
| Y93Q S95D D118K A136P D139R P183G S202R R210G Q243K W260F L288I L294P S295V | 10.8 | A & H | 44 C. | 40 hr | 50.1 | 165.7 |
| H80R Y93Q S95D D118K A136P D139R S202R R210G Q243K W260F L288I L294P S295V | 10.8 | A & H | 44 C. | 40 hr | 45.4 | 341.3 |
| Y93Q S95D D118K A136P D139R E177Y S202R R210G Q243K W260F L288I L294P S295V | 10.8 | A & H | 44 C. | 40 hr | 39.3 | 1213.0 |
| S8T Y93Q S95D D118K A136P D139R S202R R210G W260F A276E L288I L294P S295V | 10.8 | A & H | 44 C. | 40 hr | 38.9 | 820.5 |
| Y93Q S95D D118K A136P D139R S202R Q203T R210G Q243K W260F L288I L294P S295V | 10.8 | A & H | 44 C. | 40 hr | 32.6 | 920.2 |
| Y6M Y93Q S95D D118K A136P D139R S202R R210G W260F A276E L288I L294P S295V | 10.8 | A & H | 44 C. | 40 hr | 43.8 | 516.9 |
| E41V Y93Q S95D D118K A136P D139R S202R R210G Q243K W260F L288I L294P S295V | 10.8 | A & H | 44 C. | 40 hr | 42.1 | 899.6 |
| Y93Q S95D S111K D118K A136P D139R S202R R210G Q243K W260F L288I L294P S295V | 10.8 | A & H | 44 C. | 40 hr | 38.8 | 1165.6 |
| Y93Q S95D D118K A136P D139R R185G S202R R210G W260F A276E L288I L294P S295V | 10.8 | A & H | 44 C. | 40 hr | 39.9 | 1420.7 |
| Y93Q S95D D118K A136P D139R S202R Q203T R210G W260F A276E L288I L294P S295V | 10.8 | A & H | 44 C. | 40 hr | 24.9 | 1530.3 |
| Y93Q S95D D118K A136P D139R S202R R210G Q243K W260F N273D L288I L294P S295V | 10.8 | A & H | 44 C. | 40 hr | 41.4 | 1313.7 |
| Y93Q S95D D118K A136P D139R S202R R210G E234F Q243K W260F L288I L294P S295V | 10.8 | A & H | 44 C. | 40 hr | 41.3 | 1607.1 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| N71S Y93Q S95D D118K A136P D139R S202R R210G Q243K W260F L288I L294P S295V | 10.8 | A & H | 44 C. | 40 hr | 40.9 | 1693.9 |
| Y93Q S95D N100H D118K A136P D139R S202R R210G W260F A276E L288I L294P S295V | 10.8 | A & H | 44 C. | 40 hr | 34.8 | 1271.7 |
| E77K Y93Q S95D D118K A136P D139R S202R R210G Q243K W260F L288I L294P S295V | 10.8 | A & H | 44 C. | 40 hr | 21.6 | 1710.6 |
| Y93Q S95D D118K A136P D139R S202R R210G W260F S266A A276E L288I L294P S295V | 10.8 | A & H | 44 C. | 40 hr | 24.1 | 1908.7 |
| N45G Y93Q S95D D118K A136P D139R S202R R210G W260F A276E L288I L294P S295V | 10.8 | A & H | 44 C. | 40 hr | 36.0 | 1986.4 |
| Y93Q S95D S111A D118K A136P D139R S202R R210G W260F A276E L288I L294P S295V | 10.8 | A & H | 44 C. | 40 hr | 35.0 | 929.1 |
| Y93Q S95D S98D D118K A136P D139R S202R R210G W260F A276E L288I L294P S295V | 10.8 | A & H | 44 C. | 40 hr | 22.7 | 435.3 |
| A1V Y93Q S95D D118K A136P D139R S202R R210G Q243K W260F L288I L294P S295V | 10.8 | A & H | 44 C. | 40 hr | 36.5 | 432.0 |
| Y93Q S95D D118K A136P D139R S202R R210G Q243K W260F N272T L288I L294P S295V | 10.8 | A & H | 44 C. | 40 hr | 34.7 | 431.2 |
| T37P Y93Q S95D D118K A136P D139R S202R R210G Q243K W260F L288I L294P S295V | 10.8 | A & H | 44 C. | 40 hr | 41.6 | 1025.9 |
| N71S Y93Q S95D D118K A136P D139R S202R R210G W260F A276E L288I L294P S295V | 10.8 | A & H | 44 C. | 40 hr | 30.9 | 427.7 |
| T37P Y93Q S95D D118K A136P D139R S202R R210G W260F A276E L288I L294P S295V | 10.8 | A & H | 44 C. | 40 hr | 47.8 | 1091.1 |
| G47A Y93Q S95D D118K A136P D139R S202R R210G W260F A276E L288I L294P S295V | 10.8 | A & H | 44 C. | 40 hr | 22.1 | 1228.7 |
| T37R Y93Q S95D D118K A136P D139R S202R R210G Q243K W260F L288I L294P S295V | 10.8 | A & H | 44 C. | 40 hr | 34.5 | 1144.7 |
| E77T Y93Q S95D D118K A136P D139R S202R R210G W260F A276E L288I L294P S295V | 10.8 | A & H | 44 C. | 40 hr | 31.9 | 842.1 |
| Y93Q S95D S111R D118K A136P D139R S202R R210G W260F A276E L288I L294P S295V | 10.8 | A & H | 44 C. | 40 hr | 32.1 | 717.2 |
| Y93Q S95D D118K A136P D139R Q184K S202R R210G W260F A276E L288I L294P S295V | 10.8 | A & H | 44 C. | 40 hr | 34.7 | 543.2 |
| Y93Q S95D I114W D118K A136P D139R S202R R210G W260F A276E L288I L294P S295V | 10.8 | A & H | 44 C. | 40 hr | 20.8 | 836.3 |
| Y93Q S95D D118K A136P D139R S202R R210G Q243K W260F N273E L288I L294P S295V | 10.8 | A & H | 44 C. | 40 hr | 32.9 | 932.7 |
| Y93Q S95D D118K A136P D139R N150S S202R R210G Q243K W260F L288I L294P S295V | 10.8 | A & H | 44 C. | 40 hr | 35.4 | 1186.9 |
| Y93Q S95D D118K A136P D139R S202R R210G G257A W260F A276E L288I L294P S295V | 10.8 | A & H | 44 C. | 40 hr | 30.3 | 723.2 |
| R70K Y93Q S95D D118K A136P D139R S202R R210G Q243K W260F L288I L294P S295V | 10.8 | A & H | 44 C. | 40 hr | 32.1 | 955.5 |
| Y93Q S95D S111I D118K A136P D139R S202R R210G Q243K W260F L288I L294P S295V | 10.8 | A & H | 44 C. | 40 hr | 31.8 | 578.9 |
| Y93Q S95D D118K A136P D139R S202R R210G Q243K W260F N283W L288I L294P S295V | 10.8 | A & H | 44 C. | 40 hr | 31.7 | 933.9 |
| Y93Q S95D D118K A136P D139R Q169K S202R R210G Q243K W260F L288I L294P S295V | 10.8 | A & H | 44 C. | 40 hr | 36.1 | 1395.8 |
| Y93Q S95D D118K A136P D139R Q184K S202R R210G Q243K W260F L288I L294P S295V | 10.8 | A & H | 44 C. | 40 hr | 29.6 | 983.4 |
| Y93Q S95D S98P D118K A136P D139R S202R R210G Q243K W260F L288I L294P S295V | 10.8 | A & H | 44 C. | 40 hr | 25.9 | 1183.3 |
| Y93Q S95D D104G D118K A136P D139R S202R R210G W260F A276E L288I L294P S295V | 10.8 | A & H | 44 C. | 40 hr | 34.8 | 1081.8 |
| Y93Q S95D D118K A136P D139R S202R R210G Q243K W260F A276W L288I L294P S295V | 10.8 | A & H | 44 C. | 40 hr | 30.8 | 929.3 |
| Y93Q S95D D118K A136P D139R Q184E S202R R210G Q243K W260F L288I L294P S295V | 10.8 | A & H | 44 C. | 40 hr | 29.9 | 1051.1 |
| D65E Y93Q S95D D118K A136P D139R S202R R210G W260F A276E L288I L294P S295V | 10.8 | A & H | 44 C. | 40 hr | 27.0 | 1252.3 |
| Y93Q S95D D118K A136P D139R Y174L S202R R210G W260F A276E L288I L294P S295V | 10.8 | A & H | 44 C. | 40 hr | 28.0 | 1956.5 |
| Y93Q S95D A97S D118K A136P D139R S202R R210G Q243K W260F L288I L294P S295V | 10.8 | A & H | 44 C. | 40 hr | 22.9 | 1557.5 |
| V82I Y93Q S95D D118K A136P D139R S202R R210G Q243K W260F L288I L294P S295V | 10.8 | A & H | 44 C. | 40 hr | 28.2 | 356.9 |
| N18V Y93Q S95D D118K A136P D139R S202R R210G W260F A276E L288I L294P S295V | 10.8 | A & H | 44 C. | 40 hr | 48.9 | 622.1 |
| N18R Y93Q S95D D118K A136P D139R S202R R210G W260F A276E L288I L294P S295V | 10.8 | A & H | 44 C. | 40 hr | 27.1 | 354.0 |
| Y93Q S95D S98D D118K A136P D139R S202R R210G Q243K W260F L288I L294P S295V | 10.8 | A & H | 44 C. | 40 hr | 21.9 | 350.8 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| Y93Q S95D D118K A136P D139R K142M S202R R210G Q243K W260F L288I L294P S295V | 10.8 | A & H | 44 C. | 40 hr | 20.8 | 341.0 |
| Y93Q S95D D118K A136P D139R R185G S202R R210G Q243K W260F L288I L294P S295V | 10.8 | A & H | 44 C. | 40 hr | 26.6 | 340.9 |
| Y93Q S95D D118K A136P D139R Q169R S202R R210G Q243K W260F L288I L294P S295V | 10.8 | A & H | 44 C. | 40 hr | 26.0 | 337.2 |
| Y93Q S95D D118K A136P D139R S202R R210G Q243K W260F S266A L288I L294P S295V | 10.8 | A & H | 44 C. | 40 hr | 25.8 | 336.3 |
| Y93Q S95D D118K A136P D139R Q169A S202R R210G W260F A276E L288I L294P S295V | 10.8 | A & H | 44 C. | 40 hr | 37.5 | 494.8 |
| Y93Q S95D D118K A136P D139R N200T S202R R210G Q243K W260F L288I L294P S295V | 10.8 | A & H | 44 C. | 40 hr | 25.8 | 334.1 |
| Y6M Y93Q S95D D118K A136P D139R S202R R210G Q243K W260F L288I L294P S295V | 10.8 | A & H | 44 C. | 40 hr | 26.9 | 332.2 |
| Y93Q S95D D118K A136P D139R E177S S202R R210G W260F A276E L288I L294P S295V | 10.8 | A & H | 44 C. | 40 hr | 40.5 | 492.0 |
| Y93Q S95D D118K A136P D139R E177Y S202R R210G W260F A276E L288I L294P S295V | 10.8 | A & H | 44 C. | 40 hr | 46.5 | 589.4 |
| Y93Q S95D D118K A136P D139R Q184S S202R R210G Q243K W260F L288I L294P S295V | 10.8 | A & H | 44 C. | 40 hr | 25.5 | 330.5 |
| Y93Q S95D D118K A136P D139R Q184E S202R R210G W260F A276E L288I L294P S295V | 10.8 | A & H | 44 C. | 40 hr | 41.5 | 587.3 |
| Y93Q S95D S111A D118K A136P D139R S202R R210G Q243K W260F L288I L294P S295V | 10.8 | A & H | 44 C. | 40 hr | 25.3 | 329.0 |
| Y93Q S95D D118K A136P D139R Q184S S202R R210G W260F A276E L288I L294P S295V | 10.8 | A & H | 44 C. | 40 hr | 35.7 | 460.2 |
| Y93Q S95D D118K A136P D139R S202R R210G T228S W260F A276E L288I L294P S295V | 10.8 | A & H | 44 C. | 40 hr | 21.9 | 326.3 |
| Y93Q S95D D118K A136P D139R S202R R210G E234F W260F A276E L288I L294P S295V | 10.8 | A & H | 44 C. | 40 hr | 41.9 | 518.2 |
| Y93Q S95D D118K A136P D139R S202R R210G A235R Q243K W260F L288I L294P S295V | 10.8 | A & H | 44 C. | 40 hr | 25.0 | 325.9 |
| Y93Q S95D E108S D118K A136P D139R S202R R210G W260F A276E L288I L294P S295V | 10.8 | A & H | 44 C. | 40 hr | 21.7 | 321.7 |
| Y93Q S95D K116R D118K A136P D139R S202R R210G W260F A276E L288I L294P S295V | 10.8 | A & H | 44 C. | 40 hr | 36.1 | 424.6 |
| Y93Q S95D D118K T119R A136P D139R S202R R210G W260F A276E L288I L294P S295V | 10.8 | A & H | 44 C. | 40 hr | 22.6 | 304.8 |
| Y93Q S95D D118K A136P D139R N200T S202R R210G W260F A276E L288I L294P S295V | 10.8 | A & H | 44 C. | 40 hr | 44.9 | 550.6 |
| Y93Q S95D D118K A136P D139R N180R S202R R210G Q243K W260F L288I L294P S295V | 10.8 | A & H | 44 C. | 40 hr | 29.4 | 320.9 |
| Y93Q S95D D118K A136P D139R P183G S202R R210G W260F A276E L288I L294P S295V | 10.8 | A & H | 44 C. | 40 hr | 37.8 | 426.7 |
| Y93Q S95D D118K A136P D139R P183T S202R R210G W260F A276E L288I L294P S295V | 10.8 | A & H | 44 C. | 40 hr | 37.1 | 421.8 |
| Y93Q S95D D118K A136P D139R S202R R205K R210G Q243K W260F L288I L294P S295V | 10.8 | A & H | 44 C. | 40 hr | 27.0 | 319.7 |
| Q35L Y93Q S95D D118K A136P D139R S202R R210G W260F A276E L288I L294P S295V | 10.8 | A & H | 44 C. | 40 hr | 23.0 | 319.1 |
| Y93Q S95D D118K A136P D139R S202R R210G W260F A276E N279D L288I L294P S295V | 10.8 | A & H | 44 C. | 40 hr | 40.5 | 440.8 |
| N18R Y93Q S95D D118K A136P D139R S202R R210G Q243K W260F L288I L294P S295V | 10.8 | A & H | 44 C. | 40 hr | 24.3 | 318.7 |
| G47S Y93Q S95D D118K A136P D139R S202R R210G W260F A276E L288I L294P S295V | 10.8 | A & H | 44 C. | 40 hr | 24.5 | 316.5 |
| D57N Y93Q S95D D118K A136P D139R S202R R210G W260F A276E L288I L294P S295V | 10.8 | A & H | 44 C. | 40 hr | 25.7 | 342.9 |
| E77K Y93Q S95D D118K A136P D139R S202R R210G W260F A276E L288I L294P S295V | 10.8 | A & H | 44 C. | 40 hr | 26.5 | 532.8 |
| Y93Q S95D D118K A136P D139R S202R R210G A235K Q243K W260F L288I L294P S295V | 10.8 | A & H | 44 C. | 40 hr | 23.8 | 315.7 |
| Y6H Y93Q S95D D118K A136P D139R S202R R210G Q243K W260F L288I L294P S295V | 10.8 | A & H | 44 C. | 40 hr | 23.8 | 314.8 |
| N45G Y93Q S95D D118K A136P D139R S202R R210G Q243K W260F L288I L294P S295V | 10.8 | A & H | 44 C. | 40 hr | 23.8 | 314.1 |
| G47S Y93Q S95D D118K A136P D139R S202R R210G Q243K W260F L288I L294P S295V | 10.8 | A & H | 44 C. | 40 hr | 24.4 | 297.8 |
| Y93Q S95D K116R D118K A136P D139R S202R R210G Q243K W260F L288I L294P S295V | 10.8 | A & H | 44 C. | 40 hr | 21.3 | 291.6 |
| D57N Y93Q S95D D118K A136P D139R S202R R210G Q243K W260F L288I L294P S295V | 10.8 | A & H | 44 C. | 40 hr | 20.6 | 285.5 |
| Y93Q S95D D118K A136P D139R S202R R210G Q243K W260F N272M L288I L294P S295V | 10.8 | A & H | 44 C. | 40 hr | 20.4 | 284.0 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| Y93Q S95D D118K A136P D139R H172R S202R R210G Q243K W260F L288I L294P S295V | 10.8 | A & H | 44 C. | 40 hr | 20.3 | 283.3 |
| G47A Y93Q S95D D118K A136P D139R S202R R210G Q243K W260F L288I L294P S295V | 10.8 | A & H | 44 C. | 40 hr | 20.1 | 281.0 |
| Y93Q S95D I114Q D118K A136P D139R S202R R210G Q243K W260F L288I L294P S295V | 10.8 | A & H | 44 C. | 40 hr | 50.1 | 357.4 |
| Y93Q S95D D104G D118K A136P D139R S202R R210G Q243K W260F L288I L294P S295V | 10.8 | A & H | 44 C. | 40 hr | 21.4 | 251.9 |
| Y93Q S95D D118K A136P D139R S202R R210G K254Y W260F A276E L288I L294P S295V | 10.8 | A & H | 44 C. | 40 hr | 29.4 | 275.5 |
| Y93Q S95D S98T D118K A136P D139R S202R R210G W260F A276E L288I L294P S295V | 10.8 | A & H | 44 C. | 40 hr | 26.2 | 372.4 |
| Y93Q S95D D118K A136P D139R S202R R210G N213D W260F A276E L288I L294P S295V | 10.8 | A & H | 44 C. | 40 hr | 49.2 | 529.3 |
| Y93Q S95D D118K E133R A136P D139R S202R R210G W260F A276E L288I L294P S295V | 10.8 | A & H | 44 C. | 40 hr | 26.7 | 370.9 |
| Y93Q S95D D118K A136P D139R K142S S202R R210G W260F A276E L288I L294P S295V | 10.8 | A & H | 44 C. | 40 hr | 27.6 | 289.4 |
| Y93Q S95D D118K A136P D139R K142V S202R R210G W260F A276E L288I L294P S295V | 10.8 | A & H | 44 C. | 40 hr | 42.1 | 421.7 |
| A30T Q60R Y93Q S95D D118K A136P D139R P183G S202R R210G W260F L288I L294P S295V | 10.8 | A & H | 44 C. | 65 hr | 47.3 | 2795.3 |
| A30T Q60R Y93Q S95D I114Q D118K A136P D139R S202R R210G W260F L288I L294P S295V | 10.8 | A & H | 44 C. | 65 hr | 49.2 | 2933.3 |
| A30T Q60R Y93Q S95D D118K A136P D139R Q143R S202R R210G W260F L288I L294P S295V | 10.8 | A & H | 44 C. | 65 hr | 42.0 | 2748.0 |
| A1V A30T Q60R Y93Q S95D D118K A136P D139R S202R R210G W260F L288I L294P S295V | 10.8 | A & H | 44 C. | 65 hr | 45.7 | 2697.6 |
| A30T Q60R K63Q Y93Q S95D D118K A136P D139R S202R R210G W260F L288I L294P S295V | 10.8 | A & H | 44 C. | 65 hr | 26.6 | 1637.9 |
| A30T T37P Q60R Y93Q S95D D118K A136P D139R S202R R210G W260F L288I L294P S295V | 10.8 | A & H | 44 C. | 65 hr | 47.1 | 2909.1 |
| S8T A30T Q60R Y93Q S95D D118K A136P D139R S202R R210G W260F L288I L294P S295V | 10.8 | A & H | 44 C. | 65 hr | 53.1 | 3150.8 |
| A30T G47S Q60R Y93Q S95D D118K A136P D139R S202R R210G W260F L288I L294P S295V | 10.8 | A & H | 44 C. | 65 hr | 38.6 | 2182.8 |
| A30T Q60R Y93Q S95D D118K A136P D139R S202R R210G G257A W260F L288I L294P S295V | 10.8 | A & H | 44 C. | 65 hr | 36.9 | 2145.4 |
| A30T Q60R E77N Y93Q S95D D118K A136P D139R S202R R210G W260F L288I L294P S295V | 10.8 | A & H | 44 C. | 65 hr | 42.7 | 2545.4 |
| A30T Q60R Y93Q S95D D104A D118K A136P D139R S202R R210G W260F L288I L294P S295V | 10.8 | A & H | 44 C. | 65 hr | 39.0 | 2295.9 |
| A30T Q60R Y93Q S95D S111A D118K A136P D139R S202R R210G W260F L288I L294P S295V | 10.8 | A & H | 44 C. | 65 hr | 39.1 | 2359.6 |
| A30T Q60R Y93Q S95D S111R D118K A136P D139R S202R R210G W260F L288I L294P S295V | 10.8 | A & H | 44 C. | 65 hr | 39.0 | 2282.4 |
| A30T N45G Q60R Y93Q S95D D118K A136P D139R S202R R210G W260F L288I L294P S295V | 10.8 | A & H | 44 C. | 65 hr | 45.2 | 2715.3 |
| N18V A30T Q60R Y93Q S95D D118K A136P D139R S202R R210G W260F L288I L294P S295V | 10.8 | A & H | 44 C. | 65 hr | 46.1 | 2807.8 |
| N18R A30T Q60R Y93Q S95D D118K A136P D139R S202R R210G W260F L288I L294P S295V | 10.8 | A & H | 44 C. | 65 hr | 38.8 | 2293.7 |
| A30T Q60R N71S Y93Q S95D D118K A136P D139R S202R R210G W260F L288I L294P S295V | 10.8 | A & H | 44 C. | 65 hr | 42.3 | 2463.6 |
| A30T Q60R S74K Y93Q S95D D118K A136P D139R S202R R210G W260F L288I L294P S295V | 10.8 | A & H | 44 C. | 65 hr | 44.8 | 2612.3 |
| A30T Q60R Y93Q S95D D118K A136P D139R Y174L S202R R210G W260F L288I L294P S295V | 10.8 | A & H | 44 C. | 65 hr | 45.2 | 2795.8 |
| A30T Q60R Y93Q S95D D118K A136P D139R N180R S202R R210G W260F L288I L294P S295V | 10.8 | A & H | 44 C. | 65 hr | 49.3 | 3079.7 |
| A30T Q60R Y93Q S95D D118K A136P D139R Q169K S202R R210G W260F L288I L294P S295V | 10.8 | A & H | 44 C. | 65 hr | 42.8 | 2554.2 |
| A30T Q60R Y93Q S95D D118K A136P D139R E177S S202R R210G W260F L288I L294P S295V | 10.8 | A & H | 44 C. | 65 hr | 46.5 | 2609.2 |
| A30T Q60R Y93Q S95D D118K A136P D139R Q184K S202R R210G W260F L288I L294P S295V | 10.8 | A & H | 44 C. | 65 hr | 43.1 | 2535.5 |
| A30T Q60R Y93Q S95D D118K A136P D139R R185G S202R R210G W260F L288I L294P S295V | 10.8 | A & H | 44 C. | 65 hr | 48.6 | 2857.7 |
| A30T Q60R Y93Q S95D D118K A136P D139R S202R R210G E234Y W260F L288I L294P S295V | 10.8 | A & H | 44 C. | 65 hr | 39.8 | 2357.7 |
| A30T Q60R Y93Q S95D D118K A136P D139R S202R R210G A235R W260F L288I L294P S295V | 10.8 | A & H | 44 C. | 65 hr | 37.1 | 2135.0 |
| A30T Q60R Y93Q S95D K116R D118K A136P D139R S202R R210G W260F L288I L294P S295V | 10.8 | A & H | 44 C. | 65 hr | 50.8 | 3230.0 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Q60R Y93Q S95D D118K T119R A136P D139R S202R R210G W260F L288I L294P S295V | 10.8 | A & H | 44 C. | 65 hr | 31.3 | 2027.8 |
| A30T Q60R Y93Q S95D D118K A136P D139R N200T S202R R210G W260F L288I L294P S295V | 10.8 | A & H | 44 C. | 65 hr | 48.9 | 3039.0 |
| A30T Q60R Y93Q S95D D118K A136P D139R S202R R205K R210G W260F L288I L294P S295V | 10.8 | A & H | 44 C. | 65 hr | 45.5 | 2711.0 |
| A30T Q60R Y93Q S95D D118K A136P D139R S202R R210G W260F N273E L288I L294P S295V | 10.8 | A & H | 44 C. | 65 hr | 46.5 | 2814.1 |
| Y6H A30T Q60R Y93Q S95D D118K A136P D139R S202R R210G W260F L288I L294P S295V | 10.8 | A & H | 44 C. | 65 hr | 47.2 | 2848.1 |
| Y6M A30T Q60R Y93Q S95D D118K A136P D139R S202R R210G W260F L288I L294P S295V | 10.8 | A & H | 44 C. | 65 hr | 47.1 | 2798.1 |
| T11K A30T Q60R Y93Q S95D D118K A136P D139R S202R R210G W260F L288I L294P S295V | 10.8 | A & H | 44 C. | 65 hr | 37.8 | 2188.6 |
| A30T Q60R Y93Q S95D E108S D118K A136P D139R S202R R210G W260F L288I L294P S295V | 10.8 | A & H | 44 C. | 65 hr | 39.0 | 2182.0 |
| A30T Q60R Y93Q S95D D118K A136P D139R S202R R210G K254Y W260F L288I L294P S295V | 10.8 | A & H | 44 C. | 65 hr | 32.5 | 1854.4 |
| A30T Q60R Y93Q S95D D118K A136P D139R S202R R210G W260F S266A L288I L294P S295V | 10.8 | A & H | 44 C. | 65 hr | 39.9 | 2369.3 |
| A30T Q60R Y93Q S95D D118K A136P D139R S202R R210G W260F A270N L288I L294P S295V | 10.8 | A & H | 44 C. | 65 hr | 25.9 | 1681.4 |
| A30T Q60R Y93Q S95D D118K A136P D139R S202R R210G W260F L288I L294P S295G | 10.8 | A & H | 44 C. | 65 hr | 24.7 | 1394.7 |
| A30T Q60R Y93Q S95D A97R D118K A136P D139R S202R R210G W260F L288I L294P S295V | 10.8 | A & H | 44 C. | 65 hr | 39.1 | 2310.5 |
| A30T Q60R Y93Q S95D A97S D118K A136P D139R S202R R210G W260F L288I L294P S295V | 10.8 | A & H | 44 C. | 65 hr | 40.1 | 2255.1 |
| A30T Q60R Y93Q S95D S98P D118K A136P D139R S202R R210G W260F L288I L294P S295V | 10.8 | A & H | 44 C. | 65 hr | 52.3 | 3335.3 |
| A30T Q60R Y93Q S95D I114M D118K A136P D139R S202R R210G W260F L288I L294P S295V | 10.8 | A & H | 44 C. | 65 hr | 44.1 | 2532.9 |
| A30T Q60R Y93Q S95D I114W D118K A136P D139R S202R R210G W260F L288I L294P S295V | 10.8 | A & H | 44 C. | 65 hr | 46.9 | 2651.3 |
| A30T Q60R Y93Q S95D S98D D118K A136P D139R S202R R210G W260F L288I L294P S295V | 10.8 | A & H | 44 C. | 65 hr | 54.3 | 3517.2 |
| A30T Q60R Y93Q S95D D118K A136P D139R N200D S202R R210G W260F L288I L294P S295V | 10.8 | A & H | 44 C. | 65 hr | 37.3 | 2087.7 |
| A30T Q60R Y93Q S95D D118K A136P D139R S202R Q203T R210G W260F L288I L294P S295V | 10.8 | A & H | 44 C. | 65 hr | 43.8 | 2657.3 |
| A30T Q60R Y93Q S95D D118K A136P D139R S202R R210G W260F L288I E290A L294P S295V | 10.8 | A & H | 44 C. | 65 hr | 37.4 | 2218.5 |
| A30T Q60R Y93Q S95D D118K A136P D139R S202R R210G W260F L288I L294P S295V T296S | 10.8 | A & H | 44 C. | 65 hr | 41.7 | 2490.0 |
| A30T Q60R Y93Q S95D D118K A136P D139R S202R R210G N213D W260F L288I L294P S295V | 10.8 | A & H | 44 C. | 65 hr | 49.2 | 3067.7 |
| A30T D34N Q60R Y93Q S95D D118K A136P D139R S202R R210G W260F L288I L294P S295V | 10.8 | A & H | 44 C. | 65 hr | 28.7 | 1761.0 |
| A30T Q60R Y93Q S95D D118K A136P D139R K142S S202R R210G W260F L288I L294P S295V | 10.8 | A & H | 44 C. | 65 hr | 43.9 | 2588.9 |
| A30T Q60R Y93Q S95D D118K A136P D139R K142V S202R R210G W260F L288I L294P S295V | 10.8 | A & H | 44 C. | 65 hr | 47.6 | 2852.4 |
| A30T D57N Q60R Y93Q S95D D118K A136P D139R S202R R210G W260F L288I L294P S295V | 10.8 | A & H | 44 C. | 65 hr | 35.6 | 2011.7 |
| A30T Q60R Y93Q S95D D118K A136P D139R S202R R210G W260F L288I L294P S295V | 10.8 | A & H | 44 C. | 65 hr | 48.2 | 2825.5 |
| A30T Q60R Y93Q S95D D118K A136P D139R S202R R210G W260F T280L L288I L294P S295V | 10.8 | A & H | 44 C. | 65 hr | 55.5 | 3502.1 |
| A30T Q60R Y93Q S95D D118K A136P D139R Y196W S202R R210G W260F L288I L294P S295V | 10.8 | A & H | 44 C. | 65 hr | 31.5 | 1838.6 |
| A30T Q60R Y93Q S95D D118K A136P D139R S202R R210G Q243H W260F L288I L294P S295V | 10.8 | A & H | 44 C. | 65 hr | 49.7 | 3163.0 |
| A30T Q60R K63R Y93Q S95D D118K A136P D139R S202R R210G W260F L288I L294P S295V | 10.8 | A & H | 44 C. | 65 hr | 46.5 | 2717.0 |
| S3P A30T Q60R Y93Q S95D D118K A136P D139R S202R R210G W260F L288I L294P S295V | 10.8 | A & H | 44 C. | 65 hr | 51.4 | 3013.0 |
| A30T Q60R A83P Y93Q S95D D118K A136P D139R S202R R210G W260F L288I L294P S295V | 10.8 | A & H | 44 C. | 65 hr | 49.7 | 2658.0 |
| A30T G47A Q60R Y93Q S95D D118K A136P D139R S202R R210G W260F L288I L294P S295V | 10.8 | A & H | 44 C. | 65 hr | 39.1 | 2187.5 |
| A30T Q60R E77T Y93Q S95D D118K A136P D139R S202R R210G W260F L288I L294P S295V | 10.8 | A & H | 44 C. | 65 hr | 51.6 | 3136.9 |
| A30T Q60R H80K Y93Q S95D D118K A136P D139R S202R R210G W260F L288I L294P S295V | 10.8 | A & H | 44 C. | 65 hr | 47.4 | 2961.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Q60R Y93Q S95D D118K S131T A136P D139R S202R R210G W260F L288I L294P S295V | 10.8 | A & H | 44 C. | 65 hr | 47.1 | 2775.9 |
| A30T Q60R Y93F S95D D118K A136P D139R S202R R210G W260F L288I L294P S295V | 10.8 | A & H | 44 C. | 65 hr | 21.5 | 1286.1 |
| A30T Q60R A83S Y93Q S95D D118K A136P D139R S202R R210G W260F L288I L294P S295V | 10.8 | A & H | 44 C. | 65 hr | 50.3 | 3011.0 |
| F5H A30T Q60R Y93Q S95D D118K A136P D139R S202R R210G W260F L288I L294P S295V | 10.8 | A & H | 44 C. | 65 hr | 20.3 | 1252.3 |
| A30T E41V Q60R Y93Q S95D D118K A136P D139R S202R R210G W260F L288I L294P S295V | 10.8 | A & H | 44 C. | 65 hr | 45.3 | 2662.8 |
| A30T Q60R Y93Q S95D D104G D118K A136P D139R S202R R210G W260F L288I L294P S295V | 10.8 | A & H | 44 C. | 65 hr | 41.3 | 2462.0 |
| A30T Q60R D65E Y93Q S95D D118K A136P D139R S202R R210G W260F L288I L294P S295V | 10.8 | A & H | 44 C. | 65 hr | 41.4 | 2349.2 |
| A30T Q60R R70K Y93Q S95D D118K A136P D139R S202R R210G W260F L288I L294P S295V | 10.8 | A & H | 44 C. | 65 hr | 51.0 | 2992.6 |
| A30T Q60R Y93Q S95D D118K A136P D139R Q169A S202R R210G W260F L288I L294P S295V | 10.8 | A & H | 44 C. | 65 hr | 52.9 | 3075.6 |
| A30T Q60R Y93Q S95D D118K A136P D139R E177Y S202R R210G W260F L288I L294P S295V | 10.8 | A & H | 44 C. | 65 hr | 55.7 | 3891.6 |
| A30T Q60R Y93Q S95D D118K A136P D139R Q184E S202R R210G W260F L288I L294P S295V | 10.8 | A & H | 44 C. | 65 hr | 49.8 | 3312.0 |
| A30T Q60R Y93Q S95D D118K A136P D139R Q184S S202R R210G W260F L288I L294P S295V | 10.8 | A & H | 44 C. | 65 hr | 50.8 | 3160.9 |
| A30T Q60R Y93Q S95D D118K A136P D139R S202R R210G R244K W260F L288I L294P S295V | 10.8 | A & H | 44 C. | 65 hr | 48.9 | 2634.7 |
| A30T Q60R Y93Q S95D D118K A136P D139R S202R R210G W260F N279D L288I L294P S295V | 10.8 | A & H | 44 C. | 65 hr | 56.0 | 3092.3 |
| A30T Q60R Y93Q S95D D118K A136P D139R S202R R210G W260F N279E L288I L294P S295V | 10.8 | A & H | 44 C. | 65 hr | 66.6 | 5117.4 |
| A30T Q60R Y93Q S95D N100Y D118K A136P D139R S202R R210G W260F L288I L294P S295V | 10.8 | A & H | 44 C. | 65 hr | 49.8 | 3141.8 |
| A30T Q60R Y93Q S95D N100H D118K A136P D139R S202R R210G W260F L288I L294P S295V | 10.8 | A & H | 44 C. | 65 hr | 50.3 | 3157.7 |
| A30T Q60R Y93Q S95D D118K A136P D139R S202R R210G W260F N273D L288I L294P S295V | 10.8 | A & H | 44 C. | 65 hr | 53.3 | 3241.2 |
| A30T Q60R Y93Q S95D D118K A136P D139R S202R R210G W260F N272M L288I L294P S295V | 10.8 | A & H | 44 C. | 65 hr | 47.0 | 2320.0 |
| A30T Q60R Y93Q S95D D118K A136P D139R S202R R210G W260F N272T L288I L294P S295V | 10.8 | A & H | 44 C. | 65 hr | 49.4 | 2768.5 |
| A30T Q60R Y93Q S95D D118K A136P D139R S202R R210G W260F N283W L288I L294P S295V | 10.8 | A & H | 44 C. | 65 hr | 54.3 | 3740.8 |
| A30T Q60R Y93Q S95D D118K A136P D139R S202R R210G W260F A276D L288I L294P S295V | 10.8 | A & H | 44 C. | 65 hr | 60.1 | 4037.2 |
| T11R A30T Q60R Y93Q S95D D118K A136P D139R S202R R210G W260F L288I L294P S295V | 10.8 | A & H | 44 C. | 65 hr | 44.0 | 2371.8 |
| A30T Q60R Y93Q S95D D118K A136P D139R H172R S202R R210G W260F L288I L294P S295V | 10.8 | A & H | 44 C. | 65 hr | 39.2 | 2255.2 |
| A30T Q60R Y93Q S95D D118K A136P D139R S202R R210G T228S W260F L288I L294P S295V | 10.8 | A & H | 44 C. | 65 hr | 32.1 | 1697.7 |
| Y6F A30T Q60R Y93Q S95D D118K A136P D139R S202R R210G W260F L288I L294P S295V | 10.8 | A & H | 44 C. | 65 hr | 53.6 | 3125.0 |
| Y6W A30T Q60R Y93Q S95D D118K A136P D139R S202R R210G W260F L288I L294P S295V | 10.8 | A & H | 44 C. | 65 hr | 53.9 | 3398.1 |
| Y13F A30T Q60R Y93Q S95D D118K A136P D139R S202R R210G W260F L288I L294P S295V | 10.8 | A & H | 44 C. | 65 hr | 49.6 | 2960.8 |
| Y13W A30T Q60R Y93Q S95D D118K A136P D139R S202R R210G W260F L288I L294P S295V | 10.8 | A & H | 44 C. | 65 hr | 47.4 | 2383.8 |
| A30T Q60R Y93Q S95D Y105W D118K A136P D139R S202R R210G W260F L288I L294P S295V | 10.8 | A & H | 44 C. | 65 hr | 26.1 | 1360.3 |
| A30T Q60R Y93Q S95D D118K A136P D139R Y196F S202R R210G W260F L288I L294P S295V | 10.8 | A & H | 44 C. | 65 hr | 42.7 | 2379.9 |
| A30T Y32F Q60R Y93Q S95D D118K A136P D139R S202R R210G W260F L288I L294P S295V | 10.8 | A & H | 44 C. | 65 hr | 52.2 | 2971.5 |
| A30T Y32W Q60R Y93Q S95D D118K A136P D139R S202R R210G W260F L288I L294P S295V | 10.8 | A & H | 44 C. | 65 hr | 53.3 | 3465.5 |
| A30T Q60R Y93W S95D D118K A136P D139R S202R R210G W260F L288I L294P S295V | 10.8 | A & H | 44 C. | 65 hr | 24.5 | 1463.7 |
| A30T Q60R Y93Q S95D D118K A136P D139R S202R R210G W260F Y262F L288I L294P S295V | 10.8 | A & H | 44 C. | 65 hr | 31.8 | 1852.5 |
| A30T Q60R Y93Q S95D D118K A136P D139R S202R R210G W260F Y286W L288I L294P S295V | 10.8 | A & H | 44 C. | 65 hr | 26.7 | 1607.2 |
| A30T Q60R Y93Q S95D D118K A136P D139R S202R R210G Q243K W260F L288I L294P S295V | 10.8 | A & H | 44 C. | 65 hr | 29.1 | 1630.3 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T G47K Q60R Y93Q S95D D118K A136P D139R S202R R210G W260F L288I L294P S295V | 10.8 | A & H | 44 C. | 65 hr | 38.1 | 2019.5 |
| A30T Q60R Y93Q S95D D118K A136P D139R N150T S202R R210G W260F L288I L294P S295V | 10.8 | A & H | 44 C. | 65 hr | 54.4 | 3989.6 |
| A30T Y93Q S95D D118K A136P D139R N180R N200T S202R R210G W260F L288I L294P S295V | 10.8 | A & H | 44 C. | 90 hr | 34.0 | 1648.9 |
| A30T Y93Q S95D D118K A136P D139R Q184K N200T S202R R210G W260F L288I L294P S295V | 10.8 | A & H | 44 C. | 90 hr | 29.6 | 1503.4 |
| Y6M A30T Y93Q S95D D118K A136P D139R N200T S202R R210G W260F L288I L294P S295V | 10.8 | A & H | 44 C. | 90 hr | 30.8 | 1487.3 |
| A30T Y93Q S95D D118K A136P D139R N200T S202R R210G W260F T280L L288I L294P S295V | 10.8 | A & H | 44 C. | 90 hr | 32.0 | 1483.9 |
| A1V A30T Y93Q S95D D118K A136P D139R N200T S202R R210G W260F L288I L294P S295V | 10.8 | A & H | 44 C. | 90 hr | 33.9 | 1534.7 |
| A30T Y93Q S95D D118K A136P D139R N200T S202R R210G Q243Y W260F L288I L294P S295V | 10.8 | A & H | 44 C. | 90 hr | 35.2 | 1649.1 |
| A30T Y93Q S95D D118K A136P D139R N200T S202R R210G Q243K W260F L288I L294P S295V | 10.8 | A & H | 44 C. | 90 hr | 35.6 | 1592.4 |
| A30T Y93Q S95D D118K A136P D139R N200T S202R R210G Q243H W260F L288I L294P S295V | 10.8 | A & H | 44 C. | 90 hr | 37.6 | 1862.2 |
| A30T K63R Y93Q S95D D118K A136P D139R N200T S202R R210G W260F L288I L294P S295V | 10.8 | A & H | 44 C. | 90 hr | 30.3 | 1518.5 |
| S3P A30T Y93Q S95D D118K A136P D139R N200T S202R R210G W260F L288I L294P S295V | 10.8 | A & H | 44 C. | 90 hr | 33.7 | 1687.5 |
| A30T T37P Y93Q S95D D118K A136P D139R N200T S202R R210G W260F L288I L294P S295V | 10.8 | A & H | 44 C. | 90 hr | 27.4 | 1334.2 |
| A30T G47A Y93Q S95D D118K A136P D139R N200T S202R R210G W260F L288I L294P S295V | 10.8 | A & H | 44 C. | 90 hr | 21.9 | 1179.0 |
| S8T A30T Y93Q S95D D118K A136P D139R N200T S202R R210G W260F L288I L294P S295V | 10.8 | A & H | 44 C. | 90 hr | 30.3 | 1497.9 |
| A30T G47S Y93Q S95D D118K A136P D139R N200T S202R R210G W260F L288I L294P S295V | 10.8 | A & H | 44 C. | 90 hr | 29.4 | 1474.2 |
| A30T H80K Y93Q S95D D118K A136P D139R N200T S202R R210G W260F L288I L294P S295V | 10.8 | A & H | 44 C. | 90 hr | 34.9 | 1724.2 |
| A30T V82I Y93Q S95D D118K A136P D139R N200T S202R R210G W260F L288I L294P S295V | 10.8 | A & H | 44 C. | 90 hr | 26.5 | 1300.2 |
| A30T A83S Y93Q S95D D118K A136P D139R N200T S202R R210G W260F L288I L294P S295V | 10.8 | A & H | 44 C. | 90 hr | 36.0 | 1626.1 |
| A30T G47K Y93Q S95D D118K A136P D139R N200T S202R R210G W260F L288I L294P S295V | 10.8 | A & H | 44 C. | 90 hr | 32.1 | 1677.0 |
| A30T H80R Y93Q S95D D118K A136P D139R N200T S202R R210G W260F L288I L294P S295V | 10.8 | A & H | 44 C. | 90 hr | 38.1 | 1699.1 |
| A30T Y93Q S95D S111K D118K A136P D139R N200T S202R R210G W260F L288I L294P S295V | 10.8 | A & H | 44 C. | 90 hr | 34.2 | 1626.1 |
| A30T D65E Y93Q S95D D118K A136P D139R N200T S202R R210G W260F L288I L294P S295V | 10.8 | A & H | 44 C. | 90 hr | 24.9 | 1205.6 |
| A30T T37R Y93Q S95D D118K A136P D139R N200T S202R R210G W260F L288I L294P S295V | 10.8 | A & H | 44 C. | 90 hr | 42.5 | 2123.6 |
| A30T R70K Y93Q S95D D118K A136P D139R N200T S202R R210G W260F L288I L294P S295V | 10.8 | A & H | 44 C. | 90 hr | 38.7 | 1961.5 |
| A30T N45G Y93Q S95D D118K A136P D139R N200T S202R R210G W260F L288I L294P S295V | 10.8 | A & H | 44 C. | 90 hr | 28.9 | 1308.4 |
| N18V A30T Y93Q S95D D118K A136P D139R N200T S202R R210G W260F L288I L294P S295V | 10.8 | A & H | 44 C. | 90 hr | 39.2 | 1811.9 |
| N18R A30T Y93Q S95D D118K A136P D139R N200T S202R R210G W260F L288I L294P S295V | 10.8 | A & H | 44 C. | 90 hr | 36.3 | 1722.7 |
| A30T N71S Y93Q S95D D118K A136P D139R N200T S202R R210G W260F L288I L294P S295V | 10.8 | A & H | 44 C. | 90 hr | 29.7 | 1411.0 |
| A30T S74K Y93Q S95D D118K A136P D139R N200T S202R R210G W260F L288I L294P S295V | 10.8 | A & H | 44 C. | 90 hr | 32.8 | 1520.0 |
| A30T Y93Q S95D D118K A136P D139R Y174R N200T S202R R210G W260F L288I L294P S295V | 10.8 | A & H | 44 C. | 90 hr | 27.9 | 1362.6 |
| A30T Y93Q S95D D118K A136P D139R Y174L N200T S202R R210G W260F L288I L294P S295V | 10.8 | A & H | 44 C. | 90 hr | 24.8 | 1250.7 |
| A30T Y93Q S95D D118K A136P D139R Q169R N200T S202R R210G W260F L288I L294P S295V | 10.8 | A & H | 44 C. | 90 hr | 34.9 | 1585.4 |
| A30T Y93Q S95D D118K A136P D139R Q169K N200T S202R R210G W260F L288I L294P S295V | 10.8 | A & H | 44 C. | 90 hr | 29.0 | 1449.3 |
| A30T Y93Q S95D D118K A136P D139R E177S N200T S202R R210G W260F L288I L294P S295V | 10.8 | A & H | 44 C. | 90 hr | 32.5 | 1560.9 |
| A30T Y93Q S95D D118K A136P D139R N150S N200T S202R R210G W260F L288I L294P S295V | 10.8 | A & H | 44 C. | 90 hr | 32.6 | 1574.2 |
| A30T Y93Q S95D D118K A136P D139R N150R N200T S202R R210G W260F L288I L294P S295V | 10.8 | A & H | 44 C. | 90 hr | 30.6 | 1427.1 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R R185G N200T S202R R210G W260F L288I L294P S295V | 10.8 | A & H | 44 C. | 90 hr | 37.4 | 2024.0 |
| A30T Y93Q S95D D118K A136P D139R N200T S202R R210G E234F W260F L288I L294P S295V | 10.8 | A & H | 44 C. | 90 hr | 22.3 | 1152.3 |
| A30T Y93Q S95D D118K A136P D139R N200T S202R R210G E234Y W260F L288I L294P S295V | 10.8 | A & H | 44 C. | 90 hr | 32.4 | 1743.7 |
| A30T Y93Q S95D D118K A136P D139R N200T S202R R210G A235R W260F L288I L294P S295V | 10.8 | A & H | 44 C. | 90 hr | 33.5 | 1457.1 |
| A30T Y93Q S95D D118K A136P D139R N200T S202R R210G A235K W260F L288I L294P S295V | 10.8 | A & H | 44 C. | 90 hr | 33.9 | 1412.3 |
| A30T Y93Q S95D D118K A136P D139R N200T S202R R210G R244K W260F L288I L294P S295V | 10.8 | A & H | 44 C. | 90 hr | 36.0 | 1587.9 |
| A30T Y93Q S95D K116R D118K A136P D139R N200T S202R R210G W260F L288I L294P S295V | 10.8 | A & H | 44 C. | 90 hr | 41.4 | 1842.3 |
| A30T Y93Q S95D D118K A136P D139R N200T S202R R210G W260F N279E L288I L294P S295V | 10.8 | A & H | 44 C. | 90 hr | 45.5 | 2149.3 |
| A30T Y93Q S95D N100Y D118K A136P D139R N200T S202R R210G W260F L288I L294P S295V | 10.8 | A & H | 44 C. | 90 hr | 33.0 | 1741.2 |
| A30T Y93Q S95D N100H D118K A136P D139R N200T S202R R210G W260F L288I L294P S295V | 10.8 | A & H | 44 C. | 90 hr | 38.8 | 1838.0 |
| A30T Y93Q S95D D118K A136P D139R N200T S202R R210G W260F N273D L288I L294P S295V | 10.8 | A & H | 44 C. | 90 hr | 39.0 | 1881.0 |
| A30T Y93Q S95D D118K A136P D139R N200T S202R R210G W260F N273E L288I L294P S295V | 10.8 | A & H | 44 C. | 90 hr | 36.5 | 1799.3 |
| A30T Y93Q S95D D118K A136P D139R N200T S202R R210G W260F N272T L288I L294P S295V | 10.8 | A & H | 44 C. | 90 hr | 32.8 | 1638.4 |
| A30T Y93Q S95D D118K A136P D139R N200T S202R R210G W260F N283W L288I L294P S295V | 10.8 | A & H | 44 C. | 90 hr | 32.1 | 1506.8 |
| A30T Y93Q S95D D118K A136P D139R N200T S202R R210G W260F N283H L288I L294P S295V | 10.8 | A & H | 44 C. | 90 hr | 48.9 | 2550.1 |
| A30T Y93Q S95D D118K A136P D139R N200T S202R R210G W260F A276W L288I L294P S295V | 10.8 | A & H | 44 C. | 90 hr | 30.6 | 1421.9 |
| T11K A30T Y93Q S95D D118K A136P D139R N200T S202R R210G W260F L288I L294P S295V | 10.8 | A & H | 44 C. | 90 hr | 32.5 | 1434.9 |
| T11R A30T Y93Q S95D D118K A136P D139R N200T S202R R210G W260F L288I L294P S295V | 10.8 | A & H | 44 C. | 90 hr | 28.8 | 1357.2 |
| A30T D57N Y93Q S95D D118K A136P D139R N200T S202R R210G W260F L288I L294P S295V | 10.8 | A & H | 44 C. | 90 hr | 35.7 | 1691.4 |
| A30T Y93Q S95D E108S D118K A136P D139R N200T S202R R210G W260F L288I L294P S295V | 10.8 | A & H | 44 C. | 90 hr | 29.1 | 1448.2 |
| A30T Y93Q S95D D118K A136P D139R H172R N200T S202R R210G W260F L288I L294P S295V | 10.8 | A & H | 44 C. | 90 hr | 30.7 | 1425.1 |
| A30T Y93Q S95D D118K A136P D139R N200T S202R R210G T228S W260F L288I L294P S295V | 10.8 | A & H | 44 C. | 90 hr | 20.2 | 1075.2 |
| A30T Y93Q S95D D118K A136P D139R N200T S202R R210G W260F S266A L288I L294P S295V | 10.8 | A & H | 44 C. | 90 hr | 37.8 | 1680.7 |
| A30T Y93Q S95D D118K A136P D139R N200T S202R R210G W260F L288I L294K S295G | 10.8 | A & H | 44 C. | 90 hr | 23.7 | 1147.5 |
| A30T Y93Q S95D D118K A136P D139R N200T S202R R210G W260F L288I L294P S295V | 10.8 | A & H | 44 C. | 90 hr | 33.6 | 1575.8 |
| Y6F A30T Y93Q S95D D118K A136P D139R N200T S202R R210G W260F L288I L294P S295V | 10.8 | A & H | 44 C. | 90 hr | 27.3 | 1331.5 |
| A1G A30T Y93Q S95D D118K A136P D139R N200T S202R R210G W260F L288I L294P S295V | 10.8 | A & H | 44 C. | 90 hr | 37.9 | 1718.8 |
| A30T E77T Y93Q S95D D118K A136P D139R N200T S202R R210G W260F L288I L294P S295V | 10.8 | A & H | 44 C. | 90 hr | 36.1 | 1832.4 |
| A30T Y93Q S95D D118K S131T A136P D139R N200T S202R R210G W260F L288I L294P S295V | 10.8 | A & H | 44 C. | 90 hr | 37.7 | 1520.1 |
| A30T G59Q Y93Q S95D D118K A136P D139R N200T S202R R210G W260F L288I L294P S295V | 10.8 | A & H | 44 C. | 90 hr | 32.3 | 1258.3 |
| A30T Y32W Y93Q S95D D118K A136P D139R N200T S202R R210G W260F L288I L294P S295V | 10.8 | A & H | 44 C. | 90 hr | 45.5 | 1710.8 |
| A30T Y93Q S95D D118K A136P D139R N200T S202R R210G G257A W260F L288I L294P S295V | 10.8 | A & H | 44 C. | 90 hr | 54.1 | 2621.3 |
| A30T Y93Q S95D D104G D118K A136P D139R N200T S202R R210G W260F L288I L294P S295V | 10.8 | A & H | 44 C. | 90 hr | 30.7 | 1433.7 |
| A30T Q35L Y93Q S95D D118K A136P D139R N200T S202R R210G W260F L288I L294P S295V | 10.8 | A & H | 44 C. | 90 hr | 29.8 | 1459.5 |
| A30T Y93Q S95D D118K A136P D139R Q169A N200T S202R R210G W260F L288I L294P S295V | 10.8 | A & H | 44 C. | 90 hr | 32.0 | 1473.3 |
| A30T Y93Q S95D D118K A136P D139R Q184E N200T S202R R210G W260F L288I L294P S295V | 10.8 | A & H | 44 C. | 90 hr | 39.1 | 1756.9 |
| A30T Y93Q S95D D118K A136P D139R Q184S N200T S202R R210G W260F L288I L294P S295V | 10.8 | A & H | 44 C. | 90 hr | 34.9 | 1619.3 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R N200T S202R R210G W260F A276D L288I L294P S295V | 10.8 | A & H | 44 C. | 90 hr | 44.8 | 2089.3 |
| A30T Y93Q S95D D118K A136P D139R N200T S202R R210G N229D W260F L288I L294P S295V | 10.8 | A & H | 44 C. | 90 hr | 22.3 | 1256.7 |
| A30T Y93Q S95D D118K A136P D139R N200T S202R R210G W260F A270D L288I L294P S295V | 10.8 | A & H | 44 C. | 90 hr | 24.0 | 1226.4 |
| A30T Y93Q S95D A97R D118K A136P D139R N200T S202R R210G W260F L288I L294P S295V | 10.8 | A & H | 44 C. | 90 hr | 28.3 | 1441.4 |
| A30T Y93Q S95D A97S D118K A136P D139R N200T S202R R210G W260F L288I L294P S295V | 10.8 | A & H | 44 C. | 90 hr | 29.0 | 1362.3 |
| A30T Y93Q S95D S98P D118K A136P D139R N200T S202R R210G W260F L288I L294P S295V | 10.8 | A & H | 44 C. | 90 hr | 34.4 | 1591.0 |
| A30T Y93F S95D D118K A136P D139R N200T S202R R210G W260F L288I L294P S295V | 10.8 | A & H | 44 C. | 90 hr | 27.2 | 1431.9 |
| A30T Y93Q S95D I114M D118K A136P D139R N200T S202R R210G W260F L288I L294P S295V | 10.8 | A & H | 44 C. | 90 hr | 33.0 | 1543.4 |
| A30T Y93Q S95D S98D D118K A136P D139R N200T S202R R210G W260F L288I L294P S295V | 10.8 | A & H | 44 C. | 90 hr | 41.4 | 1784.8 |
| A30T Y93Q S95D I114W D118K A136P D139R N200T S202R R210G W260F L288I L294P S295V | 10.8 | A & H | 44 C. | 90 hr | 43.5 | 1831.3 |
| A30T Y93Q S95D S98T D118K A136P D139R N200T S202R R210G W260F L288I L294P S295V | 10.8 | A & H | 44 C. | 90 hr | 31.9 | 1389.5 |
| A30T Y93Q S95D I114Q D118K A136P D139R N200T S202R R210G W260F L288I L294P S295V | 10.8 | A & H | 44 C. | 90 hr | 37.3 | 1722.1 |
| A30T Y93Q S95D D118K A136P D139R N200T S202R R210G W260F L288I E290A L294P S295V | 10.8 | A & H | 44 C. | 90 hr | 24.8 | 972.4 |
| A30T Y93Q S95D D118K A136P D139R N200T S202R R210G W260F L288I L294P S295V T296S | 10.8 | A & H | 44 C. | 90 hr | 32.7 | 1586.6 |
| A30T Y93Q S95D D118K A136P D139R N200T S202R R210G W260F L288I L294P S295V F298Y | 10.8 | A & H | 44 C. | 90 hr | 29.5 | 1534.0 |
| A30T Y93Q S95D D118K A136P D139R N200T S202R R210G N213V W260F L288I L294P S295V | 10.8 | A & H | 44 C. | 90 hr | 40.3 | 1870.9 |
| A30T Y93Q S95D D118K A136P D139R K142M N200T S202R R210G W260F L288I L294P S295V | 10.8 | A & H | 44 C. | 90 hr | 37.4 | 1637.0 |
| A30T Y93Q S95D D118K A136P D139R K142S N200T S202R R210G W260F L288I L294P S295V | 10.8 | A & H | 44 C. | 90 hr | 25.5 | 1345.5 |
| A30T Y93Q S95D D118K A136P D139R K142V N200T S202R R210G W260F L288I L294P S295V | 10.8 | A & H | 44 C. | 90 hr | 25.9 | 1287.8 |
| Y6W A30T Y93Q S95D D118K A136P D139R N200T S202R R210G W260F L288I L294P S295V | 10.8 | A & H | 44 C. | 90 hr | 37.9 | 1736.3 |
| Y13F A30T Y93Q S95D D118K A136P D139R N200T S202R R210G W260F L288I L294P S295V | 10.8 | A & H | 44 C. | 90 hr | 34.5 | 1581.6 |
| A30T Y93Q S95D D118K A136P D139R Y174F N200T S202R R210G W260F L288I L294P S295V | 10.8 | A & H | 44 C. | 90 hr | 36.5 | 1665.3 |
| A30T Y93Q S95D D118K A136P D139R Y174W N200T S202R R210G W260F L288I L294P S295V | 10.8 | A & H | 44 C. | 90 hr | 32.2 | 1490.2 |
| A30T Y32F Y93Q S95D D118K A136P D139R N200T S202R R210G W260F L288I L294P S295V | 10.8 | A & H | 44 C. | 90 hr | 43.7 | 1695.0 |
| A30T Y93Q S95D D118K A136P D139R N200T S202R R210G W260F Y286F L288I L294P S295V | 10.8 | A & H | 44 C. | 90 hr | 36.1 | 1638.2 |
| A30T Q60R Y93Q S95D D118K A136P D139R Q184K S202R R210G W260F N279E L288I L294P S295V | 10.8 | A & H | 46 C. | 65 hr | 35.6 | 2881.6 |
| A30T Q60R Y93Q S95D D118K A136P D139R N200T S202R R210G W260F N279E L288I L294P S295V | 10.8 | A & H | 46 C. | 65 hr | 42.2 | 3258.3 |
| A30T Q60R Y93Q S95D D118K A136P D139R S202R R210G W260F N272T N279E L288I L294P S295V | 10.8 | A & H | 46 C. | 65 hr | 36.8 | 2859.1 |
| A30T Q60R Y93Q S95D I114W D118K A136P D139R S202R R210G W260F N279E L288I L294P S295V | 10.8 | A & H | 46 C. | 65 hr | 33.0 | 2763.9 |
| A30T Q60R Y93Q S95D D118K A136P D139R S202R Q203T R210G W260F N279E L288I L294P S295V | 10.8 | A & H | 46 C. | 65 hr | 38.4 | 3073.3 |
| A1V A30T Q60R Y93Q S95D D118K A136P D139R S202R R210G W260F N279E L288I L294P S295V | 10.8 | A & H | 46 C. | 65 hr | 42.8 | 3390.6 |
| A30T Q60R Y93Q S95D D118K A136P D139R S202R R210G Q243Y W260F N279E L288I L294P S295V | 10.8 | A & H | 46 C. | 65 hr | 43.7 | 3511.5 |
| A30T Q60R Y93Q S95D D118K A136P D139R S202R R210G Q243K W260F N279E L288I L294P S295V | 10.8 | A & H | 46 C. | 65 hr | 43.3 | 3542.4 |
| S3P A30T Q60R Y93Q S95D D118K A136P D139R S202R R210G W260F N279E L288I L294P S295V | 10.8 | A & H | 46 C. | 65 hr | 44.3 | 3584.8 |
| A30T T37P Q60R Y93Q S95D D118K A136P D139R S202R R210G W260F N279E L288I L294P S295V | 10.8 | A & H | 46 C. | 65 hr | 37.4 | 3031.7 |
| A30T G47A Q60R Y93Q S95D D118K A136P D139R S202R R210G W260F N279E L288I L294P S295V | 10.8 | A & H | 46 C. | 65 hr | 28.9 | 2315.8 |
| S8T A30T Q60R Y93Q S95D D118K A136P D139R S202R R210G W260F N279E L288I L294P S295V | 10.8 | A & H | 46 C. | 65 hr | 40.6 | 3234.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Q60R E77T Y93Q S95D D118K A136P D139R S202R R210G W260F N279E L288I L294P S295V | 10.8 | A & H | 46 C. | 65 hr | 22.0 | 1640.0 |
| A30T G47S Q60R Y93Q S95D D118K A136P D139R S202R R210G W260F N279E L288I L294P S295V | 10.8 | A & H | 46 C. | 65 hr | 30.4 | 2542.5 |
| A30T Q60R H80K Y93Q S95D D118K A136P D139R S202R R210G W260F N279E L288I L294P S295V | 10.8 | A & H | 46 C. | 65 hr | 38.0 | 2954.9 |
| A30T Q60R Y93Q S95D D118K S131T A136P D139R S202R R210G W260F N279E L288I L294P S295V | 10.8 | A & H | 46 C. | 65 hr | 40.7 | 3104.4 |
| A30T Q60R A83S Y93Q S95D D118K A136P D139R S202R R210G W260F N279E L288I L294P S295V | 10.8 | A & H | 46 C. | 65 hr | 48.0 | 3945.5 |
| A30T Q60R E77N Y93Q S95D D118K A136P D139R S202R R210G W260F N279E L288I L294P S295V | 10.8 | A & H | 46 C. | 65 hr | 36.6 | 2891.0 |
| A30T G47K Q60R Y93Q S95D D118K A136P D139R S202R R210G W260F N279E L288I L294P S295V | 10.8 | A & H | 46 C. | 65 hr | 32.7 | 2634.8 |
| A30T Q60R H80R Y93Q S95D D118K A136P D139R S202R R210G W260F N279E L288I L294P S295V | 10.8 | A & H | 46 C. | 65 hr | 36.1 | 2891.2 |
| A30T E41V Q60R Y93Q S95D D118K A136P D139R S202R R210G W260F N279E L288I L294P S295V | 10.8 | A & H | 46 C. | 65 hr | 27.5 | 2038.5 |
| A30T Q60R Y93Q S95D S111K D118K A136P D139R S202R R210G W260F N279E L288I L294P S295V | 10.8 | A & H | 46 C. | 65 hr | 41.8 | 3337.2 |
| A30T T37R Q60R Y93Q S95D D118K A136P D139R S202R R210G W260F N279E L288I L294P S295V | 10.8 | A & H | 46 C. | 65 hr | 52.2 | 3975.3 |
| A30T Q60R R70K Y93Q S95D D118K A136P D139R S202R R210G W260F N279E L288I L294P S295V | 10.8 | A & H | 46 C. | 65 hr | 37.1 | 3124.8 |
| A30T N45G Q60R Y93Q S95D D118K A136P D139R S202R R210G W260F N279E L288I L294P S295V | 10.8 | A & H | 46 C. | 65 hr | 39.0 | 2947.1 |
| N18V A30T Q60R Y93Q S95D D118K A136P D139R S202R R210G W260F N279E L288I L294P S295V | 10.8 | A & H | 46 C. | 65 hr | 43.4 | 3304.6 |
| N18R A30T Q60R Y93Q S95D D118K A136P D139R S202R R210G W260F N279E L288I L294P S295V | 10.8 | A & H | 46 C. | 65 hr | 32.0 | 2642.5 |
| A30T Q60R N71S Y93Q S95D D118K A136P D139R S202R R210G W260F N279E L288I L294P S295V | 10.8 | A & H | 46 C. | 65 hr | 45.8 | 3839.1 |
| A30T Q60R Y93Q S95D D118K A136P D139R N180R S202R R210G W260F N279E L288I L294P S295V | 10.8 | A & H | 46 C. | 65 hr | 39.0 | 3111.0 |
| A30T Q60R Y93Q S95D D118K A136P D139R Q169R S202R R210G W260F N279E L288I L294P S295V | 10.8 | A & H | 46 C. | 65 hr | 39.9 | 3254.8 |
| A30T Q60R Y93Q S95D D118K A136P D139R E177S S202R R210G W260F N279E L288I L294P S295V | 10.8 | A & H | 46 C. | 65 hr | 35.2 | 2874.7 |
| A30T Q60R Y93Q S95D D118K A136P D139R N150T S202R R210G W260F N279E L288I L294P S295V | 10.8 | A & H | 46 C. | 65 hr | 39.2 | 3337.4 |
| A30T Q60R Y93Q S95D D118K A136P D139R N150S S202R R210G W260F N279E L288I L294P S295V | 10.8 | A & H | 46 C. | 65 hr | 40.8 | 3202.1 |
| A30T Q60R Y93Q S95D D118K A136P D139R N150R S202R R210G W260F N279E L288I L294P S295V | 10.8 | A & H | 46 C. | 65 hr | 38.3 | 3091.3 |
| A30T Q60R Y93Q S95D D118K A136P D139R Q184E S202R R210G W260F N279E L288I L294P S295V | 10.8 | A & H | 46 C. | 65 hr | 44.9 | 3681.2 |
| A30T Q60R Y93Q S95D D118K A136P D139R Q184S S202R R210G W260F N279E L288I L294P S295V | 10.8 | A & H | 46 C. | 65 hr | 36.4 | 2548.9 |
| A30T Q60R Y93Q S95D D118K A136P D139R R185G S202R R210G W260F N279E L288I L294P S295V | 10.8 | A & H | 46 C. | 65 hr | 38.7 | 3190.8 |
| A30T Q60R Y93Q S95D D118K A136P D139R S202R R210G E234Y W260F N279E L288I L294P S295V | 10.8 | A & H | 46 C. | 65 hr | 29.9 | 2460.6 |
| A30T Q60R Y93Q S95D D118K A136P D139R S202R R210G A235R W260F N279E L288I L294P S295V | 10.8 | A & H | 46 C. | 65 hr | 31.3 | 2401.4 |
| A30T Q60R Y93Q S95D D118K A136P D139R S202R R210G A235K W260F N279E L288I L294P S295V | 10.8 | A & H | 46 C. | 65 hr | 35.5 | 2723.2 |
| A30T Q60R Y93Q S95D K116R D118K A136P D139R S202R R210G W260F N279E L288I L294P S295V | 10.8 | A & H | 46 C. | 65 hr | 45.1 | 3500.9 |
| A30T Q60R Y93Q S95D D118K T119R A136P D139R S202R R210G W260F N279E L288I L294P S295V | 10.8 | A & H | 46 C. | 65 hr | 31.9 | 2771.9 |
| A30T Q60R Y93Q S95D N100H D118K A136P D139R S202R R210G W260F N279E L288I L294P S295V | 10.8 | A & H | 46 C. | 65 hr | 35.3 | 2706.2 |
| A30T Q60R Y93Q S95D D118K A136P D139R S202R R210G W260F N273D N279E L288I L294P S295V | 10.8 | A & H | 46 C. | 65 hr | 37.4 | 3060.8 |
| A30T Q60R Y93Q S95D D118K A136P D139R S202R R210G W260F N273E N279E L288I L294P S295V | 10.8 | A & H | 46 C. | 65 hr | 39.2 | 3145.5 |
| Y6H A30T Q60R Y93Q S95D D118K A136P D139R S202R R210G W260F N279E L288I L294P S295V | 10.8 | A & H | 46 C. | 65 hr | 37.1 | 2783.9 |
| Y6M A30T Q60R Y93Q S95D D118K A136P D139R S202R R210G W260F N279E L288I L294P S295V | 10.8 | A & H | 46 C. | 65 hr | 39.2 | 3121.4 |
| A30T Q60R Y93Q S95D D118K A136P D139R S202R R210G W260F A276E N279E L288I L294P S295V | 10.8 | A & H | 46 C. | 65 hr | 44.4 | 3317.0 |
| T11K A30T Q60R Y93Q S95D D118K A136P D139R S202R R210G W260F N279E L288I L294P S295V | 10.8 | A & H | 46 C. | 65 hr | 34.7 | 2624.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| T11R A30T Q60R Y93Q S95D D118K A136P D139R S202R R210G W260F N279E L288I L294P S295V | 10.8 | A & H | 46 C. | 65 hr | 31.8 | 2663.3 |
| A30T Q60R Y93F S95D D118K A136P D139R S202R R210G W260F N279E L288I L294P S295V | 10.8 | A & H | 46 C. | 65 hr | 35.2 | 2637.3 |
| A30T Q60R Y93Q S95D I114M D118K A136P D139R S202R R210G W260F N279E L288I L294P S295V | 10.8 | A & H | 46 C. | 65 hr | 41.7 | 3445.3 |
| A30T Q60R Y93Q S95D D118K A136P D139R S202R R210G W260F A276W N279E L288I L294P S295V | 10.8 | A & H | 46 C. | 65 hr | 37.7 | 2883.4 |
| A30T Q60R Y93Q S95D D118K A136P D139R S202R R210G W260F A276D N279E L288I L294P S295V | 10.8 | A & H | 46 C. | 65 hr | 39.1 | 3107.7 |
| A30T Q60R Y93Q S95D D118K A136P D139R S202R R210G W260F N279E T280L L288I L294P S295V | 10.8 | A & H | 46 C. | 65 hr | 36.9 | 3012.1 |
| A30T Q60R Y93Q S95D D118K A136P D139R S202R R210G W260F N279E N283W L288I L294P S295V | 10.8 | A & H | 46 C. | 65 hr | 32.7 | 2644.7 |
| A30T Q60R Y93Q S95D D118K A136P D139R S202R R210G W260F N279E N283H L288I L294P S295V | 10.8 | A & H | 46 C. | 65 hr | 38.8 | 3000.0 |
| A30T Q60R Y93Q S95D S98D D118K A136P D139R S202R R210G W260F N279E L288I L294P S295V | 10.8 | A & H | 46 C. | 65 hr | 46.0 | 3689.0 |
| A30T Q60R Y93Q S95D D118K A136P D139R N200D S202R R210G W260F N279E L288I L294P S295V | 10.8 | A & H | 46 C. | 65 hr | 35.4 | 2809.9 |
| A30T Q60R Y93Q S95D D118K A136P D139R S202R R210G W260F N279E L288I L294P S295V T296S | 10.8 | A & H | 46 C. | 65 hr | 36.3 | 2755.5 |
| A30T Q60R Y93Q S95D D118K A136P D139R S202R R210G N213V W260F N279E L288I L294P S295V | 10.8 | A & H | 46 C. | 65 hr | 38.8 | 3134.1 |
| A30T Q60R Y93Q S95D D118K A136P D139R S202R R210G N213D W260F N279E L288I L294P S295V | 10.8 | A & H | 46 C. | 65 hr | 35.7 | 2924.9 |
| A30T Q60R Y93Q S95D D118K A136P D139R K142M S202R R210G W260F N279E L288I L294P S295V | 10.8 | A & H | 46 C. | 65 hr | 36.4 | 2818.9 |
| A30T Q60R Y93Q S95D D118K A136P D139R K142V S202R R210G W260F N279E L288I L294P S295V | 10.8 | A & H | 46 C. | 65 hr | 42.7 | 3371.5 |
| A30T D57N Q60R Y93Q S95D D118K A136P D139R S202R R210G W260F N279E L288I L294P S295V | 10.8 | A & H | 46 C. | 65 hr | 36.8 | 2863.3 |
| Y6F A30T Q60R Y93Q S95D D118K A136P D139R S202R R210G W260F N279E L288I L294P S295V | 10.8 | A & H | 46 C. | 65 hr | 32.7 | 2642.5 |
| Y6W A30T Q60R Y93Q S95D D118K A136P D139R S202R R210G W260F N279E L288I L294P S295V | 10.8 | A & H | 46 C. | 65 hr | 37.9 | 3066.9 |
| Y13W A30T Q60R Y93Q S95D D118K A136P D139R S202R R210G W260F N279E L288I L294P S295V | 10.8 | A & H | 46 C. | 65 hr | 32.7 | 2600.1 |
| A30T Q60R Y93Q S95D D118K A136P D139R Y174W S202R R210G W260F N279E L288I L294P S295V | 10.8 | A & H | 46 C. | 65 hr | 33.3 | 2695.3 |
| A30T Q60R Y93Q S95D D118K A136P D139R Y196F S202R R210G W260F N279E L288I L294P S295V | 10.8 | A & H | 46 C. | 65 hr | 28.6 | 2363.9 |
| A30T Q60R Y93Q S95D D118K A136P D139R N150T Q184E S202R R210G W260F L288I L294P S295V | 10.8 | A & H | 46 C. | 65 hr | 28.4 | 1889.2 |
| A30T Q60R Y93Q S95D D118K T119R A136P D139R N150T S202R R210G W260F L288I L294P S295V | 10.8 | A & H | 46 C. | 65 hr | 22.0 | 1524.7 |
| Y6H A30T Q60R Y93Q S95D D118K A136P D139R N150T S202R R210G W260F L288I L294P S295V | 10.8 | A & H | 46 C. | 65 hr | 27.4 | 2097.1 |
| A30T Q60R Y93Q S95D D118K A136P D139R N150T S202R R210G W260F T280L L288I L294P S295V | 10.8 | A & H | 46 C. | 65 hr | 36.8 | 2701.3 |
| A30T Q60R Y93Q S95D S98D D118K A136P D139R N150T S202R R210G W260F L288I L294P S295V | 10.8 | A & H | 46 C. | 65 hr | 35.2 | 2427.4 |
| A1V A30T Q60R Y93Q S95D D118K A136P D139R N150T S202R R210G W260F L288I L294P S295V | 10.8 | A & H | 46 C. | 65 hr | 43.7 | 2601.1 |
| A30T Q60R Y93Q S95D D118K A136P D139R N150T S202R R210G Q243Y W260F L288I L294P S295V | 10.8 | A & H | 46 C. | 65 hr | 43.2 | 3216.0 |
| A30T Q60R Y93Q S95D D118K A136P D139R N150T S202R R210G Q243K W260F L288I L294P S295V | 10.8 | A & H | 46 C. | 65 hr | 43.5 | 3026.6 |
| A30T Q60R Y93Q S95D D118K A136P D139R N150T S202R R210G Q243H W260F L288I L294P S295V | 10.8 | A & H | 46 C. | 65 hr | 40.4 | 2777.9 |
| A30T T37P Q60R Y93Q S95D D118K A136P D139R N150T S202R R210G W260F L288I L294P S295V | 10.8 | A & H | 46 C. | 65 hr | 34.7 | 2415.7 |
| A30T G47A Q60R Y93Q S95D D118K A136P D139R N150T S202R R210G W260F L288I L294P S295V | 10.8 | A & H | 46 C. | 65 hr | 26.6 | 1790.0 |
| S8T A30T Q60R Y93Q S95D D118K A136P D139R N150T S202R R210G W260F L288I L294P S295V | 10.8 | A & H | 46 C. | 65 hr | 34.4 | 2322.7 |
| A30T Q60R H80K Y93Q S95D D118K A136P D139R N150T S202R R210G W260F L288I L294P S295V | 10.8 | A & H | 46 C. | 65 hr | 42.3 | 2891.5 |
| A30T Q60R Y93Q S95D D118K A136P D139R N150T S202R R210G W260F A276E L288I L294P S295V | 10.8 | A & H | 46 C. | 65 hr | 43.6 | 3149.9 |
| A30T Q60R H80R Y93Q S95D D118K A136P D139R N150T S202R R210G W260F L288I L294P S295V | 10.8 | A & H | 46 C. | 65 hr | 31.0 | 2937.8 |
| A30T Q60R Y93Q S95D S111R D118K A136P D139R N150T S202R R210G W260F L288I L294P S295V | 10.8 | A & H | 46 C. | 65 hr | 27.3 | 2290.8 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Q60R D65E Y93Q S95D D118K A136P D139R N150T S202R R210G W260F L288I L294P S295V | 10.8 | A & H | 46 C. | 65 hr | 32.3 | 2405.0 |
| A30T T37R Q60R Y93Q S95D D118K A136P D139R N150T S202R R210G W260F L288I L294P S295V | 10.8 | A & H | 46 C. | 65 hr | 38.4 | 2683.3 |
| A30T Q60R R70K Y93Q S95D D118K A136P D139R N150T S202R R210G W260F L288I L294P S295V | 10.8 | A & H | 46 C. | 65 hr | 33.0 | 2130.6 |
| A30T N45G Q60R Y93Q S95D D118K A136P D139R N150T S202R R210G W260F L288I L294P S295V | 10.8 | A & H | 46 C. | 65 hr | 36.8 | 2514.4 |
| N18R A30T Q60R Y93Q S95D D118K A136P D139R N150T S202R R210G W260F L288I L294P S295V | 10.8 | A & H | 46 C. | 65 hr | 33.2 | 2164.0 |
| A30T Q60R N71S Y93Q S95D D118K A136P D139R N150T S202R R210G W260F L288I L294P S295V | 10.8 | A & H | 46 C. | 65 hr | 36.0 | 2440.3 |
| A30T Q60R Y93Q S95D D118K A136P D139R N150T N180T S202R R210G W260F L288I L294P S295V | 10.8 | A & H | 46 C. | 65 hr | 36.3 | 2430.5 |
| A30T Q60R Y93Q S95D D118K A136P D139R N150T Q169R S202R R210G W260F L288I L294P S295V | 10.8 | A & H | 46 C. | 65 hr | 32.4 | 2305.0 |
| A30T Q60R Y93Q S95D D118K A136P D139R N150T E177S S202R R210G W260F L288I L294P S295V | 10.8 | A & H | 46 C. | 65 hr | 39.8 | 2695.4 |
| A30T Q60R Y93Q S95D D118K A136P D139R N150S S202R R210G W260F L288I L294P S295V | 10.8 | A & H | 46 C. | 65 hr | 36.7 | 2444.4 |
| A30T Q60R Y93Q S95D D118K A136P D139R N150R S202R R210G W260F L288I L294P S295V | 10.8 | A & H | 46 C. | 65 hr | 41.1 | 2760.3 |
| A30T Q60R Y93Q S95D D118K A136P D139R N150T Q184K S202R R210G W260F L288I L294P S295V | 10.8 | A & H | 46 C. | 65 hr | 35.7 | 2509.9 |
| A30T Q60R Y93Q S95D D118K A136P D139R N150T Q184S S202R R210G W260F L288I L294P S295V | 10.8 | A & H | 46 C. | 65 hr | 23.8 | 1711.4 |
| A30T Q60R Y93Q S95D D118K A136P D139R N150T R185G S202R R210G W260F L288I L294P S295V | 10.8 | A & H | 46 C. | 65 hr | 35.1 | 2340.5 |
| A30T Q60R Y93Q S95D D118K A136P D139R N150T S202R R210G A235R W260F L288I L294P S295V | 10.8 | A & H | 46 C. | 65 hr | 29.0 | 1825.1 |
| A30T Q60R Y93Q S95D D118K A136P D139R N150T S202R R210G A235K W260F L288I L294P S295V | 10.8 | A & H | 46 C. | 65 hr | 34.8 | 2426.7 |
| A30T Q60R Y93Q S95D D118K A136P D139R N150T N200T S202R R210G W260F L288I L294P S295V | 10.8 | A & H | 46 C. | 65 hr | 39.5 | 2836.9 |
| A30T Q60R Y93Q S95D D118K A136P D139R N150T S202R R210G W260F N279D L288I L294P S295V | 10.8 | A & H | 46 C. | 65 hr | 46.1 | 2769.7 |
| A30T Q60R Y93Q S95D N100H D118K A136P D139R N150T S202R R210G W260F L288I L294P S295V | 10.8 | A & H | 46 C. | 65 hr | 23.6 | 1711.4 |
| A30T Q60R Y93Q S95D D118K A136P D139R N150T S202R R210G W260F N273D L288I L294P S295V | 10.8 | A & H | 46 C. | 65 hr | 51.7 | 3157.8 |
| A30T Q60R Y93Q S95D D118K A136P D139R N150T S202R R210G W260F N273E L288I L294P S295V | 10.8 | A & H | 46 C. | 65 hr | 27.7 | 2016.5 |
| Y6M A30T Q60R Y93Q S95D D118K A136P D139R N150T S202R R210G W260F L288I L294P S295V | 10.8 | A & H | 46 C. | 65 hr | 31.1 | 2149.0 |
| A30T Q60R Y93Q S95D D118K A136P D139R N150T S202R R210G W260F N272M L288I L294P S295V | 10.8 | A & H | 46 C. | 65 hr | 34.7 | 2194.5 |
| A30T Q60R Y93Q S95D D118K A136P D139R N150T S202R R210G W260F N272T L288I L294P S295V | 10.8 | A & H | 46 C. | 65 hr | 39.9 | 2527.9 |
| A30T Q60R Y93Q S95D D118K A136P D139R N150T S202R R210G W260F N283W L288I L294P S295V | 10.8 | A & H | 46 C. | 65 hr | 38.5 | 2288.2 |
| A30T Q60R Y93Q S95D D118K A136P D139R N150T S202R R210G W260F N283H L288I L294P S295V | 10.8 | A & H | 46 C. | 65 hr | 43.4 | 2810.4 |
| A30T Q60R Y93Q S95D D118K A136P D139R N150T S202R R210G W260F A276W L288I L294P S295V | 10.8 | A & H | 46 C. | 65 hr | 45.9 | 2725.6 |
| A30T Q60R Y93Q S95D D118K A136P D139R N150T S202R R210G W260F A276D L288I L294P S295V | 10.8 | A & H | 46 C. | 65 hr | 29.4 | 2120.6 |
| T11K A30T Q60R Y93Q S95D D118K A136P D139R N150T S202R R210G W260F L288I L294P S295V | 10.8 | A & H | 46 C. | 65 hr | 28.0 | 2038.5 |
| T11R A30T Q60R Y93Q S95D D118K A136P D139R N150T S202R R210G W260F L288I L294P S295V | 10.8 | A & H | 46 C. | 65 hr | 29.2 | 2046.6 |
| A30T Q60R Y93Q S95D D118K A136P D139R N150T S202R Q203T R210G W260F L288I L294P S295V | 10.8 | A & H | 46 C. | 65 hr | 37.6 | 2271.6 |
| A30T Q60R Y93Q S95D D118K A136P D139R N150T S202R R210G W260F L288I L294P S295V T296S | 10.8 | A & H | 46 C. | 65 hr | 28.8 | 2052.5 |
| A30T Q60R Y93Q S95D D118K A136P D139R N150T S202R R210G W260F L288I L294P S295V F298Y | 10.8 | A & H | 46 C. | 65 hr | 36.1 | 2465.8 |
| A30T Q60R Y93Q S95D D118K A136P D139R N150T S202R R210G N213D W260F L288I L294P S295V | 10.8 | A & H | 46 C. | 65 hr | 42.3 | 2753.1 |
| A30T Q60R Y93Q S95D D118K A136P D139R K142M N150T S202R R210G W260F L288I L294P S295V | 10.8 | A & H | 46 C. | 65 hr | 41.2 | 2823.7 |
| A30T Q60R Y93Q S95D D118K A136P D139R K142V N150T S202R R210G W260F L288I L294P S295V | 10.8 | A & H | 46 C. | 65 hr | 35.0 | 2438.7 |
| A30T D57N Q60R Y93Q S95D D118K A136P D139R N150T S202R R210G W260F L288I L294P S295V | 10.8 | A & H | 46 C. | 65 hr | 35.7 | 2173.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y6F A30T Q60R Y93Q S95D D118K A136P D139R N150T S202R R210G W260F L288I L294P S295V | 10.8 | A & H | 46 C. | 65 hr | 30.7 | 1988.5 |
| Y6W A30T Q60R Y93Q S95D D118K A136P D139R N150T S202R R210G W260F L288I L294P S295V | 10.8 | A & H | 46 C. | 65 hr | 33.4 | 2310.0 |
| Y13F A30T Q60R Y93Q S95D D118K A136P D139R N150T S202R R210G W260F L288I L294P S295V | 10.8 | A & H | 46 C. | 65 hr | 39.1 | 2559.7 |
| A30T Q60R Y93Q S95D D118K A136P D139R N150T Y174W S202R R210G W260F L288I L294P S295V | 10.8 | A & H | 46 C. | 65 hr | 21.8 | 1712.3 |
| A30T Q60R Y93Q S95D D118K A136P D139R N150T Y196F S202R R210G W260F L288I L294P S295V | 10.8 | A & H | 46 C. | 65 hr | 24.8 | 1719.0 |
| A30T Q60R Y93Q S95D D118K A136P D139R N150T Y196W S202R R210G W260F L288I L294P S295V | 10.8 | A & H | 46 C. | 65 hr | 22.4 | 1640.5 |
| A30T Y32W Q60R Y93Q S95D D118K A136P D139R S202R R210G W260F N279E L288I L294P S295V | 10.8 | A & H | 46 C. | 65 hr | 43.5 | 3997.8 |
| A30T Q60R Y93W S95D D118K A136P D139R S202R R210G W260F N279E L288I L294P S295V | 10.8 | A & H | 46 C. | 65 hr | 20.3 | 2132.1 |
| A30T Q60R Y93Q S95D D118K A136P D139R S202R R210G W260F Y262F N279E L288I L294P S295V | 10.8 | A & H | 46 C. | 65 hr | 20.3 | 2082.8 |
| A30T Q60R Y93Q S95D D118K A136P D139R S202R R210G W260F N279E Y286F L288I L294P S295V | 10.8 | A & H | 46 C. | 65 hr | 31.9 | 3054.0 |
| A30T Q60R Y93Q S95D D118K A136P D139R S202R R210G W260F N279E Y286W L288I L294P S295V | 10.8 | A & H | 46 C. | 65 hr | 22.6 | 2438.9 |
| A30T Q60R Y93Q S95D A136P D139R S202R R210G W260F N279E L288I L294P S295V | 10.8 | A & H | 46 C. | 65 hr | 34.1 | 3243.7 |
| A30T Q60R Y93Q S95D D118K A136P D139R R210G W260F N279E L288I L294P S295V | 10.8 | A & H | 46 C. | 65 hr | 32.7 | 2976.0 |
| A30T Y32F Q60R Y93Q S95D D118K A136P D139R N150T S202R R210G W260F L288I L294P S295V | 10.8 | A & H | 46 C. | 65 hr | 22.6 | 1640.5 |
| A30T Y32W Q60R Y93Q S95D D118K A136P D139R N150T S202R R210G W260F L288I L294P S295V | 10.8 | A & H | 46 C. | 65 hr | 26.6 | 2280.7 |
| A30T Q60R Y93Q S95D D118K A136P D139R N150T S202R R210G W260F Y286F L288I L294P S295V | 10.8 | A & H | 46 C. | 65 hr | 21.0 | 1949.9 |
| A30T Y32F Y93Q S95D D118K A136P D139R N200T S202R R210G W260F N283H L288I L294P S295V | 10.8 | A & H | 46 C. | 65 hr | 36.2 | 2897.8 |
| A30T Y32W Y93Q S95D D118K A136P D139R N200T S202R R210G W260F N283H L288I L294P S295V | 10.8 | A & H | 46 C. | 65 hr | 20.8 | 2361.1 |
| A30T Y93Q S95D D118K A136P D139R N200T S202R R210G W260F N283H Y286F L288I L294P S295V | 10.8 | A & H | 46 C. | 65 hr | 20.2 | 1973.7 |
| A30T Y93Q S95D D118K A136P D139R E177Y N200T S202R R210G W260F N283H L288I L294P S295V | 10.8 | A & H | 46 C. | 65 hr | 31.7 | 2229.3 |
| A30T Y93Q S95D D118K A136P D139R N200T S202R R210G A235R W260F N283H L288I L294P S295V | 10.8 | A & H | 46 C. | 65 hr | 24.3 | 1923.2 |
| Y6M A30T Y93Q S95D D118K A136P D139R N200T S202R R210G W260F N283H L288I L294P S295V | 10.8 | A & H | 46 C. | 65 hr | 28.4 | 1979.1 |
| A30T D57N Y93Q S95D D118K A136P D139R N200T S202R R210G W260F N283H L288I L294P S295V | 10.8 | A & H | 46 C. | 65 hr | 28.0 | 2061.9 |
| A30T Y93Q S95D D118K A136P D139R N200T S202R R210G W260F N279D N283H L288I L294P S295V | 10.8 | A & H | 46 C. | 65 hr | 32.5 | 2191.2 |
| A1G A30T Y93Q S95D D118K A136P D139R N200T S202R R210G W260F N283H L288I L294P S295V | 10.8 | A & H | 46 C. | 65 hr | 34.5 | 2510.0 |
| A1V A30T Y93Q S95D D118K A136P D139R N200T S202R R210G W260F N283H L288I L294P S295V | 10.8 | A & H | 46 C. | 65 hr | 35.3 | 2341.9 |
| A30T Y93Q S95D D118K A136P D139R N200T S202R R210G Q243Y W260F N283H L288I L294P S295V | 10.8 | A & H | 46 C. | 65 hr | 39.0 | 2677.5 |
| A30T Y93Q S95D D118K A136P D139R N200T S202R R210G Q243K W260F N283H L288I L294P S295V | 10.8 | A & H | 46 C. | 65 hr | 40.9 | 2686.4 |
| A30T Y93Q S95D D118K A136P D139R N200T S202R R210G Q243H W260F N283H L288I L294P S295V | 10.8 | A & H | 46 C. | 65 hr | 33.7 | 2380.1 |
| A30T K63R Y93Q S95D D118K A136P D139R N200T S202R R210G W260F N283H L288I L294P S295V | 10.8 | A & H | 46 C. | 65 hr | 26.8 | 2057.0 |
| A30T T37P Y93Q S95D D118K A136P D139R N200T S202R R210G W260F N283H L288I L294P S295V | 10.8 | A & H | 46 C. | 65 hr | 30.3 | 2085.2 |
| A30T G47A Y93Q S95D D118K A136P D139R N200T S202R R210G W260F N283H L288I L294P S295V | 10.8 | A & H | 46 C. | 65 hr | 24.6 | 1875.9 |
| S8T A30T Y93Q S95D D118K A136P D139R N200T S202R R210G W260F N283H L288I L294P S295V | 10.8 | A & H | 46 C. | 65 hr | 35.8 | 2485.6 |
| A30T G47S Y93Q S95D D118K A136P D139R N200T S202R R210G W260F N283H L288I L294P S295V | 10.8 | A & H | 46 C. | 65 hr | 33.8 | 2601.8 |
| A30T H80K Y93Q S95D D118K A136P D139R N200T S202R R210G W260F N283H L288I L294P S295V | 10.8 | A & H | 46 C. | 65 hr | 31.4 | 2232.0 |
| A30T Y93Q S95D D118K S131T A136P D139R N200T S202R R210G W260F N283H L288I L294P S295V | 10.8 | A & H | 46 C. | 65 hr | 28.6 | 1997.2 |
| A30T Y93Q S95D D118K A136P D139R N200T S202R R210G W260F A276E N283H L288I L294P S295V | 10.8 | A & H | 46 C. | 65 hr | 37.5 | 2607.4 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| A30T E77N Y93Q S95D D118K A136P D139R N200T S202R R210G W260F N283H L288I L294P S295V | 10.8 | A & H | 46 C. | 65 hr | 31.7 | 2443.3 |
| A30T G47K Y93Q S95D D118K A136P D139R N200T S202R R210G W260F N283H L288I L294P S295V | 10.8 | A & H | 46 C. | 65 hr | 31.6 | 2377.1 |
| A30T H80R Y93Q S95D D118K A136P D139R N200T S202R R210G W260F N283H L288I L294P S295V | 10.8 | A & H | 46 C. | 65 hr | 25.4 | 1742.6 |
| A30T E41V Y93Q S95D D118K A136P D139R N200T S202R R210G W260F N283H L288I L294P S295V | 10.8 | A & H | 46 C. | 65 hr | 37.3 | 2653.0 |
| A30T Y93Q S95D S111K D118K A136P D139R N200T S202R R210G W260F N283H L288I L294P S295V | 10.8 | A & H | 46 C. | 65 hr | 33.4 | 2327.5 |
| A30T D65E Y93Q S95D D118K A136P D139R N200T S202R R210G W260F N283H L288I L294P S295V | 10.8 | A & H | 46 C. | 65 hr | 27.3 | 1902.6 |
| A30T T37R Y93Q S95D D118K A136P D139R N200T S202R R210G W260F N283H L288I L294P S295V | 10.8 | A & H | 46 C. | 65 hr | 33.5 | 2236.0 |
| A30T R70K Y93Q S95D D118K A136P D139R N200T S202R R210G W260F N283H L288I L294P S295V | 10.8 | A & H | 46 C. | 65 hr | 33.2 | 2364.3 |
| A30T N45G Y93Q S95D D118K A136P D139R N200T S202R R210G W260F N283H L288I L294P S295V | 10.8 | A & H | 46 C. | 65 hr | 34.8 | 2478.3 |
| A30T Q35L Y93Q S95D D118K A136P D139R N200T S202R R210G W260F N283H L288I L294P S295V | 10.8 | A & H | 46 C. | 65 hr | 26.5 | 1994.9 |
| N18V A30T Y93Q S95D D118K A136P D139R N200T S202R R210G W260F N283H L288I L294P S295V | 10.8 | A & H | 46 C. | 65 hr | 38.8 | 2723.0 |
| N18R A30T Y93Q S95D D118K A136P D139R N200T S202R R210G W260F N283H L288I L294P S295V | 10.8 | A & H | 46 C. | 65 hr | 23.5 | 1820.4 |
| A30T N71S Y93Q S95D D118K A136P D139R N200T S202R R210G W260F N283H L288I L294P S295V | 10.8 | A & H | 46 C. | 65 hr | 30.6 | 2090.8 |
| A30T Y93Q S95D D118K A136P D139R N180R N200T S202R R210G W260F N283H L288I L294P S295V | 10.8 | A & H | 46 C. | 65 hr | 31.1 | 2339.1 |
| A30T Y93Q S95D D118K A136P D139R Q169R N200T S202R R210G W260F N283H L288I L294P S295V | 10.8 | A & H | 46 C. | 65 hr | 36.7 | 2373.8 |
| A30T Y93Q S95D D118K A136P D139R E177S N200T S202R R210G W260F N283H L288I L294P S295V | 10.8 | A & H | 46 C. | 65 hr | 35.8 | 2339.7 |
| A30T Y93Q S95D D118K A136P D139R N150T N200T S202R R210G W260F N283H L288I L294P S295V | 10.8 | A & H | 46 C. | 65 hr | 32.0 | 2334.4 |
| A30T Y93Q S95D D118K A136P D139R N150S N200T S202R R210G W260F N283H L288I L294P S295V | 10.8 | A & H | 46 C. | 65 hr | 33.8 | 2281.6 |
| A30T Y93Q S95D D118K A136P D139R N150N N200T S202R R210G W260F N283H L288I L294P S295V | 10.8 | A & H | 46 C. | 65 hr | 32.0 | 2219.7 |
| A30T Y93Q S95D D118K A136P D139R Q184E N200T S202R R210G W260F N283H L288I L294P S295V | 10.8 | A & H | 46 C. | 65 hr | 32.7 | 2331.0 |
| A30T Y93Q S95D D118K A136P D139R Q184K N200T S202R R210G W260F N283H L288I L294P S295V | 10.8 | A & H | 46 C. | 65 hr | 31.4 | 2150.7 |
| A30T Y93Q S95D D118K A136P D139R R185G N200T S202R R210G W260F N283H L288I L294P S295V | 10.8 | A & H | 46 C. | 65 hr | 36.6 | 2471.9 |
| A30T Y93Q S95D D118K A136P D139R N200T S202R R210G E234Y W260F N283H L288I L294P S295V | 10.8 | A & H | 46 C. | 65 hr | 20.2 | 1483.1 |
| A30T Y93Q S95D D118K A136P D139R N200T S202R R210G A235K W260F N283H L288I L294P S295V | 10.8 | A & H | 46 C. | 65 hr | 30.4 | 2146.6 |
| A30T Y93Q S95D K116R D118K A136P D139R N200T S202R R210G W260F N283H L288I L294P S295V | 10.8 | A & H | 46 C. | 65 hr | 29.6 | 2266.8 |
| A30T Y93Q S95D D118K T119R A136P D139R N200T S202R R210G W260F N283H L288I L294P S295V | 10.8 | A & H | 46 C. | 65 hr | 21.5 | 1742.8 |
| A30T Y93Q S95D N100H D118K A136P D139R N200T S202R R210G W260F N283H L288I L294P S295V | 10.8 | A & H | 46 C. | 65 hr | 30.5 | 2074.7 |
| A30T Y93Q S95D D118K A136P D139R N200T S202R R210G W260F N273D N283H L288I L294P S295V | 10.8 | A & H | 46 C. | 65 hr | 37.2 | 2553.3 |
| A30T Y93Q S95D D118K A136P D139R N200T S202R R210G W260F N273E N283H L288I L294P S295V | 10.8 | A & H | 46 C. | 65 hr | 34.6 | 2413.6 |
| Y6H A30T Y93Q S95D D118K A136P D139R N200T S202R R210G W260F N283H L288I L294P S295V | 10.8 | A & H | 46 C. | 65 hr | 35.7 | 2497.5 |
| A30T Y93Q S95D D118K A136P D139R N200T S202R R210G W260F N272M N283H L288I L294P S295V | 10.8 | A & H | 46 C. | 65 hr | 28.0 | 2016.5 |
| A30T Y93Q S95D D118K A136P D139R N200T S202R R210G W260F N272T N283H L288I L294P S295V | 10.8 | A & H | 46 C. | 65 hr | 36.1 | 2693.8 |
| A30T Y93Q S95D D118K A136P D139R N200T S202R R210G W260F A276W N283H L288I L294P S295V | 10.8 | A & H | 46 C. | 65 hr | 33.9 | 2510.5 |
| A30T Y93Q S95D D118K A136P D139R N200T S202R R210G W260F A276D N283H L288I L294P S295V | 10.8 | A & H | 46 C. | 65 hr | 40.3 | 2695.7 |
| T11K A30T Y93Q S95D D118K A136P D139R N200T S202R R210G W260F N283H L288I L294P S295V | 10.8 | A & H | 46 C. | 65 hr | 34.6 | 2250.0 |
| T11R A30T Y93Q S95D D118K A136P D139R N200T S202R R210G W260F N283H L288I L294P S295V | 10.8 | A & H | 46 C. | 65 hr | 30.7 | 2269.2 |
| A30T Q60R Y93Q S95D D118K A136P D139R N200T S202R R210G W260F N283H L288I L294P S295V | 10.8 | A & H | 46 C. | 65 hr | 35.2 | 2401.7 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D S98P D118K A136P D139R N200T S202R R210G W260F N283H L288I L294P S295V | 10.8 | A & H | 46 C. | 65 hr | 34.1 | 2485.3 |
| A30T Y93F S95D D118K A136P D139R N200T S202R R210G W260F N283H L288I L294P S295V | 10.8 | A & H | 46 C. | 65 hr | 31.5 | 2246.3 |
| A30T Y93Q S95D I114Q D118K A136P D139R N200T S202R R210G W260F N283H L288I L294P S295V | 10.8 | A & H | 46 C. | 65 hr | 33.3 | 2457.4 |
| A30T Y93Q S95D D118K A136P D139R N200T S202R R210G W260F N279E N283H L288I L294P S295V | 10.8 | A & H | 46 C. | 65 hr | 36.9 | 2528.8 |
| A30T Y93Q S95D D118K A136P D139R N200T S202R R210G W260F T280L N283H L288I L294P S295V | 10.8 | A & H | 46 C. | 65 hr | 30.0 | 2167.4 |
| A30T Y93Q S95D S98D D118K A136P D139R N200T S202R R210G W260F N283H L288I L294P S295V | 10.8 | A & H | 46 C. | 65 hr | 37.3 | 2426.6 |
| A30T Y93Q S95D D118K A136P D139R N200T S202R R210G W260F N283H L288I L294P S295V T296S | 10.8 | A & H | 46 C. | 65 hr | 30.0 | 2120.6 |
| A30T Y93Q S95D D118K A136P D139R N200T S202R R210G W260F N283H L288I L294P S295V F298Y | 10.8 | A & H | 46 C. | 65 hr | 32.4 | 2350.7 |
| A30T Y93Q S95D D118K A136P D139R N200T S202R R210G N213V W260F N283H L288I L294P S295V | 10.8 | A & H | 46 C. | 65 hr | 33.8 | 2458.0 |
| A30T Y93Q S95D D118K A136P D139R N200T S202R R210G N213D W260F N283H L288I L294P S295V | 10.8 | A & H | 46 C. | 65 hr | 42.4 | 2944.5 |
| A30T Y93Q S95D D118K A136P D139R K142M N200T S202R R210G W260F N283H L288I L294P S295V | 10.8 | A & H | 46 C. | 65 hr | 37.6 | 2858.1 |
| A30T Y93Q S95D D118K A136P D139R K142V N200T S202R R210G W260F N283H L288I L294P S295V | 10.8 | A & H | 46 C. | 65 hr | 37.3 | 2740.1 |
| Y6F A30T Y93Q S95D D118K A136P D139R N200T S202R R210G W260F N283H L288I L294P S295V | 10.8 | A & H | 46 C. | 65 hr | 34.5 | 2471.2 |
| Y6W A30T Y93Q S95D D118K A136P D139R N200T S202R R210G W260F N283H L288I L294P S295V | 10.8 | A & H | 46 C. | 65 hr | 30.8 | 2239.3 |
| Y13F A30T Y93Q S95D D118K A136P D139R N200T S202R R210G W260F N283H L288I L294P S295V | 10.8 | A & H | 46 C. | 65 hr | 34.3 | 2524.5 |
| A30T Y93Q S95D D118K A136P D139R Y174F N200T S202R R210G W260F N283H L288I L294P S295V | 10.8 | A & H | 46 C. | 65 hr | 34.8 | 2344.0 |
| A30T Y93Q S95D D118K A136P D139R Y174W N200T S202R R210G W260F N283H L288I L294P S295V | 10.8 | A & H | 46 C. | 65 hr | 32.6 | 2249.1 |
| A30T T37R Y93Q S95D D118K A136P D139R Q184K N200T S202R R210G W260F L288I L294P S295V | 10.8 | A & H | 46 C. | 65 hr | 23.1 | 1737.1 |
| A30T T37R Y93Q S95D N100H D118K A136P D139R N200T S202R R210G W260F L288I L294P S295V | 10.8 | A & H | 46 C. | 65 hr | 20.4 | 1483.1 |
| A30T T37R Y93Q S95D S98P D118K A136P D139R N200T S202R R210G W260F L288I L294P S295V | 10.8 | A & H | 46 C. | 65 hr | 25.5 | 1742.6 |
| A30T T37R Y93Q S95D D118K A136P D139R N200T S202R R210G N213V W260F L288I L294P S295V | 10.8 | A & H | 46 C. | 65 hr | 23.6 | 1711.4 |
| A1G A30T T37R Y93Q S95D D118K A136P D139R N200T S202R R210G W260F L288I L294P S295V | 10.8 | A & H | 46 C. | 65 hr | 31.1 | 2072.8 |
| A1V A30T T37R Y93Q S95D D118K A136P D139R N200T S202R R210G W260F L288I L294P S295V | 10.8 | A & H | 46 C. | 65 hr | 30.7 | 1983.3 |
| A30T T37R Y93Q S95D D118K A136P D139R N200T S202R R210G Q243K W260F L288I L294P S295V | 10.8 | A & H | 46 C. | 65 hr | 36.7 | 2364.6 |
| A30T T37R K63R Y93Q S95D D118K A136P D139R N200T S202R R210G W260F L288I L294P S295V | 10.8 | A & H | 46 C. | 65 hr | 22.2 | 1605.4 |
| S3P A30T T37R Y93Q S95D D118K A136P D139R N200T S202R R210G W260F L288I L294P S295V | 10.8 | A & H | 46 C. | 65 hr | 27.0 | 1856.8 |
| S8T A30T T37R Y93Q S95D D118K A136P D139R N200T S202R R210G W260F L288I L294P S295V | 10.8 | A & H | 46 C. | 65 hr | 27.9 | 1938.2 |
| A30T T37R E77T Y93Q S95D D118K A136P D139R N200T S202R R210G W260F L288I L294P S295V | 10.8 | A & H | 46 C. | 65 hr | 28.0 | 1845.2 |
| A30T T37R G47S Y93Q S95D D118K A136P D139R N200T S202R R210G W260F L288I L294P S295V | 10.8 | A & H | 46 C. | 65 hr | 22.9 | 1670.4 |
| A30T T37R H80K Y93Q S95D D118K A136P D139R N200T S202R R210G W260F L288I L294P S295V | 10.8 | A & H | 46 C. | 65 hr | 32.9 | 1997.6 |
| A30T T37R Y93Q S95D D118K S131T A136P D139R N200T S202R R210G W260F L288I L294P S295V | 10.8 | A & H | 46 C. | 65 hr | 24.1 | 1569.1 |
| A30T T37R Y93Q S95D D118K A136P D139R N200T S202R R210G W260F A276E L288I L294P S295V | 10.8 | A & H | 46 C. | 65 hr | 35.4 | 2257.6 |
| A30T T37R A83S Y93Q S95D D118K A136P D139R N200T S202R R210G W260F L288I L294P S295V | 10.8 | A & H | 46 C. | 65 hr | 29.1 | 1818.8 |
| A30T T37R E77N Y93Q S95D D118K A136P D139R N200T S202R R210G W260F L288I L294P S295V | 10.8 | A & H | 46 C. | 65 hr | 29.9 | 2007.4 |
| A30T T37R G47K Y93Q S95D D118K A136P D139R N200T S202R R210G W260F L288I L294P S295V | 10.8 | A & H | 46 C. | 65 hr | 23.7 | 1631.2 |
| A30T T37R H80R Y93Q S95D D118K A136P D139R N200T S202R R210G W260F L288I L294P S295V | 10.8 | A & H | 46 C. | 65 hr | 33.6 | 2189.4 |
| A30T T37R Y93Q S95D S111K D118K A136P D139R N200T S202R R210G W260F L288I L294P S295V | 10.8 | A & H | 46 C. | 65 hr | 33.1 | 1943.1 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| A30T T37R D65E Y93Q S95D D118K A136P D139R N200T S202R R210G W260F L288I L294P S295V | 10.8 | A & H | 46 C. | 65 hr | 22.8 | 1654.2 |
| A30T T37R N45G Y93Q S95D D118K A136P D139R N200T S202R R210G W260F L288I L294P S295V | 10.8 | A & H | 46 C. | 65 hr | 26.1 | 1799.7 |
| N18V A30T T37R Y93Q S95D D118K A136P D139R N200T S202R R210G W260F L288I L294P S295V | 10.8 | A & H | 46 C. | 65 hr | 31.3 | 1990.7 |
| N18R A30T T37R Y93Q S95D D118K A136P D139R N200T S202R R210G W260F L288I L294P S295V | 10.8 | A & H | 46 C. | 65 hr | 21.9 | 1599.8 |
| A30T T37R N71S Y93Q S95D D118K A136P D139R N200T S202R R210G W260F L288I L294P S295V | 10.8 | A & H | 46 C. | 65 hr | 30.7 | 2043.5 |
| A30T T37R Y93Q S95D D118K A136P D139R N180R N200T S202R R210G W260F L288I L294P S295V | 10.8 | A & H | 46 C. | 65 hr | 30.7 | 2062.9 |
| A30T T37R Y93Q S95D D118K A136P D139R Q169R N200T S202R R210G W260F L288I L294P S295V | 10.8 | A & H | 46 C. | 65 hr | 27.4 | 1828.2 |
| A30T T37R Y93Q S95D D118K A136P D139R E177Y N200T S202R R210G W260F L288I L294P S295V | 10.8 | A & H | 46 C. | 65 hr | 27.1 | 1804.2 |
| A30T T37R Y93Q S95D D118K A136P D139R N150T N200T S202R R210G W260F L288I L294P S295V | 10.8 | A & H | 46 C. | 65 hr | 29.2 | 1924.3 |
| A30T T37R Y93Q S95D D118K A136P D139R N150S N200T S202R R210G W260F L288I L294P S295V | 10.8 | A & H | 46 C. | 65 hr | 31.4 | 2075.1 |
| A30T T37R Y93Q S95D D118K A136P D139R N150R N200T S202R R210G W260F L288I L294P S295V | 10.8 | A & H | 46 C. | 65 hr | 29.6 | 1880.4 |
| A30T T37R Y93Q S95D D118K A136P D139R Q184E N200T S202R R210G W260F L288I L294P S295V | 10.8 | A & H | 46 C. | 65 hr | 33.7 | 1974.6 |
| A30T T37R Y93Q S95D D118K A136P D139R N200T S202R R210G E234Y W260F L288I L294P S295V | 10.8 | A & H | 46 C. | 65 hr | 25.3 | 1789.8 |
| A30T T37R Y93Q S95D D118K A136P D139R N200T S202R R210G A235R W260F L288I L294P S295V | 10.8 | A & H | 46 C. | 65 hr | 23.7 | 1663.9 |
| A30T T37R Y93Q S95D D118K A136P D139R N200T S202R R210G A235K W260F L288I L294P S295V | 10.8 | A & H | 46 C. | 65 hr | 23.7 | 1747.9 |
| A30T T37R Y93Q S95D K116R D118K A136P D139R N200T S202R R210G W260F L288I L294P S295V | 10.8 | A & H | 46 C. | 65 hr | 23.1 | 1664.0 |
| A30T T37R Y93Q S95D D118K A136P D139R N200T S202R R210G W260F N279D L288I L294P S295V | 10.8 | A & H | 46 C. | 65 hr | 38.4 | 2453.7 |
| A30T T37R Y93Q S95D D118K A136P D139R N200T S202R R210G W260F N279E L288I L294P S295V | 10.8 | A & H | 46 C. | 65 hr | 44.7 | 2929.8 |
| A30T T37R Y93Q S95D D118K A136P D139R N200T S202R R210G W260F N273E L288I L294P S295V | 10.8 | A & H | 46 C. | 65 hr | 33.5 | 2020.4 |
| Y6H A30T T37R Y93Q S95D D118K A136P D139R N200T S202R R210G W260F L288I L294P S295V | 10.8 | A & H | 46 C. | 65 hr | 21.5 | 1647.8 |
| Y6M A30T T37R Y93Q S95D D118K A136P D139R N200T S202R R210G W260F L288I L294P S295V | 10.8 | A & H | 46 C. | 65 hr | 23.2 | 1704.6 |
| A30T T37R Y93Q S95D D118K A136P D139R N200T S202R R210G W260F N272M L288I L294P S295V | 10.8 | A & H | 46 C. | 65 hr | 23.0 | 1633.3 |
| A30T T37R Y93Q S95D D118K A136P D139R N200T S202R R210G W260F N272T L288I L294P S295V | 10.8 | A & H | 46 C. | 65 hr | 36.6 | 2155.6 |
| A30T T37R Y93Q S95D D118K A136P D139R N200T S202R R210G W260F N283W L288I L294P S295V | 10.8 | A & H | 46 C. | 65 hr | 38.8 | 2351.7 |
| A30T T37R Y93Q S95D D118K A136P D139R N200T S202R R210G W260F A276W L288I L294P S295V | 10.8 | A & H | 46 C. | 65 hr | 25.4 | 1786.1 |
| A30T T37R Y93Q S95D D118K A136P D139R N200T S202R R210G W260F A276D L288I L294P S295V | 10.8 | A & H | 46 C. | 65 hr | 36.5 | 2274.5 |
| A30T T37R Y93Q S95D D118K A136P D139R N200T S202R R210G W260F T280L L288I L294P S295V | 10.8 | A & H | 46 C. | 65 hr | 29.5 | 1898.1 |
| T11K A30T T37R Y93Q S95D D118K A136P D139R N200T S202R R210G W260F L288I L294P S295V | 10.8 | A & H | 46 C. | 65 hr | 23.7 | 1672.6 |
| T11R A30T T37R Y93Q S95D D118K A136P D139R N200T S202R R210G W260F L288I L294P S295V | 10.8 | A & H | 46 C. | 65 hr | 22.1 | 1610.5 |
| A30T T37R D57N Y93Q S95D D118K A136P D139R N200T S202R R210G W260F L288I L294P S295V | 10.8 | A & H | 46 C. | 65 hr | 28.3 | 1886.8 |
| A30T T37R Q60R Y93Q S95D D118K A136P D139R N200T S202R R210G W260F L288I L294P S295V | 10.8 | A & H | 46 C. | 65 hr | 38.3 | 2453.4 |
| A30T T37R Y93Q S95D I114M D118K A136P D139R N200T S202R R210G W260F L288I L294P S295V | 10.8 | A & H | 46 C. | 65 hr | 22.6 | 1594.1 |
| A30T T37R Y93Q S95D I114Q D118K A136P D139R N200T S202R R210G W260F L288I L294P S295V | 10.8 | A & H | 46 C. | 65 hr | 27.7 | 1871.8 |
| A30T T37R Y93Q S95D I114W D118K A136P D139R N200T S202R R210G W260F L288I L294P S295V | 10.8 | A & H | 46 C. | 65 hr | 26.9 | 1735.6 |
| A30T T37R Y93Q S95D S98D D118K A136P D139R N200T S202R R210G W260F L288I L294P S295V | 10.8 | A & H | 46 C. | 65 hr | 28.0 | 1827.9 |
| A30T T37R Y93Q S95D D118K A136P D139R N200T S202R R210G W260F L288I L294P S295V T296S | 10.8 | A & H | 46 C. | 65 hr | 31.2 | 2035.1 |
| A30T T37R Y93Q S95D D118K A136P D139R N200T S202R R210G W260F L288I L294P S295V F298Y | 10.8 | A & H | 46 C. | 65 hr | 32.6 | 2113.8 |

TABLE 2-continued

Variants of the present invention having an improved half life Improvement Factor (HIF)
measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T T37R Y93Q S95D D118K A136P D139R N200T S202R R210G N213D W260F L288I L294P S295V | 10.8 | A & H | 46 C. | 65 hr | 31.8 | 2050.4 |
| A30T T37R Y93Q S95D D118K A136P D139R K142M N200T S202R R210G W260F L288I L294P S295V | 10.8 | A & H | 46 C. | 65 hr | 34.6 | 1961.1 |
| A30T T37R Y93Q S95D D118K A136P D139R K142V N200T S202R R210G W260F L288I L294P S295V | 10.8 | A & H | 46 C. | 65 hr | 27.3 | 1972.1 |
| Y6F A30T T37R Y93Q S95D D118K A136P D139R N200T S202R R210G W260F L288I L294P S295V | 10.8 | A & H | 46 C. | 65 hr | 27.5 | 1759.5 |
| Y6W A30T T37R Y93Q S95D D118K A136P D139R N200T S202R R210G W260F L288I L294P S295V | 10.8 | A & H | 46 C. | 65 hr | 28.6 | 1982.6 |
| Y13F A30T T37R Y93Q S95D D118K A136P D139R N200T S202R R210G W260F L288I L294P S295V | 10.8 | A & H | 46 C. | 65 hr | 26.6 | 1754.7 |
| Y13W A30T T37R Y93Q S95D D118K A136P D139R N200T S202R R210G W260F L288I L294P S295V | 10.8 | A & H | 46 C. | 65 hr | 23.9 | 1621.2 |
| A30T T37R Y93Q S95D D118K A136P D139R Y174F N200T S202R R210G W260F L288I L294P S295V | 10.8 | A & H | 46 C. | 65 hr | 31.0 | 1993.8 |
| A30T Y32F T37R Y93Q S95D D118K A136P D139R N200T S202R R210G W260F L288I L294P S295V | 10.8 | A & H | 46 C. | 65 hr | 32.6 | 1944.6 |
| A30T Y32W T37R Y93Q S95D D118K A136P D139R N200T S202R R210G W260F L288I L294P S295V | 10.8 | A & H | 46 C. | 65 hr | 28.2 | 1865.3 |
| A30T Y93Q S95D D118K A136P D139R E177Y S202R R210G W260F A276E L288I L294P S295V | 10.8 | A & H | 46 C. | 65 hr | 26.1 | 2035.6 |
| A1G A30T Y93Q S95D D118K A136P D139R S202R R210G W260F A276E L288I L294P S295V | 10.8 | A & H | 46 C. | 65 hr | 24.1 | 2002.8 |
| A30T Y93Q S95D D118K A136P D139R S202R R210G Q243K W260F A276E L288I L294P S295V | 10.8 | A & H | 46 C. | 65 hr | 33.3 | 2598.9 |
| A30T Y93Q S95D D118K A136P D139R S202R R210G Q243H W260F A276E L288I L294P S295V | 10.8 | A & H | 46 C. | 65 hr | 23.0 | 1923.1 |
| S8T A30T Y93Q S95D D118K A136P D139R S202R R210G W260F A276E L288I L294P S295V | 10.8 | A & H | 46 C. | 65 hr | 24.6 | 2010.3 |
| A30T H80K Y93Q S95D D118K A136P D139R S202R R210G W260F A276E L288I L294P S295V | 10.8 | A & H | 46 C. | 65 hr | 23.7 | 1929.8 |
| A30T A83S Y93Q S95D D118K A136P D139R S202R R210G W260F A276E L288I L294P S295V | 10.8 | A & H | 46 C. | 65 hr | 21.0 | 1817.2 |
| A30T H80R Y93Q S95D D118K A136P D139R S202R R210G W260F A276E L288I L294P S295V | 10.8 | A & H | 46 C. | 65 hr | 28.0 | 2324.8 |
| A30T E41V Y93Q S95D D118K A136P D139R S202R R210G W260F A276E L288I L294P S295V | 10.8 | A & H | 46 C. | 65 hr | 29.3 | 2383.7 |
| A30T Y93Q S95D S111A D118K A136P D139R S202R R210G W260F A276E L288I L294P S295V | 10.8 | A & H | 46 C. | 65 hr | 22.0 | 1847.5 |
| A30T Y93Q S95D S111K D118K A136P D139R S202R R210G W260F A276E L288I L294P S295V | 10.8 | A & H | 46 C. | 65 hr | 25.1 | 2057.5 |
| A30T T37R Y93Q S95D D118K A136P D139R S202R R210G W260F A276E L288I L294P S295V | 10.8 | A & H | 46 C. | 65 hr | 27.4 | 2139.1 |
| A30T R70K Y93Q S95D D118K A136P D139R S202R R210G W260F A276E L288I L294P S295V | 10.8 | A & H | 46 C. | 65 hr | 30.8 | 2473.1 |
| A30T N45G Y93Q S95D D118K A136P D139R S202R R210G W260F A276E L288I L294P S295V | 10.8 | A & H | 46 C. | 65 hr | 25.9 | 2058.6 |
| N18V A30T Y93Q S95D D118K A136P D139R S202R R210G W260F A276E L288I L294P S295V | 10.8 | A & H | 46 C. | 65 hr | 28.1 | 2194.3 |
| A30T N71S Y93Q S95D D118K A136P D139R S202R R210G W260F A276E L288I L294P S295V | 10.8 | A & H | 46 C. | 65 hr | 24.1 | 2086.3 |
| A30T Y93Q S95D D118K A136P D139R N180R S202R R210G W260F A276E L288I L294P S295V | 10.8 | A & H | 46 C. | 65 hr | 24.5 | 2119.1 |
| A30T Y93Q S95D D118K A136P D139R Q169R S202R R210G W260F A276E L288I L294P S295V | 10.8 | A & H | 46 C. | 65 hr | 29.3 | 2336.3 |
| A30T Y93Q S95D D118K A136P D139R E177S S202R R210G W260F A276E L288I L294P S295V | 10.8 | A & H | 46 C. | 65 hr | 26.4 | 2145.2 |
| A30T Y93Q S95D D118K A136P D139R N150S S202R R210G W260F A276E L288I L294P S295V | 10.8 | A & H | 46 C. | 65 hr | 30.1 | 2433.7 |
| A30T Y93Q S95D D118K A136P D139R Q184E S202R R210G W260F A276E L288I L294P S295V | 10.8 | A & H | 46 C. | 65 hr | 25.1 | 1902.6 |
| A30T Y93Q S95D D118K A136P D139R Q184K S202R R210G W260F A276E L288I L294P S295V | 10.8 | A & H | 46 C. | 65 hr | 22.1 | 1965.7 |
| A30T Y93Q S95D D118K A136P D139R Q184S S202R R210G W260F A276E L288I L294P S295V | 10.8 | A & H | 46 C. | 65 hr | 24.2 | 2036.7 |
| A30T Y93Q S95D D118K A136P D139R R185G S202R R210G W260F A276E L288I L294P S295V | 10.8 | A & H | 46 C. | 65 hr | 32.3 | 2752.6 |
| A30T Y93Q S95D D118K A136P D139R S202R R210G A235R W260F A276E L288I L294P S295V | 10.8 | A & H | 46 C. | 65 hr | 23.4 | 2166.2 |
| A30T Y93Q S95D D118K A136P D139R S202R R210G A235K W260F A276E L288I L294P S295V | 10.8 | A & H | 46 C. | 65 hr | 23.7 | 2066.5 |
| A30T Y93Q S95D K116R D118K A136P D139R S202R R210G W260F A276E L288I L294P S295V | 10.8 | A & H | 46 C. | 65 hr | 20.8 | 1844.9 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R N200T S202R R210G W260F A276E L288I L294P S295V | 10.8 | A & H | 46 C. | 65 hr | 28.1 | 2233.3 |
| A30T Y93Q S95D D118K A136P D139R S202R R210G W260F A276E N283W L288I L294P S295V | 10.8 | A & H | 46 C. | 65 hr | 32.0 | 2542.7 |
| A30T Y93Q S95D D118K A136P D139R S202R R210G W260F A276E N283H L288I L294P S295V | 10.8 | A & H | 46 C. | 65 hr | 35.3 | 2754.1 |
| A30T Y93Q S95D D118K A136P D139R S202R R210G W260F A276E N279E L288I L294P S295V | 10.8 | A & H | 46 C. | 65 hr | 28.9 | 2349.9 |
| A30T Y93Q S95D D118K A136P D139R S202R R210G W260F A276E N279D L288I L294P S295V | 10.8 | A & H | 46 C. | 65 hr | 23.8 | 1979.7 |
| T11K A30T Y93Q S95D D118K A136P D139R S202R R210G W260F A276E L288I L294P S295V | 10.8 | A & H | 46 C. | 65 hr | 22.2 | 1917.1 |
| T11R A30T Y93Q S95D D118K A136P D139R S202R R210G W260F A276E L288I L294P S295V | 10.8 | A & H | 46 C. | 65 hr | 22.4 | 1913.3 |
| A30T Q60R Y93Q S95D D118K A136P D139R S202R R210G W260F A276E L288I L294P S295V | 10.8 | A & H | 46 C. | 65 hr | 27.3 | 2195.4 |
| A30T Y93F S95D D118K A136P D139R S202R R210G W260F A276E L288I L294P S295V | 10.8 | A & H | 46 C. | 65 hr | 20.0 | 1660.0 |
| A30T Y93Q S95D I114Q D118K A136P D139R S202R R210G W260F A276E L288I L294P S295V | 10.8 | A & H | 46 C. | 65 hr | 24.9 | 2080.1 |
| A30T Y93Q S95D I114W D118K A136P D139R S202R R210G W260F A276E L288I L294P S295V | 10.8 | A & H | 46 C. | 65 hr | 22.4 | 2088.0 |
| A30T Y93Q S95D D118K A136P D139R S202R Q203T R210G W260F A276E L288I L294P S295V | 10.8 | A & H | 46 C. | 65 hr | 25.2 | 2078.1 |
| A30T Y93Q S95D D118K A136P D139R S202R R210G W260F A276E L288I L294P S295V F298Y | 10.8 | A & H | 46 C. | 65 hr | 23.1 | 2039.5 |
| A30T Y93Q S95D D118K A136P D139R S202R R210G N213V W260F A276E L288I L294P S295V | 10.8 | A & H | 46 C. | 65 hr | 20.2 | 1841.1 |
| A30T Y93Q S95D D118K A136P D139R S202R R210G N213D W260F A276E L288I L294P S295V | 10.8 | A & H | 46 C. | 65 hr | 26.4 | 2114.7 |
| A30T Y93Q S95D D118K A136P D139R K142M S202R R210G W260F A276E L288I L294P S295V | 10.8 | A & H | 46 C. | 65 hr | 27.0 | 2168.5 |
| A30T Y93Q S95D D118K A136P D139R K142V S202R R210G W260F A276E L288I L294P S295V | 10.8 | A & H | 46 C. | 65 hr | 20.5 | 1532.7 |
| A30T Y93Q S95D D118K A136P D139R S202R R210G W260F N272T A276E L288I L294P S295V | 10.8 | A & H | 46 C. | 65 hr | 25.7 | 2105.4 |
| A30T Y93Q S95D D118K A136P D139R S202R R210G W260F N273D A276E L288I L294P S295V | 10.8 | A & H | 46 C. | 65 hr | 29.1 | 2349.3 |
| A30T Y93Q S95D D118K A136P D139R S202R R210G W260F N273E A276E L288I L294P S295V | 10.8 | A & H | 46 C. | 65 hr | 29.6 | 2260.5 |
| A30T Y93Q S95D D118K A136P D139R S202R R210G W260F A276E T280L L288I L294P S295V | 10.8 | A & H | 46 C. | 65 hr | 34.6 | 2693.5 |
| Y6F A30T Y93Q S95D D118K A136P D139R S202R R210G W260F A276E L288I L294P S295V | 10.8 | A & H | 46 C. | 65 hr | 21.9 | 1839.0 |
| Y13W A30T Y93Q S95D D118K A136P D139R S202R R210G W260F A276E L288I L294P S295V | 10.8 | A & H | 46 C. | 65 hr | 23.0 | 1744.4 |
| A30T Y93Q S95D D118K A136P D139R S202R R210G W260F A276E L288I L294P S295V | 10.8 | A & H | 46 C. | 65 hr | 27.2 | 2191.5 |
| A30T Y93Q S95D D118K A136P D139R Y174F S202R R210G W260F A276E L288I L294P S295V | 10.8 | A & H | 46 C. | 65 hr | 27.5 | 2422.3 |
| A30T Y32F Y93Q S95D D118K A136P D139R S202R R210G W260F A276E L288I L294P S295V | 10.8 | A & H | 46 C. | 65 hr | 34.9 | 2838.3 |
| A30T Y32W Y93Q S95D D118K A136P D139R S202R R210G W260F A276E L288I L294P S295V | 10.8 | A & H | 46 C. | 65 hr | 29.7 | 2472.2 |
| A30T Y93Q S95D D118K A136P D139R S202R R210G W260F Y262F A276E L288I L294P S295V | 10.8 | A & H | 46 C. | 65 hr | 25.8 | 2192.0 |
| A30T Y93Q S95D D118K A136P D139R S202R R210G W260F Y262W A276E L288I L294P S295V | 10.8 | A & H | 46 C. | 65 hr | 25.1 | 2188.7 |
| A30T Y93Q S95D D118K A136P D139R S202R R210G W260F A276E Y286F L288I L294P S295V | 10.8 | A & H | 46 C. | 65 hr | 25.6 | 2136.2 |
| A30T Y93Q S95D D118K A136P D139R S202R R210G W260F L288I L294P S295V A276E K142R | 10.8 | A & H | 46 C. | 65 hr | 21.7 | 1909.6 |
| A30T Y93Q S95D D118K A136P D139R S202R R210G W260F L288I L294P S295V A276E K142Q | 10.8 | A & H | 46 C. | 65 hr | 24.4 | 2180.0 |
| A30T Q60R Y93Q S95D D118K A136P D139R S202R R210G W260F A276D L288I L294P S295V T119R | 10.8 | A & H | 46 C. | 65 hr | 20.6 | 1861.0 |
| A30T Q60R Y93Q S95D D118K A136P D139R S202R R210G W260F A276D L288I L294P S295V I114W | 10.8 | A & H | 46 C. | 65 hr | 35.9 | 3168.3 |
| A30T Q60R Y93Q S95D D118K A136P D139R S202R R210G W260F A276D L288I L294P S295V N272T | 10.8 | A & H | 46 C. | 65 hr | 37.9 | 3280.9 |
| A30T Q60R Y93Q S95D D118K A136P D139R S202R R210G Q243Y W260F A276D L288I L294P S295V | 10.8 | A & H | 46 C. | 65 hr | 44.0 | 3877.9 |
| A30T Q60R Y93Q S95D D118K A136P D139R S202R R210G W260F A276D L288I L294P S295V Q243K | 10.8 | A & H | 46 C. | 65 hr | 42.0 | 3543.5 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Q60R Y93Q S95D D118K A136P D139R S202R R210G W260F A276D L288I L294P S295V S3P | 10.8 | A & H | 46 C. | 65 hr | 32.9 | 2532.5 |
| A30T Q60R Y93Q S95D D118K A136P D139R S202R R210G W260F A276D L288I L294P S295V T37P | 10.8 | A & H | 46 C. | 65 hr | 33.8 | 2805.2 |
| A30T Q60R Y93Q S95D D118K A136P D139R S202R R210G W260F A276D L288I L294P S295V G47S | 10.8 | A & H | 46 C. | 65 hr | 27.1 | 2377.8 |
| A30T Q60R Y93Q S95D D118K A136P D139R S202R R210G W260F A276D L288I L294P S295V S131T | 10.8 | A & H | 46 C. | 65 hr | 29.8 | 2644.1 |
| A30T Q60R Y93Q S95D D118K A136P D139R S202R R210G W260F A276D L288I L294P S295V A83S | 10.8 | A & H | 46 C. | 65 hr | 34.3 | 3092.7 |
| A30T Q60R Y93Q S95D D118K A136P D139R S202R R210G W260F A276D L288I L294P S295V E77N | 10.8 | A & H | 46 C. | 65 hr | 33.5 | 2760.3 |
| A30T Q60R Y93Q S95D D118K A136P D139R S202R R210G W260F A276D L288I L294P S295V G47K | 10.8 | A & H | 46 C. | 65 hr | 21.0 | 1998.4 |
| A30T Q60R Y93Q S95D D118K A136P D139R S202R R210G W260F A276D L288I L294P S295V E41V | 10.8 | A & H | 46 C. | 65 hr | 36.0 | 2984.9 |
| A30T Q60R Y93Q S95D D118K A136P D139R S202R R210G W260F A276D L288I L294P S295V S111R | 10.8 | A & H | 46 C. | 65 hr | 39.0 | 3278.9 |
| A30T Q60R Y93Q S95D D118K A136P D139R S202R R210G W260F A276D L288I L294P S295V S111K | 10.8 | A & H | 46 C. | 65 hr | 28.7 | 2610.3 |
| A30T Q60R Y93Q S95D D118K A136P D139R S202R R210G W260F A276D L288I L294P S295V Q35L | 10.8 | A & H | 46 C. | 65 hr | 24.2 | 2374.9 |
| A30T Q60R Y93Q S95D D118K A136P D139R S202R R210G W260F A276D L288I L294P S295V D65E | 10.8 | A & H | 46 C. | 65 hr | 21.9 | 2191.4 |
| A30T Q60R Y93Q S95D D118K A136P D139R S202R R210G W260F A276D L288I L294P S295V T37R | 10.8 | A & H | 46 C. | 65 hr | 35.3 | 3174.7 |
| A30T Q60R Y93Q S95D D118K A136P D139R S202R R210G W260F A276D L288I L294P S295V R70K | 10.8 | A & H | 46 C. | 65 hr | 32.7 | 2889.1 |
| A30T Q60R Y93Q S95D D118K A136P D139R S202R R210G W260F A276D L288I L294P S295V N45G | 10.8 | A & H | 46 C. | 65 hr | 37.1 | 3138.7 |
| N18V A30T Q60R Y93Q S95D D118K A136P D139R S202R R210G W260F A276D L288I L294P S295V | 10.8 | A & H | 46 C. | 65 hr | 49.5 | 4404.9 |
| A30T Q60R Y93Q S95D D118K A136P D139R S202R R210G W260F A276D L288I L294P S295V N71S | 10.8 | A & H | 46 C. | 65 hr | 33.5 | 2960.4 |
| A30T Q60R Y93Q S95D D118K A136P D139R S202R R210G W260F A276D L288I L294P S295V N180R | 10.8 | A & H | 46 C. | 65 hr | 29.9 | 2660.6 |
| A30T Q60R Y93Q S95D D118K A136P D139R S202R R210G W260F A276D L288I L294P S295V E177S | 10.8 | A & H | 46 C. | 65 hr | 36.0 | 3135.5 |
| A30T Q60R Y93Q S95D D118K A136P D139R S202R R210G W260F A276D L288I L294P S295V E177Y | 10.8 | A & H | 46 C. | 65 hr | 42.9 | 3456.8 |
| A30T Q60R Y93Q S95D D118K A136P D139R S202R R210G W260F A276D L288I L294P S295V N150R | 10.8 | A & H | 46 C. | 65 hr | 37.1 | 3207.9 |
| A30T Q60R Y93Q S95D D118K A136P D139R S202R R210G W260F A276D L288I L294P S295V Q184E | 10.8 | A & H | 46 C. | 65 hr | 32.7 | 2781.0 |
| A30T Q60R Y93Q S95D D118K A136P D139R S202R R210G W260F A276D L288I L294P S295V Q184K | 10.8 | A & H | 46 C. | 65 hr | 33.6 | 2947.7 |
| A30T Q60R Y93Q S95D D118K A136P D139R S202R R210G W260F A276D L288I L294P S295V E234Y | 10.8 | A & H | 46 C. | 65 hr | 29.6 | 2711.9 |
| A30T Q60R Y93Q S95D D118K A136P D139R S202R R210G W260F A276D L288I L294P S295V A235R | 10.8 | A & H | 46 C. | 65 hr | 29.4 | 2610.7 |
| A30T Q60R Y93Q S95D D118K A136P D139R S202R R210G W260F A276D L288I L294P S295V A235K | 10.8 | A & H | 46 C. | 65 hr | 32.9 | 2860.0 |
| A30T Q60R Y93Q S95D D118K A136P D139R S202R R210G W260F A276D L288I L294P S295V K116R | 10.8 | A & H | 46 C. | 65 hr | 36.1 | 3121.0 |
| A30T Q60R Y93Q S95D D118K A136P D139R S202R R210G W260F A276D L288I L294P S295V N200T | 10.8 | A & H | 46 C. | 65 hr | 36.8 | 3023.5 |
| A30T Q60R Y93Q S95D D118K A136P D139R S202R R210G W260F A276D L288I L294P S295V Y6M | 10.8 | A & H | 46 C. | 65 hr | 30.9 | 2720.4 |
| A30T Q60R Y93Q S95D D118K A136P D139R S202R R210G W260F A276D L288I L294P S295V N279D | 10.8 | A & H | 46 C. | 65 hr | 39.2 | 3327.0 |
| A30T Q60R Y93Q S95D D118K A136P D139R S202R R210G W260F A276D L288I L294P S295V T11R | 10.8 | A & H | 46 C. | 65 hr | 24.8 | 2415.8 |
| A30T Q60R Y93Q S95D D118K A136P D139R S202R R210G W260F A276D L288I L294P S295V S98P | 10.8 | A & H | 46 C. | 65 hr | 35.6 | 3143.0 |
| A30T Q60R Y93Q S95D D118K A136P D139R S202R R210G W260F A276D L288I L294P S295V I114M | 10.8 | A & H | 46 C. | 65 hr | 40.0 | 3251.3 |
| A30T Q60R Y93Q S95D D118K A136P D139R S202R R210G W260F A276D L288I L294P S295V S98D | 10.8 | A & H | 46 C. | 65 hr | 42.7 | 3675.1 |
| A30T Q60R Y93Q S95D D118K A136P D139R S202R R210G W260F A276D L288I L294P S295V T296S | 10.8 | A & H | 46 C. | 65 hr | 33.2 | 2917.9 |
| A30T Q60R Y93Q S95D D118K A136P D139R S202R R210G W260F A276D L288I L294P S295V F298Y | 10.8 | A & H | 46 C. | 65 hr | 30.2 | 2655.1 |
| A30T Q60R Y93Q S95D D118K A136P D139R S202R R210G W260F A276D L288I L294P S295V N213V | 10.8 | A & H | 46 C. | 65 hr | 32.1 | 2727.3 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Q60R Y93Q S95D D118K A136P D139R S202R R210G W260F A276D L288I L294P S295V K142V | 10.8 | A & H | 46 C. | 65 hr | 32.0 | 2711.6 |
| A30T Q60R Y93Q S95D D118K A136P D139R S202R R210G W260F A276D L288I L294P S295V D57N | 10.8 | A & H | 46 C. | 65 hr | 30.5 | 2577.5 |
| A30T Q60R Y93Q S95D D118K A136P D139R S202R R210G W260F A276D L288I L294P S295V N272M | 10.8 | A & H | 46 C. | 65 hr | 35.8 | 2923.8 |
| A30T Q60R Y93Q S95D D118K A136P D139R S202R R210G W260F N273D A276E L288I L294P S295V | 10.8 | A & H | 46 C. | 65 hr | 45.5 | 3939.5 |
| A30T Q60R Y93Q S95D D118K A136P D139R S202R R210G W260F A276D L288I L294P S295V N273E | 10.8 | A & H | 46 C. | 65 hr | 40.6 | 3352.8 |
| A30T Q60R Y93Q S95D D118K A136P D139R S202R R210G W260F A276D L288I L294P S295V T280L | 10.8 | A & H | 46 C. | 65 hr | 43.9 | 3792.8 |
| A30T Q60R Y93Q S95D D118K A136P D139R S202R R210G W260F A276D L288I L294P S295V Y6F | 10.8 | A & H | 46 C. | 65 hr | 32.9 | 2715.6 |
| A30T Q60R Y93Q S95D D118K A136P D139R S202R R210G W260F A276D L288I L294P S295V Y6W | 10.8 | A & H | 46 C. | 65 hr | 31.4 | 2638.0 |
| A30T Q60R Y93Q S95D D118K A136P D139R S202R R210G W260F A276D L288I L294P S295V Y13F | 10.8 | A & H | 46 C. | 65 hr | 40.2 | 3510.2 |
| A30T Q60R Y93Q S95D D118K A136P D139R S202R R210G W260F A276D L288I L294P S295V Y13W | 10.8 | A & H | 46 C. | 65 hr | 31.4 | 2746.1 |
| A30T Q60R Y93Q S95D D118K A136P D139R S202R R210G W260F A276D L288I L294P S295V Y174F | 10.8 | A & H | 46 C. | 65 hr | 32.7 | 2827.8 |
| A30T Q60R Y93Q S95D D118K A136P D139R S202R R210G W260F A276D L288I L294P S295V Y32F | 10.8 | A & H | 46 C. | 65 hr | 41.1 | 3502.9 |
| A30T Q60R K63R Y93Q S95D D118K A136P D139R S202R R210G W260F A276D L288I L294P S295V | 10.8 | A & H | 46 C. | 65 hr | 25.0 | 2219.9 |
| A30T Q60R Y93Q S95D D118K A136P D139R S202R R210G W260F A276D L288I L294P S295V Y6H | 10.8 | A & H | 46 C. | 65 hr | 27.4 | 2311.4 |
| A30T Y32W Q60R Y93Q S95D D118K A136P D139R S202R R210G W260F N272T L288I L294P S295V | 10.8 | A & H | 46 C. | 65 hr | 26.1 | 2770.3 |
| A30T Y32W Q60R Y93Q S95D I114M D118K A136P D139R S202R R210G W260F L288I L294P S295V | 10.8 | A & H | 46 C. | 65 hr | 20.8 | 2182.2 |
| A1G A30T Y32W Q60R Y93Q S95D D118K A136P D139R S202R R210G W260F L288I L294P S295V | 10.8 | A & H | 46 C. | 65 hr | 29.5 | 2676.0 |
| S8T A30T Y32W Q60R Y93Q S95D D118K A136P D139R S202R R210G W260F L288I L294P S295V | 10.8 | A & H | 46 C. | 65 hr | 26.9 | 2603.0 |
| A30T Y32W Q60R E77T Y93Q S95D D118K A136P D139R S202R R210G W260F L288I L294P S295V | 10.8 | A & H | 46 C. | 65 hr | 25.1 | 2452.8 |
| A30T Y32W Q60R H80K Y93Q S95D D118K A136P D139R S202R R210G W260F L288I L294P S295V | 10.8 | A & H | 46 C. | 65 hr | 20.8 | 2340.4 |
| A30T Y32W Q60R Y93Q S95D D118K A136P D139R S202R R210G W260F A276E L288I L294P S295V | 10.8 | A & H | 46 C. | 65 hr | 30.0 | 3128.6 |
| A30T Y32W Q60R A83S Y93Q S95D D118K A136P D139R S202R R210G W260F L288I L294P S295V | 10.8 | A & H | 46 C. | 65 hr | 25.1 | 2573.4 |
| A30T Y32W Q60R E77N Y93Q S95D D118K A136P D139R S202R R210G W260F L288I L294P S295V | 10.8 | A & H | 46 C. | 65 hr | 25.3 | 2671.2 |
| A30T Y32W T37R Q60R Y93Q S95D D118K A136P D139R S202R R210G W260F L288I L294P S295V | 10.8 | A & H | 46 C. | 65 hr | 30.0 | 2841.1 |
| A30T Y32W Q60R R70K Y93Q S95D D118K A136P D139R S202R R210G W260F L288I L294P S295V | 10.8 | A & H | 46 C. | 65 hr | 29.3 | 3021.7 |
| N18V A30T Y32W Q60R Y93Q S95D D118K A136P D139R S202R R210G W260F L288I L294P S295V | 10.8 | A & H | 46 C. | 65 hr | 28.6 | 2844.1 |
| A30T Y32W Q60R Y93Q S95D D118K A136P D139R Q169R S202R R210G W260F L288I L294P S295V | 10.8 | A & H | 46 C. | 65 hr | 26.5 | 2589.2 |
| A30T Y32W Q60R Y93Q S95D D118K A136P D139R N150S S202R R210G W260F L288I L294P S295V | 10.8 | A & H | 46 C. | 65 hr | 27.1 | 2931.9 |
| A30T Y32W Q60R Y93Q S95D D118K A136P D139R N150N S202R R210G W260F L288I L294P S295V | 10.8 | A & H | 46 C. | 65 hr | 21.6 | 2326.0 |
| A30T Y32W Q60R Y93Q S95D D118K A136P D139R Q184E S202R R210G W260F L288I L294P S295V | 10.8 | A & H | 46 C. | 65 hr | 22.0 | 2319.1 |
| A30T Y32W Q60R Y93Q S95D D118K A136P D139R R185G S202R R210G W260F L288I L294P S295V | 10.8 | A & H | 46 C. | 65 hr | 21.5 | 2280.7 |
| A30T Y32W Q60R Y93Q S95D D118K A136P D139R S202R R210G E234Y W260F L288I L294P S295V | 10.8 | A & H | 46 C. | 65 hr | 27.6 | 2847.9 |
| A30T Y32W Q60R Y93Q S95D D118K A136P D139R S202R R210G A235R W260F L288I L294P S295V | 10.8 | A & H | 46 C. | 65 hr | 20.4 | 2052.8 |
| A30T Y32W Q60R Y93Q S95D D118K A136P D139R S202R R210G A235K W260F L288I L294P S295V | 10.8 | A & H | 46 C. | 65 hr | 22.6 | 2465.6 |
| A30T Y32W Q60R Y93Q S95D D118K A136P D139R N200T S202R R210G W260F L288I L294P S295V | 10.8 | A & H | 46 C. | 65 hr | 25.2 | 2566.9 |
| A30T Y32W Q60R Y93Q S95D D118K A136P D139R S202R R210G W260F N279D L288I L294P S295V | 10.8 | A & H | 46 C. | 65 hr | 30.2 | 2959.5 |
| Y6M A30T Y32W Q60R Y93Q S95D D118K A136P D139R S202R R210G W260F L288I L294P S295V | 10.8 | A & H | 46 C. | 65 hr | 21.9 | 2249.3 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y32W Q60R Y93Q S95D D118K A136P D139R S202R R210G W260F N283W L288I L294P S295V | 10.8 | A & H | 46 C. | 65 hr | 23.6 | 2429.8 |
| A30T Y32W Q60R Y93Q S95D D118K A136P D139R S202R R210G W260F N283H L288I L294P S295V | 10.8 | A & H | 46 C. | 65 hr | 32.8 | 3105.0 |
| A30T Y32W Q60R Y93Q S95D D118K A136P D139R S202R R210G W260F T280L L288I L294P S295V | 10.8 | A & H | 46 C. | 65 hr | 32.3 | 3099.4 |
| A30T Y32W Q60R Y93F S95D D118K A136P D139R S202R R210G W260F L288I L294P S295V | 10.8 | A & H | 46 C. | 65 hr | 24.1 | 2534.3 |
| A30T Y32W Q60R Y93Q S95D I114W D118K A136P D139R S202R R210G W260F L288I L294P S295V | 10.8 | A & H | 46 C. | 65 hr | 20.9 | 2284.1 |
| A30T Y32W Q60R Y93Q S95D S98D D118K A136P D139R S202R R210G W260F L288I L294P S295V | 10.8 | A & H | 46 C. | 65 hr | 24.2 | 2505.5 |
| A30T Y32W Q60R Y93Q S95D D118K A136P D139R S202R Q203T R210G W260F L288I L294P S295V | 10.8 | A & H | 46 C. | 65 hr | 21.4 | 2262.9 |
| A30T Y32W Q60R Y93Q S95D D118K A136P D139R K142M S202R R210G W260F L288I L294P S295V | 10.8 | A & H | 46 C. | 65 hr | 38.3 | 3633.1 |
| A30T Y32W Q60R Y93Q S95D D118K A136P D139R Y174F S202R R210G W260F L288I L294P S295V | 10.8 | A & H | 46 C. | 65 hr | 29.0 | 2917.3 |
| A30T Y32W K33Q Q60R Y93Q S95D D118K A136P D139R S202R R210G W260F L288I L294P S295V | 10.8 | A & H | 46 C. | 65 hr | 20.6 | 2261.6 |
| N18V A30T S74K Y93Q S95D D118K A136P D139R N180R S202R R210G W260F A276D N283H L288I L294P S295V | 10.8 | A & H | 46 C. | 65 hr | 50.6 | 2992.9 |
| S8T A30T Y93Q S95D D118K A136P D139R N150T S202R R210G Q243K W260F A276D L288I L294P S295V | 10.8 | A & H | 46 C. | 65 hr | 53.7 | 3146.2 |
| S8T A30T Y93Q S95D D118K A136P D139R N150T S202R R210G Q243K W260F A276D L288I L294P S295V | 10.8 | A & H | 46 C. | 65 hr | 51.7 | 2965.8 |
| A30T Y93Q S95D D118K A136P D139R P183T N200T R202S R210G W260F D276A N279E L288I L294P S295V | 10.8 | A & H | 46 C. | 65 hr | 51.5 | 3048.8 |
| A30T Y93Q S95D D118K A136P D139R S202R R205K R210G Q243K W260F A276D L288I L294P S295V | 10.8 | A & H | 46 C. | 65 hr | 45.8 | 2853.8 |
| A1V A30T Y93Q D118K A136P D139R S202R R210G A257G W260F A276D L288I L294P S295V | 10.8 | A & H | 46 C. | 65 hr | 62.3 | 4024.9 |
| A1V A30T Y93Q D118K A136P D139R E177Y S202R R210G G257A W260F A276D L288I L294P S295V | 10.8 | A & H | 46 C. | 65 hr | 48.8 | 2649.5 |
| A1V Y6H A30T T37P G47T Q60R Y93Q D118K A136P D139R S202R R210G A257G W260F A276D L288I L294P S295V | 10.8 | A & H | 46 C. | 65 hr | 46.9 | 2511.9 |
| A1V A30T T37P G47T Y93Q D118K A136P D139R S202R R210G A257G W260F A276D L288I L294P S295V | 10.8 | A & H | 46 C. | 65 hr | 42.8 | 2243.1 |
| A1V A30T T37P G47T Y93Q D118K A136P D139R S202R R210G G257A W260F A276D L288I L294P S295V | 10.8 | A & H | 46 C. | 65 hr | 41.1 | 2141.6 |
| A1V A30T Y93Q D118K A136P D139R N150T S202R R210G Q243K G257A W260F A276D L288I L294P S295V | 10.8 | A & H | 46 C. | 65 hr | 37.4 | 2345.2 |
| A1V A30T Y93Q D118K A136P D139R P183T S202R R205K R210G Q243K G257A W260F A276D L288I L294P S295V | 10.8 | A & H | 46 C. | 65 hr | 61.5 | 4442.8 |
| A1V A30T Y93Q D118K A136P D139R P183T S202R R210G Q243K G257A W260F A276D L288I L294P S295V | 10.8 | A & H | 46 C. | 65 hr | 60.4 | 4294.3 |
| A1V A30T R70K Y93Q D118K A136P D139R P183T S202R R210G G257A W260F D276A N279D L288I L294P S295V | 10.8 | A & H | 46 C. | 65 hr | 52.8 | 3531.0 |
| A1V S8T A30T Q60R Y93Q D118K A136P D139R N150T S202R R210G G257A W260F A276D L288I L294P S295V | 10.8 | A & H | 46 C. | 65 hr | 35.8 | 2247.7 |
| A1V A30T Y93Q D118K A136P D139R P183T S202R R210G G257A W260F D276A N279D L288I L294P S295V | 10.8 | A & H | 46 C. | 65 hr | 36.2 | 2219.6 |
| A1V A30T Y93Q D118K A136P D139R P183T S202R R210G G257A W260F D276A N279E L288I L294P S295V | 10.8 | A & H | 46 C. | 65 hr | 46.8 | 2967.7 |
| A1V A30T Y93Q D118K A136P D139R N150S S202R R210G R244V G257A W260F A276D L288I L294P S295V | 10.8 | A & H | 46 C. | 65 hr | 40.4 | 2195.2 |
| A1V A30T Y93Q D118K A136P D139R N150S R176Q S202R R210G R244V G257A W260F A276D L288I L294P S295V | 10.8 | A & H | 46 C. | 65 hr | 44.9 | 2482.1 |
| A1V G4D A30T Y93Q D118K A136P D139R S202R R205K R210G Q243K G257A W260F A276D L288I L294P S295V | 10.8 | A & H | 46 C. | 65 hr | 36.2 | 2130.3 |
| A1V A30T Y93Q D118K A136P D139R S202R R205K R210G Q243K G257A W260F A276D L288I L294P S295V | 10.8 | A & H | 46 C. | 65 hr | 41.1 | 2431.5 |
| A1V A30T Y93Q D118K A136P D139R P183T S202R R210G G257A W260F A276D L288I L294P S295V | 10.8 | A & H | 46 C. | 65 hr | 43.1 | 2678.2 |
| A30T Y93Q S95D D118K A136P D139R S202R R210G W260F A276D L288I L294P S295V | 10.8 | A & H | 46 C. | 65 hr | 35.0 | 2814.1 |
| A30T Y93Q S95D S98P D118K A136P D139R N180R S202R R210G W260F A276D N283H L288I L294P S295V | 10.8 | A & H | 46 C. | 65 hr | 49.7 | 2915.3 |
| A30T Y93Q S95D D118K A136P D139R S202R R210G Q243K W260F A276D L288I L294P S295V | 10.8 | A & H | 46 C. | 65 hr | 51.9 | 2985.8 |
| S8P A30T Y93Q S95D D118K A136P D139R N150T S202R R210G Q243K W260F A276D L288I L294P S295V | 10.8 | A & H | 46 C. | 65 hr | 57.2 | 3506.0 |
| A30T R70K Y93Q S95D D118K A136P D139R P183T S202R R210G W260F D276A N279E L288I L294P S295V | 10.8 | A & H | 46 C. | 65 hr | 51.0 | 2998.2 |

TABLE 2-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A30T Y93Q S95D D118K A136P D139R N150S R176Q S202R R210G R244V W260F A276D L288I L294P S295V | 10.8 | A & H | 46 C. | 65 hr | 53.1 | 2975.6 |
| A30T Y93Q S95D D118K A136P D139R P183T S202R R205K R210G Q243K W260F A276D L288I L294P S295V | 10.8 | A & H | 46 C. | 65 hr | 48.7 | 3099.0 |
| A30T Y93Q S95D D118K A136P D139R P183T S202R R205K R210G W260F A276D L288I L294P S295V | 10.8 | A & H | 46 C. | 65 hr | 48.6 | 3092.3 |
| A1V S8R A30T Y93Q D118K A136P D139R S202R R210G G257A W260F A276D L288I L294P S295V | 10.8 | A & H | 42 C. | 65 hr | 34.8 | 2469.2 |
| A1V S8R A30T N45S Y93Q D118K A136P D139R S202R R210G G257A W260F A276D L288I L294P S295V | 10.8 | A & H | 42 C. | 65 hr | 30.6 | 2349.3 |
| A1V A30T Y93Q A97E D118K E133Q A136P D139R S202R R210G G257A W260F A276D L288I L294P S295V | 10.8 | A & H | 42 C. | 65 hr | 34.5 | 2465.4 |
| A1V A30T E41N Y93Q D118K E133Q A136P D139R S202R R210G G257A W260F A276D L288I L294P S295V | 10.8 | A & H | 42 C. | 65 hr | 34.7 | 2466.4 |
| A1V A30T E41N R70Q Y93Q A97E D118K A136P D139R S202R R210G G257A W260F A276D L288I L294P S295V | 10.8 | A & H | 42 C. | 65 hr | 41.6 | 2764.4 |
| A1V A30T Y93Q D118K E133Q A136P D139R S202R R210G G257A W260F A276D L288I L294P S295V | 10.8 | A & H | 42 C. | 65 hr | 33.2 | 2423.1 |
| A1V A30T E41N Y93Q A97E D118K A136P D139R S202R R210G G257A W260F A276D L288I L294P S295V | 10.8 | A & H | 42 C. | 65 hr | 36.5 | 2503.6 |
| A1V A30T Y93Q A97E D118K A136P D139R S202R R210G G257A W260F A276D L288I L294P S295V | 10.8 | A & H | 42 C. | 65 hr | 41.1 | 2512.9 |
| A1V A30T E41N Y93Q A97E D118K A136P D139R S202R R210G G257A W260F A276D L288I L294P S295V | 10.8 | A & H | 42 C. | 65 hr | 36.1 | 2469.2 |
| A1V N2E A30T Y93Q A97E D118K E133Q A136P D139R S202R R210G G257A W260F A276D L288I L294P S295V | 10.8 | A & H | 42 C. | 65 hr | 37.8 | 2651.9 |
| A1V N2E A30T E41N Y93Q A97E D118K E133Q A136P D139R S202R R210G G257A W260F A276D L288I L294P S295V | 10.8 | A & H | 42 C. | 65 hr | 35.4 | 2472.3 |
| A1V A30T R70Q Y93Q A97E D118K A136P D139R S202R R210G G257A W260F A276D L288I L294P S295V | 10.8 | A & H | 42 C. | 65 hr | 38.9 | 2685.4 |
| A1V A30T R70Q Y93Q A97E D118K E133Q A136P D139R S202R R210G G257A W260F A276D L288I L294P S295V | 10.8 | A & H | 42 C. | 65 hr | 37.2 | 2651.9 |
| A1V A30T E41N R70Q Y93Q A97E D118K E133Q A136P D139R S202R R210G G257A W260F A276D L288I L294P S295V | 10.8 | A & H | 42 C. | 65 hr | 41.1 | 2378.8 |
| A1V A30T Y93Q D118K D135V A136P D139R S202R R210G G257A W260F A276D L288I L294P S295V | 10.8 | A & H | 42 C. | 65 hr | 45.1 | 1834.2 |
| A1V A30T Y93Q D118K A136P D139R P183A S202R R210G G257A W260F A276D L288I L294P S295V | 10.8 | A & H | 42 C. | 65 hr | 41.7 | 2809.1 |

TABLE 3

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| G47A G257W | 9 | Model O | 40 C. | 16 hr | 76.9 | 3.7 |
| G47S A83P | 9 | Model O | 40 C. | 16 hr | 74.0 | 4.2 |
| G47A G257L | 9 | Model O | 40 C. | 16 hr | 73.7 | 3.5 |
| G47A G257A | 9 | Model O | 40 C. | 16 hr | 70.7 | 3.0 |
| G47S A136P | 9 | Model O | 40 C. | 16 hr | 69.1 | 3.5 |
| S3P G47S E77T K116R A136P G257W | 9 | Model O | 40 C. | 16 hr | 68.9 | 2.0 |
| G47S S241C | 9 | Model O | 40 C. | 16 hr | 68.2 | 2.8 |
| G47S K116R G257W | 9 | Model O | 40 C. | 16 hr | 67.2 | 2.4 |
| G47A G257S | 9 | Model O | 40 C. | 16 hr | 63.8 | 2.7 |
| G47A A83P | 9 | Model O | 40 C. | 16 hr | 61.5 | 2.6 |
| G47S Y93Q | 9 | Model O | 40 C. | 16 hr | 60.6 | 2.7 |
| G47A Y93C | 9 | Model O | 40 C. | 16 hr | 59.8 | 2.4 |
| G47A A136P | 9 | Model O | 40 C. | 16 hr | 59.7 | 2.4 |
| G47S S98P | 9 | Model O | 40 C. | 16 hr | 58.9 | 2.5 |
| G47S V82I | 9 | Model O | 40 C. | 16 hr | 58.8 | 2.1 |
| T37P G47S | 9 | Model O | 40 C. | 16 hr | 58.7 | 2.3 |
| G47S G257A | 9 | Model O | 40 C. | 16 hr | 57.7 | 2.3 |
| G47A D135P | 9 | Model O | 40 C. | 16 hr | 57.6 | 2.1 |
| G47A G257Y | 9 | Model O | 40 C. | 16 hr | 57.3 | 2.1 |
| G47S D135P | 9 | Model O | 40 C. | 16 hr | 56.9 | 2.2 |
| G47S G257L | 9 | Model O | 40 C. | 16 hr | 56.4 | 2.1 |
| S98P G257W | 9 | Model O | 40 C. | 16 hr | 56.0 | 2.3 |
| G47S K116R | 9 | Model O | 40 C. | 16 hr | 55.7 | 2.1 |
| G47S G257F | 9 | Model O | 40 C. | 16 hr | 55.6 | 2.0 |

TABLE 3-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
| --- | --- | --- | --- | --- | --- | --- |
| E77T G257F | 9 | Model O | 40 C. | 16 hr | 55.4 | 2.1 |
| G47A S98P | 9 | Model O | 40 C. | 16 hr | 55.0 | 2.0 |
| G47A Y93I | 9 | Model O | 40 C. | 16 hr | 54.6 | 1.9 |
| T37P G47A | 9 | Model O | 40 C. | 16 hr | 54.4 | 1.9 |
| G47S Y93I | 9 | Model O | 40 C. | 16 hr | 54.1 | 1.9 |
| T37P G257W | 9 | Model O | 40 C. | 16 hr | 54.0 | 1.9 |
| G47A Y93Q | 9 | Model O | 40 C. | 16 hr | 53.9 | 2.0 |
| G47A Y93F | 9 | Model O | 40 C. | 16 hr | 53.7 | 2.0 |
| G47S G257S | 9 | Model O | 40 C. | 16 hr | 53.6 | 2.0 |
| G47A Y93A | 9 | Model O | 40 C. | 16 hr | 53.5 | 2.1 |
| G47S Y93F | 9 | Model O | 40 C. | 16 hr | 52.8 | 1.7 |
| G47A E77T | 9 | Model O | 40 C. | 16 hr | 52.7 | 1.8 |
| E77T G257W | 9 | Model O | 40 C. | 16 hr | 52.1 | 2.1 |
| G47A V82I | 9 | Model O | 40 C. | 16 hr | 52.1 | 2.0 |
| G47S Y93R | 9 | Model O | 40 C. | 16 hr | 51.7 | 2.0 |
| A136P G257W | 9 | Model O | 40 C. | 16 hr | 51.6 | 2.0 |
| G47S G257Y | 9 | Model O | 40 C. | 16 hr | 51.3 | 1.8 |
| G47S G257W | 9 | Model O | 40 C. | 16 hr | 51.1 | 1.9 |
| G47A K1166R | 9 | Model O | 40 C. | 16 hr | 50.9 | 1.8 |
| Y93Q G257W | 9 | Model O | 40 C. | 16 hr | 50.8 | 2.2 |
| G47S Y93A | 9 | Model O | 40 C. | 16 hr | 50.0 | 1.7 |
| T37P G257L | 9 | Model O | 40 C. | 16 hr | 48.5 | 1.7 |
| G47S Y93C | 9 | Model O | 40 C. | 16 hr | 48.4 | 1.7 |
| K116R G257W | 9 | Model O | 40 C. | 16 hr | 46.6 | 1.8 |
| E77T G257A | 9 | Model O | 40 C. | 16 hr | 46.3 | 1.7 |
| G257W P258Q | 9 | Model O | 40 C. | 16 hr | 44.8 | 1.6 |
| S98P A136P | 9 | Model O | 40 C. | 16 hr | 44.1 | 1.5 |
| E77T S241C | 9 | Model O | 40 C. | 16 hr | 43.9 | 1.4 |
| T37P G257A | 9 | Model O | 40 C. | 16 hr | 43.9 | 1.5 |
| T37P S241O | 9 | Model O | 40 C. | 16 hr | 43.6 | 1.4 |
| G257E P258Q | 9 | Model O | 40 C. | 16 hr | 42.0 | 1.4 |
| Y93Q A136P | 9 | Model O | 40 C. | 16 hr | 41.8 | 1.5 |
| E77T A136P | 9 | Model O | 40 C. | 16 hr | 40.1 | 1.4 |
| T37P A136P | 9 | Model O | 40 C. | 16 hr | 37.7 | 1.2 |
| E77T G257Y | 9 | Model O | 40 C. | 16 hr | 36.6 | 1.1 |
| T37P G257Y | 9 | Model O | 40 C. | 16 hr | 36.5 | 1.2 |
| E77T Y93R | 9 | Model O | 40 C. | 16 hr | 36.1 | 1.2 |
| T37P A83P | 9 | Model O | 40 C. | 16 hr | 36.1 | 1.1 |
| E77T K116R | 9 | Model O | 40 C. | 16 hr | 35.8 | 1.2 |
| G47A S241C | 9 | Model O | 40 C. | 16 hr | 35.6 | 1.6 |
| T37P G257S | 9 | Model O | 40 C. | 16 hr | 35.3 | 1.2 |
| E77T Y93A | 9 | Model O | 40 C. | 16 hr | 34.6 | 1.1 |
| E77T Y93I | 9 | Model O | 40 C. | 16 hr | 33.9 | 1.1 |
| E77T Y93C | 9 | Model O | 40 C. | 16 hr | 32.6 | 1.0 |
| Y93Q K116R | 9 | Model O | 40 C. | 16 hr | 32.1 | 1.1 |
| T37P S98P | 9 | Model O | 40 C. | 16 hr | 31.7 | 1.0 |
| E77T Y93F | 9 | Model O | 40 C. | 16 hr | 31.6 | 1.1 |
| T37P E77T | 9 | Model O | 40 C. | 16 hr | 31.1 | 1.0 |
| S98P K116R | 9 | Model O | 40 C. | 16 hr | 30.8 | 1.1 |
| T37P Y93Q | 9 | Model O | 40 C. | 16 hr | 30.0 | 1.0 |
| T37P Y93C | 9 | Model O | 40 C. | 16 hr | 30.0 | 1.0 |
| T37P V82I | 9 | Model O | 40 C. | 16 hr | 29.6 | 1.0 |
| T37P Y93A | 9 | Model O | 40 C. | 16 hr | 29.3 | 1.0 |
| E77T V82I | 9 | Model O | 40 C. | 24 hr | 24.4 | 1.3 |
| E77T A83P | 9 | Model O | 40 C. | 24 hr | 25.1 | 1.3 |
| V82I A83P | 9 | Model O | 40 C. | 24 hr | 44.8 | 2.2 |
| D135P A136P | 9 | Model O | 40 C. | 24 hr | 31.3 | 1.6 |
| E77T D135P | 9 | Model O | 40 C. | 24 hr | 24.2 | 1.3 |
| E77T G257L | 9 | Model O | 40 C. | 24 hr | 37.3 | 1.9 |
| V82I K116R | 9 | Model O | 40 C. | 24 hr | 22.3 | 1.2 |
| V82I D135P | 9 | Model O | 40 C. | 24 hr | 26.4 | 1.4 |
| V82I S241C | 9 | Model O | 40 C. | 24 hr | 34.6 | 1.7 |
| V82I G257A | 9 | Model O | 40 C. | 24 hr | 29.7 | 1.5 |
| V82I G257F | 9 | Model O | 40 C. | 24 hr | 37.3 | 2.0 |
| V82I G257W | 9 | Model O | 40 C. | 24 hr | 43.9 | 2.3 |
| V82I G257S | 9 | Model O | 40 C. | 24 hr | 24.4 | 1.3 |
| V82I G257Y | 9 | Model O | 40 C. | 24 hr | 24.9 | 1.3 |
| V82I G257L | 9 | Model O | 40 C. | 24 hr | 37.9 | 1.8 |
| Y93C S241C | 9 | Model O | 40 C. | 24 hr | 37.0 | 1.8 |
| Y93C G257A | 9 | Model O | 40 C. | 24 hr | 28.6 | 1.4 |
| Y93C G257W | 9 | Model O | 40 C. | 24 hr | 48.0 | 2.3 |
| Y93C G257S | 9 | Model O | 40 C. | 24 hr | 21.5 | 1.2 |
| Y93C G257Y | 9 | Model O | 40 C. | 24 hr | 21.5 | 1.2 |
| Y93C G257L | 9 | Model O | 40 C. | 24 hr | 38.5 | 1.9 |

TABLE 3-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| A83P Y93R | 9 | Model O | 40 C. | 24 hr | 26.9 | 1.4 |
| A83P Y93A | 9 | Model O | 40 C. | 24 hr | 22.0 | 1.2 |
| A83P Y93I | 9 | Model O | 40 C. | 24 hr | 24.0 | 1.2 |
| A83P Y93C | 9 | Model O | 40 C. | 24 hr | 26.7 | 1.4 |
| A83P Y93F | 9 | Model O | 40 C. | 24 hr | 25.2 | 1.3 |
| A83P Y93Q | 9 | Model O | 40 C. | 24 hr | 27.4 | 1.4 |
| A83P S98P | 9 | Model O | 40 C. | 24 hr | 32.1 | 1.6 |
| A83P K116R | 9 | Model O | 40 C. | 24 hr | 23.8 | 1.3 |
| A83P D135P | 9 | Model O | 40 C. | 24 hr | 35.2 | 1.8 |
| A83P A136P | 9 | Model O | 40 C. | 24 hr | 24.6 | 1.3 |
| A83P S241C | 9 | Model O | 40 C. | 24 hr | 40.7 | 2.1 |
| A83P G257A | 9 | Model O | 40 C. | 24 hr | 38.9 | 1.9 |
| A83P G257F | 9 | Model O | 40 C. | 24 hr | 49.4 | 2.4 |
| A83P G257W | 9 | Model O | 40 C. | 24 hr | 50.6 | 2.7 |
| A83P G257S | 9 | Model O | 40 C. | 24 hr | 34.9 | 1.8 |
| A83P G257Y | 9 | Model O | 40 C. | 24 hr | 31.6 | 1.6 |
| A83P G257L | 9 | Model O | 40 C. | 24 hr | 47.0 | 2.3 |
| Y93A D135P | 9 | Model O | 40 C. | 24 hr | 23.5 | 1.2 |
| Y93A S241C | 9 | Model O | 40 C. | 24 hr | 29.5 | 1.5 |
| Y93A G257A | 9 | Model O | 40 C. | 24 hr | 28.8 | 1.5 |
| Y93A G257S | 9 | Model O | 40 C. | 24 hr | 21.4 | 1.2 |
| Y93A G257L | 9 | Model O | 40 C. | 24 hr | 31.1 | 1.6 |
| Y93C D135P | 9 | Model O | 40 C. | 24 hr | 26.4 | 1.4 |
| Y93F D135P | 9 | Model O | 40 C. | 24 hr | 22.9 | 1.2 |
| Y93F A136P | 9 | Model O | 40 C. | 24 hr | 25.1 | 1.3 |
| Y93F G257A | 9 | Model O | 40 C. | 24 hr | 62.0 | 3.8 |
| Y93F G257W | 9 | Model O | 40 C. | 24 hr | 42.9 | 2.3 |
| Y93F G257Y | 9 | Model O | 40 C. | 24 hr | 24.4 | 1.3 |
| Y93F G257L | 9 | Model O | 40 C. | 24 hr | 38.0 | 1.9 |
| Y93I D135P | 9 | Model O | 40 C. | 24 hr | 23.9 | 1.3 |
| Y93I A136P | 9 | Model O | 40 C. | 24 hr | 24.7 | 1.3 |
| Y93I S241C | 9 | Model O | 40 C. | 24 hr | 31.5 | 1.6 |
| Y93I G257A | 9 | Model O | 40 C. | 24 hr | 25.9 | 1.3 |
| Y93I G257W | 9 | Model O | 40 C. | 24 hr | 43.2 | 2.2 |
| Y93I G257S | 9 | Model O | 40 C. | 24 hr | 20.2 | 1.1 |
| Y93I G257Y | 9 | Model O | 40 C. | 24 hr | 24.9 | 1.3 |
| Y93I G257L | 9 | Model O | 40 C. | 24 hr | 48.7 | 2.6 |
| Y93Q D135P | 9 | Model O | 40 C. | 24 hr | 25.9 | 1.3 |
| Y93Q S241C | 9 | Model O | 40 C. | 24 hr | 33.0 | 1.6 |
| Y93Q G257A | 9 | Model O | 40 C. | 24 hr | 27.6 | 1.4 |
| Y93Q G257F | 9 | Model O | 40 C. | 24 hr | 34.6 | 1.8 |
| Y93Q G257S | 9 | Model O | 40 C. | 24 hr | 22.2 | 1.2 |
| G47S G257E | 9 | Model O | 40 C. | 24 hr | 57.9 | 3.4 |
| V82R G257W | 9 | Model O | 40 C. | 24 hr | 51.9 | 2.5 |
| D135P G257F | 9 | Model O | 40 C. | 24 hr | 49.9 | 2.4 |
| D135P G257W | 9 | Model O | 40 C. | 24 hr | 48.6 | 2.3 |
| A136P G257F | 9 | Model O | 40 C. | 24 hr | 48.3 | 2.2 |
| D135P G257A | 9 | Model O | 40 C. | 24 hr | 45.5 | 2.1 |
| Y93Q G257L | 9 | Model O | 40 C. | 24 hr | 44.2 | 2.2 |
| D135P G257E | 9 | Model O | 40 C. | 24 hr | 40.7 | 2.0 |
| A136P G257L | 9 | Model O | 40 C. | 24 hr | 38.4 | 1.8 |
| V82R G257E | 9 | Model O | 40 C. | 24 hr | 37.9 | 1.8 |
| D135P G257L | 9 | Model O | 40 C. | 24 hr | 37.5 | 1.7 |
| S98P S241C | 9 | Model O | 40 C. | 24 hr | 36.9 | 2.0 |
| G47S P258Q | 9 | Model O | 40 C. | 24 hr | 36.9 | 1.8 |
| S98P G257F | 9 | Model O | 40 C. | 24 hr | 35.7 | 2.0 |
| S98P G257L | 9 | Model O | 40 C. | 24 hr | 35.6 | 1.8 |
| V82R G47S | 9 | Model O | 40 C. | 24 hr | 35.5 | 1.6 |
| K116R G257L | 9 | Model O | 40 C. | 24 hr | 34.9 | 1.8 |
| A136P S241C | 9 | Model O | 40 C. | 24 hr | 34.5 | 1.6 |
| Y93R G257E | 9 | Model O | 40 C. | 24 hr | 34.4 | 1.7 |
| D135P S241C | 9 | Model O | 40 C. | 24 hr | 33.5 | 1.7 |
| Y93R G257L | 9 | Model O | 40 C. | 24 hr | 32.0 | 1.7 |
| V82I G257E | 9 | Model O | 40 C. | 24 hr | 31.5 | 1.6 |
| A136P G257A | 9 | Model O | 40 C. | 24 hr | 30.9 | 1.5 |
| D135P G257S | 9 | Model O | 40 C. | 24 hr | 30.5 | 1.7 |
| Y93R G257A | 9 | Model O | 40 C. | 24 hr | 30.4 | 1.5 |
| Y93R G257W | 9 | Model O | 40 C. | 24 hr | 30.3 | 1.4 |
| Y93R S241C | 9 | Model O | 40 C. | 24 hr | 30.2 | 1.5 |
| S98P G257A | 9 | Model O | 40 C. | 24 hr | 29.9 | 1.5 |

TABLE 3-continued

Variants of the present invention having an improved half life Improvement Factor (HIF) measured as improved stability compared to the parent mannanase (SEQ ID NO: 1)

| Substitutions introduced in SEQ ID NO: 1 | pH | Detergent | Temperature | Time | % Residual Activity | HIF |
|---|---|---|---|---|---|---|
| Y93R G257F | 9 | Model O | 40 C. | 24 hr | 29.5 | 1.4 |
| Y93F G257E | 9 | Model O | 40 C. | 24 hr | 28.7 | 1.5 |
| V82R Y93R | 9 | Model O | 40 C. | 24 hr | 28.1 | 1.5 |
| D135P G257Y | 9 | Model O | 40 C. | 24 hr | 28.1 | 1.3 |
| K116R G257F | 9 | Model O | 40 C. | 24 hr | 28.1 | 1.2 |
| A136P G257Y | 9 | Model O | 40 C. | 24 hr | 26.4 | 1.3 |
| S98P D135P | 9 | Model O | 40 C. | 24 hr | 26.3 | 1.5 |
| A136P G257S | 9 | Model O | 40 C. | 24 hr | 26.0 | 1.3 |
| K116R S241C | 9 | Model O | 40 C. | 24 hr | 25.5 | 1.4 |
| K116R D135P | 9 | Model O | 40 C. | 24 hr | 24.6 | 1.3 |
| K116R G257A | 9 | Model O | 40 C. | 24 hr | 24.3 | 1.3 |
| V82R Y93F | 9 | Model O | 40 C. | 24 hr | 22.0 | 1.2 |
| Y93R A136P | 9 | Model O | 40 C. | 24 hr | 21.9 | 1.2 |
| Y93R D135P | 9 | Model O | 40 C. | 24 hr | 20.4 | 1.1 |
| S241C G257A | 9 | Model O | 40 C. | 24 hr | 47.7 | 2.4 |
| S241C G257F | 9 | Model O | 40 C. | 24 hr | 28.8 | 1.5 |
| S241C G257W | 9 | Model O | 40 C. | 24 hr | 49.2 | 2.2 |
| S241C G257S | 9 | Model O | 40 C. | 24 hr | 36.4 | 1.7 |
| S241C G257Y | 9 | Model O | 40 C. | 24 hr | 27.3 | 1.4 |
| S241C G257L | 9 | Model O | 40 C. | 24 hr | 51.7 | 2.7 |
| V82R D135P | 9 | Model O | 40 C. | 24 hr | 36.8 | 1.8 |
| T37P V82R | 9 | Model O | 40 C. | 24 hr | 20.3 | 1.1 |
| G47A V82R | 9 | Model O | 40 C. | 24 hr | 26.2 | 1.4 |
| G47S V82R | 9 | Model O | 40 C. | 24 hr | 31.6 | 1.6 |
| E77T V82R | 9 | Model O | 40 C. | 24 hr | 23.3 | 1.2 |
| V82R Y93A | 9 | Model O | 40 C. | 24 hr | 25.2 | 1.3 |
| V82R Y93I | 9 | Model O | 40 C. | 24 hr | 36.2 | 1.9 |
| V82R Y93C | 9 | Model O | 40 C. | 24 hr | 26.2 | 1.3 |
| V82R Y93Q | 9 | Model O | 40 C. | 24 hr | 28.2 | 1.5 |
| V82R S98P | 9 | Model O | 40 C. | 24 hr | 26.3 | 1.4 |
| V82R K116R | 9 | Model O | 40 C. | 24 hr | 20.7 | 1.2 |
| V82R A136P | 9 | Model O | 40 C. | 24 hr | 33.8 | 1.6 |
| V82R S241C | 9 | Model O | 40 C. | 24 hr | 39.0 | 1.9 |
| V82R G257A | 9 | Model O | 40 C. | 24 hr | 43.1 | 2.2 |
| V82R G257F | 9 | Model O | 40 C. | 24 hr | 35.5 | 1.8 |
| V82R G257S | 9 | Model O | 40 C. | 24 hr | 21.7 | 1.2 |
| V82R G257Y | 9 | Model O | 40 C. | 24 hr | 31.6 | 1.5 |
| V82R G257L | 9 | Model O | 40 C. | 24 hr | 41.4 | 2.0 |

Example 4: Protease Stability of Mannanase Variants

Variants of the present invention and generated as described in Example 1 and 2, were tested for protease stability in Model O detergent at pH 9.0 and Model A detergent at pH 7.8. Stability test was performed by incubating the variants in detergent for 4 weeks and at a temperature of either 37° C., 40° C. or 50° C. (see tables below) and comparing the activity against a control sample that was stored at −18° C. for the same duration.

To the Model O detergent and Model A detergents was added a protease as disclosed in the tables below.

The residual activity was measured by using the PAHBAH reducing sugar method, using carob-galactomannan from Megazyme. Substrate was incubated with detergent containing the mannanase enzyme for 30 min at 50° C. The enzymatic hydrolysis reaction was stopped by adding an alkaline reagent containing PAHBAH and $Bi^{3+}$, which reacts with reducing sugars for 20 minutes. The resulting yellow color is measured by reading the optical density at 405 nm. The residual activity was calculated by taking the ratio of Stress response to Un-stress response and expressing in terms of % RA.

TABLE 4 protease stability at pH 9.0 and 37° C. in Model O detergent (see Table 1). The protease used is a variant of SEQ ID NO: 4 with the following modifications: S9E + N42R + N74D + V199I + Q200L + Y203W + S253D + N255W + L256E added in a 0.2% (w/w) concentration.

| Sample | Incubation time | Residual activity % |
|---|---|---|
| Reference (SEQ ID NO: 2) | 4 weeks | 0 |
| SEQ ID NO: 2 + S202R + W260F + L288I + L294P + S295V | 4 weeks | 69 |
| SEQ ID NO: 2 + S202R + W260F + L288I + L294P + S295V +A136P | 4 weeks | 79 |
| SEQ ID NO: 2 + Y93Q + A136P + S202R + W260F + L288I + L294P + S295V | 4 weeks | 94 |
| SEQ ID NO: 2 + S98P + A136P + S202R + W260F + L288I + L294P + S295V | 4 weeks | 89 |

TABLE 5 protease stability at pH 7.8 at 40° C. and 50° C. in Model A detergent (see Table 1). The protease used is a variant of 4 with the following modifications: Y161A + R164S + A188P added in a 0.7% (w/w) concentration.

| Sample | Temperature | Incubation time | Residual activity % |
| --- | --- | --- | --- |
| Reference (SEQ ID NO: 2) | 40° C. | 4 weeks | 33 |
| SEQ ID NO: 2 + A30T + Y93Q + S95D + D118K + A136P + D139R + N200T + S202R + R210G + W260F + N283H + L288I + L294P + S295V | 40° C. | 4 weeks | 91 |
| Reference (SEQ ID NO: 2) | 50° C. | 4 weeks | 15 |
| SEQ ID NO: 2 + A30T + Y93Q + S95D + D118K + A136P + D139R + N200T + S202R + R210G + W260F + N283H + L288I + L294P + S295V | 50° C. | 4 weeks | 83 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

SEQUENCE LISTING

```
<160> NUMBER OF SEQ ID NOS: 4

<210> SEQ ID NO 1
<211> LENGTH: 326
<212> TYPE: PRT
<213> ORGANISM: Bacillus bogoriensis
<220> FEATURE:
<221> NAME/KEY: mat_peptide
<222> LOCATION: (29)..(326)

<400> SEQUENCE: 1

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Ala Asn Ser Gly
        -10                  -5                  -1   1

Phe Tyr Val Ser Gly Thr Thr Leu Tyr Asp Ala Asn Gly Asn Pro Phe
  5                  10                  15                  20

Val Met Arg Gly Ile Asn His Gly His Ala Trp Tyr Lys Asp Gln Ala
                 25                  30                  35

Thr Thr Ala Ile Glu Gly Ile Ala Asn Thr Gly Ala Asn Thr Val Arg
                 40                  45                  50

Ile Val Leu Ser Asp Gly Gly Gln Trp Thr Lys Asp Ile His Thr
                 55                  60                  65

Val Arg Asn Leu Ile Ser Leu Ala Glu Asp Asn His Leu Val Ala Val
 70                  75                  80

Leu Glu Val His Asp Ala Thr Gly Tyr Asp Ser Ile Ala Ser Leu Asn
 85                  90                  95                 100

Arg Ala Val Asp Tyr Trp Ile Glu Met Arg Ser Ala Leu Ile Gly Lys
                105                 110                 115

Glu Asp Thr Val Ile Ile Asn Ile Ala Asn Glu Trp Phe Gly Ser Trp
                120                 125                 130

Glu Gly Asp Ala Trp Ala Asp Gly Tyr Lys Gln Ala Ile Pro Arg Leu
                135                 140                 145

Arg Asn Ala Gly Leu Asn His Thr Leu Met Val Asp Ala Ala Gly Trp
                150                 155                 160
```

```
Gly Gln Phe Pro Gln Ser Ile His Asp Tyr Gly Arg Glu Val Phe Asn
165                 170                 175                 180

Ala Asp Pro Gln Arg Asn Thr Met Phe Ser Ile His Met Tyr Glu Tyr
                185                 190                 195

Ala Gly Gly Asn Ala Ser Gln Val Arg Thr Asn Ile Asp Arg Val Leu
            200                 205                 210

Asn Gln Asp Leu Ala Leu Val Ile Gly Glu Phe Gly His Arg His Thr
        215                 220                 225

Asn Gly Asp Val Asp Glu Ala Thr Ile Met Ser Tyr Ser Glu Gln Arg
    230                 235                 240

Gly Val Gly Trp Leu Ala Trp Ser Trp Lys Gly Asn Gly Pro Glu Trp
245                 250                 255                 260

Glu Tyr Leu Asp Leu Ser Asn Asp Trp Ala Gly Asn Asn Leu Thr Ala
                265                 270                 275

Trp Gly Asn Thr Ile Val Asn Gly Pro Tyr Gly Leu Arg Glu Thr Ser
            280                 285                 290

Arg Leu Ser Thr Val Phe
        295

<210> SEQ ID NO 2
<211> LENGTH: 298
<212> TYPE: PRT
<213> ORGANISM: Bacillus bogoriensis

<400> SEQUENCE: 2

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
                20                  25                  30

Lys Asp Gln Ala Thr Thr Ala Ile Glu Gly Ile Ala Asn Thr Gly Ala
            35                  40                  45

Asn Thr Val Arg Ile Val Leu Ser Asp Gly Gly Gln Trp Thr Lys Asp
        50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
            180                 185                 190

Met Tyr Glu Tyr Ala Gly Gly Asn Ala Ser Gln Val Arg Thr Asn Ile
        195                 200                 205

Asp Arg Val Leu Asn Gln Asp Leu Ala Leu Val Ile Gly Glu Phe Gly
210                 215                 220

His Arg His Thr Asn Gly Asp Val Asp Glu Ala Thr Ile Met Ser Tyr
225                 230                 235                 240
```

```
Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
        275                 280                 285

Arg Glu Thr Ser Arg Leu Ser Thr Val Phe
        290                 295

<210> SEQ ID NO 3
<211> LENGTH: 981
<212> TYPE: DNA
<213> ORGANISM: Bacillus bogoriensis

<400> SEQUENCE: 3
```

| | | |
|---|---|---|
| atgaaacaac aaaaacggct ttacgcccga ttgctgacgc tgttatttgc gctcatcttc | 60 |
| ttgctgcctc attctgcagc cgcggcaaat tccggatttt atgtaagcgg taccactcta | 120 |
| tacgatgcca atggaaaccc atttgtaatg agagggatta ccatgggca cgcatggtat | 180 |
| aaagaccagg caactactgc aattgaaggg attgcaaata ccggtgctaa tacggtccgg | 240 |
| attgtgttat ctgatggggg acaatggaca aaagatgaca tccatacagt aagaaacctt | 300 |
| atctctttag cggaagataa tcatttggtt gctgttcttg aagttcatga tgctaccggt | 360 |
| tatgattcca ttgcttcgct caatcgtgct gttgattatt ggattgaaat gagaagtgct | 420 |
| ttaattggaa aggaagatac cgtcattatt aatattgcga tgaatggtt tggttcgtgg | 480 |
| gaaggggatg cttgggctga cgggtataaa caagcaatcc cgcgattgcg taacgccggt | 540 |
| ctaaaccata ccttgatggt agatgctgcg gggtggggac aatttccaca atcgattcat | 600 |
| gattatggaa gagaagtttt taatgctgac cctcaacgaa atacaatgtt ttcgattcat | 660 |
| atgtatgaat atgcaggtgg taatgcatcg caagttcgta ctaatattga ccgagttctt | 720 |
| aatcaagacc tcgcattagt cattggtgaa tttggacacc gtcatacaaa tggtgacgtc | 780 |
| gatgaagcaa cgattatgag ctattctgaa caaagaggag ttgggtggtt ggcgtggtca | 840 |
| tggaaaggga acggcccaga tgggagtat ttagaccttt cgaatgattg ggctggaaat | 900 |
| aaccttacag cttggggaaa tacaatagtg aatggtccat atggtttaag agaaacttcg | 960 |
| agattaagca ccgtttttg a | 981 |

```
<210> SEQ ID NO 4
<211> LENGTH: 269
<212> TYPE: PRT
<213> ORGANISM: Bacillus subtilis

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
```

|  |  |  |  |  | 85 |  |  |  |  | 90 |  |  |  |  | 95 |  |  |
|---|---|---|---|---|---|---|---|---|---|---|---|---|---|---|---|---|---|
| Ser | Gly | Ser | Gly<br>100 | Ser | Val | Ser | Ser | Ile<br>105 | Ala | Gln | Gly | Leu | Glu<br>110 | Trp | Ala |
| Gly | Asn | Asn<br>115 | Gly | Met | His | Val<br>120 | Ala | Asn | Leu | Ser | Leu<br>125 | Gly | Ser | Pro | Ser |
| Pro | Ser<br>130 | Ala | Thr | Leu | Glu | Gln<br>135 | Ala | Val | Asn | Ser | Ala<br>140 | Thr | Ser | Arg | Gly |
| Val<br>145 | Leu | Val | Val | Ala | Ala<br>150 | Ser | Gly | Asn | Ser | Gly<br>155 | Ala | Gly | Ser | Ile | Ser<br>160 |
| Tyr | Pro | Ala | Arg<br>165 | Tyr | Ala | Asn | Ala | Met | Ala<br>170 | Val | Gly | Ala | Thr<br>175 | Asp | Gln |
| Asn | Asn | Asn | Arg<br>180 | Ala | Ser | Phe | Ser | Gln<br>185 | Tyr | Gly | Ala | Gly | Leu<br>190 | Asp | Ile |
| Val | Ala | Pro<br>195 | Gly | Val | Asn | Val | Gln<br>200 | Ser | Thr | Tyr | Pro | Gly<br>205 | Ser | Thr | Tyr |
| Ala | Ser | Leu | Asn<br>210 | Gly | Thr | Ser | Met<br>215 | Ala | Thr | Pro | His | Val<br>220 | Ala | Gly | Ala |
| Ala<br>225 | Ala | Leu | Val | Lys | Gln<br>230 | Lys | Asn | Pro | Ser | Trp<br>235 | Ser | Asn | Val | Gln | Ile<br>240 |
| Arg | Asn | His | Leu | Lys<br>245 | Asn | Thr | Ala | Thr | Ser<br>250 | Leu | Gly | Ser | Thr | Asn<br>255 | Leu |
| Tyr | Gly | Ser | Gly<br>260 | Leu | Val | Asn | Ala | Glu<br>265 | Ala | Ala | Thr | Arg |  |  |  |

The invention claimed is:

1. An isolated mannanase variant of a parent mannanase, wherein the variant comprises at least two substitutions in any two or more positions corresponding to positions selected from the group consisting of 3, 37, 47, 77, 82, 83, 93, 98, 116, 136, 241, 257, and 258, wherein at least one substitution is X136P at position 136, wherein numbering is according to SEQ ID NO: 2, said variant has mannanase activity and comprises an amino acid sequence that has at least 85% but less than 100% sequence identity to the amino acid sequence of SEQ ID NO: 2.

2. The variant according to claim 1, wherein said at least two substitutions are A136P and one or more substitutions selected from the group consisting of: S3P, T37P, G47A, G47S, E77T, V82I, V82R, A83P, Y93Q, Y93C, Y93A, Y93F, Y93I, Y93R, S98P, K116R, S241C, G257W, G257E, G257L, G257A, G257S, G257Y, G257F, and P258Q.

3. A composition comprising the variant of claim 1.

4. The composition according to claim 3, wherein said composition further comprises an additional enzyme.

5. The composition of claim 3, wherein said composition further comprises a surfactant, a bleaching system, a chelating agent, a stabilizing agent, a hydrotope, a builder, a co-builder, a bleach activator, a polymer and/or a fabric-huing agent.

6. An isolated polynucleotide encoding the variant according to claim 1.

7. A nucleic acid construct comprising the polynucleotide according to claim 6.

8. An expression vector comprising the polynucleotide according to claim 6.

9. An isolated host cell comprising the polynucleotide according to claim 6.

10. A method of producing a mannanase variant, comprising:
cultivating the host cell according to claim 9 under conditions suitable for expression of said variant; and
recovering said variant.

11. A method of dishwashing in an automatic dishwashing machine comprising the steps of adding said composition of claim 3 in a detergent composition compartment in said automatic dishwashing machine, and releasing said composition during a main-wash cycle.

12. A method of laundering in an automatic laundering machine comprising the steps of adding said composition of claim 3 in a detergent composition compartment in said automatic laundering machine, and releasing said composition during a main wash cycle.

13. The variant according to claim 1, further comprising a substitution in an amino acid position selected from the positions 260, 288, 294, and 295, wherein numbering is according to SEQ ID NO: 2.

14. The variant according to claim 1, wherein said variant has an improved in-detergent stability or thermostability compared to said parent mannanase.

15. The variant according to claim 1, wherein said two or more substitutions are selected from the group consisting of positions: 3+136, 37+136, 47+136, 77+136, 82+136, 83+136, 93+136, 98+136, 116+136, 136+241, 136+257 and 136+258, wherein numbering is according to SEQ ID NO: 2.

16. The composition of claim 4, wherein the additional enzyme is a protease, an amylase or a lipase.

* * * * *